US010584159B2

(12) United States Patent
Laporte et al.

(10) Patent No.: US 10,584,159 B2
(45) Date of Patent: Mar. 10, 2020

(54) RENILLA BASED BIOSENSORS FOR MONITORING BIOMOLECULE LOCALIZATION AND TRAFFICKING IN CELLS

(71) Applicants: The Royal Institution for the Advancement of Learning/McGill University, Montréal, Québec (CA); Université de Montréal, Montréal, Québec (CA)

(72) Inventors: Stéphane Alain Laporte, Outremont (CA); Yoon Namkung, Pointe-Claire (CA); Michel Bouvier, Montréal (CA); Christian Le Gouill, Montréal (CA); Mireille Hogue, Laval (CA); Viktoriya Lukasheva, Pointe-Claire (CA); Hiroyuki Kobayashi, Montréal (CA); Denis Deblois, Montréal (CA); Étienne Durette, Saint-Jérôme (CA)

(73) Assignees: The Royal Institution for the Advancement of Learning/McGill University, Montréal, Québec (CA); Université de Montréal, Montréal, Québec (CA)

( * ) Notice: Subject to any disclaimer, the term of this patent is extended or adjusted under 35 U.S.C. 154(b) by 153 days.

(21) Appl. No.: 15/512,267

(22) PCT Filed: Sep. 21, 2015

(86) PCT No.: PCT/CA2015/050924
§ 371 (c)(1),
(2) Date: Mar. 17, 2017

(87) PCT Pub. No.: WO2016/041093
PCT Pub. Date: Mar. 24, 2016

(65) Prior Publication Data
US 2017/0313762 A1 Nov. 2, 2017

Related U.S. Application Data

(60) Provisional application No. 62/052,738, filed on Sep. 19, 2014.

(51) Int. Cl.
*C07K 14/72* (2006.01)
*G01N 33/50* (2006.01)

(52) U.S. Cl.
CPC ....... *C07K 14/723* (2013.01); *G01N 33/5035* (2013.01); *C07K 2319/60* (2013.01)

(58) Field of Classification Search
CPC .............. C07K 14/723; C07K 2319/60; G01N 33/5035
See application file for complete search history.

(56) References Cited

FOREIGN PATENT DOCUMENTS

| WO | 2005105850 | 11/2005 |
|---|---|---|
| WO | 2010/085844 | 8/2010 |
| WO | 2011/067202 | 6/2011 |
| WO | 2011130540 | 10/2011 |

OTHER PUBLICATIONS

Violin et al., G Protein coupled receptor kinase and p-arrestin mediated desensitization of the angiotensin II Type 1A receptor elucidated by diacylglycerol dynamics. J Biol. Chem. 281, 36411-36419, 2006. (Year: 2006).*
Supplementary European Search Report corresponding to European Application No. 15841561.2 dated Feb. 5, 2018.
Charest et al. "Palmitoylation of the V2 vasopressin receptor carboxyl tail enhances beta-arrestin recruitment leading to efficient receptor endocytosis and ERK1/2 activation", J. Biol. Chem. 287(42):41541-41551.
Anborgh et al. (2000). "Receptor/beta-arrestin complex formation and the differential trafficking and resensitization of beta2-adrenergic and angiotensin II type 1A receptors." Mol Endocrinol 14(12): 2040-2053.
Barberis et al, (1992), "Pharmacology of oxytocin and vasopressin receptors in the central and peripheral nervous system." Ann N Y Acad Sci 652: 39-45.
Claing et al. (2002). "Endocytosis of G protein-coupled receptors roles of G protein-coupled receptor kinases and beta-arrestin proteins." Prog Neurobiol 66(2): 61-79.
Dacres et al., "Comparison of enhanced bioluminescence energy transfer donors for protease biosensors". Analytical Biochemistry, Feb. 28, 2012 (Feb. 28, 2012), vol. 424, pp. 206-210.
Fessart et al. (2005). "c-Src regulates clathrin adapter protein 2 interaction with beta-arrestin and the angiotensin II type 1 receptor during clathrin-mediated internalization." Mol Endocrinol 19(2): 491-503.

(Continued)

*Primary Examiner* — Elly-Gerald Stoica
(74) *Attorney, Agent, or Firm* — Myers Bigel, P.A.

(57) ABSTRACT

Bioluminescence resonance energy transfer (BRET) biosensors for assessing the intracellular localization, internalization and trafficking into cellular compartments of proteins such as receptors, and other biomolecules such as second messengers, are disclosed. These biosensors, which are dependent on the concentration/density of the BRET donor and acceptor in cellular compartments rather that specific protein-protein interactions, use a *Renilla* GFP/Luc BRET pair, which allows the robust and reproducible monitoring of protein trafficking/localization, with a sensitivity compatible with high-throughput screening (HTS). The use of these biosensors for various applications, including assessing/monitoring protein endocytosis, recycling and intracellular trafficking, receptor maturation/rescue by pharmacological chaperones, various endocytosis/exocytosis processes, activation/inhibition, as well as biomolecule concentration/density in different cellular compartments, is also disclosed.

26 Claims, 40 Drawing Sheets
Specification includes a Sequence Listing.

(56) References Cited

OTHER PUBLICATIONS

Gaborik et al. (2001). "Beta-arrestin- and dynamin-dependent endocytosis of the AT1 angiotensin receptor." Mol Pharmacol 59(2): 239-247.
Goupil et al. (2012). "Biasing the prostaglandin F2alpha receptor responses toward EGFR-dependent transactivation of MAPK." Mol Endocrinol 26(7): 1189-1202.
Hanyaloglu et al. (2008). "Regulation of GPCRs by endocytic membrane trafficking and its potential implications." Annu Rev Pharmacol Toxicol 48: 537-568.
Hein et al. (1997). "Intracellular trafficking of angiotensin II and its AT1 and AT2 receptors: evidence for selective sorting of receptor and ligand," Mol Endocrinol 11(9): 1266-1277.
Hunyady et al. (2006). "Pleiotropic AT1 receptor signaling pathways mediating physiological and pathogenic actions of angiotensin II." Mol Endocrinol 20(5): 953-970.
Hunyady et al. (2002). "Differential PI 3-kinase dependence of early and late phases of recycling of the internalized AT1 angiotensin receptor." J Cell Biol 157(7): 1211-1222.
Innamorati et al. (1998). "A serine cluster prevents recycling of the V2 vasopressin receptor." Proc Natl Acad Sci U S A 95(5): 2222-2226.
Lan al., "Sensitive and High Resolution Localization and Tracking of Membrane Proteins in Live Cells with BRET" Traffic, Nov. 2012 (Nov. 2012), vol. 13(11), pp. 1450-1456.
Li et al. (2008). "Rab4 and Rab11 coordinately regulate the recycling of angiotensin II type I receptor as demonstrated by fluorescence resonance energy transfer microscopy." J Biomed Opt 13(3): 031206.
Molinari et al. (2008). "Functional complementation of high-efficiency resonance energy transfer: a new tool for the study of protein binding interactions in living cells." Biochem J 409(1): 251-261.
Morello et al., "Pharmacological chaperones rescue cell-surface expression and function of misfolded V2 vasopressin receptor mutants", J Clin Invest, 2000, 105(7): p. 887-95.
Oakley et al. (2000). "Differential affinities of visual arrestin, beta arrestin1, and beta arrestin2 for G protein-coupled receptors delineate two major classes of receptors." J Biol Chem 275(22): 17201-17210.
Posner et al. (2010). "Cellular signalling: Peptide hormones and growth factors." Prog brain Res 181: 1-16.
Quoyer et al. (2013). "Pepducin targeting the C-X-C chemokine receptor type 4 acts as a biased agonist favoring activation of the inhibitory G protein." Proceedings of the National Academy of Sciences of the United States of America 110(52): E5088-5097.
René et al. "Pharmacological Chaperones Restore Function to MC4R Mutants Responsible for Severe Early-Onset Obesity", J Pharmacol Exp Ther. Dec. 2010;335(3)520-32.
Seachrist et al. (2003). "Regulation of G protein-coupled receptor endocytosis and trafficking by Rab GTPases." Life Sci 74(2-3): 225-236.
Serradeil-Le Gal C., "An Overview of SR121463, a Selective Non-Peptide Vasopressin V2 Receptor Antagonist", Cardiovasc Drug Rev. 2001, 19(3):201-14.
Toth et al. (2012). "Acute depletion of plasma membrane phosphatidylinositol 4,5-bisphosphate impairs specific steps in endocytosis of the G-protein-coupled receptor." J Cell Sci 125(Pt 9): 2185-2197.
Tsao et al. (2000). "Type-specific sorting of G protein-coupled receptors after endocytosis." J Biol Chem 275(15): 11130-11140.
Tsao et al. (2001). "Role of endocytosis in mediating downregulation of G-protein-coupled receptors." Trends Pharmacol Sci 22(2): 91-96.
Ward et al. (1976). "Action spectrum and quantum yield for the photoinactivation of mnemiopsin, a bioluminescent photoprotein from the Ctenophore mnemiopsis SP." Photochem Photobiol 23(5): 351-363.
Wible et al., "HERG-Lite: A novel comprehensive high-throughout screen fordrug-induced hERG risk", J Pharmacol Toxicol Methods. 2005, 52(1):136-45.
Yeatman et al. (2014) "Allosteric Modulation of M1 Muscarinic Acetylcholine Receptor Internalization and Subcellular Trafficking", The Journal of Biological Chemistry vol. 289, No. 22, pp. 15856-15866.
Zhang et al. (1999). "Cellular trafficking of G protein-coupled receptor/beta-arrestin endocytic complexes." J Biol Chem 274(16): 10999-11006.
Zhang et al. (1996). "Dynamin and beta-arrestin reveal distinct mechanisms for G protein-coupled receptor internalization." J Biol Chem 271(31): 18302-18305.
Zimmerman et al. (2012). "Differential beta-arrestin-dependent conformational signaling and cellular responses revealed by angiotensin analogs." Sci Signal 5(221): ra33.
Zimmerman et al. (2011). "Role of beta-arrestins in bradykinin B2 receptor-mediated signalling," Cell Signal 23(4): 648-659.
Notification of Transmittal of the International Search Report and the Written Opinion of the International Searching Authority, or the Declaration corresponding to International Application No. PCT/CA2015/050924; dated Nov. 27, 2015.
Balla et al, "Demonstration of Angiotensin II-induced Ras Activation in the trans-Golgi Network and Endoplasmic Reticulum Using Bioluminescence Resonance Energy Transfer-based Biosensors", J. Biological Chem. 286 (7):5319-5327 (2011).
Office Action corresponding to Japanese Application No. 2017-515812 dated Jul. 16, 2019.

* cited by examiner

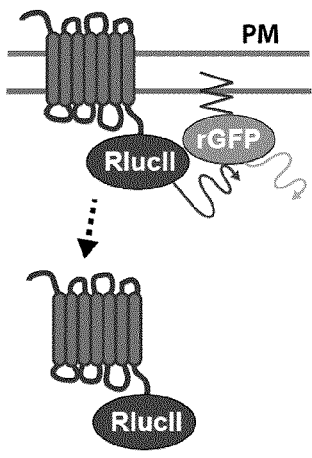
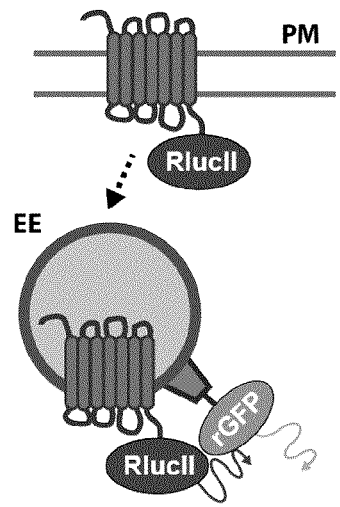
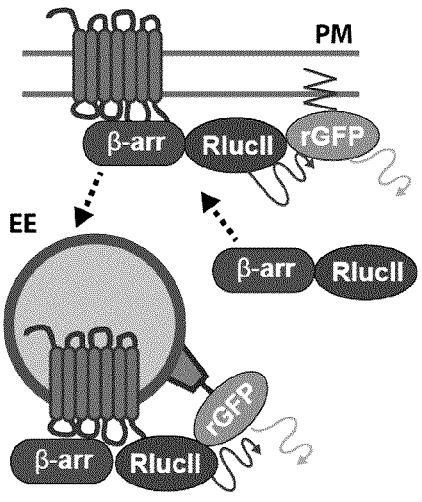
FIG. 1A  FIG. 1B  FIG. 1C
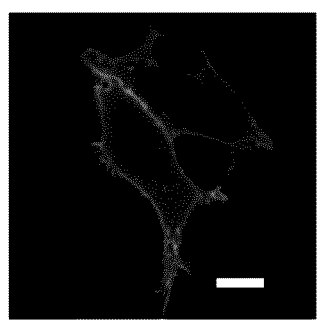
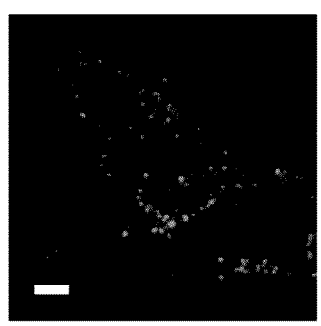
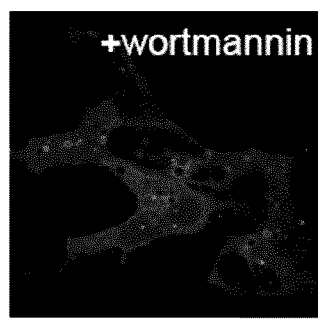
FIG. 1D  FIG. 1E
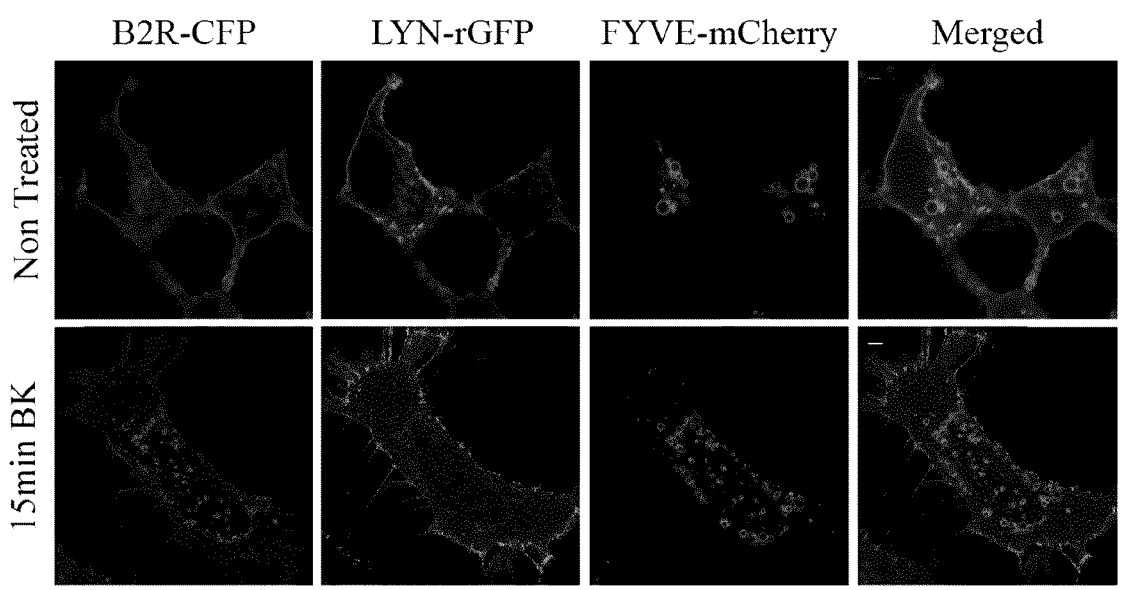
FIG. 1F

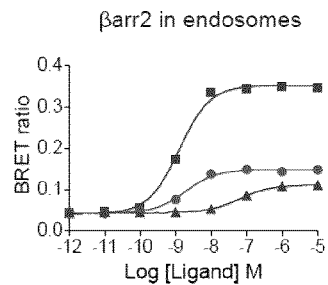
FIG. 6D
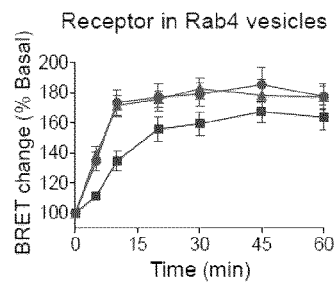
FIG. 6E
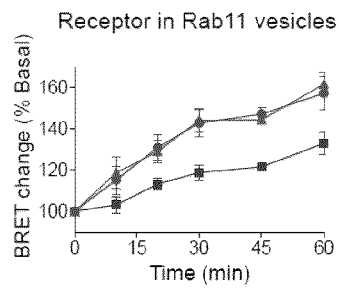
FIG. 6F
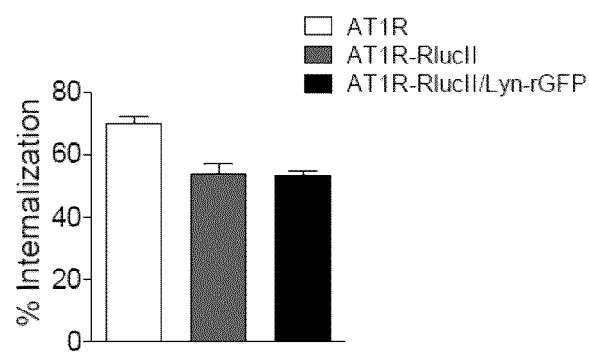
FIG. 7A
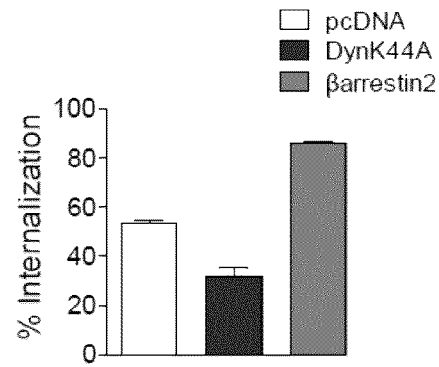
FIG. 7B
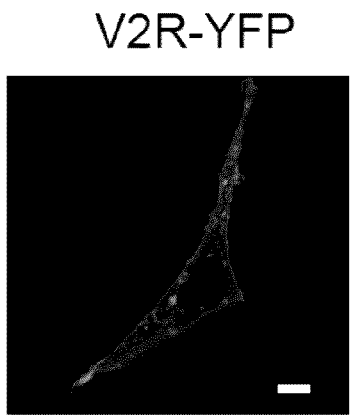
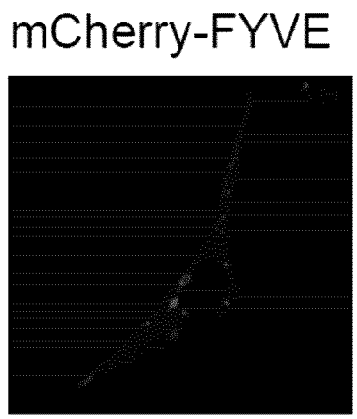
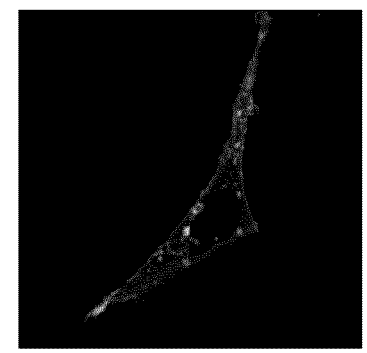
FIG. 8

| a) MC4R | 1) hMC4R wt-RlucII: human wild type Melanocortin 4 receptor tagged with RlucII |
|---|---|
| 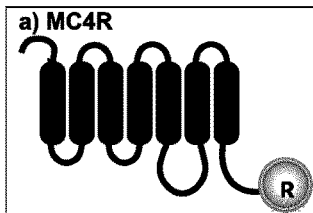 | 2) hMC4R (R165Q)-RlucII: mutant R165Q-hMC4R tagged with RlucII, intracellularly retained and PC-rescuable |
| | 3) hMC4R (P299H)-RlucII: mutant P299H-hMC4R tagged with RlucII, intracellularly retained and not PC-rescuable |
| | Linker sequence between the hMC4R and RlucII: hMC4R-VGGGGSKLPAT-RlucII  Linker1 |

FIG. 11A

| b) V2R | 1) hV2R wt-RlucII: human wild type Vasopressin 2 receptor tagged with RlucII |
|---|---|
| 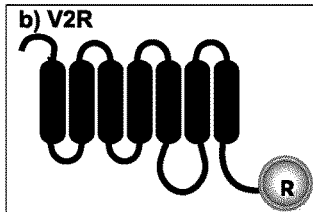 | 2) hV2R (Y128S)-RlucII: mutant Y128S-hV2R tagged with RlucII, intracellularly retained and PC-rescuable |
| | Linker sequence between the hV2R and RlucII: hV2R-GGSGLKLPAT-RlucII  Linker2 |

FIG. 11B

| c) hERG int RlucII | 1) hERK wt-RlucII: human wild type voltage-gated Potassium channel H2 (also known as hERG) with an internal RlucII-tag at position 379 with duplication of residues 373 to 379 |
|---|---|
| 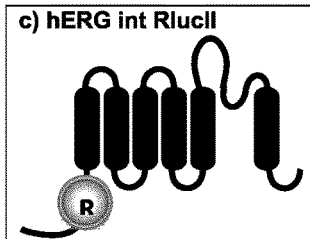 | 2)hERG (G601S): mutant G601S-hERG tagged with RlucII (pos 379) intracellularly retained and PC-rescuable |
| | Linkers and region duplicated from hERG: ...EKVTQVL$^{379}$- NAAIRSGG-RlucII- GGNAAIRS- EKVTQVL$^{379}$...  hERG      Linker 3              Linker 4      hERG |

FIG. 11C

| d) PM-rGFP & Golgi-rGFP 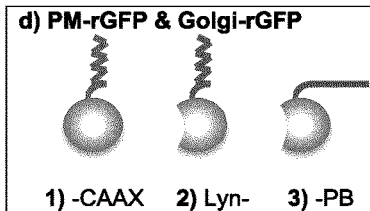<br>1) -CAAX  2) Lyn-  3) -PB | 1) Lyn-rGFP: Renilla reniformis green fluorescent protein (rGFP) tagged in N-terminal with the palmitoylation & myristoylation signal sequence from the Lyn kinase: MGCIKSKGKDS-<br>2) rGFP-CAAX (Kras): rGFP tagged in C-terminal with the plasma-membrane targetting polybasic sequence and prenylation signal sequence from kRas splice variant b: - GKKKKKKSKTKCVIM<br>3) rGFP-CAAX (Hras): rGFP tagged in C-terminal with the plasma-membrane targetting palmitoylation sequence and prenylation signal sequence from hRas: - CMSCKCVLS<br>4) rGFP-CAAX (CCIL): rGFP tagged in C-terminal with the plasma-membrane targetting palmitoylation sequence from hRas and prenylation signal sequence from Ral1: - CMSCKCCIL<br>5) rGFP-PB: rGFP tagged in C-terminal with the plasma-membrane targeting polybasic sequence from the human GRK5: - SPKKGLLQRLFKRQHQNNSKS<br>6) rGFP-Caveolin1α: Human Caveolin1α tagged in N-terminal with rGFP<br>7) Golgi-rGFP: rGFP tagged in N-terminal with the Golgi targetting sequence from the human eNOS1: - residues 1 to 73: MGNLK...PRVKN-<br><br>Linker between Lyn plasma-membrane targeting sequence (Lyn) and rGFP:<br>　　　Lyn-<u>LSNAT</u>-rGFP<br>　　　　　　Linker<br>Linker between rGFP and polybasic/prenylation sequence from Kras (CAAX):<br>　　　rGFP-<u>GSAGTMASNNTASG</u>-CAAX<br>　　　　　　Linker<br>Linker between rGFP and polybasic sequence from GRK5 (PB):<br>　　　rGFP-<u>GGSGLKLPAT</u>-PB<br>　　　　　　Linker<br>Linker between rGFP and palmitoylation/prenylation sequence from hRAS (CAAX) and hRAS/Ral1(CAAX=CCIL); Linker between rGFP and Caveolin1α:<br>　　　rGFP-<u>GSAGT</u>-CAAX & rGFP-<u>GSAGT</u>-Caveolin1α<br>　　　　　　Linker　　　　　　　　Linker<br><br>Linker between Golgi targeting sequence from eNOS (1-73) and rGFP:<br>　　　eNOS(1-73)-<u>GSNAT</u>-rGFP<br>　　　　　　　　Linker |

FIG. 11D

Class A receptor: β2AR

Class B receptor: V2R

DR: V2R, unimolecular-βarr2 recruitment sensor

DR: β2AR, unimolecular-βarr2 recruitment sensor

PLC activation

DR: H1R, DAG sensor (RlucII-C1b vs rGFP-CAAX(Kras))

DR: BKRB2, DAG sensor (RlucII-C1b vs rGFP-CAAX(Kras))

DR: D2R, DAG sensor (RlucII-C1b vs rGFP-CAAX(Kras))

DR: β2AR, DAG sensor (RlucII-C1b vs rGFP-CAAX(Kras))

Gβγ-sequestration based sensor
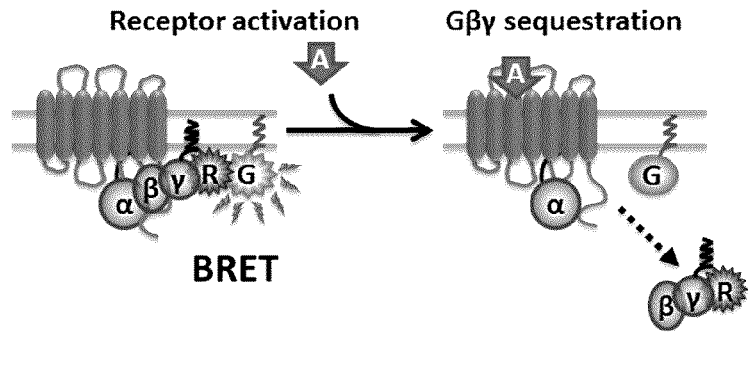
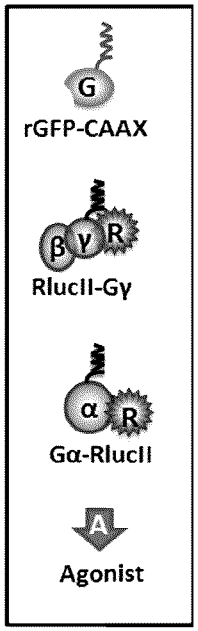
Gα-sequestration based sensor
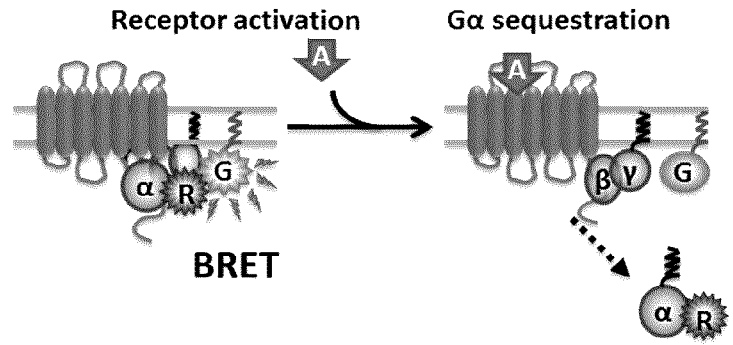
FIG. 24A
Sequestration of Gγ-RlucII from rGFP-CAAX (Kras) in response to β1AR stimulation
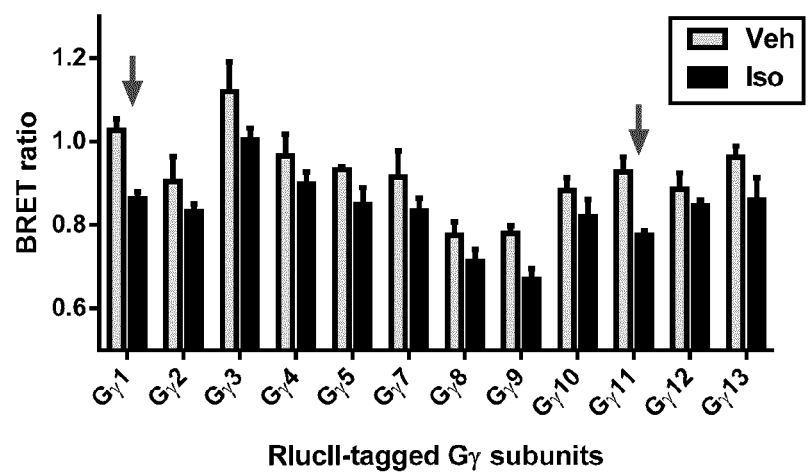
FIG. 24B ial # RENILLA BASED BIOSENSORS FOR MONITORING BIOMOLECULE LOCALIZATION AND TRAFFICKING IN CELLS

CROSS REFERENCE TO RELATED APPLICATIONS

This application claims the benefit of U.S. Provisional Application Ser. No. 62/052,738, filed on Sep. 19, 2014, which is incorporated herein by reference in its entirety.

TECHNICAL FIELD

The present invention generally relates to the assessment/monitoring of the localization, transport and trafficking of biomolecules such as proteins, for example cell surface receptor endocytosis, recycling and intracellular trafficking of receptors and effectors.

BACKGROUND ART

Protein trafficking is an active process in which proteins are re-located from one region of a cell to another. Membranes and their protein components are constantly being turned over through a mechanism that has multiple components and pathways. One of the mechanisms of modulating the activity of cell surface receptors, such as G protein-coupled receptors (GPCRs) and the Epidermal Growth Factor receptor (EGFR), is through receptor endocytosis. For GPCRs, ligand-induced receptor endocytosis can drive receptors removal from the PM through specialized compartments like clathrin-coated vesicles, which involve the recruitment of the endocytic adaptor β-arrestin to liganted receptors (Claing, Laporte et al. 2002). Internalizing receptors can be directed into divergent lysosomal and recycling pathways, producing essentially opposite effects on the strength and duration of cellular signaling via heterotrimeric G proteins, and can also promote distinct signalling events from intracellular membranes through the signalling scaffolding of β-arrestins (Hanyaloglu and von Zastrow 2008; Posner and Laporte 2010). Therapeutic advantages have been proposed for drugs promoting the intracellular targeting of GPCR/β-arrestin complexes, while for some receptors their recycling to the PM is also essential for adequate maintenance of physiological responses.

Thus, simple and reliable systems for monitoring receptor trafficking are key to study the mechanism of receptor endocytosis and to develop efficient therapeutics acting on cell surface receptors such as GPCRs. For instance the Angiotensin II type 1 receptor (AT1R) has attracted significant attention for drug development, because of its involvement in the development of cardiovascular diseases, including hypertension, hypertrophy, fibrosis and atherosclerosis (Hunyady and Catt 2006), and because ligands, which have cardioprotective function can also promote internalization of receptors and intracellular AT1R/β-arrestin signalling complexes. Great advantages can thus arise from developing assays efficiently assessing in a quantitative and high efficiency manner drugs' propensity to induce the internalization of receptors such as GPCRs.

The present description refers to a number of documents, the content of which is herein incorporated by reference in their entirety.

SUMMARY OF THE INVENTION

The present invention relates to the following items 1 to 73:

1. A biosensor for assessing the trafficking and/or localization of a protein of interest comprising;
   a first component comprising said protein of interest tagged with a *Renilla* green fluorescent protein (*Renilla* GFP) or a *Renilla* luciferase protein (*Renilla* Luc);
   a second component comprising a cellular compartment targeting moiety tagged with a *Renilla* GFP or a *Renilla* Luc;
   wherein if said first protein is tagged with said *Renilla* GFP, said cellular compartment targeting moiety is tagged with said *Renilla* Luc, and if said first protein is tagged with said *Renilla* Luc, said cellular compartment targeting moiety is tagged with said *Renilla* GFP.

2. The biosensor of item 1, wherein said protein of interest is tagged with said *Renilla* Luc and said cellular compartment targeting moiety is tagged with said *Renilla* GFP.

3. The biosensor of item 1 or 2, wherein said protein of interest is a Rho-binding polypeptide, a β-arrestin polypeptide, a cell surface receptor or a G protein subunit polypeptide.

4. The biosensor of item 3, wherein said protein of interest is a Rho-binding polypeptide.

5. The biosensor of item 3, wherein said protein of interest is a cell surface receptor.

6. The biosensor of item 5, wherein said cell surface receptor is a G protein-coupled receptor (GPCR).

7. The biosensor of any one of items 1 to 6, wherein said cellular compartment targeting moiety is a plasma membrane (PM) targeting moiety, an endosomal targeting moiety, a Golgi targeting moiety, a lysosomal targeting moiety, a peroxisomal targeting moiety, an autophagosomal targeting moiety, a ribosome targeting moiety, a mitochondria targeting moiety, a cytoskeleton targeting moiety or a nuclear targeting moiety.

8. The biosensor of item 7, wherein said cellular compartment targeting moiety is a plasma membrane (PM) targeting moiety.

9. The biosensor of item 8, wherein said PM targeting moiety is a PM protein or a fragment thereof that localizes to the PM.

10. The biosensor of item 9, wherein said PM protein or fragment thereof comprises (a) a palmitoylation, myristoylation, and/or prenylation signal sequence and/or (b) a polybasic sequence.

11. The biosensor of item 10, wherein said palmitoylation and/or myristoylation signal sequence is from the human Src family kinase Lyn.

12. The biosensor of item 11, wherein said PM targeting moiety comprises the amino acid sequence MGCIKSK-GKDS (SEQ ID NO:1).

13. The biosensor of item 12, wherein said polybasic sequence and prenylation signal sequence are from human KRAS splice variant b.

14. The biosensor of item 13, wherein said PM targeting moiety comprises the amino acid sequence GKKKK-KKSKTKCVIM (SEQ ID NO:7).

15. The biosensor of item 10, wherein said PM targeting moiety comprises a palmitoylation sequence and prenylation signal sequence from hRas.

16. The biosensor of item 15, wherein said PM targeting moiety comprises the amino acid sequence CMSCK-CVLS (SEQ ID NO:47).

17. The biosensor of item 10, wherein said PM targeting moiety comprises a palmitoylation sequence from hRas and prenylation signal sequence from Ral1.

18. The biosensor of item 17, wherein said PM targeting moiety comprises the amino acid sequence CMSCKCCIL (SEQ ID NO:43).
19. The biosensor of item 9, wherein said PM protein or fragment thereof is Caveolin1α.
20. The biosensor of item 10, wherein said PM targeting polybasic sequence is from human GRKS.
21. The biosensor of item 20, wherein said PM targeting moiety comprises the amino acid sequence SPKK-GLLQRLFKRQHQNNSKS (SEQ ID NO:8).
22. The biosensor of item 8 to 21, wherein (i) said PM targeting moiety comprises a palmitoylation and/or myristoylation signal sequence from the human Src family kinase Lyn, and is fused to the N-terminal end of said *Renilla* Luc or said *Renilla* GFP or (ii) said PM targeting moiety comprises (a) a polybasic sequence and prenylation signal sequence from human KRAS splice variant b or HRAS; (b) a palmitoylation sequence from HRAS and prenylation signal sequence from Ral1; (c) Caveolin1α or a fragment thereof; or (d) a polybasic sequence from human GRKS, and is fused to the C-terminal end of said *Renilla* Luc or said *Renilla* GFP.
23. The biosensor of item 7, wherein said cellular compartment targeting moiety is an endosomal targeting moiety.
24. The biosensor of item 23, wherein said endosomal targeting moiety is an endosomal protein or a fragment thereof that localizes to the endosomes.
25. The biosensor of item 24, wherein said endosomal protein or fragment thereof comprises a FYVE domain.
26. The biosensor of any one of items 23 to 25, wherein said endosomal targeting moiety comprises the FYVE domain of human endofin.
27. The biosensor of item 26, wherein said endosomal targeting moiety comprises residues 739 to 806 of human endofin (SEQ ID NO:20).
28. The biosensor of item 23, wherein said endosomal protein or fragment thereof is a Rab protein or a fragment thereof.
29. The biosensor of item 28, wherein said Rab protein is Rab4 or Rab 11.
30. The biosensor of any one of items 23 to 29, wherein said endosomal targeting moiety is fused to the C-terminal end of said *Renilla* Luc or said *Renilla* GFP.
31. The biosensor of any one of items 23 to 30, wherein said protein of interest is fused to the N-terminal end of said *Renilla* Luc or said *Renilla* GFP.
32. The biosensor of item 7, wherein said cellular compartment targeting moiety is a Golgi targeting moiety.
33. The biosensor of item 32, wherein said Golgi targeting moiety is a Golgi protein or a fragment thereof that localizes to the Golgi.
34. The biosensor of item 33, wherein said Golgi targeting moiety is eNOS1 or a fragment thereof that localizes to the Golgi.
35. The biosensor of item 34, wherein said Golgi targeting moiety comprises residues 1 to 73 of human eNOS1 (SEQ ID NO: 42).
36. The biosensor of any one of items 1 to 35, wherein said first and second component are covalently linked through a flexible linker.
37. The biosensor of item 36, wherein said flexible linker is a polypeptide of about 50 to about 500 amino acids.
38. The biosensor of item 37, wherein said flexible linker is a polypeptide of about 300 amino acids.
39. A nucleic acid encoding the first and/or second components of the biosensor of any one of items 1 to 38.
40. A vector comprising the nucleic acid of item 39.
41. A host cell expressing the biosensor of any one of items 1 to 38.
42. A method for determining whether an agent modulates the trafficking of a protein of interest in a cell, said method comprising: measuring the BRET signal in the biosensor of any one of items 1 to 38 in the presence and absence of said agent;
wherein a difference in said BRET signal in the presence of said agent relative to the absence thereof is indicative that said agent modulates the trafficking of said protein of interest in said cell.
43. A method for determining whether an agent induces the internalization of a cell surface receptor of interest in a cell, said method comprising: measuring the BRET signal in the biosensor of any one of items 8 to 22 in the presence and absence of said agent;
wherein a lower BRET signal in the presence of said agent relative to the absence thereof is indicative that said agent induces the internalization of a cell surface receptor of interest.
44. A method for assessing the recycling of an internalized receptor of interest at the cell surface, said method comprising:
(a) contacting a first and a second biosensor comprising a PM targeting moiety as defined herein in the presence of a ligand that induces the internalization of said receptor;
(b) measuring a BRET signal in the first biosensor after said contacting;
(c) washing said second biosensor to remove said ligand;
(d) measuring a BRET signal in the second biosensor after said washing; and
(e) determining the recycling of an internalized receptor of interest at the cell surface by comparing the BRET signal in the first and second biosensors,
wherein a higher BRET signal in said second biosensor relative to said first biosensor is indicative of recycling of the internalized receptor of interest at the cell surface.
45. The method of item 44, further comprising repeating steps (d) and (e) at different times after washing to study the kinetics of recycling of the internalized receptor of interest.
46. A method for determining whether an agent induces the trafficking of a cell surface receptor of interest at an endosomal compartment, said method comprising: measuring the BRET signal in the biosensor of any one of items 23 to 31 in the presence and absence of said agent; wherein a higher BRET signal in the presence of said agent relative to the absence thereof is indicative that said agent induces the trafficking of said cell surface receptor of interest in said endosomal compartment.
47. The method of item 46, wherein said method is performed using a plurality of biosensors, and wherein each of said biosensors comprises a different endosomal targeting moiety.
48. A method for determining whether an agent acts as a pharmacological chaperone for a receptor of interest, said method comprising: measuring the BRET signal in the biosensor of any one of items 8 to 22 in the presence and absence of said agent; wherein a higher BRET signal in the presence of said agent relative to the absence thereof is indicative that said agent acts as a pharmacological chaperone for said receptor of interest.
49. A method for determining whether an agent acts as a pharmacological chaperone for a receptor of interest, said method comprising:
providing a biosensor comprising: said receptor of interest tagged with a *Renilla* green fluorescent protein (*Renilla*

GFP) or a *Renilla* luciferase protein (*Renilla* Luc); and an endoplasmic reticulum (ER) targeting moiety tagged with a *Renilla* GFP or a *Renilla* Luc; wherein if said receptor is tagged with said *Renilla* GFP, said ER targeting moiety is tagged with said *Renilla* Luc, and if said receptor is tagged with said *Renilla* Luc, said ER targeting moiety is tagged with said *Renilla* GFP; and measuring the BRET acceptor signal in the presence and absence of said agent;

wherein a decrease in the BRET signal in the presence of said agent relative to the absence thereof is indicative that said agent acts as a pharmacological chaperone for said receptor.

50. The method of item 48 or 49, wherein said receptor is a mutated receptor.
51. The method of any one of items 48 to 50, wherein said receptor is a G protein-coupled receptor (GPCR).
52. The method of item 51, wherein said GPCR is a melanocortin-4 receptor (MC4R) or a vasopressin 2 receptor (V2R).
53. The method of any one of items 48 to 52, wherein said receptor is an ion channel.
54. The method of item 53, wherein said ion channel is a voltage-gated potassium channel.
55. The method of item 54, wherein said voltage-gated potassium channel is hERG.
56. The method of any one of items 48 to 55, wherein said receptor is tagged with said *Renilla* Luc, and said PM targeting moiety or ER targeting moiety is tagged with said *Renilla* GFP.
57. The method of any one of items 48 to 56, wherein said PM targeting is the PM targeting moiety defined in any one of items 9 to 22.
58. A method for determining whether an agent induces the recruitment of a β-arrestin to the plasma membrane, said method comprising:
    providing a biosensor comprising a cell or membrane preparation comprising: said β-arrestin tagged with a *Renilla* green fluorescent protein (*Renilla* GFP) or a *Renilla* luciferase protein (*Renilla* Luc); a plasma membrane (PM) targeting moiety tagged with a *Renilla* GFP or a *Renilla* Luc; and a GPCR; wherein if said β-arrestin is tagged with said *Renilla* GFP, said PM targeting moiety is tagged with said *Renilla* Luc, and if said β-arrestin is tagged with said *Renilla* Luc, said PM targeting moiety is tagged with said *Renilla* GFP; and
    measuring the BRET acceptor signal in the presence and absence of said agent;
wherein an increase in the BRET signal in the presence said agent relative to the absence thereof is indicative that said agent induces the recruitment of said β-arrestin to the plasma membrane.
59. The method of item 58, wherein said β-arrestin is tagged with said *Renilla* Luc.
60. The method of item 58 or 59, wherein said PM targeting moiety PM targeting is the PM targeting moiety defined in any one of items 9 to 22.
61. A method for assessing a modulation in the amount of a biomolecule at a cellular compartment between a first and a second condition, said method comprising:
    providing a biosensor comprising: a first component comprising a *Renilla* green fluorescent protein (*Renilla* GFP) tagged with a protein marker that binds to said biomolecule; and a second component comprising a *Renilla* luciferase protein (*Renilla* Luc) tagged with said protein marker;
    measuring the BRET acceptor signal in said first and second conditions;

wherein a difference in the BRET signal between said first and second conditions is indicative of a modulation in the amount of said biomolecule at said cellular compartment between said first and second conditions.

62. The method of item 61, wherein said first condition is the presence of an agent and said second condition is the absence of said agent.
63. The method of item 61 or 62, wherein said biomolecule is a phospholipid.
64. The method of item 63, wherein said phospholipid is phosphatidylinositol 4,5-bisphosphate ($PIP_2$).
65. The method of item 64, wherein said protein marker comprises a Pleckstrin homology (PH) domain.
66. The method of item 65, wherein said PH domain is the PH domain of PLCδ1.
67. The method of item 61 or 62, wherein said biomolecule is a second messenger.
68. The method of item 67, wherein said second messenger is diacylglycerol (DAG).
69. The method of item 68, wherein said protein marker comprises a phorbol esters/diacylglycerol binding domain.
70. The method of item 69, wherein said protein marker comprises the phorbol esters/diacylglycerol binding domain domain of PKC (C1b).
71. The method of item 70, wherein said protein marker comprises the amino acid sequence of SEQ ID NO:72.
72. The method of any one of items 42 to 71, wherein the BRET signal is measured using a plate reader or by microscopy.
73. The biosensor of any one of items 1 to 38, or the method of any one of items 42 to 72, wherein said *Renilla* Luc is *Renilla reniformis* luciferase II (RlucII) and/or said *Renilla* GFP is a *Renilla reniformis* GFP (rGFP).

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIGS. 1A to 1F show the generation of Bioluminescence Resonance Energy Transfer (BRET)-based GPCR endocytosis sensor. FIGS. 1A to 1C: Three configurations of BRET-based sensors for assessing/monitoring GPCR endocytosis. To monitor the receptor (FIG. 1A) and β-arrestin (FIG. 1C) amounts at the plasma membrane, anchor rGFP at the plasma membrane by tagging an acylation moiety of lyn-kinase (MGCIKSKGKDS) in N-terminus of rGFP. FIGS. 1B, 1C: To examine targeting of either receptor (FIG. 1B) or β-arrestin (FIG. 1C) to the endosomes, FYVE domain of endofin (amino acids 739 to 806), which tethers the sensor in the endosomes, fused to the C-terminus of rGFP. HEK293SL cells expressing either lyn-rGFP (FIG. 1D) or rGFP-endofinFYVE (FIG. 1E) were subjected to confocal fluorescent microscopy. rGFP-endofinFYVE expressing cells were treated with 500 nM wortmannin for 40 min (FIG. 1E, right panel). Scale bars, 10 µm. FIG. 1F: Simultaneous visualization of receptor, lyn-rGFP, and FYVE domain upon receptor endocytosis. HEK293SL cells were transiently transfected with B2R-CFP, lyn-rGFP, and mCherry-endofinFYVE. Top panel showed basal status and the bottom panel showed a bradykinin induced B2R endocytosis. Scale bars, 10 μm.

FIG. 2A: HEK293SL cells were transfected with AT1R-RlucII along with either lyn-GFP10 (□) or lyn-rGFP (■). Cells were incubated with various concentrations of AngII for 40 min then BRET was measured as described under "materials and methods". FIG. 2B: HEK293SL cells were transfected with AT1R-RlucII along with either GFP10-endofinFYVE or rGFP-endofinFYVE. FIG. 2C: HEK293SL cells were transfected with AT1R and βarr2-RlucII along with either GFP10-endofinFYVE or rGFP-endofinFYVE. AT1R-RlucII along with either lyn-rGFP (FIG. 2D) or rGFP-endofinFYVE (FIG. 2E) transfected cells were incubated in the absence or presence of 100 nM AngII at 37° C. for the indicated times then BRET was measured. The BRET ratio change is expressed as percentage of BRET ratio observed in the control (no AngII treatment) group. Data are represented as the means±S.E. from 2-6 independent experiments. FIG. 2F: Data in FIGS. 2D and 2E were normalized to the maximal responses, respectively and plotted together.

FIG. 3F: endocytosis of AT1R in the presence of the vesicle acidification inhibitors bafilomycin A (Baf) and Chloroquine (CQ). Cells were incubated in various concentrations of AngII for 40 min before BRET measurement. Values shown are the means±S.E. from at least three independent experiments.

FIG. 4A: HEK293SL cells were transfected with lyn-rGFP along with either AT1R-RlucII, B2R-RlucII, V2R-RlucII, or $β_2$AR-RlucII. FIG. 4B: HEK293SL cells were transfected with rGFP-endofinFYVE along with either AT1R-RlucII, B2R-RlucII, V2R-RlucII, or $β_2$AR-RlucII. Cells were incubated with various concentrations of respective cognate ligand as described in the figure for 30 min (FIG. 4A) or 40 min (FIG. 4B) at 37° C. then BRET were measured. FIG. 4C: HEK293SL cells were transfected with βarr2-RlucII and rGFP-endofinFYVE along with either AT1R, B2R, V2R, $β_2$AR, or FP receptor constructs. Cells were incubated with various concentrations of respective cognate ligand for 40 min before BRET measurement. The cognate ligands for each receptor were as follows: AT1R, AngII (squares); B2R, Bradykinin (BK, triangles); V2R, AVP (circles) or Oxytocin (OT, stars); $β_2$AR, isoproterenol (ISO, inverted triangles); FP, PGF2α (lozenges). Data for (a) to (c) are expressed as the means±S.E. of 2-3 independent experiments. FIG. 4D: Monitoring of EGFR endocytosis by BRET between RlucII-GRB2 and rGFP-endofinFYVE (GRB2 interacts with EGFR and participates in EGFR internalization). HEK293SL cells were transfected with EGFR along with RlucII-GRB2 and rGFP-endofinFYVE. Cells were incubated with various concentrations of EGF for 30 min at 37° C. then BRET were measured. Results for FIG. 4D are means±SE of triplicates in a single representative experiment out of two independent experiments. FIG. 4E: Assessment of Z' factors as an indication of robustness of the assays for High-Throughput Screening (HTS). HEK293 were co-transfected with AT1R-RlucII/lyn-rGFP, AT1R-RlucII/rGFP-endofinFYVE or AT1R/βarr2-RlucII/rGFP-endofinFYVE and plated in a 48-well plate and stimulated with 100 nM AngII at 37° C. for 20 min to allow receptor receptor dissaperance from the plasma membrane and the accumulation of both receptor and βarrestin2 in endosomes. Cell surface receptor endocytosis was evaluated in BRET2. BRET values are expressed per well in the presented graphs and Z' factor evaluated over 0.64, 0.73 and 0.79 for the AngII-treated group, respectively, which indicates a robust assay for receptor internalization in endosomes.

FIG. 5A: HEK293SL cells were transfected with AT1R-RlucII along with lyn-rGFP. Cells were incubated in the absence (control) or presence of 100 nM AngII for 30 min then cells were washed and further incubated in the absence of AngII for 45 min. The BRET ratio change is expressed as percentage of BRET ratio observed in the control (no AngII treatment) group. Data are represented as the means±S.E. from four independent experiments. FIG. 5B: HEK293SL cells expressing lyn-rGFP along with either V2R-RlucII, B2R-RlucII, AT1R-RlucII, or $β_2$AR-RlucII were subjected to the receptor recycling as described in FIG. 5A with their cognate ligands, 100 nM AVP for V2R, 100 nM BK for B2R, 100 nM AngII for AT1R, and 1 μM ISO for β2AR. Receptor recycling is expressed as a percent increase in the BRET ratio 45 min after ligand wash-out. All values are expressed as the means±±S.E. from 3-4 independent experiments. FIG. 5C: HEK293SL cells were transfected with AT1R-RlucII along with rGFP-endofinFYVE. Cells were incubated in the absence (control) or presence of 100 nM AngII for 30 min then cells were washed and further incubated in the absence of AngII for 45 min. The BRET ratio change is expressed as percentage of BRET ratio observed in the control (no AngII treatment) group. Data represent as the means±S.E. from three independent experiments.

FIGS. 6A to 6F show the effects of AngII analogs on AT1R trafficking and sorting. FIG. 6A: HEK293SL cells expressing AT1R-RlucII/rGFPendofinFYVE were incubated either with 100 nM AngII (squares), 100 nM SI (triangles), or 1 μM DVG (circles) for indicated times then BRET were measured. BRET ratios were normalized to the maximal AngII response (60 min) as a 100% and the basal (no ligand) as a 0%. Data are expressed as the means±S.E. from at least three independent experiments. HEK293SL cells were transfected with AT1R-RlucII/lyn-rGFP (FIG. 6B), AT1R-RlucII/rGFP-endofinFYVE (FIG. 6C) or AT1R/βarr2-RlucII/rGFP-endofinFYVE (FIG. 6D). Cells were incubated with various concentrations of AngII (squares), SI (triangles), or DVG (circles) for 30 min (FIG. 6B) or 40 min (FIGS. 6C, 6D) before BRET measurement. Data are represented as the means±S.E. from at least three independent experiments. FIGS. 6E and 6F: HEK293SL cells were transfected with AT1R-RlucII along with either rGFP-rab4 (FIG. 6E) or rGFP-rab11 (FIG. 6F). Cells were incubated either with 100 nM AngII (squares), 100 nM SI (triangles), or 1 μM DVG (circles) for indicated times then BRET were measured. The BRET ratio change is expressed as percentage of BRET ratio observed in the control (no ligand treatment) group. Data represent the mean±S.E. from three independent experiments.

FIGS. 7A and B show AT1R internalization accessed by intact cell [$^{125}$I]AngII-binding assay. FIG. 7A: HEK293SL cells were transiently transfected either AT1R alone (☐), AT1R-RlucII alone (■), or AT1R-RlucII along with lyn-rGFP (■). The cells were incubated in the absence or presence of 100 nM AngII for 30 min at 37° C. then subjected to intact-cell [$^{125}$I]AngII-binding assay as describe under "materials and methods". FIG. 7B: HEK293SL cells expressing AT1R-RlucII/Lyn-rGFP along with either pcDNA (☐), dynamin K44A (■), or β-arrestin2 (■) were incubated in the absence or presence of 100 nM AngII for 30 min at 37° C. then subjected to an intact-cell [$^{125}$I]AngII-binding assay as describe below (Example 1). Receptor endocytosis was expressed as the percent loss of cell surface receptors. Data are represented as the means±S.E. of three independent experiments.

FIG. 8 shows the high basal endosomal localization of V2R. HEK293SL cells transiently expressing V2R-YFP along with mCherry-endofinFYVE, were subjected to a confocal microscopy. Scale bar, 10 μm.

FIG. 9B: HEK293SL cells were transfected with AT1R-RlucII along with Lyn-rGFP. Cells were incubated in the absence (−Ubo) or presence of 100 nM Ubo (+Ubo) for 30 min then stimulated with various concentrations of AngII for 30 min before BRET measurement. FIG. 9C: HEK293SL cells were transfected with AT1R-RlucII along with rGFP-FYVE. Cells were incubated in the absence (−Ubo) or presence of 100 nM Ubo (+Ubo) for 30 min then stimulated with various concentrations of either AngII, SI, or DVG for 40 min before BRET measurement. FIG. 9D: Cells were transfected with AT1R-RlucII along with either rGFP-rab4 or rGFP-rab11. Cells were incubated in the absence (−Ubo) or presence of 100 nM Ubo (+Ubo) for 30 min then stimulated either with 100 nM AngII, 100 nM SI, or 1 μM DVG for 10 min for the rGFP-rab4 and 30 min for the rGFP-rab11 then BRET were measured. The BRET ratio change is expressed as percentage of BRET ratio observed in the control (no ligand treatment) group. Data represent the mean±S.E. from three independent experiments.

FIG. 10A: The pharmacological chaperone (PC) assay is based on relocalization of a pharmacological chaperone-rescued protein that would, otherwise, be retained in a different subcellular compartment. Relocalization detected and measured using BRET, preferentially with rGFP with a plasma-membrane targeting sequence (rGFP-CAAX, Lyn-rGFP or rGFP-PB; for a description, see FIG. 11D). Misfolded receptors and channels such as hERG are retained in intracellular compartments and translocate to the plasma membrane upon pharmalogical chaperone-mediated rescue. In this assay, the receptor is preferentially tagged with RlucII and the membrane with rGFP; the BRET signal is proportional to the density of the RlucII-tagged protein at the membrane. The misfolded protein could either be a mutant or the WT protein. For receptors that internalize upon agonist exposure, the functionality of the rescued receptor may then be assessed using the agonist-induced sequestration assay depicted in FIG. 10B (which essentially corresponds to the BRET-based sensor depicted in FIG. 1A). FIG. 10B: principle of a BRET-based agonist-induced sequestration assay. A plasma membrane (PM) marker is tagged with a BRET acceptor such as GFP (G) and the PC-rescued receptor of interest (e.g., a PC-rescued GPCR) is tagged with a BRET donor such as RLuc (R). In the absence of agonist (left), the receptors are retained at the PM and co-localize with the BRET acceptor-tagged PM marker, thus resulting in a strong BRET acceptor signal. However, in the presence of an agonist (right), the receptors are internalized, thus decreasing the density of the BRET donor-tagged receptor at the PM, which results in a decrease in the BRET acceptor signal. This assay can be performed following PC-mediated cell-surface rescue of receptors, in the same well, thus in a homogenous assay that monitor two different aspects of the receptor biology.

FIGS. 11A to D show the constructs used to validate and optimize a sensor to detect pharmacological chaperone properties. FIGS. 11A to C: the chaperone-rescue assay was developed and tested with wild type (WT) and naturally-occurring substitutions of human GPCRs (Melanocortin receptor 4: hMC4R and the vasopressin receptor 2: hV2R) and a voltage-gated Potassium channel H2 (hERG) tagged with a BRET donor. The receptors were tagged in C-terminal with RlucII. The hERG channel was internally tagged with RlucII at the equivalent position of residue 379 and, the sequence from residues 373-379 was duplicated on each side of linker3 and linker 4 (see FIG. 11C). Flexible linkers were used between the receptor/channel and the RlucII tag. The sequence of the linkers is indicated in FIG. 11A for the MC4R constructs (Linker1), in FIG. 11B for the V2R constructs (Linker2) and in FIG. 11C for the hERG constructs (Linker3 & 4). FIG. 11D: A BRET acceptor (rGFP) was tagged with different plasma-membrane or Golgi apparatus targeting sequences: in N-terminal with the palmitoylation & myristoylation signal sequence from the Lyn kinase (Lyn-), in C-terminal with the polybasic sequence and prenylation signal sequence from KRAS splice variant b (-CAAX), in C-terminal with the polybasic sequence from the human GRK5 (-PB), in C-terminal with the plasma-membrane targetting palmitoylation sequence and prenylation signal sequence from hRas, in C-terminal with the plasma-membrane targetting palmitoylation sequence from hRas and prenylation signal sequence from Ral1, in C-terminal with human Caveolin1α (a marker of caveolae); and in N-terminal with the Golgi targetting sequence (residues 1-73) from human eNOS1. Linkers 5, 6 and 7 were used between the rGFP and the plasma-membrane targeting sequence: lyn, CAAX and PB, respectively. Llinker 8 was used between rGFP and palmitoylation/prenylation sequence from hRAS (CAAX) and hRAS/Ral1 (CAAX=CCIL), and between rGFP and Caveolin1α. Llinker 9 was used between the golgi targetting sequence from eNOS (1-73) and rGFP.

FIG. 18B) hERG at different ratios of hERG to rGFP-CAAX. HEK293 cells were co-transfected with an rGFP-CAAX construct (72 ng of plasmid for 10 wells of a 96-well plate) and 3 different quantities (as indicated on the graphs: 6, 12 and 24 ng for 10 wells) of hERG wt-RlucII (FIG. 18A) and hERG (G601S)-RlucII (FIG. 18B). The PC-mediated rescue of cell surface expression was evaluated in BRET2, following a 16 h-treatment with either a chaperone: (Astemizole, 10 µM; solid black bars) or vehicle (DMSO; white bars). Astemizole-treatment induces an increase in cell surface expression, as revealed by an increase in BRET signal, compared to vehicle-treated cells. The wt (FIG. 18A) and G601S mutant (FIG. 18B) hERG were both sensitive to a PC-treatment and were used to characterize ligands known to bind and act with different efficacy as chaperones on hERG (FIGS. 18C and D). In FIG. 18E, robustness of the assay with the hERG (G601S)-RlucII construct was evaluated with a Z' factor. Cell surface expression was evaluated in BRET2, following a 16 h-treatment with 10 μM Astemizole (48 wells) vs. vehicle (DMSO) (48 wells). BRET values are expressed per well in the presented graphs and Z' factor evaluated at 0.622, which indicates a robust assay that would be amenable to high throughput screening application.

FIG. 24A shows a schematic representation of a biosensor for measuring G protein translocation and activation. The biosensor comprises a PM-targeting domain/moiety (e.g., CAAX domain) attached to a BRET acceptor (e.g., rGFP) and a BRET donor (e.g., RlucII) attached to a protein G subunit, for example Gγ (Gβγ-sequestration based sensor) or Gα (Gα-sequestration based sensor). Upon activation of the GPCR by an agonist (A), the G protein subunit is released from the GPCR, thus reducing the amount/density of G protein subunit at the plasma membrane, leading to a lower BRET signal. A change in BRET could also reflect translo-cation from (decrease in BRET) or to (an increase in BRET) a subdomain of the membrane or sub-cellular compartment tagged with an rGFP-marker.

FIGS. 24B and 24C show the sequestration of various RlucII-tagged Gγ subunit from the plasma membrane (rGFP-CAAX Kras) in response to β1AR (FIG. 24B) or β2AR (FIG. 24C) stimulation with isoproterenol. Prior to the experiment, HEK293 cells were cotransfected with con-structs encoding a β-adrenergic receptor, a WT Gβ1 subunit, an RlucII-tagged Gγ subunit (as indicated) and WT Gα15. The combination with RlucII-Gγ1 subunit is giving the best window to establish dose-response curves for those 2 recep-tors.

FIG. 26A shows the difference of energy transfer when RlucII is paired with Venus, GFP2, and rGFP. FIG. 26B shows the BRET ratio calculated from Venus-, GFP2- and rGFP-fused-constructs.

DISCLOSURE OF INVENTION

Figure 1G:
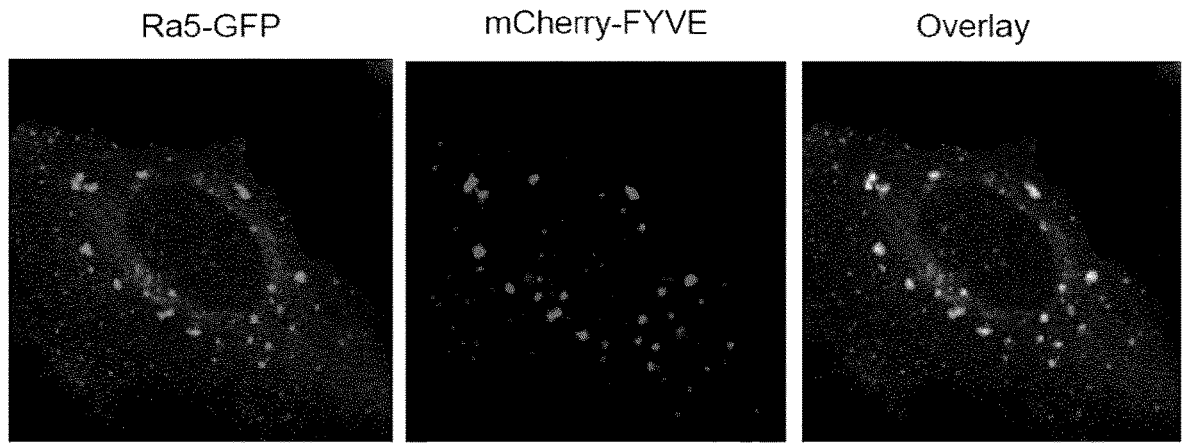
FIG. 1G: A mCherry-labeled variant of the endofin FYVE sensor also co-localized with Rab5, which populates EE.

In the studies described herein, the present inventors have developed BRET-based biosensors that permit to assess/monitor the intracellular localization and trafficking (e.g., receptor internalization, recycling, exocytosis) of proteins, such as receptors and other proteins. Using GPCRs and an ion channel as models, the present inventors have developed sensitive means, based on the *renilla*'s BRET pair RlucII-rGFP, for real-time monitoring and pharmacological profiling of receptor and β-arrestin internalization and their trafficking into different cellular compartments, as well as for the identification of trafficking regulators. These sensors rely on changes in concentrations or densities of the donor relative to the acceptor at a given cellular localization or in a given cellular compartment, which is promoted by a modulator, independently of direct protein-protein interactions (as it is often the case for conventional BRET assays) it is more versatile and amenable to most proteins trafficking between different cellular localizations/compartments. It was found that the use of a *renilla*'s BRET pair, such as the representative RlucII/rGFP BRET pair, system gives very robust and reproducible response, which increases the dynamic range over ~5 to 10-fold compared to that of the traditional BRET1 (Rluc/Venus) or BRET2 (RlucII/GFP10) pairs. In general, the dynamic range of the signal is very narrow using the Rluc/Venus pair (BRET ratios of 0.04-0.08), similar to the one obtained with the version of the biosensors using the RlucII/GFP10 pair (see Examples 3 and 12, FIGS. 2A to 2C and 19A to 19E). This very shallow dynamic range greatly limits the analysis of subtle changes in receptor and effector trafficking and renders the assay inefficiently sensitive for high-throughput screening (HTS). The sensitive biosensors described herein may be useful for:

Real-time monitoring of cell surface receptor internalization and recycling (i.e. receptors returning to the plasma membrane after internalization): They allow vetting removal of different receptors (e.g., GPCRs, RTKs) from the plasma membrane, and conversely, after inducing endocytosis, monitoring recycling of receptors through the regain of BRET signal at the PM following ligand removal. They also allow the study of regulation, the pharmacology and pathway-specificity of endocytosis of receptor trafficking.

Real-time monitoring of receptor and β-arrestin trafficking in different intracellular compartments. They allow assessing the clathrin- and β-arrestin-dependent internalization of receptors (e.g., GPCRs) and the differential trafficking of receptor/β-arrestin complexes into distinct cellular compartments such as the recycling endosomes (ENDs).

Pharmacological profiling of receptor (e.g., GPCR) and β-arrestin trafficking: They allow assessing the propensity of ligands to regulate the trafficking of receptor/β-arrestin complexes into distinct cellular compartments, and monitor the effects of drugs on both the initial internalization of receptor and the cycling of receptors (e.g., GPCRs) at the PM.

Identification of trafficking modulators through high-throughput screening (HTS): Because the assays are reproducible and sensitive, they allow high-throughput screening for identifying modulators of receptor (e.g., GPCR) and other protein trafficking. Proof-of-principle was provided with the AT1R, and the identification of new small molecule regulators of this receptor trafficking, and also other GPCRs like the B2R (Example 17).

Identification of agents (chaperones) capable of rescuing the expression of receptors. The chaperone assay is independent on receptor signalling and is mostly a binding assay to detect ligands that stabilize or influence the conformation of a specific target (receptor). It is thus an interesting assay for screening orthosteric and allosteric ligands, in a signalling unbiased way. This binding assay could be further used to identify an "off-target" effect of an agent, i.e. to determine whether an agent identified against a particular target also cross-reacts with one or more additional targets (which could be assessed by determining whether the agent "rescues" these one or more additional targets using the biosensor described herein.

Monitoring/assessing the recruitment of proteins (e.g., adaptor or signalling proteins) to receptors (e.g., β-arrestin recruitment to GPCRs, G protein subunit sequestration, Grb2 recruitment to Receptor Tyrosine kinase (RTK), which reflects receptor activation.

Because the different cellular compartment markers remain in their selective compartments (e.g. plasma membrane (PM) or endosomes (ENDs)), and because only the receptor (or other tagged proteins such as βarrestin, G protein subunits, effectors, etc.) moves from one compartment to the other upon modulation by a ligand (e.g., agonist stimulation, antagonist inhibition or pharmacological chaperones), it allows the tracking of trafficking proteins from the PM to ENDs, which may be revealed by a decrease (for the PM-rGFP/receptor-RlucII assay) and/or an increase (for the END-rGFP/receptor-RlucII assay) BRET signals, respectively. In addition, using the PM-rGFP/receptor-RlucII system, the receptor recycling can be monitored with ligand wash-off after its endocytosis. This assay is not limited to assessing endocytosis/recycling of receptors, but is also amenable to identification and characterisation of pharmacological chaperones (see Examples 7 to 11), and to also assess/monitor exocytosis and protein translocation processes. Therefore any type of protein movement (trafficking) between different intracellular compartments can be accessed quantitatively with high sensitivity using the biosensors described herein.

Figure 22A:
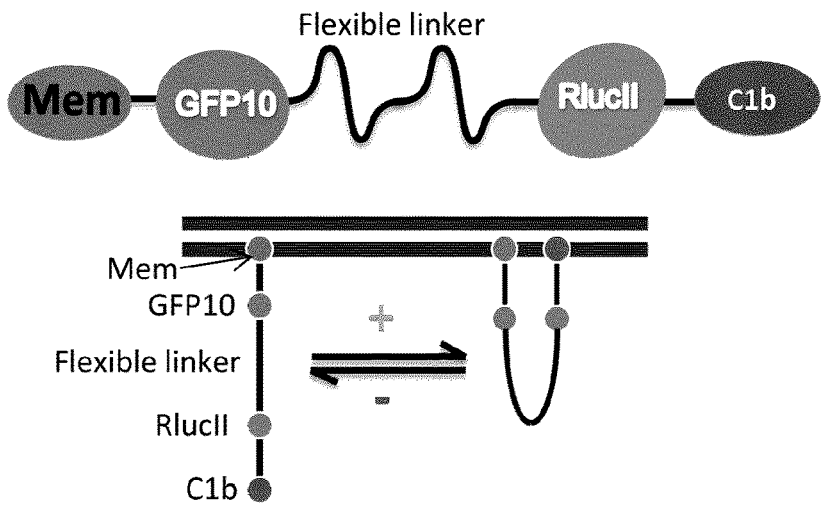
FIG. 22A shows a schematic representation of a unimolecular biosensor for measuring the translocation of the diacylglycerol-(DAG-) binding domain of PKCdelta (C1b) to the plasma-membrane. The biosensor comprises a PM-targeting domain/moiety (Mem), a BRET acceptor (e.g., GFP10), a flexible linker, a BRET donor (e.g., RlucII) and the DAG-binding domain of PKCδ, C1b. Upon activation of PLC, membrane PIP$_2$ is hydrolysed into IP$_3$ and DAG. The DAG enrichment causes the C1b domain to bind to the membrane, bringing the BRET acceptor (e.g., GFP10) and BRET donor (e.g., RlucII) closer to each other, inducing a higher BRET signal.
Figure 23A:
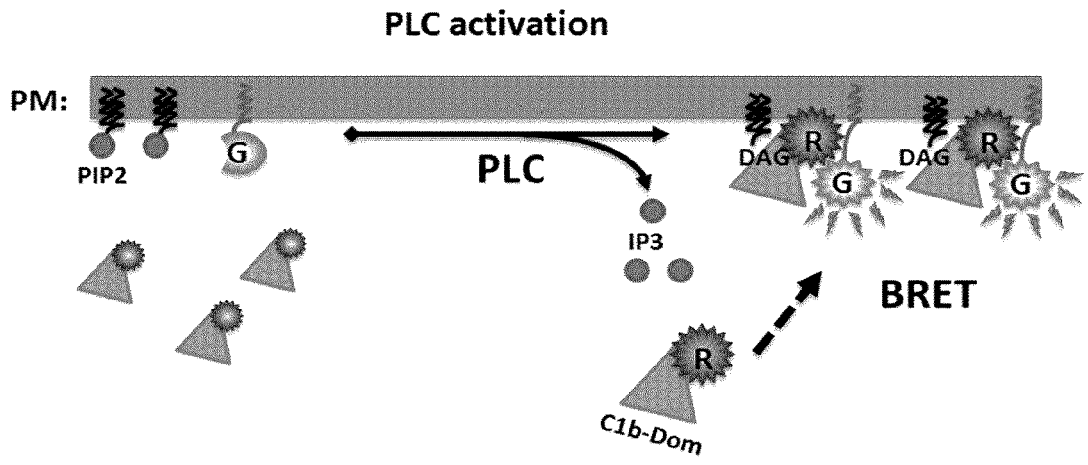
FIG. 23A shows a schematic representation of a biosensor for measuring the translocation of the diacylglycerol- (DAG-) binding domain of PKCdelta (C1b) to the plasma-membrane. The biosensor comprises a PM-targeting domain/moiety attached to a BRET acceptor (e.g., rGFP) and a BRET donor (e.g., RlucII) linked to the DAG-binding domain of PKCδ, C1b. Upon activation of PLC, membrane $PIP_2$ is hydrolysed into $IP_3$ and DAG. The DAG enrichment causes the C1b domain to bind to the membrane, bringing the BRET acceptor (e.g., rGFP) and BRET donor (e.g., RlucII) closer to each other, inducing a higher BRET signal.

These biosensors can also be applied not only to protein (e.g., receptor, intracellular proteins) trafficking but also to monitoring any type of local concentration or density changes of proteins and other biomolecules in the cells. It can be done in two ways: First, if the rGFP or the RlucII are tagged with specific intracellular organelle or cellular compartment markers, it may be possible to follow the protein of interest in different intracellular localization upon any specific condition. Second, the biosensors of the invention can be applied to monitoring local concentration or density of proteins, as well as the local density of lipids or other biomolecules (e.g., second messengers). The RlucII-rGFP pair was applied to detect membrane $PI(4,5)P_2$ generation using PLCδ1-PH domain (Example 13, FIGS. 20A and B). In the basal state, PLCδ1-PH-RlucII and PLCδ1-PH-rGFP (or rGFP fused to a PM targeting moiety such as Lyn or CAAX) are localized in the PM where $PI(4,5) P_2$ is located, so their local concentration is high enough to generate a BRET. When the phospholipase C (PLC) is activated, $PI(4,5)P_2$ is hydrolyzed, and the PLCδ1-PH domain tagged RlucII and rGFP diffuse into the cytosol reducing the local concentration of rGFP and RlucII, hence reducing the BRET signal. Similarly, the DAG-binding domain of PKCdelta (C1b) may be used to measure $PIP_2$ hydrolysation into $IP_3$ and DAG (FIGS. 22A and 23A). DAG enrichment causes the C1b domain to bind to the membrane, bringing the BRET acceptor (e.g., rGFP, linked to a PM targeting moiety) and BRET donor (e.g., RlucII, linked to C1b) closer to each other, inducing a higher BRET signal. With the same rationale, any kind of protein segregation also could be detected. In an embodiment, the trafficking is receptor internalization and/or recycling.

Accordingly, in a first aspect, the present invention provides biosensor for assessing the localization and/or trafficking of a protein/polypeptide of interest comprising: a first component comprising the protein/polypeptide of interest tagged with a *Renilla* green fluorescent protein (*Renilla* GFP) or a *Renilla* luciferase protein (*Renilla* Luc); a second component comprising a cellular compartment targeting moiety tagged with a *Renilla* GFP or a *Renilla* Luc; wherein if said protein/polypeptide of interest is tagged with said *Renilla* GFP, said cellular compartment targeting moiety is tagged with said *Renilla* Luc, and if said protein/polypeptide of interest is tagged with said *Renilla* Luc, said cellular compartment targeting moiety is tagged with said *Renilla* GFP.

The term "protein/polypeptide of interest" refers to any protein/polypeptide (native, mutated, soluble or membrane-bound) or fragments/portions thereof, whose localization, translocation and/or recruitment to one or more cellular compartments is to be assessed. The protein of interest may be, for example, a receptor, a protein recruited to, or sequestered away from, the plasma membrane upon receptor stimulation, a protein translocating to the nucleus, etc. In an embodiment, the protein of interest is a receptor (i.e., a protein found attached to or embedded within the plasma membrane). In an embodiment, the receptor is internalized upon ligand (e.g., agonist) binding. In an embodiment, the receptor is a G-protein coupled receptor (GPCR). "GPCR" refers to full length native GPCR molecules as well as mutant GPCR molecules. A list of GPCRs is given in Foord et al (2005) Pharmacol Rev. 57, 279-288, which is incorporated herein by reference, and an updated list of GPCRs is available in the IUPHAR-DB database (Harmar A J, et al. (2009) IUPHAR-DB: the IUPHAR database of G protein-coupled receptors and ion channels. *Nucl. Acids Res.* 37 (Database issue): D680-D685; Sharman J L, et al., (2013) IUPHAR-DB: updated database content and new features. *Nucl. Acids Res.* 41 (Database Issue): D1083-8).

In another embodiment, the receptor is an ion channel, for example a voltage-gated ion channel (e.g., a sodium, calcium, potassium channel). A list of ion channels is available in the IUPHAR-DB database (see references above).

In another embodiment, the protein/polypeptide of interest is an adaptor protein (e.g., a signal transducing adaptor protein) a variant/fragment thereof. Adaptor proteins are proteins that are accessory to main proteins in a signal transduction pathway, and contain a variety of protein-binding modules (e.g., SH2 and/or SH3 domains) that link protein-binding partners together and facilitate the creation of larger signaling complexes. These proteins usually lack any intrinsic enzymatic activity themselves, but instead mediate specific protein-protein interactions that drive the formation of protein complexes. Examples of adaptor proteins include MyD88, Grb2 and SHC1.

In another embodiment, the protein of interest is a β-arrestin, a β-arrestin variant, or an active portion/fragment thereof, for example β-arrestin-1 (RefSeq: NP_004032.2 for isoform 1; NP_064647.1 for isoform 2) or β-arrestin-2 (RefSeq: NP_004304.1 for isoform 1; NP_945355.1 for isoform 2; NP_001244257.1 for isoform 3; NP_001244258.1 for isoform 4; NP_001244259.1 for isoform 5; and NP_001244260.1 for isoform 6).

In another embodiment, the protein of interest is a G protein subunit, a G protein subunit variant, or an active portion/fragment thereof, e.g., a Gα, Gγ or Gβ subunit or an active fragment thereof.

Thus, in another aspect, the present invention provides a biosensor for assessing G protein and/or GPCR activation, said biosensor comprising: a first component comprising a G protein subunit or an active fragment thereof tagged with a *Renilla* green fluorescent protein (*Renilla* GFP) or a *Renilla* luciferase protein (*Renilla* Luc); a second component comprising a PM targeting moiety tagged with a *Renilla* GFP or a *Renilla* Luc; wherein if said G protein subunit is tagged with said *Renilla* GFP, said PM targeting moiety is tagged with said *Renilla* Luc, and if said G protein subunit is tagged with said *Renilla* Luc, said PM targeting moiety is tagged with said *Renilla* GFP.

In another aspect, the present invention provides a biosensor for assessing whether a GPCR ligand modulates the activity of a G protein subunit, said biosensor comprising: a first component comprising said G protein subunit or an active fragment thereof tagged with a *Renilla* green fluorescent protein (*Renilla* GFP) or a *Renilla* luciferase protein (*Renilla* Luc); a second component comprising a PM targeting moiety tagged with a *Renilla* GFP or a *Renilla* Luc; wherein if said G protein subunit is tagged with said *Renilla* GFP, said PM targeting moiety is tagged with said *Renilla* Luc, and if said G protein subunit is tagged with said *Renilla* Luc, said PM targeting moiety is tagged with said *Renilla* GFP.

In an embodiment, said G protein subunit or active fragment thereof is tagged with said *Renilla* Luc, said PM targeting moiety is tagged with said *Renilla* GFP. In an embodiment, the G protein subunit is a Gγ subunit, e.g., Gγ1, Gγ2, Gγ3, Gγ4, Gγ5, Gγ6, Gγ7, Gγ8, Gγ9, Gγ10, Gγ11, Gγ12 or Gγ13. In another embodiment, the G protein subunit is a Gα subunit, e.g., Gq, Gs, Gi1, Gi2, Gi3, Gt-cone, Gt-rod, Gt-gus, Gz, GoA, GoB, Golf, G11, G12, G13, G14, or G15/G16. In another embodiment, the G protein subunit is a Gβ, e.g., Gβ1, Gβ2, Gβ3, Gβ4 or Gβ5 (Gβ5-S or Gβ5-L).

In another embodiment, the protein of interest is a protein that binds to DAG, or an active portion/fragment thereof, e.g., a phorbol esters/diacylglycerol binding domain (DAG-binding domain). In an embodiment, the DAG-binding domain is from PKCδ (C1b). Other proteins that comprise a DAG-binding domain (commonly refererred to as C1 domain) include, for example AKAP13; ARAF; ARHGAP29; ARHGEF2; BRAF; CDC42BPA; CDC42BPB; CDC42BPG; CHN1; CHN2; CIT; DGKA; DGKB; DGKD; DGKE; DGKG; DGKH; DGKI; DGKK; DGKQ; DGKZ; GMIP; HMHA1; KSR1; KSR2; MYO9A; MYO9B; PDZD8; PRKCA; PRKCB1; PRKCD; PRKCE; PRKCG; PRKCH; PRKCI; PRKCN; PRKCQ; PRKCZ; PRKD1; PRKD2; PRKD3; RACGAP1; RAF1; RASGRP; RASGRP1; RASGRP2; RASGRP3; RASGRP4; RASSF1; RASSF5; ROCK1; ROCK2; STAC; STAC2; STAC3; TENC1; UNC13A; UNC13B; UNC13C; VAV1; VAV2 and VAV3.

In another embodiment, the protein of interest is PLCδ1 or or an active portion/fragment thereof capable of binding to PI(4,5)P$_2$, e.g., the pleckstrin homology (PH) domain of PLCδ1.

In another embodiment, the protein of interest is a protein that binds to a small GTPase (Expasy ENZYME entry: EC 3.6.5.2). Small GTPases are a family of about 50 enzymes with a molecular mass of 21 kDa distantly related to the a subunit of G proteins, and which are involved in cell-growth regulation (Ras subfamily), membrane vesicle traffic and uncoating (Rab and ARF subfamilies), nuclear protein import (Ran subfamily) and organization of the cytoskeleton (Rho and Rac subfamilies). In an embodiment, the protein of interest is a protein that binds to one or more members of of the Ras superfamily of small GTPases, e.g., Ras, Rho, Ran, Rab and Arf families of GTPases. The localization/translocation of such small GTPases may be assessed using a polypeptide comprising a Ras-binding domain (RBD), for example the RBD of RAF1 or a variant thereof that comprises an A85K substitution (which has a higher affinity for Ras). Other proteins that comprise a RBD include ARAF, BRAF, RGS12, RGS14, TIAM1 and PI3K. The protein of interest may thus comprises the entire/native sequence of a protein that binds to a small GTPase, or a variant of fragment thereof that maintains the ability to bind to a small GTPase.

In a further embodiment, the protein of interest is a protein that binds to one or more members of the Rho superfamily of small GTPases, Rho (A, B & C), Rac (rac1, 2, 3 or RhoG) or Cdc42 (Cdc42, RhoQ or RhoJ). In another embodiment, the protein of interest is a protein that binds to a Rho protein (RhoA, RhoB and/or RhoC, preferably RhoA), or an active fragment thereof, for example a Cdc42/Rac interactive binding (CRIB) domain. The CRIB domain (EMBL-EBI/Interpro accession No. IPR000095) is a conserved region within the N-terminal portion of the GTPase binding domain (GBD, also called p21 binding domain, PBD) that is present in many putative downstream effectors of small GTPases (e.g., Cdc42p- and/or Rho-like small GTPases), and comprises about 15-16 amino acids. Proteins that comprise a CRIB domain include mammalian activated Cdc42-associated kinases (ACKs), mammalian p21-activated kinases (PAK1 to PAK4), Rhotekin (RTKN), mammalian Wiskott-Aldrich Syndrome Proteins (WASPs), kinases of the protein kinase C superfamily, such as serine/threonine protein kinase N (PKN, also known as protein kinase C-related kinase, PRK). In an embodiment, the protein of interest comprises the CRIB domain of human PKN1 (Uniprot reference: Q16512-1) or PKN2 (Uniprot reference: Q16513), preferably PKN1. The CRIB domain of human PKN1 comprises the sequence VQSEPRSWSLLEQLG (SEQ ID NO:40), which corresponds to residues 6-20 of native human PKN1 (Uniprot reference: Q16512-1).

Thus, in another aspect, the present invention provides a biosensor for assessing the activation of a small GTPase (e.g., Rho), said biosensor comprising: a first component comprising a polypeptide comprising a domain that binds to said small GTPase (e.g., a CRIB domain) tagged with a *Renilla* green fluorescent protein (*Renilla* GFP) or a *Renilla* luciferase protein (*Renilla* Luc); a second component comprising a PM or endosomal targeting moiety tagged with a *Renilla* GFP or a *Renilla* Luc; wherein if said polypeptide comprising a domain that binds to said small GTPase (e.g., a CRIB domain) is tagged with said *Renilla* GFP, said PM or endosomal targeting moiety is tagged with said *Renilla* Luc, and if said polypeptide comprising a domain that binds to said small GTPase (e.g., a CRIB domain) is tagged with said *Renilla* Luc, said PM or endosomal targeting moiety is tagged with said *Renilla* GFP. In an embodiment, the small GTPase is a Rho protein (e.g., RhoA). In an embodiment, the domain that binds to the small GTPase is a CRIB domain, such as the CRIB domain of human PKN1. In an embodiment, the second component comprises a PM targeting moiety.

The term *Renilla* luciferase as used herein refers to an oxidative enzyme used in bioluminescence and that is derived from an organism of the genus *Renilla*, such as *Renilla reniformis* or *Renilla mulleri*. It includes the native luciferase from a *Renilla* organism, or variants thereof, for example the native form (in terms of amino acid sequence) of *Renilla reniformis* luciferase (Rluc) or variants thereof such as RlucII or Rluc8. The term "RlucII" refers to a mutant form of *Renilla reniformis* luciferase that comprises the following amino acid substitutions: A55T, C124A and M185V relative to a native *Renilla* luciferase. In an embodiment, the RlucII comprises the sequence depicted in Example 1 (SEQ ID NO:10). The term "Rluc8" refers to a mutant form of *Renilla reniformis* luciferase that comprises the following amino acid substitutions: A55T, C124A, S130A, K136R, A143M, M185V, M253L, and S287L relative to a native *Renilla* luciferase. The amino acid sequence of native *Renilla mulleri* luciferase is disclosed in GenBank accession No. AAG54094.1.

The term "*Renilla* GFP" refers to a green fluorescent protein that is derived from organisms of the genus *Renilla*, such as *Renilla reniformis* or *Renilla mulleri*. It includes the native GFP from a *Renilla* organism, or variants thereof. In an embodiment, the *Renilla* GFP is a *Renilla reniformis* GFP (referred to herein as "rGFP"), in a further embodiment, the native form (in terms of amino acid sequence) of *Renilla reniformis* GFP. In an embodiment, the rGFP comprises the sequence depicted in Example 1 (SEQ ID NO:11). The amino acid sequence of native *Renilla mulleri* GFP is disclosed in GenBank accession No. AAG54098.1. The nucleic acid sequence of the *Renilla* luciferase and/or *Renilla* GFP may be codon-optimized for expression in human cells (i.e. "humanized", see, e.g., WO 2002057451 for a humanized version of *Renilla mulleri* GFP).

Resonance energy transfer (abbreviated RET) is a mechanism describing energy transfer between two chromophores, having overlapping emission/absorption spectra. When the two chromophores (the "donor" and the "acceptor"), are within a short distance (e.g., 10-100 Angstroms) of one another and their transition dipoles are appropriately oriented, the donor chromophore is able to transfer its excited-state energy to the acceptor chromophore through non-radiative dipole-dipole coupling. Bioluminescence Resonance Energy Transfer (BRET) is based on the non-radiative transfer of energy between a donor bioluminophore (bioluminescent enzyme such as *renilla* luciferase) and an acceptor fluorophore (e.g., *renilla* GFP).

The term "cellular compartment targeting moiety" refers to a biomolecule, preferably a polypeptide or peptide, which, when attached to the *Renilla* GFP or *Renilla* Luc (as a fusion protein, for example), targets them to a particular compartment, organelle or localization within the cell, such as for example the plasma membrane (or a particular subdomain of the plasma membrane, such as lipid rafts), the endosomes (e.g. early and/or late endosomes), the lysosomes, the phagosomes, the ribosomes, the mitochondria, the endoplasmic reticulum, the Golgi apparatus, the nucleus, etc., thereby increasing the effective concentration of the *Renilla* GFP or *Renilla* Luc. Such markers are typically proteins (or suitable fragments thereof) that are normally found at high levels in the targeted particular compartment. Peptides that target proteins to specific compartment, organelle or localization within the cell are known in the art and include endoplasmic reticulum (ER) signal peptide or ER-retrieval sequence, nuclear localization signal (NLS) peptide, and mitochondrial localization signal (MLS) peptide, for example.

In an embodiment, the cellular compartment targeting moiety is a plasma membrane (PM) targeting moiety. Any moiety capable of recruiting the *Renilla* GFP or *Renilla* Luc to the PM may be used in the biosensors. The *Renilla* GFP or *Renilla* Luc may thus be fused to any protein found at the plasma membrane (e.g., receptors or any other protein found at the PM), or fragments thereof. An example of such proteins is Caveolin-1, which the main component of the caveolae (a type of lipid raft that correspond to small (50-100 nm) invaginations of the plasma membrane) found in many cell types. Two isoforms of Caveolin-1, generated by alternative splicing of the CAV1 gene, have been identified: Caveolin-1α (comprising residues 2-178) and Caveolin-1β (corresponding to the 32-178 sequence). Other examples of such moiety include peptides/polypeptides comprising a signal sequence for protein lipidation/fatty acid acylation, such as myristoylation, palmitoylation and prenylation, as well as polybasic domains. Several proteins are known to be myristoylated, palmitoylated and/or prenylated (e.g., protein kinases and phosphatases such as Yes, Fyn, Lyn, Lck, Hck, Fgr, G$_\alpha$ proteins, nitric oxide synthase, ADP-ribosylation factors (ARFs), calcium binding proteins and membrane or cytoskeleton-associated structural proteins such as MARCKS (see, e.g., Wright et al., *J Chem Biol.* March 2010; 3(1): 19-35; Alcart-Ramos et al., *Biochimica et Biophysica Acta (BBA)—Biomembranes*, Volume 1808, Issue 12, December 2011, Pages 2981-2994), and thus the myristoylation, palmitoylation and prenylation signal sequences from any of these proteins may be used in the biosensor. In an embodiment, the myristoylation and/or palmitoylation sequence is from the Lyn kinase.

In an embodiment, the PM membrane targeting moiety comprises a CAAX motif (C is cysteine residue, AA are two aliphatic residues, and X represents any amino acid. CAAX motifs are found in "CAAX proteins" that are defined as a group of proteins with a specific amino acid sequence at C-terminal that directs their post translational modification. CAAX proteins encompass a wide variety of molecules that include nuclear lamins (intermediate filaments) such as prelamin A, lamin B1 and lamin B2, Ras and a multitude of GTP-binding proteins (G proteins) such as Ras, Rho, Rac, and Cdc42, several protein kinases and phosphatases, etc. (see, e.g., Gao et al., *Am J Transl Res.* 2009; 1(3): 312-325). The proteins that have a CAAX motif or box at the end of the C-terminus typically need a prenylation process before the proteins migrate to the plasma membrane or nuclear membrane and exert different functions. In an embodiment, the CAAX box is derived from a human RAS family protein, for example HRAS, NRAS, Ral-A, KRAS4A or KRAS4b. The last C-terminal residues of RAS, NRAS, KRAS4A or KRAS4b (referred to as the hypervariable region or HVR) are depicted below, with the putative minimal plasma membrane targeting region in italics and the CAAX box underlined (see, e.g., Ahearn et al., *Nature Reviews Molecular Cell Biology* 13: 39-51, January 2012): HRAS: KLNPPDESGPGCMSCK<u>CVLS</u>; (SEQ ID NO:33); NRAS: KLNSSDDGTQGCMGLP<u>CVVM</u>; (SEQ ID NO:34); KRAS4A: KISKEEKTPGCVK/KK<u>CIIM</u>; (SEQ ID NO:35); KRAS4b: KMSKDGKKKKKKSKTK<u>CVIM</u>; (SEQ ID NO:36); Ral-A/Ral1: KNGKKKRKSLAKRIRER<u>CCIL</u> (SEQ ID NO:37).

In an embodiment, the PM targeting moiety comprises the sequence GKKKKKKSKTKCVIM (SEQ ID NO:7) from KRAS4b. In another embodiment, the PM targeting moiety comprises the the plasma-membrane targetting palmitoylation sequence from hRas and prenylation signal sequence from Ral-A/Ral1 (sequence: CMSCKCCIL, SEQ ID NO:43).

Several proteins also contain a non-lipid, polybasic domain that targets the PM such as Ras small GTPases, phosphatase PTEN, nonreceptor tyrosine kinase Src, actin regulators WASP and MARCKS, and G protein-coupled receptor kinases (GRKs) such as GRK5. In an embodiment, the polybasic domain is from GRK5, and comprises the sequence SPKKGLLQRLFKRQHQNNSKS (SEQ ID NO:8).

In a particular aspect, the present invention provides a biosensor comprising: a cell or membrane preparation comprising: (i) a first component comprising a β-arrestin tagged with a *Renilla* GFP or a *Renilla* Luc; (ii) a second component comprising a plasma membrane (PM) targeting moiety tagged with a *Renilla* GFP or a *Renilla* Luc; and a GPCR; wherein if said β-arrestin is tagged with said *Renilla* GFP, said PM targeting moiety is tagged with said *Renilla* Luc, and if said β-arrestin is tagged with said *Renilla* Luc, said PM targeting moiety is tagged with said *Renilla* GFP. Such biosensor may be useful to monitor/measure the recruitment of a β-arrestin to a GPCR located at the plasma membrane.

In an embodiment, the cellular compartment targeting moiety is an endosomal targeting moiety. Several endosomal targeting moieties/markers are known in the art and include the Rab family of proteins (RAB4, RAB5, RAB7, RAB9 and RAB11), mannose 6-phosphate receptor (M6PR), caveolin-1 and -2, transferrin and its receptor, clathrin, as well as proteins comprising a FYVE domain such as early endosome autoantigen 1 (EEA1), Rabenosyn-5, Smad anchor for receptor activation (SARA), Vps27p and Endofin. Some markers are more specific to early endosomes (e.g., RAB4, Transferrin and its receptor, and proteins comprising a FYVE domain), others are more specific to late endosomes (e.g., RAB7, RAB9, and M6PR) and others are more specific to recycling endosomes (e.g., RAB11, RAB4). Thus, these proteins or suitable fragments thereof may be fused to *Renilla* Luc or *Renilla* GFP to link/target them to an endosomal localization.

In an embodiment, the endosomal targeting moiety comprises a FYVE domain. The FYVE domain is defined by the three conserved elements: the N-terminal WxxD, the central RR/KHHCR, and the C-terminal RVC motifs. In an embodiment, the endosomal targeting moiety comprises the FYVE domain of Endofin, for example about residues 739 to 806 human Endofin.

In an embodiment, the cellular compartment targeting moiety is a lysosomal targeting moiety, such as for example LAMP1 and LAMP2. Thus, these proteins or suitable fragments thereof may be fused to *Renilla* Luc or *Renilla* GFP to link/target them to a lysosomal localization.

In an embodiment, the cellular compartment targeting moiety is a peroxisomal targeting moiety, such as for example PMP70, PXMP2 and Catalase. Thus, these proteins or suitable fragments thereof may be fused to *Renilla* Luc or *Renilla* GFP to link/target them to a peroxisomal localization.

In an embodiment, the cellular compartment targeting moiety is an autophagosomal targeting moiety, such as for example ATG (AuTophaGy related) family proteins (ATG4, ATG5, ATG16, ATG12, see Lamb et al., *Nature Reviews Molecular Cell Biology* 14, 759-774 (2013)), LC3A/B and SQSTM1/p62. Thus, these proteins or suitable fragments thereof may be fused to *Renilla* Luc or *Renilla* GFP to link/target them to an autophagosomal localization.

In an embodiment, the cellular compartment targeting moiety is a ribosome targeting moiety. Several endosomal targeting moieties/markers are known in the art and include the Ribosomal Proteins (L7a, S3 and S6). Thus, these proteins or suitable fragments thereof may be fused to *Renilla* Luc or *Renilla* GFP to link/target them to a ribosomal localization.

In an embodiment, the cellular compartment targeting moiety is an endoplasmic reticulum (ER) targeting moiety. Several ER targeting moieties/markers are known in the art and include ERp72, ERp29, Protein disulphide isomerase (PDI), HSP70 family proteins such as GRP78 (HSPA5), GRP94 (HSP90B1) and GRP58 (PDIA3), Calnexin and Calreticulin. Thus, these proteins or suitable fragments thereof may be fused to *Renilla* Luc or *Renilla* GFP to link/target them to an ER localization.

In an embodiment, the cellular compartment targeting moiety is a Golgi targeting moiety. Several Golgi targeting moieties/markers are known in the art and include eNOS (e.g., the N-terminal portion thereof, J. Liu et al., Biochemistry, 35 (1996), pp. 13277-13281), GM130, Golgin-97, the 58K protein, Trans-Golgi network membrane protein 2 (TGOLN2), TGN46, TGN38, Mannosidase 2, Syntaxin 6, GM130 (GOLGA2), Golgin-160, Membrin (GS27), GS28, Coatomer proteins, Rbet1 and RCAS1. Thus, these proteins or suitable fragments thereof may be fused to *Renilla* Luc or *Renilla* GFP to link/target them to a Golgi apparatus localization. In an embodiment, the Golgi targeting moiety the N-terminal portion of a human eNOS protein, for example residues 1 to 73 of human eNOS1 (SEQ ID NO: 42).

In an embodiment, the cellular compartment targeting moiety is a mitochondria targeting moiety. Several mitochondria targeting moieties/markers are known in the art and include AIF, COX IV, Cytochrome C, hexokinase I, SOD1, SDHA, Pyruvate dehydrogenase, VDAC, TOMM22, UCP1, UCP2, UCP3, PHB1 Galpha12 (or the N-terminal portion thereof; Andreeva et al., FASEB J. 2008 August; 22(8): 2821-31. Epub 2008 Mar. 26), a protein of the Bcl-family member or a fragment thereof, for example a fragment of Bcl-XL (RKGQERFNRWFLTGMTVAGVVLLGSLFSRK, SEQ ID NO:87, Mossalam et al., Mol Pharm. 2012 May 7; 9(5): 1449-1458). Thus, these proteins or suitable fragments thereof may be fused to *Renilla* Luc or rGFP to link/target them to a mitochondrial localization. The nuclear targeting moiety may also comprise a mitochondrial targeting signal, which is a 10-70 amino acid long peptide that directs newly synthesized proteins to the mitochondria. It is found at the N-terminus and consists of an alternating pattern of hydrophobic and positively charged amino acids to form an amphipathic helix. Mitochondrial targeting signals can contain additional signals that subsequently target the protein to different regions of the mitochondria, such as the mitochondrial matrix.

In an embodiment, the cellular compartment targeting moiety is a nuclear targeting moiety. Several nuclear targeting moieties/markers are known in the art and include Lamin A/C, Nucleoporins (NUP), ASHL2, ESET, Histones, LSD1, DNA repair enzymes such as PARP, and P84/THOC1. Thus, these proteins or suitable fragments thereof may be fused to *Renilla* Luc or *Renilla* GFP to link/target them to a nuclear localization. The nuclear targeting moiety may also comprises a nuclear localization signal or sequence (NLS), which is an amino acid sequence that tags a protein for import into the cell nucleus by nuclear transport. Typically, this signal consists of one or more short sequences of positively charged lysines or arginines exposed on the protein surface. The best characterized transport signal is the classical NLS (cNLS) for nuclear protein import, which consists of either one (monopartite) or two (bipartite) stretches of basic amino acids. Monopartite cNLSs are exemplified by the SV40 large T antigen NLS ($^{126}$PKK-KRRV$^{132}$) (SEQ ID NO:38) and bipartite cNLSs are exemplified by the nucleoplasmin NLS ($^{155}$KRPAATKK-AGQAKKKK$^{170}$) (SEQ ID NO:39).

In an embodiment, the cellular compartment targeting moiety is a nuclear export sequence (NES). NES is a short amino acid sequence (typically 4 hydrophobic residues) in a protein that targets it for export from the cell nucleus to the cytoplasm through the nuclear pore complex using nuclear transport. The sequence of such NES may be for example LxxxLxxLxL, where "L" is a hydrophobic residue (often leucine) and "x" is any other amino acid. In proteins that are translocated from cytosol to nucleus (such as ERK or MDM2), a decrease in the BRET signal is detected using an NES moiety.

In an embodiment, the cellular compartment targeting moiety is a cytoskeleton targeting moiety, for example actin or a fragment thereof, or a protein comprising an actin-binding domain (ABD), such as the N-terminal F-actin binding domain of Inositol-1,4,5-trisphosphate-3-kinase-A (ITPKA) (Johnson and Schell, *Mol. Biol. Cell* Dec. 15, 2009 vol. 20 no. 24 5166-5180). In an embodiment, the cytoskeleton targeting moiety is a peptide comprising the sequence MGVADLIKKFESISKEE (SEQ ID NO: 88) ("Lifeact", Riedl et al., *Nat Methods.* 2008 July; 5(7): 605).

In another aspect, the present invention provides a biosensor for assessing a modulation (increase or decrease) in the amount of a biomolecule at a cellular compartment between a first and a second condition, said biosensor comprising: a first component comprising a *Renilla* green fluorescent protein (*Renilla* GFP) tagged with a protein marker that binds to said biomolecule; and a second component comprising a *Renilla* luciferase protein (*Renilla* Luc) tagged with said protein marker.

In another aspect, the present invention provides a biosensor for assessing a modulation (increase or decrease) in the amount of a biomolecule at a cellular compartment between a first and a second condition, said biosensor comprising: a first component comprising a protein marker that binds to said biomolecule tagged with a *Renilla* GFP or *Renilla* Luc; and a second component comprising a cellular compartment targeting moiety tagged with a *Renilla* GFP or *Renilla* Luc; wherein if said protein marker is tagged with *Renilla* GFP, said cellular compartment targeting moiety is tagged with *Renilla* Luc and vice-versa.

Such biosensors may be used in a method for assessing a modulation in the amount of a biomolecule at a cellular compartment between a first and a second condition, e.g., in the presence and absence of an agent. If the agent increase the amount of biomolecule at the cellular compartment (e.g., PM) the BRET signal will be increased in the presence of the agent and vice-versa.

The protein marker may be any protein or fragment thereof that binds to said biomolecule, and thus whose concentration or density at said cellular compartment is dependent on the concentration or density of said biomolecule (e.g., a second messenger, including cyclic nucleotides such as cAMP and cGMP, $IP_3$, DAG, $PIP_3$, $Ca^{2+}$ ions) at said cellular compartment. For example, PLCδ1 localization at the PM is dependent on the presence of $PIP_2$ and/or $PIP_3$ If the concentration of $PI(4,5)P_2$ at the PM decreases (which occurs when phospholipase C (PLC) is activated because $PI(4,5)P_2$ is hydrolyzed), PLCδ1 diffuse into the cytosol reducing its concentration/density at the PM. Thus, the concentration/density of PLCδ1 (or a fragment thereof that binds to $PIP_2$ and/or $PIP_3$, such as its PH domain) at the PM, which may be measured by BRET using *Renilla* Luc- and *Renilla* GFP-tagged PLCδ1 (or a fragment thereof, e.g., SEQ ID NO:25), or with a *Renilla* Luc or GFP-tagged PLCδ1 and a *Renilla* Luc or GFP-tagged PM-targeting moiety, may be used as an indicator of the concentration or density of the biomolecule at the PM. Similarly, the PH domain and Phox homology domain (PX domain) of certain proteins, (ex: akt and PLD1) interact with $PIP_3$, thus a protein marker comprising a PH or PX domain selective for $PIP_3$ binding, could be used to as an indicator of the concentration or density of $PIP_3$ at the PM. Another example is the C1 domain (also known as phorbol esters/diacylglycerol binding domain, which is found for example in the N-terminal portion of protein kinase. Also, PLCγ1 can bind to different phospholipids including $PIP_3$. The C1 domain binds to diacylglycerol (DAG), and thus a protein marker comprising a C1 domain could be used to as an indicator of the concentration or density of DAG at the PM. Thus, any protein or protein domain capable of binding to a biomolecule such as a second messenger and whose concentration or density at said cellular compartment is dependent on the concentration or density of said biomolecule could be used in such biosensor.

The term "biomolecule" refer to any molecule that may be produced by or present in a cell, for example a protein, a peptide, an amino acid, a nucleic acid (DNA or RNA), a lipid or fatty acid, a phospholipid, a sugar (polysaccharide), or any other compound such as ATP, AMP, ADP, histamine, etc. In an embodiment, the biomolecule is a second messenger (i.e. a molecules that relay signals received at receptors on the cell surface to target molecules in the cytosol and/or nucleus), e.g., Cyclic AMP, Cyclic GMP, Inositol Triphosphate ($IP_3$), phosphatidylinositols (e.g., Phosphatidylinositol 4,5-bisphosphate or $PIP_2$, Phosphatidylinositol 3,4,5-triphosphate or $PIP_3$, Diacylglycerol (DAG), $Ca^{2+}$. In an embodiment, the biomolecule is a hydrophobic molecule (e.g., a phospholipid) found at the PM, such as diacylglycerol and phosphatidylinositols.

The variant as used herein refers to a protein/polypeptide having has an identity or similarity of at least 60% with a reference (e.g., native) sequence and retains a desired activity thereof, for example the capacity to bind to a target protein and/or to translocation to a cellular compartment. In further embodiments, the variant has a similarity or identity of at least 65, 70, 75, 80, 85, 90, 91, 92, 93, 94, 95, 96, 97, 98 or 99% with a reference (e.g., native) sequence and retains a desired activity thereof. "Similarity" and "identity" refers to sequence similarity/identity between two polypeptide molecules. The similarity or identity can be determined by comparing each position in the aligned sequences. A degree of similarity or identity between amino acid sequences is a function of the number of matching or identical amino acids at positions shared by the sequences. Optimal alignment of sequences for comparisons of similarity or identity may be conducted using a variety of algorithms, such as the local homology algorithm of Smith and Waterman, 1981, Adv. Appl. Math 2: 482, the homology alignment algorithm of Needleman and Wunsch, 1970, J. Mol. Biol. 48: 443, the search for similarity method of Pearson and Lipman, 1988, Proc. Natl. Acad. Sci. USA 85: 2444, and the computerized implementations of these algorithms (such as GAP, BESTFIT, FASTA and TFASTA in the Wisconsin Genetics Software Package, Genetics Computer Group, Madison, Wis., U.S.A.). Sequence similarity or identity may also be determined using the BLAST algorithm, described in Altschul et al., 1990, J. Mol. Biol. 215: 403-10 (using the published default settings). Software for performing BLAST analysis may be available through the National Center for Biotechnology Information web site (http://www.ncbi.nlm.nih.gov/).

The *Renilla* Luc or *Renilla* GFP may be fused N-terminal, within or C-terminal relative to the cellular compartment targeting moiety. In an embodiment, the cellular compartment targeting moiety is a PM targeting moiety, and it is fused to the N-terminal end of said *Renilla* Luc or said *Renilla* GFP. In an embodiment, the cellular compartment targeting moiety is an endosomal targeting moiety, and it is fused to the C-terminal end of said *Renilla* Luc or said *Renilla* GFP.

The *Renilla* Luc or *Renilla* GFP may be fused N-terminal, within (see, e.g., Gα subunit with internal RlucII described in the examples), or C-terminal relative to the protein of interest. In an embodiment, the *Renilla* Luc or *Renilla* GFP is fused to the N-terminal end of the protein of interest. In another embodiment, the *Renilla* Luc or *Renilla* GFP is fused to the C-terminal end of the protein of interest.

In an embodiment, the protein of interest is tagged with a *Renilla* Luc and the cellular compartment marker is tagged with a *Renilla* GFP.

Other domains or linkers may be present at the N-terminal, C-terminal or within the above-noted first and/or second components. In embodiments, the *Renilla* Luc or *Renilla* GFP may be covalently linked to the protein of interest or the cellular compartment targeting moiety either directly (e.g., through a peptide bond) or "indirectly" via a suitable linker moiety, e.g., a linker of one or more amino acids (e.g., a polyglycine linker) or another type of chemical linker (e.g., a carbohydrate linker, a lipid linker, a fatty acid linker, a polyether linker, PEG, etc. In an embodiment, one or more additional domain(s) may be inserted before (N-terminal), between or after (C-terminal) the components defined above. In an embodiment, the *Renilla* Luc and/or *Renilla* GFP are covalently linked through a peptide bond to the protein of interest and/or the cellular compartment targeting moiety. In an embodiment, a peptide linker is present between *Renilla* Luc or *Renilla* GFP and the protein of interest or the cellular compartment targeting moiety. In embodiments, the linker comprises about 4 to about 50 amino acids, about 4 to about 40, 30 or 20 amino acids, or about 5 to about 15 amino acids, e.g., 4, 5, 6, 7, 8, 9, 10, 11, 12, 13, 14, 15, 16, 17, 18, 19 or 20 amino acids. In a further embodiment, the linker is one of the linker described in Example 1 below and/or FIGS. 11A-11D).

In an embodiment, the first and second components are linked together to provide a unimolecular biosensor. The first and second components are covalently attached by a linker, preferably a flexible polypeptide linker. In an embodiment, the flexible polypeptide linker has a length corresponding to the length of a random amino acid sequence of about 50 to about 500-1000 amino acids, for example corresponding to the length of a random amino acid sequence of about 100 to about 400-500 amino acids, preferably about 200-400 amino acids, for example about 300. In a further embodiment, the flexible linker comprises a random amino acid sequence of about 50 to about 500-1000 amino acids, for example a random amino acid sequence of about 100 to about 400-500 amino acids, preferably a random amino acid sequence of about 200-400 amino acids, for example about 300 amino acids. Methods for designing flexible amino acid linkers, and more specifically linkers with minimal globularity and maximal disorder, are known in the art. This may be achieved, for example, using the Globplot 2.3 program. The sequence may be further optimized to eliminate putative aggregation hotspots, localization domains, and/or interaction and phosphorylation motifs. Such a unimolecular biosensor allows the assessment of BRET in intact cells as well as in membrane preparations.

In another aspect, the present invention provides a nucleic acid encoding the above-defined first and/or second component(s). In an embodiment, the nucleic acid is present in a vector/plasmid, in a further embodiment an expression vector/plasmid. Such vectors comprise a nucleic acid sequence capable of encoding the above-defined first and/or second component(s) operably linked to one or more transcriptional regulatory sequence(s), such as promoters, enhancers and/or other regulatory sequences. In an embodiment, the nucleic acid encodes the first and second components (polycistronic construct).

The term "vector" refers to a nucleic acid molecule, which is capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". A recombinant expression vector of the present invention can be constructed by standard techniques known to one of ordinary skill in the art and found, for example, in Sambrook et al. (1989) in *Molecular Cloning: A Laboratory Manual*. A variety of strategies are available for ligating fragments of DNA, the choice of which depends on the nature of the termini of the DNA fragments and can be readily determined by persons skilled in the art. The vectors of the present invention may also contain other sequence elements to facilitate vector propagation and selection in bacteria and host cells. In addition, the vectors of the present invention may comprise a sequence of nucleotides for one or more restriction endonuclease sites. Coding sequences such as for selectable markers and reporter genes are well known to persons skilled in the art.

A recombinant expression vector comprising a nucleic acid sequence of the present invention may be introduced into a cell (a host cell), which may include a living cell capable of expressing the protein coding region from the defined recombinant expression vector. The living cell may include both a cultured cell and a cell within a living organism. Accordingly, the invention also provides host cells containing the recombinant expression vectors of the invention. The terms "cell", "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Vector DNA can be introduced into cells via conventional transformation or transfection techniques. The terms "transformation" and "transfection" refer to techniques for introducing foreign nucleic acid into a host cell, including calcium phosphate or calcium chloride co-precipitation, DEAE-dextran-mediated transfection, lipofection, electroporation, microinjection and viral-mediated transfection. Suitable methods for transforming or transfecting host cells can for example be found in Sambrook et al. (*Molecular Cloning: A Laboratory Manual*, $2^{nd}$ Edition, Cold Spring Harbor Laboratory press (1989)), and other laboratory manuals. "Transcriptional regulatory sequence/element" is a generic term that refers to DNA sequences, such as initiation and termination signals, enhancers, and promoters, splicing signals, polyadenylation signals which induce or control transcription of protein coding sequences with which they are operably linked. A first nucleic acid sequence is "operably-linked" with a second nucleic acid sequence when the first nucleic acid sequence is placed in a functional relationship with the second nucleic acid sequence. For instance, a promoter is operably-linked to a coding sequence if the promoter affects the transcription or expression of the coding sequences. Generally, operably-linked DNA sequences are contiguous and, where necessary to join two protein coding regions, in reading frame. However, since for example enhancers generally function when separated from the promoters by several kilobases and intronic sequences may be of variable lengths, some polynucleotide elements may be operably-linked but not contiguous.

In another aspect, the present invention provides a kit comprising a first nucleic acid encoding the first component and a second nucleic acid encoding the second component.

In another aspect, the present invention provides a cell comprising or expressing the above-defined first and/or second component(s). In an embodiment, the cell has been transfected or transformed with a nucleic acid encoding the above-defined first and/or second component(s). The invention further provides a recombinant expression system, vectors and cells, such as those described above, for the expression of the first and/or second component(s) of the invention, using for example culture media and reagents well known in the art. The cell may be any cell capable of expressing the first and second component(s) defined above. Suitable host cells and methods for expression of proteins are well known in the art. Any cell capable of expressing the component(s) defined above may be used. For example, eukaryotic host cells such as mammalian cells may be used (e.g., rodent cells such as mouse, rat and hamster cell lines, human cells/cell lines). In another embodiment, the above-mentioned cell is a human cell line, for example an embryonic kidney cell line (e.g., HEK293 or HEK293T cells).

In an embodiment, the above-mentioned biosensor comprises a cell comprising or expressing the first and second components. In another embodiment, the above-mentioned biosensor comprises a membrane preparation comprising the first and second components.

In another aspect, the present invention provides a method for comparing the trafficking of a protein of interest in a cell under a first and a second condition, said method comprising: measuring the BRET signal in the biosensor defined herein under said first condition; and measuring the BRET signal in the biosensor defined herein under said second condition; wherein a difference in said BRET signal between said first and second conditions is indicative of a difference in the trafficking of said protein of interest under said first and second conditions. In an embodiment, the first condition is no activation and the second condition is activation (e.g., using an agonist) or vice-versa. In another embodiment, the first condition is no inhibition and the second condition is inhibition (e.g., using an antagonist) or vice-versa.

In another aspect, the present invention provides a method for determining whether an agent modulates (increases or decreases) the density or concentration of a protein of interest at a cellular compartment, said method comprising: measuring the BRET signal in the biosensor defined herein in the presence and absence of said agent; wherein a difference in said BRET signal in the presence of said agent relative to the absence thereof is indicative that said agent modulates (increases or decreases) the density or concentration of said protein of interest at the cellular compartment. An increase in the BRET signal being indicative that the agent increases the density or concentration of said protein of interest at the cellular compartment, whereas a decrease in the BRET signal being indicative that the agent decreases the density or concentration of said protein of interest at the cellular compartment.

Methods and devices to measure the BRET signal are well known in the art. The BRET signal may be measured, for example, by determining the intensity of the *Renilla* GFP signal (light intensity), and/or by calculating the ratio of the signal or light intensity emitted by the *Renilla* GFP over the signal or light intensity emitted by the *Renilla* Luc (BRET ratio). The BRET signal may be measured using a microplate reader or microscope with a suitable filter set for detecting the *Renilla* luciferase (donor) and/or rGFP (acceptor) light emissions.

By choosing an appropriate cellular compartment targeting moiety, it is possible to assess/monitor the trafficking of a protein of interest to any cellular compartment (PM, ER, Golgi, mitochondria, endosomes, etc.). For example, to determine whether a given condition or an agent affects the trafficking of a protein of interest to the mitochondria, a biosensor comprising a mitochondrial targeting moiety tagged with *Renilla* GFP or *Renilla* Luc may be used. An increase in the BRET signal in the presence of the agent or under the given condition (relative to the absence of the agent or to a different condition) is indicative of the "recruitment" of the protein of interest to the mitochondria (i.e., an increase in the concentration/density of the protein of interest at the mitochondria). In contrast, a decrease in the BRET signal in the presence of the agent or under the given condition (relative to the absence of the agent or to a different condition) is indicative of a decrease in the concentration/density of the protein of interest at the mitochondria. Using suitable cellular compartment targeting moieties, a similar approach may be used to study the trafficking of proteins to different cellular compartments.

In an embodiment, the method comprises determining whether an agent or condition induces (i.e. increases) the trafficking of a cell surface receptor of interest in an endosomal compartment (i.e., increases the concentration/density of the protein of interest in the endosomes), Accordingly, in another aspect, the present invention provides a method for comparing the trafficking of a cell surface receptor of interest at an endosomal compartment, said method comprising: measuring the BRET signal in the biosensor comprising an endosomal targeting moiety as defined herein under said first condition; and measuring the BRET signal in the biosensor comprising an endosomal targeting moiety as defined herein under said second condition; wherein a difference in the BRET signal between said first and second conditions is indicative of a difference in the trafficking of said protein of interest at said endosomal compartment under said first and second conditions.

In another aspect, the present invention provides a method for determining whether an agent induces (i.e. increases) the trafficking of a cell surface receptor of interest in a cell at an endosomal compartment, said method comprising: measuring the BRET signal in the biosensor comprising an endosomal targeting moiety, preferably an endosomal targeting moiety comprising a FYVE domain (e.g., the FYVE domain of Endofin) as defined herein in the presence and absence of said agent; wherein a higher BRET signal in the presence of said agent relative to the absence thereof is indicative that said agent induces (i.e. increases) the trafficking of a cell surface receptor of interest in a cell in said endosomal compartment (i.e. increase the concentration/density of the protein of interest in the endosomes).

As shown in the experiments described herein, it is possible to assess/monitor the trafficking of a protein across the endosomal pathway, for example by using a plurality of biosensors, each comprising a different endosomal targeting moiety (e.g., a first biosensor comprising a targeting moiety for the early endosomes and a second biosensor comprising a targeting moiety for the late endosomes).

In another aspect, the present invention provides a method for comparing the internalization of a cell surface receptor of interest in a cell under a first and a second condition, said method comprising: measuring the BRET signal in the biosensor comprising a PM targeting moiety as defined herein under said first condition; and measuring the BRET signal in the biosensor comprising a PM targeting moiety as defined herein under said second condition; wherein a difference in said BRET signal between said first and second conditions is indicative of a difference in the internalization of said cell surface receptor of interest under said first and second conditions.

In another aspect, the present invention provides a method for determining whether an agent induces the internalization and/or sequestration of a cell surface receptor of interest in a cell, said method comprising: measuring the BRET signal in the biosensor comprising a PM targeting moiety as defined herein in the presence and absence of said agent; wherein a lower BRET signal in the presence of said agent relative to the absence thereof is indicative that said agent induces the internalization and/or sequestration of the cell surface receptor of interest.

The biosensors described herein further permit to determine whether internalized receptors are recycled back at the cell surface, and if so to assess the kinetics of receptor recycling.

In another aspect, the present invention provides a method for monitoring the recycling of an internalized receptor of interest at the cell surface, said method comprising: (a) contacting the biosensor comprising a PM targeting moiety as defined herein in the presence of a ligand that induces the internalization of said receptor; (b) measuring a first BRET signal in the biosensor; (c) washing said biosensor to remove said ligand; (d) measuring a second BRET signal in the biosensor after said washing; and (e) determining the recycling of an internalized receptor of interest at the cell surface by comparing said first and second signals, wherein a higher second BRET signal relative to said first BRET signal is indicative of recycling of the internalized receptor of interest at the cell surface.

In another aspect, the present invention provides a method for monitoring the recycling of an internalized receptor of interest at the cell surface, said method comprising: (a) contacting a first and a second biosensor comprising a PM targeting moiety as defined herein in the presence of a ligand that induces the internalization of said receptor; (b) measuring a BRET signal in the first biosensor after said contacting; (c) washing said second biosensor to remove said ligand; (d) measuring a BRET signal in the second biosensor after said washing; and (e) determining the recycling of an internalized receptor of interest at the cell surface by comparing the BRET signal in the first and second biosensors, wherein a higher BRET signal in said second biosensor relative to said first biosensor is indicative of recycling of the internalized receptor of interest at the cell surface.

In an embodiment, the method further comprises repeating steps (d) and (e) at different times after washing to study the kinetics of recycling of the internalized receptor of interest.

In another aspect, the present invention provides a method for monitoring a modulation of G protein and/or GPCR activity between a first condition and a second condition, said method comprising: measuring the BRET signal in the biosensor for monitoring G protein and/or GPCR modulation as defined herein under said first condition; and measuring the BRET signal in the biosensor for monitoring G protein and/or GPCR modulation as defined herein under said second condition; wherein a difference in the BRET signal between said first and second conditions is indicative of a modulation of G protein and/or GPCR activity between said first and second conditions.

In an embodiment, the first condition is absence of a test compound (e.g., putative inhibitor or agonist) and the second condition is presence of a test compound, or vice-versa. A lower BRET signal in the presence of the test compound is indicative that the test compound is an agonist.

In another aspect, the present invention provides a method for determining whether a GPCR ligand modulates the activity of a G protein subunit of interest, said method comprising: measuring the BRET signal in the biosensor for monitoring G protein and/or GPCR modulation as defined herein in the presence or absence of said GPCR ligand; wherein a difference in the BRET signal in the presence vs. absence of said GPCR ligand is indicative that said GPCR ligand modulates the activity of the G protein subunit of interest.

In another aspect, the present invention provides a method for monitoring a modulation of the activity of a small GTPase between a first condition and a second condition, said method comprising: measuring the BRET signal in the biosensor for assessing the activation of a small GTPase as defined herein under said first condition; and measuring the BRET signal in the biosensor for for assessing the activation of a small GTPase as defined herein under said second condition; wherein a difference in the BRET signal between said first and second conditions is indicative of a modulation of the activity of a small GTPase between said first and second conditions.

In an embodiment, the first condition is absence of a test compound (e.g., putative inhibitor or agonist) and the second condition is presence of a test compound, or vice-versa. A higher BRET signal in the presence of the test compound is indicative that the test compound is an agonist (recruitment of the small GTPase at the PM or endosomes).

In another aspect, the present invention provides a method for determining whether a test agent modulates the activity of a small GTPase (e.g., a Rho protein), said method comprising: measuring the BRET signal in the biosensor for assessing the activation of a small GTPase as defined herein in the presence or absence of said test agent; wherein a difference in the BRET signal in the presence vs. absence of said test agent is indicative that said test agent modulates the activity of said small GTPase.

Using the biosensors described herein, it is also possible to assess/monitor the "rescue" of a protein of interest (for example, a defective protein that does not properly exit from the ER) by a pharmacological chaperone (PC). The term "pharmacological chaperone" ("PC") as used herein refers to a molecule that binds to a protein (e.g., a receptor) and has one or more of the following effects: (i) enhancing the formation of a stable molecular conformation of the protein; (ii) enhances proper trafficking of the protein from the ER to another cellular location, preferably a native cellular location, i.e., preventing ER-associated degradation of the protein; (iii) preventing aggregation of conformationally unstable, i.e., misfolded proteins; (iv) restoring or enhancing at least partial wild-type function, stability, and/or activity of the protein and/or (v) inducing a different folding of the protein. Thus, a pharmacological chaperone for a protein is a molecule that binds to the protein, resulting in proper folding, trafficking, non-aggregation, and/or activity of the protein, and/or to modulate the folding of the protein (inducing a folding of the protein that is different than the folding in the absence of the chaperone).

It has previously been shown that small molecule inhibitors of enzymes associated with lysosomal storage disorders (LSDs) can both rescue folding and activity of the mutant enzyme, and enhance folding and activity of the wild-type enzyme (see U.S. Pat. Nos. 6,274,597; 6,583,158; 6,589,964; 6,599,919; and 6,916,829). In particular, it was discovered that administration of small molecule derivatives of glucose and galactose, which were specific competitive inhibitors of mutant enzymes associated with LSDs, effectively increased in vitro and in vivo stability of the mutant enzymes and enhanced the mutant enzyme activity. The original theory behind this strategy is as follows: since the mutant enzyme protein folds improperly in the ER (Ishii et al., Biochem. Biophys. Res. Comm. 1996; 220: 812-815), the enzyme protein is retarded in the normal transport pathway (ER→Golgi apparatus→endosome→lysosome) and rapidly degraded. Therefore, a compound which stabilizes the correct folding of a mutant protein will serve as an active site-specific chaperone for the mutant protein to promote its smooth escape from the ER quality control system. Enzyme inhibitors occupy the catalytic center, resulting in stabilization of enzyme conformation in cells and in animals. These specific chaperones were designated "active site-specific chaperones (ASSCs)" since they bound in the active site of the enzyme.

In addition to rescuing the mutant enzymes, the ASSCs enhance ER secretion and activity of recombinant wild-type enzymes. An ASSC facilitates folding of overexpressed wild-type enzyme, which is otherwise retarded in the ER quality control system because overexpression and over production of the enzyme exceeds the capacity of the ER and leads to protein aggregation and degradation. Thus, a compound that induces a stable molecular conformation of an enzyme during folding serves as a "chaperone" to stabilize the enzyme in a proper conformation for exit from the ER. As noted above, for enzymes, one such compound unexpectedly turned out to be a competitive inhibitor of the enzyme.

In addition to the LSDs, a large and diverse number of diseases are now recognized as "conformational diseases" that are caused by adoption of non-native protein conformations, which may lead to retardation of the protein in the ER and ultimate degradation of the proteins (Kuznetsov et al., N. Engl. J. Med. 1998; 339:1688-1695; Thomas et al., Trends Biochem. Set 1995; 20:456-459; Bychkova et al., *FEBS Lett.* 1995; 359:6-8; Brooks, *FEBS Lett.* 1997; 409: 115-120). For example, small synthetic compounds were found to stabilize the DNA binding domain of mutant forms of the tumor suppressor protein p53, thereby allowing the protein to maintain an active conformation (Foster et al., Science 1999; 286:2507-10). Synthesis of receptors has been shown to be rescued by small molecule receptor antagonists and ligands (Morello et al., J Clin. Invest. 2000; 105: 887-95; Petaja-Repo et al., EMBO J. 2002; 21: 1628-37). Even pharmacological rescue of membrane channel proteins and other plasma membrane transporters has been demonstrated using channel-blocking drugs or substrates (Rajamani et al., *Circulation* 2002; 105:2830-5; Zhou et al., *J Biol. Chem.* 1999; 274:31123-26; Loo et al., *J. Biol. Chem.* 1997; 272: 709-12; Pedemonte et al., *J. Clin. Invest.* 2005; 115: 2564-71). Thus, the biosensors described herein may be useful to identify chaperones that rescue the expression and/or proper maturation of proteins, and in turn which may be useful for the treatment of diseases associated with defects in the expression and/or proper maturation of one or more proteins, as described above.

In another aspect, the present invention provides a method for determining whether an agent acts as a pharmacological chaperone for a receptor of interest, said method comprising:

providing a biosensor comprising: a cell comprising: said receptor of interest tagged with a *Renilla* GFP or a *Renilla*

Luc, preferably a *Renilla* Luc; and a plasma membrane (PM) targeting moiety tagged with *Renilla* GFP or a *Renilla* Luc, preferably a *Renilla* GFP; wherein if said receptor is tagged with said a *Renilla* GFP, said PM targeting moiety is tagged with said *Renilla* Luc, and if said receptor is tagged with said *Renilla* Luc, said PM targeting moiety is tagged with said a *Renilla* GFP; and measuring the BRET acceptor signal in the presence and absence of said agent; wherein an increase in the BRET signal in the presence of said agent relative to the absence thereof is indicative that said agent acts as a pharmacological chaperone for said receptor.

In another aspect, the present invention provides a method for determining whether an agent acts as a pharmacological chaperone for a protein of interest, said method comprising:

providing a biosensor comprising: a cell comprising: said protein of interest tagged with a *Renilla* GFP or a *Renilla* Luc; and an endoplasmic reticulum (ER) targeting moiety tagged with a rGFP or a *Renilla* Luc; wherein if said protein is tagged with said *Renilla* GFP, said ER targeting moiety is tagged with said *Renilla* Luc, and if said protein is tagged with said *Renilla* Luc, said ER targeting moiety is tagged with said *Renilla* GFP; and measuring the BRET acceptor signal in the presence and absence of said agent; wherein a decrease in the BRET signal in the presence of said agent relative to the absence thereof is indicative that said agent acts as a pharmacological chaperone for said receptor.

The above-mentioned method may be performed using a native protein/receptor, or a mutated receptor, as shown in the experiments described herein. The experiments described herein further shows that the biosensors are suitable to measure rescue of a GPCR as well as of a non-GPCR receptor (a voltage-dependent potassium channel), providing evidence that they may be used to monitor the rescue of any protein or receptor. In an embodiment, the protein is a native GPCR or a mutated GPCR. In a further embodiment, the GPCR is a native melanocortin-4 receptor (MC4R) or a mutated MC4R. In an embodiment, the mutated MC4R contains one or more mutations that result in reduced or improper intracellular folding of the MC4R polypeptide. Exemplary mutations are as follows: P78L, R165Q, R165W, I125K, C271Y, A175T, I316L, I316S, I317T, N97D, G98R, N62S, C271R, S58C, N62S, N97D, Y157S, I102S, L106P, L250Q, Y287X, P299H, S58C, CTCT at codon 211, and TGAT insertion at codon 244. In another embodiment, the GPCR is a native V2R or a mutated V2R. In a further embodiment, the mutated V2R comprises a Y128S or W164S substitution. In another embodiment, the protein is an ion channel, a native ion channel or a mutated ion channel, in a further embodiment a voltage-gated potassium channel, such as hERG.

In an embodiment, the above method for determining whether an agent acts as a pharmacological chaperone further comprises determining whether the rescued protein/receptor is functional, e.g., using a ligand.

In another aspect, the present invention provides a method for determining whether an agent induces the recruitment of a β-arrestin at the plasma membrane (PM), said method comprising:

providing a biosensor comprising a cell or membrane preparation comprising: said β-arrestin tagged with a *Renilla* GFP or a *Renilla* Luc), preferably a *Renilla* Luc; a plasma membrane (PM) targeting moiety tagged with a *Renilla* GFP or a *Renilla* Luc, preferably a *Renilla* GFP; and a GPCR; wherein if said β-arrestin is tagged with said *Renilla* GFP, said PM targeting moiety is tagged with said *Renilla* Luc, and if said β-arrestin is tagged with said *Renilla* Luc, said PM targeting moiety is tagged with said *Renilla* GFP; and measuring the BRET acceptor signal in the presence and absence of said agent;

wherein an increase in the BRET signal in the presence said agent relative to the absence thereof is indicative that said agent induces the recruitment of said β-arrestin at the PM.

The above-mentioned methods comprise contacting the biosensor with a substrate for a *Renilla* Luc, such as a luciferin, to produce energy (in the form of light) that will be accepted by (excite) the rGFP. Non-limiting examples of luciferins include D-luciferin, imidazopyrazinone-based compounds such as coelenterazine (coelenterazine 400A (DeepBlueC™), coelenterazine H and analogues of e-Coelenterazine such as Prolume Purple™ from Nanolight™), ViviRen™ (from Promega), Latia luciferin ((E)-2-methyl-4-(2,6,6-trimethyl-1-cyclohex-1-yl)-1-buten-1-ol formate), bacterial luciferin, Dinoflagellate luciferin, etc. In an embodiment, the substrate is coelenterazine 400A, coelenterazine H or Prolume Purple™.

As used herein, the term "agent" is used to refer to any molecule, for example, protein, oligopeptide, small organic molecule, polysaccharide, polynucleotide, and the like, to be tested for bioactivity. Such agents can be obtained from any number of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means.

Positive controls and negative controls may be used in the methods/assays. Control and test samples may be performed multiple times to obtain statistically significant results.

In an embodiment, the above-mentioned methods are high-throughput methods (high-throughput screening, HTS). The term "high-throughput screening" (HTS) as used herein refers to a method that allow screening rapidly and in parallel large numbers of compounds (hundreds, thousands) for binding activity or biological activity against target molecules. Such HTS methods are typically performed in microtiter plates having several wells, for example 384, 1536, or 3456 wells. For HTS, it is important that the readout signal be detected with high sensitivity, accuracy and reproducibility.

MODE(S) FOR CARRYING OUT THE INVENTION

The present invention is illustrated in further details by the following non-limiting examples.

Example 1: Materials and Methods

Materials. Angiotensin II (AngII; [Asp-Arg-Val-Tyr-Ile-His-Pro-Phe], SEQ ID NO:), poly-ornithine, poly-D-lysine, isoproterenol, arginine-vasopressin (AVP), bradykinin, were from Sigma®. Prostaglandin F2α (PGF2α), Prostaglandin E2 and u46619 were from Cayman Chemical® (Ann Arbor, Mich.). [Sar$^1$, Ile$^8$]-AngII (SI) and [Asp$^1$,Val$^5$, Gly$^8$]-AngII (DVG) [Sar1-Val5-D-Phe8] AngII (SVdF) and [Sar1-D-Ala8] AngII (TRV120027), were synthesized at the Université de Sherbrooke (Canada, QC). UBO-QIC was obtained from Institute for Pharmaceutical Biology of the University of Bonn (Germany). Iodine-125 was obtained from PerkinElmer®. Dulbecco's modified Eagles medium (DMEM), fetal bovine serum, OPTI-MEM®, and other cell culture reagents were purchased from Invitrogen®. Coelenterazine 400a, Coelenterazine H and Prolume Purplel were purchased from either Goldbio®, Biotium or Nanolight® Technology. Polyethylenimine (PEI; 25 kDa linear; was purchased from Polysciences (Warrington, Pa., USA). Salmon sperm DNA was purchased from Lifetechnologies (ThermoFisher). Phusion DNA polymerase was from Thermo Scientific®. Restriction enzymes and T4 DNA ligase were obtained from NEB®.

Plasmids and constructions. For the construction of the lyn-GFP10, the coding sequence of the first 11 residues (MGCIKSKGKDS, SEQ ID NO: 1) of the human Lyn-kinase and the full coding region of GFP10 were synthesized at GeneScript® (Piscataway, N.J.) and subcloned into pcDNA 3.1/zeo (−) using infusion (Clontech®, CA). The lyn-rGFP was generated by replacing the coding sequence of GFP10 in the lyn-GFP10 construct by the humanized rGFP, which was generated by PCR amplification. StreptagII-fused GFP10 was synthesized at GenScript® and subcloned into pcDNA3.1/zeo(−) (STII-GFP10). The FYVE domain of the human endofin (amino acids 739-806), was synthesized at Bio Basic® Inc. (Ontario, Canada) and subcloned into the STII-GFP10 construct in-frame (GFP10-endofinFYVE). rGFP-endofinFYVE was generated by inserting the FYVE domain of GFP10-endofinFYVE into a vector containing humanized rGFP in pcDNA3.1(+) in-frame. rGFP-rab4 and rGFP-rab11 were generated by replacing the FYVE domain in rGFP-endofinFYVE with PCR amplified rab4 and rab11 coding sequences, respectively. To generate RlucII fused AT1R, the human AT1R coding sequences containing a signal peptide and Flag sequence were PCR amplified and subcloned into in frame in pcDNA3.1/hygro(+) also containing the RlucII via NheI and HindIII sites. Plasmids encoding human βarr2-RlucII has been previously described (Quoyer, Janz et al. 2013). RlucII-tagged receptors were obtained by PCR using published constructs of MC4R-Venus constructs (P. René et al. J Pharmacol Exp Ther. 2010 December; 335(3):520-32) and hV2R wt (Morello, J. P., et al., *J Clin Invest*, 2000. 105(7): p. 887-95). RlucII-tagged receptors were obtained by PCR using plasmids encoding hERG, a generous gift from D. Deblois (Université de Montréal, Montréal, Canada). *Renilla reniformis* GFP (rGFP) constructs were obtained by PCR from the synthetized coding sequence (from GenScript, USA). PH domain tagged RlucII and rGFP: PH domain of PLCδ1 was PCR amplified using PLCδ1 image clone (IMAGE:5769665) as a template. The PCR product was used to replace endofinFYVE domain in GFP10-endofinFYVE by subcloning into XbaI and HindIII sites. The PH domain of GFP10-PH (PLCδ) was inserted either into a vector containing humanized rGFP in pcDNA3.1(+) or a vector containing HA-RlucII in pcDNA3.1(+) in-frame (rGFP-PH(PLCδ1) and HA-RlucII-PH(PLCδ1), respectively). hMC4R-RlucII: Plasmids encoding the fusion protein hMC4Rwt-RlucII, hMC4R (R165Q)-RlucII and hMC4R-(P299H)-RlucII were obtained by PCR amplification of MC4R from MC4R-venus constructs and, subcloned in frame at the N-terminus to the humanized *Renilla* luciferase II (hRlucII) sequence (a variant of the hRluc previously reported (Leduc, Breton et al. 2009)) into pcDNA3.1 RlucII vector (linker sequence: VGGGGSKLPAT, SEQ ID NO:2). hV2R-RlucII: The V2R substitution Y128S was created using the site-directed mutagenesis with the Quick Change™ mutation kit (Agilent Technologies, Santa-Clara, USA). Plasmids encoding the fusion protein hV2R wt-RlucII and hV2R (Y128S)-RlucII were obtained by PCR amplification of V2R coding sequence, subcloned in frame at the N-terminus to the hRlucII sequence into pcDNA3.1 RlucII vector (linker sequence: GGSGLKLPAT, SEQ ID NO:3). hERG-RlucII: Plasmids encoding the fusion protein hERG wt-RlucII and hERG (0601S)-RlucII were obtained by PCR amplification of 3 fragments encoding: residues 1-379 of hERG, 373-1159 of hERG and the RlucII, and subcloned by Gibson Assembly (New England Biolabs) pcDNA3.1 (+) vector (linker at the N-terminal of RlucII: NAAIRSGG, SEQ ID NO:4 and at the C-terminal of RlucII: GGNAAIRS, SEQ ID NO:5). rGFP-CAAX: Plasmid encoding the fusion protein rGFP-CAAX was obtained by PCR amplification of rGFP coding sequence with a reverse primer encoding a linker (sequence: GSAGTMASNNTASG, SEQ ID NO:6) and the plasma-membrane targeting polybasic sequence and prenylation signal sequence from KRAS splice variant b: -GKKKK-KKSKTKCVIM (named: CAAX, SEQ ID NO:7). The CAAX plasma-membrane targeting sequence is in frame at the C-terminus of the rGFP coding sequence. The PCR fragment is sub-cloned into pcDNA3.1 (+) vector. rGFP-PB: Plasmids encoding the fusion protein rGFP-PB was obtained by replacing the CAAX motif of rGFP-CAAX by the GRKS-plasma membrane targeting domain (PB; sequence: SPKKGLLQRLFKRQHQNNSKS, SEQ ID NO:8) using PCR amplification and Gibson assembly. The complete vector pCDNA 3.1 (+) rGFP-CAAX is amplified by PCR using oligos encoding PB. The PCR reaction product is digested with DpnI, purified and recircularized in a Gibson assembly reaction. Cloning of RlucII-GRB2: The coding sequence of human GRB2 variant1 was PCR-amplified and subcloned at the C-terminus of RlucII in the vector pCDNA3.1 (+) RlucII with a small flexible linker (sequence: GSAGT, SEQ ID NO:9) between GRB2 and RlucII. All the PCR were done by using the Phusion® DNA polymerase. All constructs were verified by DNA sequencing prior to use.

Cell culture and Transient Transfection. Human embryonic kidney 293 (HEK293) cells were maintained in Dulbecco's Modified Eagle's Medium (DMEM) supplemented with 10% fetal bovine serum, 100 unit/ml penicillin/streptomycin at 37° C. in a humidified atmosphere with 5% $CO_2$. HEK293SL cells were cultured in DMEM supplemented with 5% fetal bovine serum and 20 μg/ml gentamycin. Cells were grown at 37° C. in 5% $CO_2$ and 90% humidity.

Transfections using calcium phosphate: HEK293SL cells were transfected using a calcium phosphate method (Fessart, Simaan et al. 2005). Cells were seeded at a density of ~7.5×10$^5$ per 100 mm dishes a day before transfection and transfection was carried out as described previously (Fessart, Simaan et al. 2005). After 18 h of transfection, the medium was replaced, and the cells were divided for subsequent experiments. All assays were performed 48 h after transfection.

Transfection using Poly(ethylenimine) (PEI): Two days before the experiments, HEK293 cells from a 6-well plate were washed with PBS containing no calcium or magnesium, detached and transfected with the indicated plasmids using PEI as a transfecting agent (at a ratio of 3 to 1, PEI/DNA) and then directly seeded in 96-well plates pretreated with poly-L-ornithine hydrobromide at a density of 35 000 cells per well.

Stable rGFP-CAAX cell lines. HEK293 cells from a 6-well plate were washed with Phosphate Buffered Saline (PBS) and transfected with 1.2 ug of rGFP-CAAX encoding construct/well using poly-ethylenimine 25-kDa linear (PEI) as a transfecting agent (at a ratio of 3 to 1, PEI/DNA) (Hamdan, Rochdi et al. 2007). The rGFP-CAAX construct also encodes for the hygromycin resistance, and transfected cells were seeded in T75 dishes and selection (hygromycin at 100 μg/ml) was maintained for 4 weeks and hygromycin-resistant cells were FACS-sorted against GFP fluorescence, in populations expressing different levels of rGFP-CAAX.

BRET measurements for FIGS. 1B to 9D, 25D to 25F. The following day of transfection, cells were detached and replated onto poly-ornithine coated white 96-well plate at a density of 25,000 cells per well. The next day, cells were washed once with pre-warmed Tyrode's buffer (140 mM NaCl, 2.7 mM KCl, 1 mM $CaCl_2$, 12 mM $NaHCO_3$, 5.6 mM D-glucose, 0.5 mM $MgCl_2$, 0.37 mM $NaH_2PO_4$, 25 mM HEPES, pH 7.4), and then stimulated with either various concentrations of ligands in Tyrode's buffer for the indicated time, or single concentration of ligands for various times at 37° C. For recycling experiment, after stimulating the cells with the ligands for 30 min at 37° C., they were washed either three times with ice-cold Tyrode's buffer or once with Tyrode's buffer/three times with acid (50 mM sodium citrate, pH 4.0)/two times with Tyrode's buffer. All the washing steps were performed on ice. Cells were then further incubated with Tyrode's buffer at 37° C. in a water bath for 45 min. The cell-permeable substrate, coelenterazine 400a was added at a final concentration of 5 μM in Tyrode's buffer 3-4 min before BRET measurements. Measurements were performed by using Synergy2 (BioTek®) microplate reader with a filter set of 410±80 nm and 515±30 nm for detecting the RlucII Renilla luciferase (donor) and GFP10 or rGFP (acceptor) light emissions, respectively. The BRET signal was determined by calculating the ratio of the light intensity emitted by the GFP10 or rGFP over the light intensity emitted by the RlucII. All the BRET measurements were performed in triplicate at 37° C.

Figure 21A:
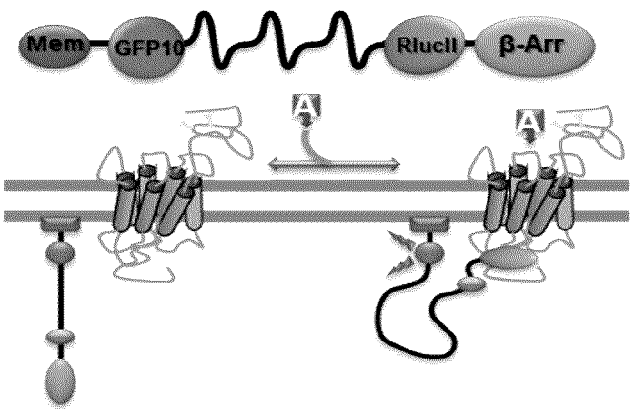
FIG. 21A shows the configuration of a unimolecular biosensor for monitoring β-arrestin recruitment to a GPCR at the plasma membrane. A BRET acceptor (e.g., rGFP, GFP10) is tagged with a PM targeting moiety (thus tethering the construct at the PM) and a flexible linker is placed between the BRET acceptor and a BRET donor (e.g., RlucII), which is attached to a β-arrestin. In the presence of a GPCR agonist (represented by A), β-arr is recruited to the GPCR, thus increasing the concentration of RlucII-β-arr at the plasma membrane, which in turn results in an increase in energy transfer (BRET) between RlucII and the PM-tagged GFP.
Figure 21B:
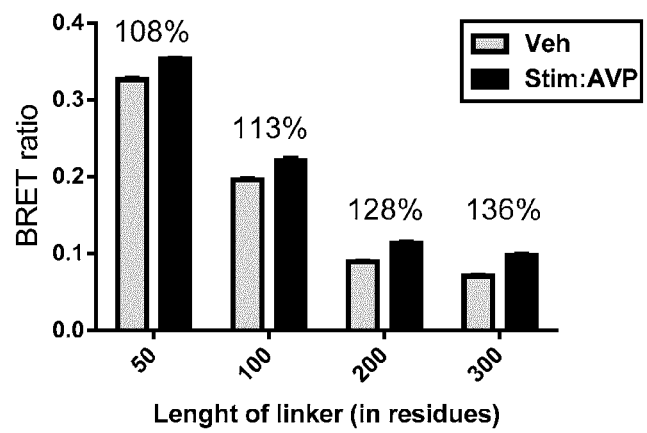
FIG. 21B shows the BRET ratio using unimolecular biosensors with flexible linkers of different lengths to assess β-arrestin$_2$ recruitment to V$_2$R following stimulation with AVP.

BRET assay for evaluation of PC rescue of cell surface expression and functionality (sequestration assay). In FIGS. 12A to 18E, Hek293 cells were transiently transfected using PEI as described in this section. The DNA transfected per well of a 96-well plate is as follow: in FIGS. 12A and 12B, with 2.4 ng of hMC4R-RlucII encoding construct and an increasing quantity of rGFP-CAAX (Kras) up to 9.6 ng for FIGS. 12A and for 12B, rGFP-PB up to 9.6 ng; in FIGS. 13A to 13C with 0.6, 1.2 or 2.4 ng of hMC4R-RlucII and 4.8 ng of rGFP-CAAX (Kras); in FIG. 13D with 2.4 ng of polycistronic rGFP-CAAX(Kras)/MC4R-RlucII construct; in FIG. 13E with 1.2 ng of hV2R-RlucII and 4.8 ng of rGFP-CAAX (Kras); in FIGS. 14A to 16B with 2.4 ng of hMC4R-RlucII and 7.2 ng of rGFP-CAAX (Kras); Hek293 cells stably expressing rGFP-CAAX(Kras) were transfected with 0.6, 1.2 or 2.4 ng of hMC4R-RlucII; in FIG. 17A or 0.6, 1.2 or 2.4 ng of hV2R_Y128S-RlucII; in FIG. 17B; in FIGS. 18A and 18B with 0.6, 1.2 or 2.4 ng of hERG-RlucII and 4.8 ng of rGFP-CAAX (Kras); and in FIGS. 18C-18E with 0.6 ng of hERG-RlucII and 7.2 ng of rGFP-CAAX (Kras). Transfected cells seeded in 96-well plates were treated with a pharmalogical chaperone (for MC4R: DCPMP(N-((2R)-3 (2,4-dichloroPhenyl)-1-(4-(2-((1-methoxypropan-2-ylamino)methyl)phenyl) piperazin-1-yl)-1-oxopropan-2-yl) propionamide) or Compound 1; for V2R: SR121463; for hERG: Astemizole, Cisapride, Quinidine, Ditiazem, Amiodarone and Acetaminophen) or vehicle for 16 h-18 h, as indicated in each figure, prior to the BRET assay performed 2-day post-transfection. For the BRET assay, cells were washed once with PBS and left in Tyrode's buffer. The cells were then optionally treated for MC4R with 10 μM of α-MSH for an hour at 37° C. to evaluate PC-rescue of functionality as a function of agonist induced sequestration of receptors that were expressed at the cell surface (FIG. 13). The Rluc substrate, Coel-400a (for BRET2 experiments) or coelenterazine H (for BRET1 experiments, FIGS. 13E and 15B and 15D), was added at a final concentration of 2.5 μM and cells were further incubated for an additional 5 minutes. BRET values were then collected using a Mithras LB940 Multimode Microplate Reader, equipped with the following filters for BRET2: 400 nm±70 nm (energy donor) and 515 nm±20 nm (energy acceptor) and for BRET1: 480 nm±20 nm (energy donor) and 530 nm±20 nm (energy acceptor). BRET values were determined by calculating the ratio of the light emitted by the acceptor over the light emitted by the RlucII.

βarrestin recruitment to plasma membrane using rGFP-markers: For FIGS. 19B to 19D, HEK293 cells were transfected with PEI, as described previously, with 3 ng of either βarrestin1-RlucII (FIGS. 19B & 19D) or βarrestin2-RlucII (FIGS. 19C & 19E)+4.8 ng of PM-marker (rGFP-CAAX=red triangles, GFP10-CAAX=circles, rGFP-PB=green triangles & Lyn-rGFP=squares)+10 ng V2R (FIGS. 19D & 19E) or 40 ng β2AR (FIGS. 19B & 19C) per well of a 96-well plate. 48 h post-transfection, cells were washed and stimulated for 10 min with the indicated doses at 37° C. Coel-400a was then added at a final concentration of 2.5 μM and incubated for an additional 5 min. BRET was measured at 37° C., using a Tristar Microplate Reader (Berthold Technologies). Data was normalized as a ratio of the max response obtained with the GFP10-CAAX (Kras) construct. For FIG. 19F, a transfection mix of 200 ng of β2AR, 20 ng β-arrestin2-RlucII, 800 ng rGFP-CAAX, complemented to 2 μg with ssDNA and PEI at a ratio of PEI:DNA of 3:1, is added to 3 ml of Hek293SL (350,000 cells/ml). Cells were seeded on poly-D-lysine pretreated plates. 48 h post-transfection, cells were washed and preincubated in Tyrode+1 mM $CaCl_2$ at 37° C. for 60 min then treated with the indicated doses of Isoproterenol for 2 min at 37° C. Coel-400a was then added at a final concentration of 2.5 μM and incubated for an additional 6 min. BRET was measured at 37° C., using a Tristar Microplate Reader (Berthold Technologies). For FIGS. 19C, 19E, 19H and 19I, HEK293 cells were transfected with PEI, as described previously with 3 ng of βarrestin2-RlucII (FIGS. 19C & 19E)+ 4.8 ng of rGFP-CAAX (Kras)+10 ng V2R (FIG. 19I) or 40 ng β2AR (FIG. 19H) per well of a 96-well plate. 48 h post-transfection, cells were washed and half of a 96-well plate stimulated for 10 min with 100 nM AVP (for FIG. 19H) or with isoproterenol at 1 μM (for FIG. 19H) and the other half of the plate with vehicle, at 37° C. Coel-400a was then added at a final concentration of 2.5 μM and incubated for an additional 5 min. BRET was measured at 37° C., using a Tristar Microplate Reader (Berthold Technologies). Z'-factor values were calculated as described by Zhang et al. (Zhang, Chung et al. 1999). For FIGS. 19J and 19G, Hek293SL cells were seed at 100 mm dish and then next day the cells were transfected with 90 ng of βarrestin2-RlucII and 480 of rGFP-CAAX (Kras) along with 600 ng AT1R (FIG. 19J) with a calcium phosphate method, as described previously. 24 h after transfection, cells were replated onto 96-well plate then next day, cells were washed and half of a 96-well plate stimulated for 6 min with 100 nM AngII (FIG. 19J) and the other half of the plate with vehicle, at room temperature before BRET measurements. (FIG. 19G) HEk293SL cells were transfected with AT1R (600 ng) and βarrestin2-RlucII (90 ng) along with either Lyn-rGFP (480 ng), rGFP-CAAX (480 ng), or GFP10-CAAX (480 ng) in 100 mm dishes. Next day, the cells were replated onto 96-well plates. 48 h post-transfection, the cells were stimulated various concentrations of AngII for 6 min before BRET measurements. Coelenterazine 400a (final concentration of 5 µM) was added after 2 min of AngII stimulation. BRET was measured at room temperature, using a Synergy2 (BioTek®) microplate reader. Z'-factor values were calculated as described by Zhang et al. (Zhang, Chung et al. 1999).

βarrestin recruitment unimolecular sensor: for FIG. 21B, 200 ng of V2R-pRK5, 50 ng of β2AR unimolecular sensor with different linkers, complemented to 1 µg with ssDNA and PEI at a ratio of PEI:DNA of 3:1, was added to 1.2 ml of HEK293SL. Cells were seeded on poly-D-lysine pretreated plates. 48 h post-transfection, cells were washed and preincubated in Tyrode +1 mM $CaCl_2$ at 37° C. for 60 min then treated with AVP (100 nM) for 10 min at 37° C. Coelenterazine 400a (coel-400a) (Biotium) was added at a final concentration of 2.5 µM and, incubated for an additional 5 min. BRET ratios were measured at 37° C., using Mithras LB940 Multimode Microplate Reader (Berthold Technologies). For FIG. 21C, 1× transfection: 400 ng sphAT1R, 200 ng of β2AR unimolecular sensor with a 200 residues-long linker, complemented to 4 µg with ssDNA and PEI at a ratio of PEI:DNA of 3:1, was added to 7 ml ml of HEK293SL. Cells were seeded on poly-D-lysine pretreated plates. 48 h post-transfection, cells were washed and preincubated in Tyrode +1 mM $CaCl_2$ at 37° C. for 60 min then treated with different concentrations of ligand for 5 min at 37° C. Coelenterazine 400a (coel-400a) (Biotium) was added at a final concentration of 2.5 µM and incubated for an additional 5 min. BRET ratios were measured at 37° C., using Mithras LB940 Multimode Microplate Reader (Berthold Technologies).

Figure 22B:
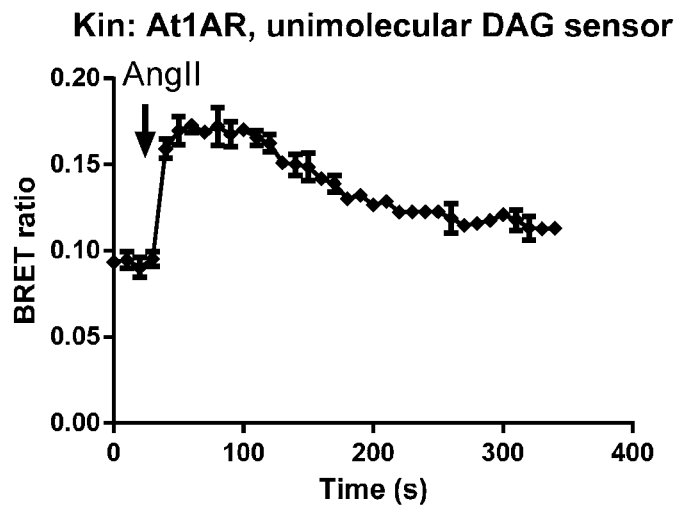
FIG. 22B shows kinetics of DAG sensor activation following AT1R exposure to angiotensin II. AT1R stably expressing HEK293 cells were transfected with a construct encoding the unimolecular DAG sensor DNA and BRET. The BRET level was monitored every 4 s. AngII (final concentration of 100 nM) was added after 16 BRET measurements (64 s). Data are mean±SD of triplicates of a representative experiment.
Figure 22C:
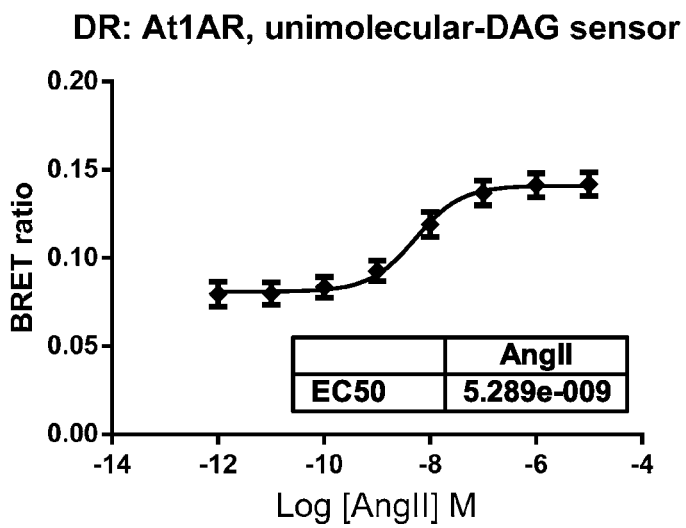
FIGS. 22C to 22E show dose-response curves obtained with the unimolecular DAG sensor representing the level DAG produced at the plasma membrane following activation of the Angiotensin II receptor (AT1R) with angiotensin II (ANGII) (FIG. 22C), Prostaglandin F receptor (FP) with two natural ligands, prostaglandin 2α (PGF2α; solid diamonds) and prostaglandin E2 (PGE2; open circles) (FIG. 22D), Urotensin II receptor (GPR14) with urotensin II (UTII) (FIG. 22E). The EC$_{50}$ values obtained for those ligands (ANGII=5.3 nM, PGF2α=11 nM, PGE2=90 nM and UTII=1.7 nM) are similar to the data already published for another related assay (calcium influx) and binding.
Figure 22D:
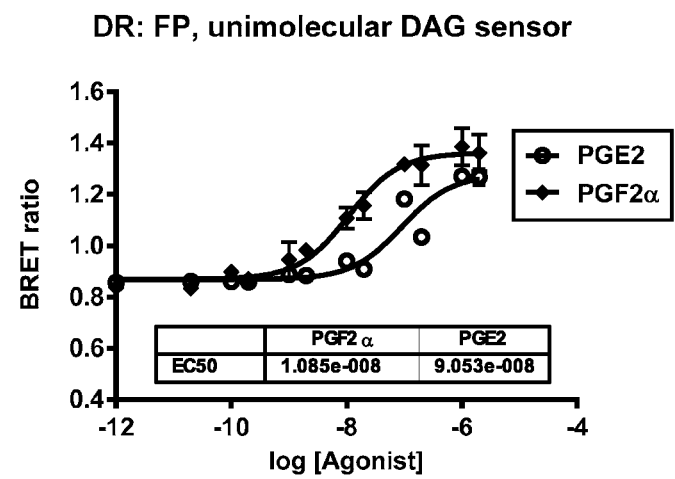
Figure 22E:
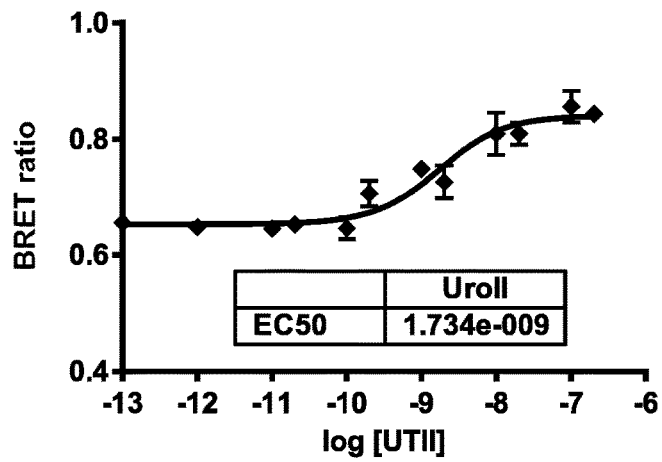

Unimolecular DAG sensor. For FIGS. 22B and C, HEK293SL cells stably expressing hAt1AR (~50 fmol/mg) were cultured in DMEM supplemented with 10% FBS and 20 µg/ml gentamycin and seeded at a density of 75,000 cells/100 mm dishes and were transiently transfected the next day with 150 ng of construct encoding for the DAG unimolecular sensor, using calcium phosphate method as described previously. 48 h post-transfection, cells were washed and Coel-400a was added to a final concentration of 5 µM and incubated 3 min. For FIG. 22B, BRET was measured every 4 sec, AngII is then added at 64 sec for a final concentration of 100 nM and, kinetics of agonist-promoted stimulation evaluated. Data are mean±SD of triplicates of a representative experiment. For FIG. 22C, cells were stimulated with the indicated concentrations of AngII for 1 min prior to BRET measurements. Data are mean±S.E. of six independent experiments. For FIGS. 22D and E, Hek293SL cells were transfected with FuGENE HD, according to Roche's protocol with a ratio of 2:1 fugene:DNA. 10 ng of construct encoding the unimolecular sensor and 400 ng for the receptor (FIGS. 22D, FP and in 2E, GPR14) complemented to 1 ug with ssDNA, were transfected per well of a 6 well plate. 48 h post-transfection, cells were washed, incubated in Tyrode's buffer for 1 h. Cells were then stimulated with the indicated doses with their respective ligands (in FIG. 22D, with PGF2α and PGE2 and in 22E, with Urotensin II) for 1 min then Coel-400a was added at a final concentration of 2.5 µM for an additional 5 min. For FIG. 22F, cells were transfected as in FIG. 22D but with just the unimolecular DAG sensor encoding construct. 48 h post-transfection, cells were washed, incubated in Tyrode's buffer for 1 h. Coel-400a was added at a final concentration of 2.5 µM for an additional 5 min. Cells were then stimulated with 5 µM m-3m3FBS or just vehicle for the indicated time. For FIGS. 22G and 22H, cells were transfected as in FIGS. 22E and 22D, respectively. 48 h post-transfection, cells were washed, incubated in Tyrode's buffer for 1 h. Half of the wells of a 96-well plate were stimulated with 100 nM of ligands (in FIGS. 22H, with PGF2α and in 22G, with Urotensin II) for 1 min and the other half with vehicle. Coel-400a was then added at a final concentration of 2.5 µM for an additional 5 min incubation. For FIGS. 22D to 22H, the BRET ratios were measured at 37° C., using Mithras LB940 Multimode Microplate Reader (Berthold Technologies).

Figure 23B:
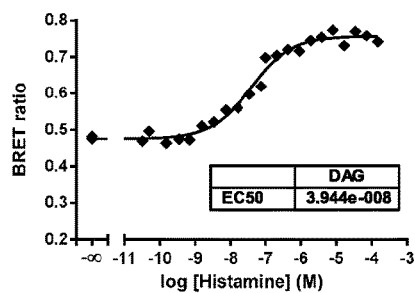
FIGS. 23B to 23D show dose-response curves for the recruitment of C1b at the plasma membrane following activation of the histamine H1 receptor (H1R) (FIG. 23B), Bradykinin Receptor B2 (BKRB2) (FIG. 23C), dopamine D2 receptor (D2R) (FIG. 23D) and β2AR (FIG. 23E) using the DAG biosensor. Gq-coupled receptors (H1R and BKRB2) activation lead to a better signal than a Gi-coupled receptor (D2R) or a Gs-coupled receptor that essentially do not lead to a detectable response in absence of co-expression of G15, a G protein of the Gq family.
Figure 23C:
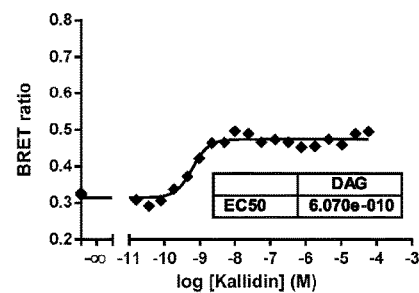
Figure 23D:
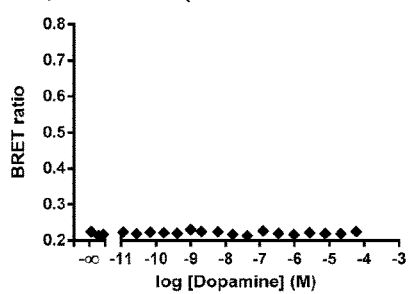
Figure 23E:
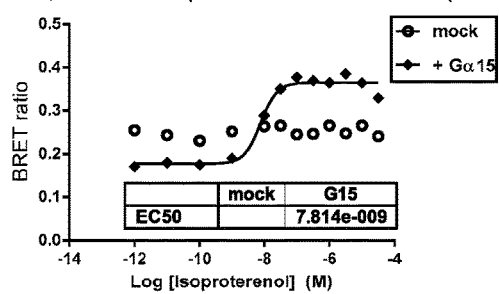

DAG sensor based on C1b recruitment to rGFP-markers. For FIGS. 23B to D, HEK293 cells were transfected using PEI, as already described, with 100 ng of RlucII-C1b, 500 ng of rGFP-CAAX (Kras) and 100 ng of either human histamine type 1 (H1R, Gq-coupled receptor, human Bradykinin type 2 (BKRB2, Gq-coupled receptor), human dopamine type 2 (D2R, Gi-coupled receptor used as negative control) receptors and complemented to 1 µg with ssDNA. 48 h post-transfection, cells were washed and incubated for 1 h at RT in Tyrode's buffer. Cells were incubated 5 min with the indicated doses of their respective agonist (Histamine for H1R, Kallidin for BKRB2 and Dopamine for D2R). Prolume Purple™ was then added at 2 µM final for an additional 5 min. BRET measurements were done using a Synergy Neo Multi-Mode Microplate Reader (BioTek Instruments, Inc). For FIG. 23E, 100 ng of β2AR, 20 ng RlucII-C1b, 400 ng of rGFP-CAAX (Kras), and either 100 ng of WT Gα15 or 100 ng of empty vector (Mock), complemented to 1 µg with ssDNA, and PEI at a ratio of PEI:DNA of 3:1, is added to 1.2 ml of Hek293SL (350 000 cells/ml). Cells were seeded on poly-D-lysine pretreated plates. 48 h post-transfection, cells were washed and preincubated in Tyrode +1 mM $CaCl_2$ at 37° C. for 60 min. Coelenterazine 400a was then added at a final concentration of 2.5 µM and incubated for 6 min. Cells were then treated with the indicated doses of Isoproterenol, for 1 min. BRET was measured at 37° C., using a Tristar Microplate Reader (Berthold Technologies).

Sensor based on Gprotein translocation: For FIGS. 24B to D, 100 ng of HA-β1AR or HA-β2AR, 5 ng of the indicated RlucII-Gγ, 100 ng of WT Gα15, 100 ng of WT Gβ1, 200 ng of rGFP-CAAX (Kras), complemented to 1 µg with ssDNA, and PEI at a ratio of PEI:DNA of 3:1, is added to 1.2 ml of Hek293SL (350,000 cells/ml) (for FIGS. 24B & C) or 2× to 3 ml of HEK293SL (350,000 cells/ml) (for FIG. 24 D). Cells were seeded on poly-D-lysine pretreated plates. 48 h post-transfection, cells were washed and preincubated in Tyrode +1 mM $CaCl_2$ at 37° C. for 60 min. Coelenterazine 400a was then added at a final concentration of 2.5 µM and incubated for 6 min. Cells were then treated with either 1 µM (FIGS. 24B and C) or the indicated doses (FIG. 24D) of Isoproterenol, for 2 min. BRET was measured at 37° C., using a Tristar® Microplate Reader (Berthold Technologies). For FIGS. 24E to G, 100 ng of HA-β1AR, 30 ng of Gαs pos67RlucII or Gα12 pos84RlucII, 100 ng of WT Gγ5, 100 ng of WT Gβ1, 400 ng of rGFP-CAAX or Golgi marker (eNOS(1-73)-rGFP), complemented to 1 µg with ssDNA, and PEI at a ratio of PEI:DNA of 3:1, is added 2× to 3 ml of HEK293SL (350,000 cells/ml). Cells were seeded on poly-D-lysine pretreated plates. 48 h post-transfection, cells were washed and preincubated in Tyrode +1 mM $CaCl_2$ at 37° C. for 60 min. Prolume Purple™ was then added at a final concentration of 2 µM and incubated for 6 min. Cells were then treated or not with either 1 µM for the indicated time (FIG. 24F) or the indicated doses (FIGS. 24E & G) of Isoproterenol, for 4 min. BRET was measured at 37° C., using a Tristar® Microplate Reader (Berthold Technologies). For FIG. 24H, 200 ng of TPαR, 30 ng of Gαq pos118RlucII, 100 ng of WT Gγ5, 100 ng of WT Gβ1, 400 ng of rGFP-CAAX or Golgi marker (eNOS(1-73)-rGFP), complemented to 1 μg with ssDNA, and PEI at a ratio of PEI:DNA of 3:1, is added to 1.2 ml of HEK293SL (350,000 cells/ml). Cells were seeded on poly-D-lysine pretreated plates. 48 h post-transfection, cells were washed and preincubated in Tyrode +1 mM $CaCl_2$ at 37° C. for 60 min. Incubated or not with 100 nM of Ubo-Qic for 20 min. Cells were then treated for the indicated doses of U46619, for 6 min. Coel-400a was then added at a final concentration of 2.5 μM and incubated for an additional 5 min. BRET was measured at 37° C., using a Tristar Microplate Reader (Berthold Technologies).

PKN-based RhoA activation assay. For FIGS. 25B-D, HEK293SL cells were grown in DMEM supplemented with 6% fetal bovine serum (FBS) and 20 μg/ml gentamycin, at 37° C. Cells were seeded at a density of $7.5 \times 10^5$ cells per 100 mm dishes and were transiently transfected the next day with constructs encoding AT1R (3 μg) along with PKN-crib-RlucII (90 ng) and rGFP-CAAX (480 ng) using calcium phosphate method as described previously. After 24 h, cells were detached and seeded onto poly-ornithine-coated 96-well white plates at a density of 25 000 cells per well in media. The next day, cells were washed once with Tyrode's buffer and left in 80 μl of Tyrode's buffer at 37° C. When indicated, cells were treated with Ubo-Qic 100 nM for 30 min or C3 toxin for 3 μg/ml (in FIG. 25I), 4 hours at 37° C. Cell stimulation and BRET measurements were done at RT. BRET signals were monitored by addition of Coel-400a to a final concentration of 5 μM using a Synergy2 (BioTek®) microplate reader. Filter set was 410±80 nm and 515±30 nm for detecting the RlucII Renilla luciferase (donor) and rGFP (acceptor) light emission. For FIG. 25B, a transfection mix of 200 ng of TPαR, 20 ng PKN-RlucII, 600 ng CAAX-rGFP, complemented to 2 μg with ssDNA and PEI at a ratio of PEI:DNA of 3:1, is added to 3 ml of Hek293SL (350 000 cells/ml). Cells were seeded on poly-D-lysine pretreated plates. 48 h post-transfection, cells were washed and preincubated in Tyrode +1 mM $CaCl_2$ at 37° C. for 30 min then with Coel-400a at a final concentration of 2.5 μM and, incubated for 6 min. Cells were stimulated for 2 min with the indicated doses of U46619. BRET was measured at 37° C., using a Tristar Microplate Reader (Berthold Technologies) equipped with BRET400-GFP2/10 filter set (acceptor, 515±20 nm; and donor, 400±70 nm filters). For FIGS. 25I and J, a transfection mix of 200 ng of TPαR, 20 ng PKN-RlucII, 600 ng CAAX-rGFP, complemented to 2 μg with ssDNA and PEI at a ratio of PEI:DNA of 3:1, is added to 3 ml of Hek293SL (350,000 cells/ml). Cells were seeded on poly-D-lysine pretreated plates. 24 h post-transfection, the Rho inhibitor (CT04; Cytoskeleton, Inc) was added when indicated, overnight at final concentration 2 μg/ml. 48 h post-transfection, cells were washed and preincubated in Tyrode +1 mM $CaCl_2$ at 37° C. for 60 min then treated, as indicated, with 100 nM of U46619 or 1 μg/ml of Rho activator II (CN03; Cytoskeleton, Inc) for 1 min at 37° C. Coel-400a was then added at a final concentration of 2.5 μM and incubated for an additional 5 min. BRET was measured at 37° C., using a Tristar Microplate Reader (Berthold Technologies).

Intact cell [$^{125}$I]-AngII binding. [$^{125}$I]-AngII was prepared with the lodogen method, and its specific radioactivity was determined from self-displacement and saturation experiments as previously described (Zimmerman, Beautrait et al. 2012) The density of cell surface receptors was evaluated with binding assays at 4° C. using [$^{125}$I]-AngII as tracer. HEK293SL cells expressing either AT1R or AT1R-RlucII were seeded 1 day after transfection at a density of ~120,000 cells per well in poly-ornithine coated 24-well plates. The following day, cells were washed once with pre-warmed DMEM with 20 mM HEPES (DMEM-H) and then incubated in the absence or presence of 100 nM AngII in DMEM-H for 30 min at 37° C. The plates were quickly washed three times with ice-cold acid (50 mM sodium citrate, pH 4.0) for 5 min each on ice to stop the stimulation and remove both the remaining surface bound and unbound AngII ligand. To remove and neutralize the residual acid, cells were further washed twice with ice-cold Tyrode's buffer. Cells were then incubated with 0.5 ml of [$^{125}$I]-AngII (~250,000 cpm) in the binding buffer (0.2% BSA, 50 mM Tris, 100 mM $NaCl_2$, 5 mM $MgCl_2$, pH 7.4) at 4° C. overnight. Nonspecific binding was determined in the presence of 1 μM AngII. Next day, the cells were washed three times with ice-cold PBS with calcium and magnesium, and 0.5 ml of 0.5 N NaOH/0.05% SDS was added. Radioactivity was counted using a PerkinElmer Wizard® 1470 automatic γ-counter. Protein amounts were measured by Bio-rad® Protein Assay kit according to the manufacture's instruction with some modifications. Briefly, the cells were treated same as above except incubation without radiolabelled AngII, and then after washing, add 2 ml of diluted Protein assay reagent instead of NaOH/SDS. After mixing by pipetting, the samples were transferred to plastic cuvettes and measured absorbance at 595 nm.

Confocal microscopy. One day before transfection, HEK293SL cells were seeded in 35 mm glass-bottom dishes at a density of 100,000 cells/dish. Cells were transfected with B2R-CFP, LYN-rGFP and mCherry-endofinFYVE. Forty-eight hours post-transfection, cells were serum starved for 30 min, either left untreated (non treated) or treated with bradykinin (1 μM) for 15 min. Samples were analyzed on a Zeiss LSM-510 Meta laser scanning microscope using argon (514 nm) and HeNe I (543 nm) lasers, and images (2048× 2048 pixels) were collected using a 63× oil immersion lens. For detecting CFP and GFP, UV and argon lasers were used with 405 nm and 514 nm excitation, and either BP 420-480 nm or BP 505-550 nm emission filters, respectively. For mCherry detection, a HeNe I laser was used with 543 nm excitation and LP 560 nm emission filter sets.

BRET microscopy/imaging. HEK293S cells were cultured in DMEM supplemented with 10% FBS, 100 units/ml penicillin and 0.1 mg/ml streptomycin and plated on poly-D-lysine coated glass-bottom 35 mm culture dishes at the density of $1-2 \times 10^5$ cells/dish. On the next day, cells were transfected with RlucII-fused (BRET donor) and rGFP-fused (BRET acceptor) constructs using X-treme GENE HP reagent (Roche) using 1 μg DNA and 3 μl reagent per dish according to the manufacturer protocol. For FIGS. 26A and 26B (luminescence spectrum measurement), cells were transfected with 100 g/dish of RlucII N-terminally fused to Venus, GFP2 or rGFP. Cells are detached from the culture surface by adding 1 ml of PBS supplemented with 5 mM EDTA, and re-suspended to PBS. As a luciferase substrate, 1 μM of Prolume purple (Nanolight Technology) was added and the luminescence spectrum was obtained with Synergy Neo plate reader (BioTek) 2 min after the addition of the substrate. For FIG. 26C (luminescence microscopy), cells were transfected with 100 ng/dish of HA-β2AR, 50 ng/dish or βarrestin2-RlucII and 500 ng/dish of rGFP-CAAX were transfected. Cells were washed once with 1 ml of modified Hank's balanced salt solution (138 mM NaCl, 5.33 mM KCl, 0.44 mM $KH_2PO_4$, 0.33 mM $Na_2HPO_4$, 4.16 mM NaHCO$_3$, 1.0 mM CaCl$_2$, 1.0 mM MgCl$_2$, 10 mM HEPES, pH 7.4) and set on the microscope. 10 μM of Prolume Purple (NanoLight Technology) was added to the dish. BRET images were obtained using Nikon® Ti-U microscope equipped with 60× objective (Apochromat TIRF, NA 1.49, Nikon) and imaging camera (PIXIS1024, Princeton instruments) with filter changer (Lambda 10-2, Sutter instrument). Immediately after the addition of coelenterazine, camera shutter was closed and a blank image was acquired for 90 sec. Then images were acquired with filters corresponding to BRET donor (410/80 nm) and BRET acceptor (480LP or 510/40 nm) wavelength for 90 sec each. Images were captured every 5 min, and blank image values were subtracted from the corresponding pixels of BRET donor and acceptor images in order to remove photon counts deriving from dark current and sampling noises of the camera. For each time points, BRET ratio images were generated using pixel arithmetic functions of MetaMorph software version 7.8 (Molecular Devices) as follows; Pixel hue: BRET level calculated by dividing the counts of acceptor images with donor images, and allocated to default rainbow hue (lowest (typically 0.0) in purple and highest (typically 2.0) in red). Pixel brightness: the value of donor images with auto brightness.

Z'-factors determination. BRET1 and BRET2 assays were performed on cells cotransfected with rGFP-CAAX construct and either the hMC4R wt-RlucII or hMC4R (R165Q)-RlucII construct (as indicated in FIGS. 15A to 15D), with half of the 96-well plate treated with the pharmacological chaperone (10 uM DCPMP) and the second half of the plate treated with the corresponding vehicle (DMSO). Z'-factor values were calculated as described by Zhang et al. (Zhang, Chung et al. 1999). A Z'-factor over 0.4 is considered a robust assay.

Evaluation of resistance to DMSO. Ligands and compound-libraries are often dissolved in DMSO. To evaluate whether the BRET-based assay for cell surface evaluation is sensitive to concentrations of DMSO usually reached with dose-response curves of ligands selected from a compound-library, transfected cells were DCPMP-treated at 10 uM or with vehicle (DMSO) in well containing different concentrations of DMSO, as indicated in FIG. 16. BRET values were then obtained as previously described.

Data Analysis. Estimation of the $t_{1/2}$ and the $EC_{50}$ values for ligand-mediated endocytosis were calculated using the GraphPad® Prism curve fitting program The curves presented throughout this study, representing the best fits, and were generated using this GraphPad® Prism program as well.

Sequences: The amino acid sequences of polypeptides and constructs used herein are depicted below.

```
RLucII
                                                        (SEQ ID NO: 10)
MTSKVYDPEQRKRMITGPQWWARCKQMNVLDSFINYYDSEKHAENAVIFLHGNATSSYLWRHVV
PHIEPVARCIIPDLIGMGKSGKSGNGSYRLLDHYKYLTAWFELLNLPKKIIFVGHDWGAALAFHYSY
EHQDKIKAIVHAESVVDVIESWDEWPDIEEDIALIKSEEGEKMVLENNFFVETVLPSKIMRKLEPEEF
AAYLEPFKEKGEVRRPTLSWPREIPLVKGGKPDVVQIVRNYNAYLRASDDLPKMFIESDPGFFSNA
IVEGAKKFPNTEFVKVKGLHFSQEDAPDEMGKYIKSFVERVLKNEQ rGFP: Renilla reniformis preen fluorescent protein
                                                        (SEQ ID NO: 11)
MDLAKLGLKEVMPTKINLEGLVGDHAFSMEGVGEGNILEGTQEVKISVTKGAPLPFAFDIVSVAFSY
GNRAYTGYPEEISDYFLQSFPEGFTYERNIRYQDGGTAIVKSDISLEDGKFIVNVDFKAKDLRRMG
PVMQQDIVGMQPSYESMYTNVTSVIGECIIAFKLQTGKHFTYHMRTVYKSKKPVETMPLYHFIQHR
LVKTNVDTASGYVVQHETAIAAHSTIKKIEGSLP GFP10
                                                        (SEQ ID NO: 12)
MVSKGEELFTGVVPILVELDGDVNGHKFSVSGEGEGDATYGKLTLKFICTTGKLPVPWPTLVTTLS
YGVQCFSRYPDHMKQHDFFKSAMPEGYVQERTIFFKDDGNYKTRAEVKFEGDTLVNRIELKGIDF
KEDGNILGHKLEYNYNPHNVYIMADKQKNGIKVNFKIRHNIEDGSVQLADHYQQNTPIGDGPVLLP
DNHYLFTQSALSKDPNEKRDHMVLLEFVTAAGITLGMDELYK hMC4R WT: human wild-type Melanocortin 4 receptor
                                                        (SEQ ID NO: 13)
MVNSTHRGMHTSLHLWNRSSYRLHSNASESLGKGYSDGGCYEQLFVSPEVFVTLGVISLLENILVI
VAIAKNKNLHSPMYFFICSLAVADMLVSVSNGSETIVITLLNSTDTDAQSFTVNIDNVIDSVICSSLLA
SICSLLSIAVDRYFTIFYALQYHNIMTVKRVGIIISCIWAACTVSGILFIIYSDSSAVIICLITMFFTMLALM
ASLYVHMFLMARLHIKRIAVLPGTGAIRQGANMKGAITLTILIGVFVVCWAPFFLHLIFYISCPQNPYC
VCFMSHFNLYLILIMCNSIIDPLIYALRSQELRKTFKEIICCYPLGGLCDLSSRY hMC4R (R165Q): mutant R165Q-hMC4R, intracellularly retained and PC-
rescuable
                                                        (SEQ ID NO: 14)
MVNSTHRGMHTSLHLWNRSSYRLHSNASESLGKGYSDGGCYEQLFVSPEVFVTLGVISLLENILVI
VAIAKNKNLHSPMYFFICSLAVADMLVSVSNGSETIVITLLNSTDTDAQSFTVNIDNVIDSVICSSLLA
SICSLLSIAVDRYFTIFYALQYHNIMTVKQVGIIISCIWAACTVSGILFIIYSDSSAVIICLITMFFTMLALM
ASLYVHMFLMARLHIKRIAVLPGTGAIRQGANMKGAITLTILIGVFVVCWAPFFLHLIFYISCPQNPYC
VCFMSHFNLYLILIMCNSIIDPLIYALRSQELRKTFKEIICCYPLGGLCDLSSRY hMC4R (P299H): mutant P299H-hMC4R, intracellularly retained and mostly
not PC-rescuable
                                                        (SEQ ID NO: 15)
MVNSTHRGMHTSLHLWNRSSYRLHSNASESLGKGYSDGGCYEQLFVSPEVFVTLGVISLLENILVI
VAIAKNKNLHSPMYFFICSLAVADMLVSVSNGSETIVITLLNSTDTDAQSFTVNIDNVIDSVICSSLLA
SICSLLSIAVDRYFTIFYALQYHNIMTVKRVGIIISCIWAACTVSGILFIIYSDSSAVIICLITMFFTMLALM
ASLYVHMFLMARLHIKRIAVLPGTGAIRQGANMKGAITLTILIGVFVVCWAPFFLHLIFYISCPQNPYC
VCFMSHFNLYLILIMCNSIIDHLIYALRSQELRKTFKEIICCYPLGGLCDLSSRY
```

-continued hV2R WT: human wild type Vasopressin 2 receptor
(SEQ ID NO: 16)
MLMASTTSAVPGHPSLPSLPSNSSQERPLDTRDPLLARAELALLSIVFVAVALSNGLVLAALARRG
RRGHWAPIHVFIGHLCLADLAVALFQVLPQLAWKATDRFRGPDALCRAVKYLQMVGMYASSYMIL
AMTLDRHRAICRPMLAYRHGSGAHWNRPVLVAWAFSLLLSLPQLFIFAQRNVEGGSGVTDCWAC
FAEPWGRRTYVTWIALMVFVAPTLGIAACQVLIFREIHASLVPGPSERPGGRRRGRRTGSPGEGA
HVSAAVAKTVRMTLVIVVVYVLCWAPFFLVQLWAAWDPEAPLEGAPFVLLMLLASLNSCTNPWIY
ASFSSSVSSELRSLLCCARGRTPPSLGPQDESCTTASSSLAKDTSS hV2R (Y128S): mutant Y128S-hV2R, intracellularly retained and PC-
rescuable
(SEQ ID NO: 17)
MLMASTTSAVPGHPSLPSLPSNSSQERPLDTRDPLLARAELALLSIVFVAVALSNGLVLAALARRG
RRGHWAPIHVFIGHLCLADLAVALFQVLPQLAWKATDRFRGPDALCRAVKYLQMVGMYASSSMIL
AMTLDRHRAICRPMLAYRHGSGAHWNRPVLVAWAFSLLLSLPQLFIFAQRNVEGGSGVTDCWAC
FAEPWGRRTYVTWIALMVFVAPTLGIAACQVLIFREIHASLVPGPSERPGGRRRGRRTGSPGEGA
HVSAAVAKTVRMTLVIVVVYVLCWAPFFLVQLWAAWDPEAPLEGAPFVLLMLLASLNSCTNPWIY
ASFSSSVSSELRSLLCCARGRTPPSLGPQDESCTTASSSLAKDTSS hERG WT: human wild type voltade-dated Potassium channel H2
(SEQ ID NO: 18)
MPVRRGHVAPQNTFLDTIIRKFEGQSRKFIIANARVENCAVIYCNDGFCELCGYSRAEVMQRPCTC
DFLHGPRTQRRAAAQIAQALLGAEERKVEIAFYRKDGSCFLCLVDVVPVKNEDGAVIMFILNFEVV
MEKDMVGSPAHDTNHRGPPTSWLAPGRAKTFRLKLPALLALTARESSVRSGGAGGAGAPGAVV
VDVDLTPAAPSSESLALDEVTAMDNHVAGLGPAEERRALVGPGSPPRSAPGQLPSPRAHSLNPD
ASGSSCSLARTRSRESCASVRRASSADDIEAMRAGVLPPPPRHASTGAMHPLRSGLLNSTSDSD
LVRYRTISKIPQITLNFVDLKGDPFLASPTSDREIIAPKIKERTHNVTEKVTQVLSLGADVLPEYKLQA
PRIHRWTILHYSPFKAVWDWLILLLVIYTAVFTPYSAAFLLKETEEGPPATECGYACQPLAVVDLIVD
IMFIVDILINFITITYVNANEEVVSHPGRIAVHYFKGWFLIDMVAAIPFDLLIFGSGSEELIGLLKTARLL
RLVRVARKLDRYSEYGAAVLFLLMCTFALIAHWLACIWYAIGNMEQPHMDSRIGWLHNLGDQIGLK
PYNSSGLGGPSIKDKYVTALYFTFSSLTSVGFGNVSPNTNSEKIFSICVMLIGSLMYASIFGNVSAII
QRLYSGTARYHTQMLRVREFIRFHQIPNPLRQRLEEYFQHAWSYTNGIDMNAVLKGFPECLQADI
CLHLNRSLLQHCKPFRGATKGCLRALAMKFKTTHAPPGDTLVHAGDLLTALYFISRGSIEILRGDVV
VAILGKNDIFGEPLNLYARPGKSNGDVRALTYCDLHKIHRDDLLEVLDMYPEFSDHFWSSLEITFNL
RDTNMIPGSPGSTELEGGFSRQRKRKLSFRRRTDKDTEQPGEVSALGPGRAGAGPSSRGRPGG
PWGESPSSGPSSPESSEDEGPGRSSSPLRLVPFSSPRPPGEPPGGEPLMEDCEKSSDTCNPLS
GAFSGVSNIFSFWGDSRGRQYQELPRCPAPTPSLLNIPLSSPGRRPRGDVESRLDALQRQLNRLE
TRLSADMATVLQLLQRQMTLVPPAYSAVTTPGPGPTSTSPLLPVSPLPTLTLDSLSQVSQFMACEE
LPPGAPELPQEGPTRRLSLPGQLGALTSQPLHRHGSDPGS hERG (G601S): mutant G601S-hERG, intracellularly retained and PC-
rescuable
(SEQ ID NO: 19)
MPVRRGHVAPQNTFLDTIIRKFEGQSRKFIIANARVENCAVIYCNDGFCELCGYSRAEVMQRPCTC
DFLHGPRTQRRAAAQIAQALLGAEERKVEIAFYRKDGSCFLCLVDVVPVKNEDGAVIMFILNFEVV
MEKDMVGSPAHDTNHRGPPTSWLAPGRAKTFRLKLPALLALTARESSVRSGGAGGAGAPGAVV
VDVDLTPAAPSSESLALDEVTAMDNHVAGLGPAEERRALVGPGSPPRSAPGQLPSPRAHSLNPD
ASGSSCSLARTRSRESCASVRRASSADDIEAMRAGVLPPPPRHASTGAMHPLRSGLLNSTSDSD
LVRYRTISKIPQITLNFVDLKGDPFLASPTSDREIIAPKIKERTHNVTEKVTQVLSLGADVLPEYKLQA
PRIHRWTILHYSPFKAVWDWLILLLVIYTAVFTPYSAAFLLKETEEGPPATECGYACQPLAVVDLIVD
IMFIVDILINFITITYVNANEEVVSHPGRIAVHYFKGWFLIDMVAAIPFDLLIFGSGSEELIGLLKTARLL
RLVRVARKLDRYSEYGAAVLFLLMCTFALIAHWLACIWYAIGNMEQPHMDSRIGWLHNLGDQIGK
PYNSSSLGGPSIKDKYVTALYFTFSSLTSVGFGNVSPNTNSEKIFSICVMLIGSLMYASIFGNVSAIIQ
RLYSGTARYHTQMLRVREFIRFHQIPNPLRQRLEEYFQHAWSYTNGIDMNAVLKGFPECLQADICL
HLNRSLLQHCKPFRGATKGCLRALAMKFKTTHAPPGDTLVHAGDLLTALYFISRGSIEILRGDVVVA
ILGKNDIFGEPLNLYARPGKSNGDVRALTYCDLHKIHRDDLLEVLDMYPEFSDHFWSSLEITFNLRD
TNMIPGSPGSTELEGGFSRQRKRKLSFRRRTDKDTEQPGEVSALGPGRAGAGPSSRGRPGGPW
GESPSSGPSSPESSEDEGPGRSSSPLRLVPFSSPRPPGEPPGGEPLMEDCEKSSDTCNPLSGAF
SGVSNIFSFWGDSRGRQYQELPRCPAPTPSLLNIPLSSPGRRPRGDVESRLDALQRQLNRLETRL
SADMATVLQLLQRQMTLVPPAYSAVTTPGPGPTSTSPLLPVSPLPTLTLDSLSQVSQFMACEELPP
GAPELPQEGPTRRLSLPGQLGALTSQPLHRHGSDPGS Lyn: palmitoylation & myristoylation signal sequence from the Lyn kinase
(SEQ ID NO: 1)
MGCIKSKGKDS CAAX-Kras: plasma-membrane targeting polybasic sequence and prenylation
signal sequence from kRas splice variant b
(SEQ ID NO: 7)
GKKKKKKSKTKCVIM PB: plasma-membrane targeting polybasic sequence from the human GRK5
(SEQ ID NO: 8)
SPKKGLLQRLFKRQHQNNSKS endofin's FYVE domain
(SEQ ID NO: 20)
QKQPTWVPDSEAPNCMNCQVKFTFTKRRHHCRACGKVFCGVCCNRKCKLQYLEKEARVCVVCY
ETISK Rab4

-continued (SEQ ID NO: 21)
MSETYDFLFKFLVIGNAGTGKSCLLHQFIEKKFKDDSNHTIGVEFGSKIINVGGKYVKLQIWDTAGQ
ERFRSVTRSYYRGAAGALLVYDITSRETYNALTNWLTDARMLASQNIVIILCGNKKDLDADREVTFL
EASRFAQENELMFLETSALTGENVEEAFVQCARKILNKIESGELDPERMGSGIQYGDAALRQLRSP
RRAQAPNAQECGC Rab11
(SEQ ID NO: 22)
MGTRDDEYDYLFKVVLIGDSGVGKSNLLSRFTRNEFNLESKSTIGVEFATRSIQVDGKTIKAQIWDT
AGQERYRAITSAYYRGAVGALLVYDIAKHLTYENVERWLKELRDHADSNIVIMLVGNKSDLRHLRA
VPIDEARAFAEKNGLSFIETSALDSTNVEAAFQTILTEIYRIVSQKQMSDRRENDMSPSNNVVPIHV
PPTTENKPKVQCCQNI signal peptide-Flag-human AT1R (spFlag-AT1R)
(SEQ ID NO: 23)
MKTIIALSYIFCLVFADYKDDDDAMILNSSTEDGIKRIQDDCPKAGRHNYIFVMIPTLYSIIFVVGIFGN
SLVVIVIYFYMKLKTVASVFLLNLALADLCFLLTLPLWAVYTAMEYRWPFGNYLCKIASASVSFNLYA
SVFLLTCLSIDRYLAIVHPMKSRLRRTMLVAKVICIIIWLLAGLASLPAIIHRNVFFIENTNITVCAFHYE
SQNSTLPIGLGLTKNILGFLFPFLIILTSYTLIWKALKKAYEIQKNKPRNDDIFKIIMAIVLFFFFSWIPHQ
IFTFLDVLIQLGIIRDCRIADIVDTAMPITICIAYFNNCLNPLFYGFLGKKFKRYFLQLLKYIPPKAKSHS
NLSTKMSTLSYRPSDNVSSSTKKPAPCFEVE hGRB2 v1; human GRB2 variant 1
(SEQ ID NO: 24)
MEAIAKYDFKATADDELSFKRGDILKVLNEECDQNWYKAELNGKDGFIPKNYIEMKPHPFGNDVQ
HPKVLRDGAGKYFLWVVKFNSLNELVDYHRSTSVSRNQQIFLRDIEQVPQQPTYVQALFDFDPQE
DGELGFRRGDFIHVMDNSDPNWWKGACHGQTGMFPRNYVTPVNRNV PH domain of PLCδ1
(SEQ ID NO: 25)
DSGRDFLTLHGLQDDEDLQALLKGSQLLKVKSSSWRRERFYKLQEDCKTIWQESRKVMRTPESQ
LFSIEDIQEVRMGHRTEGLEKFARDVPEDRCFSIVFKDQRNTLDLIAPSPADAQHWVLGLHKIIHHS
GSMDQRQKLQHWIHSCLRKADKNKDNKMSFKELQNFLKELNI HA tag
(SEQ ID NO: 26)
MYPYDVPDYA Residues 1-73 of human eNOS1
(SEQ ID NO: 42)
MGNLKSVAQEPGPPCGLGLGLGLGLCGKQGPATPAPEPSRAPASLLPPAPEHSPPSSPLTQPPE
GPKFPRVKN Calveolin1α
(SEQ ID NO: 44)
MSGGKYVDSEGHLYTVPIREQGNIYKPNNKAMADELSEKQVYDAHTKEIDLVNRDPKHLNDDVVK
IDFEDVIAEPEGTHSFDGIWKASFTTFTVTKYWFYRLLSALFGIPMALIWGIYFAILSFLHIWAVVPCI
KSFLIEIQCISRVYSIYVHTVCDPLFEAVGKIFSNVRINLQKEI Linker1: Linker sequence between the hMC4R and RlucII
(SEQ ID NO: 2)
VGGGGSKLPAT Linker2: Linker sequence between the hV2R and RlucII
(SEQ ID NO: 3)
GGSGLKLPAT Linker3: Linker sequence in N-terminal of RlucII, following residue
379 of hERG
(SEQ ID NO: 4)
NAAIRSGG Linker4: Linker sequence in N-terminal of Rlucll, preceding residue
373 of hERG
(SEQ ID NO: 5)
GGNAAIRS Linker5: Linker between Lyn's plasma-membrane targeting sequence
(Lyn) and rGFP
(SEQ ID NO: 27)
LSNAT Linker6: Linker between rGFP and polybasic/prenylation sequence from
kRAS (CAAX)
(SEQ ID NO: 28)
GSAGTMASNNTASG Linker7: Linker between rGFP and polybasic sequence from GRK5 (PB):
(SEQ ID NO: 3)
GGSGLKLPAT -continued Linker8: Linker between rGFP and palmitoylation/prenylation sequence from hRAS (CAAX) and hRAS/RaI1(CAAX = CCIL), between rGFP and Caveolin1α, and between RlucII and GRB2::

(SEQ ID NO: 9)
GSAGT

Linker9: Linker between Golgi targeting sequence from eNOS (1-73) and rGFP
(SEQ ID NO: 41)
GSNAT Linker10: between (i) rGFP and (ii) endofin's FYVE domain, Rab4 or Rab11
(SEQ ID NO: 29)
GSGGSGSGGLE Linker11: between sbFlag-AT1R and RlucII
(SEQ ID NO: 30)
GGSGGKLPAT Linker12: between RlucII and PH domain of PLCO1
(SEQ ID NO: 31)
GNASGTGSGGSGSGGLEM Linker13: between rGFP and PH domain of PLCO1
(SEQ ID NO: 29)
GSGGSGSGGLE Linker14: between HA tag and RlucII
(SEQ ID NO: 32)
SNAKL hV2R (W1645): mutant W1645-hV2R, intracellularly retained and PC-rescuable
(SEQ ID NO: 46)
MLMASTTSAVPGHPSLPSLPSNSSQERPLDTRDPLLARAELALLSIVFVAVALSNGLVLAALARRG
RRGHWAPIHVFIGHLCLADLAVALFQVLPQLAWKATDRFRGPDALCRAVKYLQMVGMYASSYMIL
AMTLDRHRAICRPMLAYRHGSGAHWNRPVLVASAFSLLLSLPQLFIFAQRNVEGGSGVTDCWAC
FAEPWGRRTYVTWIALMVFVAPTLGIAACQVLIFREIHASLVPGPSERPGGRRRGRRTGSPGEGA
HVSAAVAKTVRMTLVIVVVYVLCWAPPFFLVQLWAAWDPEAPLEGAPFVLLMLLASLNSCTNPWIY
ASFSSSVSSELRSLLCCARGRTPPSLGPQDESCTTASSSLAKDTSS.

CAAX (Hras): plasma-membrane targeting palmitoylation sequence and prenylation signal sequence from hRas
(SEQ ID NO: 47)
CMSCKCVLS CAAX (CCIL): plasma-membrane targetting palmitoylation sequence from hRas and prenylation signal sequence from RaII
(SEQ ID NO: 43)
CMSCKCCIL hMC4R N625 mutant Melanocortin 4 receptor, intracellularly retained and PC-rescuable
(SEQ ID NO: 48)
MVNSTHRGMHTSLHLWNRSSYRLHSNASESLGKGYSDGGCYEQLFVSPEVFVTLGVISLLESILVI
VAIAKNKNLHSPMYFFICSLAVADMLVSVSNGSETIVITLLNSTDTDAQSFTVNIDNVIDSVICSSLLA
SICSLLSIAVDRYFTIFYALQYHNIMTVKRVGIIISCIWAACTVSGILFIIYSDSSAVIICLITMFFTMLALM
ASLYVHMFLMARLHIKRIAVLPGTGAIRQGANMKGAITLTILIGVFVVCWAPFFLHLIFYISCPQNPYC
VCFMSHFNLYLILIMCNSIIDPLIYALRSQELRKTFKEIICCYPLGGLCDLSSRY hMC4R R165W mutant Melanocortin 4 receptor, intracellularly retained and PC-rescuable
(SEQ ID NO: 49)
MVNSTHRGMHTSLHLWNRSSYRLHSNASESLGKGYSDGGCYEQLFVSPEVFVTLGVISLLENILVI
VAIAKNKNLHSPMYFFICSLAVADMLVSVSNGSETIVITLLNSTDTDAQSFTVNIDNVIDSVICSSLLA
SICSLLSIAVDRYFTIFYALQYHNIMTVKWVGIIISCIWAACTVSGILFIIYSDSSAVIICLITMFFTMLAL
MASLYVHMFLMARLHIKRIAVLPGTGAIRQGANMKGAITLTILIGVFVVCWAPFFLHLIFYISCPQNP
YCVCFMSHFNLYLILIMCNSIIDPLIYALRSQELRKTFKEIICCYPLGGLCDLSSRY Unimolecular DAG sensor
(SEQ ID NO: 50)
MGCIKSKGKDSLSNAMVSKGEELFTGVVPILVELDGDVNGHKFSVSGEGEGDATYGKLTLKFICTT
GKLPVPWPTLVTTLSYGVQCFSRYPDHMKQHDFFKSAMPEGYVQERTIFFKDDGNYKTRAEVKF
EGDTLVNRIELKGIDFKEDGNILGHKLEYNYNPHNVYIMADKQKNGIKVNFKIRHNIEDGSVQLADH
YQQNTPIGDGPVLLPDNHYLFTQSALSKDPNEKRDHMVLLEFVTAAGITLGMDELYKGTGTAAKE
GEKQKGAMQPSEQQRGKEAQKEKNGKEPNPRPEQPKPAKVEQQEDEPEERPKREPMQLEPAE
SAKQGRNLPQKVEQGEERPQEADMPGQAQSSAMRPQLSNSEEGPARGKPAPEEPDEQLGEPEE
AQGEHADEPAPSKPSEKHMVPQMAEPEKGEEAREPQGAEDKPAPVHKPKKEEPQRPNEEKAPK
PKGRHVGRQENDDSAGKPEPGRPDRKGKEKEPEEEPAQGHSLPQEPEPMPRPKPEVRKKPHP
GASPHQVSDVEDAKGPERKVNPMEGEESAKQAQQEGPAENDEAERPERPASGGAREAMTSKV
YDPEQRKRMITGPQWWARCKQMNVLDSFINYYDSEKHAENAVIFLHGNATSSYLWRHVVPHIEP
VARCIIPDLIGMGKSGKSGNGSYRLLDHYKYLTAWFELLNLPKKIIFVGHDWGAALAFHYSYEHQD
KIKAIVHAESVVDVIESWDEWPDIEEDIALIKSEEGEKMVLENNFFVETVLPSKIMRKLEPEEFAAYL

```
EPFKEKGEVRRPTLSWPREIPLVKGGKPDVVQIVRNYNAYLRASDDLPKMFIESDPGFFSNAIVEG
AKKFPNTEFVKVKGLHFSQEDAPDEMGKYIKSFVERVLKNEQGSGSGFNIDMPHRFKVHNYMSP
TFCDHCGSLLWGLVKQGLKCEDCGMNVHHKCREKVANLCG

Unimolecular Parrestin1 sensor
                                                            (SEQ ID NO: 51)
MGCIKSKGKDSLSNAMVSKGEELFTGVVPILVELDGDVNGHKFSVSGEGEGDATYGKLTLKFICTT
GKLPVPWPTLVTTLSYGVQCFSRYPDHMKQHDFFKSAMPEGYVQERTIFFKDDGNYKTRAEVKF
EGDTLVNRIELKGIDFKEDGNILGHKLEYNYNPHNVYIMADKQKNGIKVNFKIRHNIEDGSVQLADH
YQQNTPIGDGPVLLPDNHYLFTQSALSKDPNEKRDHMVLLEFVTAAGITLGMDELYKGTGTAAKE
GEKQKGAMQPSEQQRGKEAQKEKNGKEPNPRPEQPKPAKVEQQEDEPEERPKREPMQLEPAE
SAKQGRNLPQKVEQGEERPQEADMPGQAQSAMRPQLSNSEEGPARGKPAPEEPDEQLGEPEE
AQGEHADEPAPSKPSEKHMVPQMAEPEKGEEAREPQGAEDKPAPVHKPKKEEPQRPNEEKAPK
PKGRHVGRQENDDSAGKPEPGRPDRKGKEKEPEEEPAQGHSLPQEPEPMPRPKPEVRKKPHP
GASPHQVSDVEDAKGPERKVNPMEGEESAKQAQQEGPAENDEAERPERPASGGAREAMTSKV
YDPEQRKRMITGPQWWARCKQMNVLDSFINYYDSEKHAENAVIFLHGNATSSYLWRHVVPHIEP
VARCIIPDLIGMGKSGKSGNGSYRLLDHYKYLTAWFELLNLPKKIIFVGHDWGAALAFHYSYEHQD
KIKAIVHAESVVDVIESWDEWPDIEEDIALIKSEEGEKMVLENNFFVETVLPSKIMRKLEPEEFAAYL
EPFKEKGEVRRPTLSWPREIPLVKGGKPDVVQIVRNYNAYLRASDDLPKMFIESDPGFFSNAIVEG
AKKFPNTEFVKVKGLHFSQEDAPDEMGKYIKSFVERVLKNEQGSGSAGTAGDKGTRVFKKASPN
GKLTVYLGKRDFVDHIDLVDPVDGVVLVDPEYLKERRVYVTLTCAFRYGREDLDVLGLTFRKDLFV
ANVQSFPPAPEDKKPLTRLQERLIKKLGEHAYPFTFEIPPNLPCSVTLQPGPEDTGKACGVDYEVK
AFCAENLEEKIHKRNSVRLVIRKVQYAPERPGPQPTAETTRQFLMSDKPLHLEASLDKEIYYHGEPI
SVNVHVTNNTNKTVKKIKISVRQYADICLFNTAQYKCPVAMEEADDTVAPSSTFCKVYTLTPFLANN
REKRGLALDGKLKHEDTNLASSTLLREGANREILGIIVSYKVKVKLVVSRGGLLGDLASSDVAVELP
FTLMHPKPKEEPPHREVPENETPVDTNLIELDTNDDDIVFEDFARQRLKGMKDDKEEEEDGTGSP
QLNNR Unimolecular Parrestin2 sensor
                                                            (SEQ ID NO: 52)
MGCIKSKGKDSLSNAMVSKGEELFTGVVPILVELDGDVNGHKFSVSGEGEGDATYGKLTLKFICTT
GKLPVPWPTLVTTLSYGVQCFSRYPDHMKQHDFFKSAMPEGYVQERTIFFKDDGNYKTRAEVKF
EGDTLVNRIELKGIDFKEDGNILGHKLEYNYNPHNVYIMADKQKNGIKVNFKIRHNIEDGSVQLADH
YQQNTPIGDGPVLLPDNHYLFTQSALSKDPNEKRDHMVLLEFVTAAGITLGMDELYKGTGTAAKE
GEKQKGAMQPSEQQRGKEAQKEKNGKEPNPRPEQPKPAKVEQQEDEPEERPKREPMQLEPAE
SAKQGRNLPQKVEQGEERPQEADMPGQAQSAMRPQLSNSEEGPARGKPAPEEPDEQLGEPEE
AQGEHADEPAPSKPSEKHMVPQMAEPEKGEEAREPQGAEDKPAPVHKPKKEEPQRPNEEKAPK
PKGRHVGRQENDDSAGKPEPGRPDRKGKEKEPEEEPAQGHSLPQEPEPMPRPKPEVRKKPHP
GASPHQVSDVEDAKGPERKVNPMEGEESAKQAQQEGPAENDEAERPERPASGGAREAMTSKV
YDPEQRKRMITGPQWWARCKQMNVLDSFINYYDSEKHAENAVIFLHGNATSSYLWRHVVPHIEP
VARCIIPDLIGMGKSGKSGNGSYRLLDHYKYLTAWFELLNLPKKIIFVGHDWGAALAFHYSYEHQD
KIKAIVHAESVVDVIESWDEWPDIEEDIALIKSEEGEKMVLENNFFVETVLPSKIMRKLEPEEFAAYL
EPFKEKGEVRRPTLSWPREIPLVKGGKPDVVQIVRNYNAYLRASDDLPKMFIESDPGFFSNAIVEG
AKKFPNTEFVKVKGLHFSQEDAPDEMGKYIKSFVERVLKNEQGSGSAGTAGEKPGTRVFKKSSP
NCKLTVYLGKRDFVDHLDKVDPVDGVVLVDPDYLKDRKVFVTLTCAFRYGREDLDVLGLSFRKDL
FIATYQAFPPVPNPPRPPTRLQDRLLRKLGQHAHPFFFTIPQNLPCSVTLQPGPEDTGKACGVDFE
IRAFCAKSLEEKSHKRNSVRLVIRKVQFAPEKPGPQPSAETTRHFLMSDRSLHLEASLDKEIYYHG
EPLNVNVHVTNNSTKTVKKIKVSVRQYADICLFSTAQYKCPVAQLEQDDQVSPSSTFCKVYTITPLL
SDNREKRGLALDGKLKHEDTNLASSTIVKEGANKEVLGILVSYRVKVKLVVSRGGDVSVELPFVLM
HPKPHDHIPLPRPQSAAPETDVPVDTNLIEFDTNYATDDDIVFEDFARLRLKGMKDDDYDDQLC Human GαL2 subunit with an RlucII inserted at position 84:
                                                            (SEQ ID NO: 53)
MSGVVRTLSRCLLPAEAGGARERRAGSGARDAEREARRRSRDIDALLARERRAVRRLVKILLLGA
GESGKSTFLKQMRIIHGREGSGGGGSMTSKVYDPEQRKRMITGPQWWARCKQMNVLDSFINYY
DSEKHAENAVIFLHGNAASSYLWRHVVPHIEPVARCIIPDLIGMGKSGKSGNGSYRLLDHYKYLTA
WFELLNLPKKIIFVGHDWGAALAFHYSYEHQDKIKAIVHAESVVDVIESWDEWPDIEEDIALIKSEEG
EKMVLENNFFVETVLPSKIMRKLEPEEFAAYLEPFKEKGEVRRPTLSWPREIPLVKGGKPDVVQ1V
RNYNAYLRASDDLPKMFIESDPGFFSNAIVEGAKKFPNTEFVKVKGLHFSQEDAPDEMGKYIKSFV
ERVLKNEQSGGGGSGTFDQKALLEFRDTIFDNILKGSRVLVDARDKLGIPWQYSENEEHGMFLMA
FENKAGLPVEPATFQLYVPALSALWRDSGIREAFSRRSEFQLGESVKYFLDNLDRIGQLEYMPTE
QDILLARKATKGIVEHDFVIKKIPFKMVDVGGQRSQRQKWFQCFDGITSILFMVSSSEYDQVLMED
RRTNRLVESMNIFETIVNNKLFFNVSIILFLNKMDLLVEKVKTVSIKKHFPDFRGDPHRLEDVQRYLV
QCFDRKRRNRSKPLFHHFTTAIDTENVRFVFHAVKDTILQENLKDIMLQ Human Gαg subunit with an RlucII inserted at position 118:
                                                            (SEQ ID NO: 54)
MTLESIMACCLSEEAKEARRINDEIERQLRRDKRDARRELKLLLLGTGESGKSTFIKQMRIIHGSGY
SDEDKRGFTKLVYQNIFTAMQAMIRAMDTLKIPYKYEHNKAHAQLVREVDVNAAIRSTRMTSKVYD
PEQRKRMITGPQWWARCKQMNVLDSFINYYDSEKHAENAVIFLHGNAASSYLWRHVVPHIEPVA
RCIIPDLIGMGKSGKSGNGSYRLLDHYKYLTAWFELLNLPKKIIFVGHDWGAALAFHYSYEHQDKIK
AIVHAESVVDVIESWDEWPDIEEDIALIKSEEGEKMVLENNFFVETVLPSKIMRKLEPEEFAAYLEPF
KEKGEVRRPTLSWPREIPLVKGGKPDVVQIVRNYNAYLRASDDLPKMFIESDPGFFSNAIVEGAKK
FPNTEFVKVKGLHFSQEDAPDEMGKYIKSFVERVLKNEQCTNAAIRSEKVSAFENPYVDAIKSLWN
DPGIQECYDRRREYQLSDSTKYYLNDLDRVADPAYLPTQQDVLRVRVPTTGIIEYPFDLQSVIFRM
VDVGGQRSERRKWIHCFENVTSIMFLVALSEYDQVLVESDNENRMEESKALFRTIITYPWFQNSS
VILFLNKKDLLEEKIMYSHLVDYFPEYDGPQRDAQAAREFILKMFVDLNPDSDKIIYSHFTCATDTEN
IRFVFAAVKDTILQLNLKEYNLV
```

Human GαS subunit with an RlucII inserted at position 67:

(SEQ ID NO: 55)
MGCLGNSKTEDQRNEEKAQREANKKIEKQLQKDKQVYRATHRLLLLGAGESGKSTIVKQMRILHV
NGSGGGGSMTSKVYDPEQRKRMITGPQWWARCKQMNVLDSFINYYDSEKHAENAVIFLHGNAT
SSYLWRHVVPHIEPVARCIIPDLIGMGKSGKSGNGSYRLLDHYKYLTAWFELLNLPKKIIFVGHDWG
AALAFHYSYEHQDKIKAIVHAESVVDVIESWDEWPDIEEDIALIKSEEGEKMVLENNFFVETVLPSKI
MRKLEPEEFAAYLEPFKEKGEVRRPTLSWPREIPLVKGGKPDVVQIVRNYNAYLRASDDLPKMFIE
SDPGFFSNAIVEGAKKFPNTEFVKVKGLHFSQEDAPDEMGKYIKSFVERVLKNEQSGGGGSFNGE
GGEEDPQAARSNSDGEKATKVQDIKNNLKEAIETIVAAMSNLVPPVELANPENQFRVDYILSVMNV
PDFDFPPEFYEHAKALWEDEGVRACYERSNEYQLIDCAQYFLDKIDVIKQADYVPSDQDLLRCRVL
TSGIFETKFQVDKVNFHMFDVGGQRDERRKWIQCFNDVTAIIFVVASSSYNMVIREDNQTNRLQE
ALNLFKSIWNNRWLRTISVILFLNKQDLLAEKVLAGKSKIEDYFPEFARYTTPEDATPEPGEDPRVT
RAKYFIRDEFLRISTASGDGRHYCYPHFTCAVDTENIRRVFNDCRDIIQRMHLRQYELL human Gβ1 subunit (SEQ ID NO: 56)
MSELDQLRQEAEQLKNQIRDARKACADATLSQITNNIDPVGRIQMRTRRTLRGHLAKIYAMHWGT
DSRLLVSASQDGKLIIWDSYTTNKVHAIPLRSSWVMTCAYAPSGNYVACGGLDNICSIYNLKTREG
NVRVSRELAGHTGYLSCCRFLDDNQIVTSSGDTTCALWDIETGQQTTTFTGHTGDVMSLSLAPDT
RLFVSGACDASAKLWDVREGMCRQTFTGHESDINAICFFPNGNAFATGSDDATCRLFDLRADQEL
MTYSHDNIICGITSVSFSKSGRLLLAGYDDFNCNVWDALKADRAGVLAGHDNRVSCLGVTDDGMA
VATGSWDSFLKIWN human Gγ1 subunit (SEQ ID NO: 57)
MPVINIEDLTEKDKLKMEVDQLKKEVTLERMLVSKCCEEVRDYVEERSGEDPLVKGIPEDKNPFKE
LKGGCVIS human Gγ2 subunit (SEQ ID NO: 58)
MASNNTASIAQARKLVEQLKMEANIDRIKVSKAAADLMAYCEAHAKEDPLLTPVPASENPFREKKF
FCAIL human Gγ3 subunit (SEQ ID NO: 59)
MKGETPVNSTMSIGQARKMVEQLKIEASLCRIKVSKAAADLMTYCDAHACEDPLITPVPTSENPFR
EKKFFCALL human Gγ4 subunit (SEQ ID NO: 60)
MKEGMSNNSTTSISQARKAVEQLKMEACMDRVKVSQAAADLLAYCEAHVREDPLIIPVPASENPF
REKKFFCTIL human Gγ5 subunit (SEQ ID NO: 61)
MSGSSSVAAMKKVVQQLRLEAGLNRVKVSQAAADLKQFCLQNAQHDPLLTGVSSSTNPFRPQKV
CSFL human Gγ7 subunit (SEQ ID NO: 62)
MSATNNIAQARKLVEQLRIEAGIERIKVSKAASDLMSYCEQHARNDPLLVGVPASENPFKDKKPCII
L human Gγ8 subunit (SEQ ID NO: 63)
MSNNMAKIAEARKTVEQLKLEVNIDRMKVSQAAAELLAFCETHAKDDPLVTPVPAAENPFRDKRLF
CVLL human Gγ9 subunit (SEQ ID NO: 64)
MAQDLSEKDLLKMEVEQLKKEVKNTRIPISKAGKEIKEYVEAQAGNDPFLKGIPEDKNPFKEKGGC
LIS human Gγ10 subunit (SEQ ID NO: 65)
MSSGASASALQRLVEQLKLEAGVERIKVSQAAAELQQYCMQNACKDALLVGVPAGSNPFREPRS
CALL human Gγ11 subunit (SEQ ID NO: 66)
MPALHIEDLPEKEKLKMEVEQLRKEVKLQRQQVSKCSEEIKNYIEERSGEDPLVKGIPEDKNPFKE
KGSCVIS human Gγ12 subunit (SEQ ID NO: 67)
MSSKTASTNNIAQARRTVQQLRLEASIERIKVSKASADLMSYCEEHARSDPLLIGIPTSENPFKDKK
TCIIL human Gγ13 subunit
(SEQ ID NO: 68)
MEEWDVPQMKKEVESLKYQLAFQREMASKTIPELLKWIEDGIPKDPFLNPDLMKNNPWVEKGKC
TIL human Gα15 subunit
(SEQ ID NO: 69)
MARSLTWRCCPWCLTEDEKAAARVDQEINRILLEQKKQDRGELKLLLLGPGESGKSTFIKQMRIIH
GAGYSEEERKGFRPLVYQNIFVSMRAMIEAMERLQIPFSRPESKHHASLVMSQDPYKVTTFEKRY
AAAMQWLWRDAGIRACYERRREFHLLDSAVYYLSHLERITEEGYVPTAQDVLRSRMPTTGINEYC
FSVQKTNLRIVDVGGQKSERKKW1HCFENVIALIYLASLSEYDQCLEENNQENRMKESLALFGTILE
LPWFKSTSVILFLNKTDILEEKIPTSHLATYFPSFQGPKQDAEAAKRFILDMYTRMYTGCVDGPEGS
KKGARSRRLFSHYTCATDTQNIRKVFKDVRDSVLARYLDEINLL Rho-binding domain (CRIB) of the human Protein kinase 1 (PKN)
(SEQ ID NO: 70)
VQSEPRSWSLLEQLGLAGADLAAPGVQQQLELERERLRREIRKELKLKEGAENLRRATTDLGRSL
GPVELLLRGSSRRLDLLHQQLQE Linker between RlucII and the Rho binding domain of PKN1
(SEQ ID NO: 71)
GSASAGTATMASDA DAG binding domain C1b from the human PKCO
(SEQ ID NO: 72)
FNIDMPHRFKVHNYMSPTFCDHCGSLLWGLVKQGLKCEDCGMNVHHKCREKVANLCG Human 31 adrenergic receptor (β1AR)
(SEQ ID NO: 73)
MGAGVLVLGASEPGNLSSAAPLPDGAATAARLLVPASPPASLLPPASESPEPLSQQWTAGMGLL
MALIVLLIVAGNVLVIVAIAKTPRLQTLTNLFIMSLASADLVMGLLVVPFGATIVVWGRWEYGSFFCE
LWTSVDVLCVTASIETLCVIALDRYLAITSPFRYQSLLTRARARGLVCTVWAISALVSFLPILMHWW
RAESDEARRCYNDPKCCDFVTNRAYAIASSVVSFYVPLCIMAFVYLRVFREAQKQVKKIDSCERRF
LGGPARPPSPSPSPVPAPAPPPGPPRPAAAAATAPLANGRAGKRRPSRLVALREQKALKTLGIIM
GVFTLCWLPFFLANVVKAFHRELVPDRLFVFFNWLGYANSAFNPIIYCRSPDFRKAFQGLLCCARR
AARRRHATHGDRPRASGCLARPGPPPSPGAASDDDDDDVVGATPPARLLEPWAGCNGGAAAD
SDSSLDEPCRPGFASESKV Human = adrenergic receptor (β2AR)
(SEQ ID NO: 74)
MGQPGNGSAFLLAPNRSHAPDHDVTQQRDEVWVVGMGIVMSLIVLAIVFGNVLVITAIAKFERLQT
VTNYFITSLACADLVMGLAVVPFGAAHILMKMWTFGNFWCEFWTSIDVLCVTASIETLCVIAVDRYF
AITSPFKYQSLLTKNKARVIILMVWIVSGLTSFLPIQMHWYRATHQEAINCYANETCCDFFTNQAYAI
ASSIVSFYVPLVIMVFVYSRVFQEAKRQLQKIDKSEGRFHVQNLSQVEQDGRTGHGLRRSSKFCL
KEHKALKTLGIIMGTFTLCWLPFFIVNIVHVIQDNLIRKEVYILLNWIGYVNSGFNPLIYCRSPDFRIAF
QELLCLRRSSLKAYGNGYSSNGNTGEQSGYHVEQEKENKLLCEDLPGTEDFVGHQGTVPSDNID
SQGRNCSTNDSLL Human prostaglandin 2a receptor isoform a (FP)
(SEQ ID NO: 75)
MSMNNSKQLVSPAAALLSNTTCQTENRLSVFFSVIFMTVGILSNSLAIAILMKAYQRFRQKSKASFL
LLASGLVITDFFGHLINGAIAVFVYASDKEWIRFDQSNVLCSIFGICMVFSGLCPLLLGSVMAIERCIG
VTKPIFHSTKITSKHVKMMLSGVCLFAVFIALLPILGHRDYKIQASRTWCFYNTEDIKDWEDRFYLLL
FSFLGLLALGVSLLCNAITGITLLRVKFKSQQHRQGRSHHLEMVIQLLAIMCVSCICWSPFLVTMANI
GINGNHSLETCETTLFALRMATWNQILDPWVYILLRKAVLKNLYKLASQCCGHVISLHIWELSSIK
NSLKVAAISESPVAEKSAST Human Thromboxane A2 receptor isoform a (TPaR)
(SEQ ID NO: 76)
MWPNGSSLGPCFRPTNITLEERRLIASPWFAASFCVVGLASNLLALSVLAGARQGGSHTRSSFLT
FLCGLVLTDFLGLLVTGTIVVSQHAALFEWHAVDPGCRLCRFMGVVMIFFGLSPLLLGAAMASERY
LGITRPFSRPAVASQRRAWATVGLVWAAALALGLLPLLGVGRYTVQYPGSWCFLTLGAESGDVAF
GLLFSMLGGLSVGLSFLLNTVSVATLCHVYHGQEAAQQRPRDSEVEMMAQLLGIMVVASVCWLP
LLVFIAQTVLRNPPAMSPAGQLSRTTEKELLIYLRVATWNQILDPWVYILFRRAVLRRLQPRLSTRP
RSLSLQPQLTQRSGLQ Human Urotensin II receptor (GPR14)
(SEQ ID NO: 77)
MALTPESPSSFPGLAATGSSVPEPPGGPNATLNSSWASPTEPSSLEDLVATGTIGTLLSAMGVVG
VVGNAYTLVVTCRSLRAVASMYVYVVNLALADLLYLLSIPFIVATYVTKEWHFGDVGCRVLFGLDFL
TMHASIFTLIVMSSERYAAVLRPLDTVQRPKGYRKLLALGTWLLALLLTLPVMLAMRLVRRGPKSL
CLPAWGPRAHRAYLTLLFATSIAGPGLLIGLLYARLARAYRRSQRASFKRARRPGARALRLVLGIVL
LFWACFLPFWLWQLLAQYHQAPLAPRTARIVNYLTTCLTYGNSCANPFLYTLLTRNYRDHLRGRV
RGPGSGGGRGPVPSLQPRARFORCGRSLSSCSPQPIDSLVLAPAAPARPAPEGPRAPA Human histamine type 1 receptor (H1R)
(SEQ ID NO: 78)
MSLPNSSCLLEDKMCEGNKTTMASPQLMPLVVVLSTICLVTVGLNLLVLYAVRSERKLHTVGNLYI
VSLSVADLIVGAVVMPMNILYLLMSKWSLGRPLCLFWLSMDYVASTASIFSVFILCIDRYRSVQQPL
RYLKYRTKTRASATILGAWFLSFLWVIPILGWNHFMQQTSVRREDKCETDFYDVTWFKVMTAIINF
YLPTLLMLWFYAKIYKAVRQHCQHRELINRSLPSFSEIKLRPENPKGDAKKPGKESPWEVLKRKPK
DAGGGSVLKSPSQTPKEMKSPVVFSQEDDREVDKLYCFPLDIVHMQAAAEGSSRDYVAVNRSHG
QLKTDEQGLNTHGASEISEDQMLGDSQSFSRTDSDTTTETAPGKGKLRSGSNTGLDYIKFTWKRL
RSHSRQYVSGLHMNRERKAAKQLGFIMAAFILCWIPYFIFFMVIAFCKNCCNEHLHMFTIWLGYINS
TLNPLIYPLCNENFKKTFKRILHIRS human Bradykinin type 2 receptor (BKRB2)
(SEQ ID NO: 79)
MFSPWKISMFLSVREDSVPTTASFSADMLNVTLQGPTLNGTFAQSKCPQVEWLGWLNTIQPPFL
WVLFVLATLENIFVLSVFCLHKSSCTVAEIYLGNLAAADLILACGLPFWAITISNNFDWLFGETLCRV
VNAIISMNLYSSICFLMLVSIDRYLALVKTMSMGRMRGVRWAKLYSLVIWGCTLLLSSPMLVFRTM
KEYSDEGHNVTACVISYPSLIWEVFINMLLNVVGFLLPLSVITFCTMQIMQVLRNNEMQKFKEIQTE
RRATVLVLVVLLLFIICWLPFQISTFLDTLHRLGILSSCQDERIIDVITQIASFMAYSNSCLNPLVYVIVG
KRFRKKSWEVYQGVCQKGGCRSEPIQMENSMGTLRTSISVERQIHKLQDWAGSRQ human dopamine type 2 receptor isoform 1(D2R)
(SEQ ID NO: 80)
MDPLNLSWYDDDLERQNWSRPFNGSDGKADRPHYNYYATLLTLLIAVIVFGNVLVCMAVSREKAL
QTTTNYLIVSLAVADLLVATLVMPWVVYLEVVGEWKFSRIHCDIFVTLDVMMCTASILNLCAISIDRY
TAVAMPMLYNTRYSSKRRVTVMISIVWVLSFTISCPLLFGLNNADQNECIIANPAFVVYSSIVSFYVP
FIVTLLVYIKIYIVLRRRRKRVNTKRSSRAFRAHLRAPLKGNCTHPEDMKLCTVIMKSNGSFPVNRR
RVEAARRAQELEMEMLSSTSPPERTRYSPIPPSHHQLTLPDPSHHGLHSTPDSPAKPEKNGHAKD
HPKIAKIFEIQTMPNGKTRTSLKTMSRRKLSQQKEKKATQMLAIVLGVFIICWLPFFITHILNIHCDCNI
PPVLYSAFTWLGYVNSAVNPIIYTTFNIEFRKAFLKILHC GFP2-RlucII fusion
(SEQ ID NO: 81)
MVSKGEELFTGVVPILVELDGDVNGHKFSVSGEGEGDATYGKLTLKFICTTGKLPVPWPTLVTTLS
YGVQCFSRYPDHMKQHDFFKSAMPEGYVQERTIFFKDDGNYKTRAEVKFEGDTLVNRIELKGIDF
KEDGNILGHKLEYNYNSHNVYIMADKQKNGIKVNFKIRHNIEDGSVQLADHYQQNTPIGDGPVLLP
DNHYLSTQSALSKDPNEKRDHMVLLEFVTAAGITLGMDELYKGGGGGDIEFLQPGGSSGGGMTS
KVYDPEQRKRMITGPQWWARCKQMNVLDSFINYYDSEKHAENAVIFLHGNAASSYLWRHVVPHI
EPVARCIIPDLIGMGKSGKSGNGSYRLLDHYKYLTAWFELLNLPKKIIFVGHDWGAALAFHYSYEH
QDKIKAIVHAESVVDVIESWDEWPDIEEDIALIKSEEGEKMVLENNFFVETVLPSKIMRKLEPEEFAA
YLEPFKEKGEVRRPTLSWPREIPLVKGGKPDVVQIVRNYNAYLRASDDLPKMFIESDPGFFSNAIV
EGAKKFPNTEFVKVKGLHFSQEDAPDEMGKYIKSFVERVLKNEQ rGFP-RlucII fusion
(SEQ ID NO: 82)
MDLAKLGLKEVMPTKINLEGLVGDHAFSMEGVGEGNILEGTQEVKISVTKGAPLPFAFDIVSVAFSY
GNRAYTGYPEEISDYFLQSFPEGFTYERNIRYQDGGTAIVKSDISLEDGKFIVNVDFKAKDLRRMG
PVMQQDIVGMQPSYESMYTNVTSVIGECIIAPKLQTGKHFTYHMRTVYKSKKPVETMPLYHFIQHR
LVKTNVDTASGYVVQHETAIAAHSTIKKIEGSLPGGGGGDIEFLQPGGSGGGGMTSKVYDPEQRK
RMITGPQWWARCKQMNVLDSFINYYDSEKHAENAVIFLHGNAASSYLWRHVVPHIEPVARCIIPDL
IGMGKSGKSGNGSYRLLDHYKYLTAWFELLNLPKKIIFVGHDWGAALAFHYSYEHQDKIKAIVHAE
SVVDVIESWDEWPDIEEDIALIKSEEGEKMVLENNFFVETVLPSKIMRKLEPEEFAAYLEPFKEKGE
VRRPTLSWPREIPLVKGGKPDVVQIVRNYNAYLRASDDLPKMFIESDPGFFSNAIVEGAKKFPNTE
FVKVKGLHFSQEDAPDEMGKYIKSFVERVLKNEQ Venus-Rlucll fusion
(SEQ ID NO: 83)
MVSKGEELFTGVVPILVELDGDVNGHKFSVSGEGEGDATYGKLTLKLICTTGKLPVPWPTLVTTLG
YGLQCFARYPDHMKQHDFFKSAMPEGYVQERTIFFKDDGNYKTRAEVKFEGDTLVNRIELKGIDF
KEDGNILGHKLEYNYNSHNVYITADKQKNGIKANFKIRHNIEDGSVQLADHYQQNTPIGDGPVLLP
DNHYLSYQSALSKDPNEKRDHMVLLEFVTAAGITLGMDELYKGGGGGDIEFLQPGGSSGGGMTS
KVYDPEQRKRMITGPQWWARCKQMNVLDSFINYYDSEKHAENAVIFLHGNAASSYLWRHVVPHI
EPVARCIIPDLIGMGKSGKSGNGSYRLLDHYKYLTAWFELLNLPKKIIFVGHDWGAALAFHYSYEH
QDKIKAIVHAESVVDVIESWDEWPDIEEDIALIKSEEGEKMVLENNFFVETVLPSKIMRKLEPEEFAA
YLEPFKEKGEVRRPTLSWPREIPLVKGGKPDVVQIVRNYNAYLRASDDLPKMFIESDPGFFSNAIV
EGAKKFPNTEFVKVKGLHFSQEDAPDEMGKYIKSFVERVLKNEQ Linker between parrestin (1&2) and RlucII
(SEQ ID NO: 84)
KLPAT Human Parrestin1
(SEQ ID NO: 85)
MGDKGTRVFKKASPNGKLTVYLGKRDFVDHIDLVDPVDGVVLVDPEYLKERRVYVTLTCAFRYGR
EDLDVLGLTFRKDLFVANVQSFPPAPEDKKPLTRLQERLIKKLGEHAYPFTFEIPPNLPCSVTLQPG
PEDTGKACGVDYEVKAFCAENLEEKIHKRNSVRLVIRKVQYAPERPGPQPTAETTRQFLMSDKPL
HLEASLDKEIYYHGEPISVNVHVTNNTNKTVKKIKISVRQYADICLFNTAQYKCPVAMEEADDTVAP

```
-continued
SSTFCKVYTLTPFLANNREKRGLALDGKLKHEDTNLASSTLLREGANREILGIIVSYKVKVKLVVSR
GGLLGDLASSDVAVELPFTLMHPKPKEEPPHREVPENETPVDTNLIELDTNDDDIVFEDFARQRLK
GMKDDKEEEEDGTGSPQLNNR
```

Human parrestin2

(SEQ ID NO: 86)

```
MGEKPGTRVFKKSSPNCKLTVYLGKRDFVDHLDKVDPVDGVVLVDPDYLKDRKVFVTLTCAFRY
GREDLDVLGLSFRKDLFIATYQAFPPVPNPPRPPTRLQDRLLRKLGQHAHPFFFTIPQNLPCSVTL
QPGPEDTGKACGVDFEIRAFCAKSLEEKSHKRNSVRLVIRKVQFAPEKPGPQPSAETTRHFLMSD
RSLHLEASLDKELYYHGEPLNVNVHVTNNSTKTVKKIKVSVRQYADICLFSTAQYKCPVAQLEQDD
QVSPSSTFCKVYTITPLLSDNREKRGLALDGKLKHEDTNLASSTIVKEGANKEVLGILVSYRVKVKL
VVSRGGDVSVELPFVLMHPKPHDHIPLPRPQSAAPETDVPVDTNLIEFDTNYATDDDIVFEDFARL
RLKGMKDDDYDDQLC
```

Example 2: Generation and Validation of New BRET Sensors for GPCR Trafficking New BRET acceptors based on *Renilla reniformis* GFP (rGFP) were generated for assessing receptor internalization and their targeting with β-arrestins to endosomes. These BRET acceptors were engineered for their specific expression either at the plasma membrane or in the endosomes, and for being used with the RET donors: RlucII-tagged GPCRs and β-arrestins (FIGS. 1A-C). The BRET assay disclosed herein is based on changes in the local concentration of the donor relative to the acceptor rather than a specific protein-protein interaction; hence not limited by the requirement for protein interaction and the avidity of one's complex. For its plasma membrane localization, rGFP was first tagged with a lyn domain. Lyn-rGFP localized mainly at the plasma membrane when expressed in HEK293 cells (FIGS. 1D and F). Moreover, adding the endofin FYVE domain to rGFP (rGFP-endofinFYVE) showed clear and exclusive endosomal localization (FIG. 1E, left panel). A mCherry-labeled variant of the endofin FYVE (mCherry-FYVE) sensor also co-localized with the small G protein Rab5, which populates EE (FIG. 1G). Notably, blocking PI3K using wortmannin delocalized the rGFP-endofinFYVE into the cytosol and enlarged endosomal vesicles (FIG. 1E, right panel), consistent with its tethering to endosomes through PI3P binding. To visualize GPCR trafficking, the bradykinin B2 receptor tagged with CFP (B2R-CFP) was used, and lyn-rGFP and mCherry-endofin FYVE were expressed simultaneously (FIG. 1F). At basal state, B2R-CFP localized at the plasma membrane with lyn-rGFP (top panel). Upon agonist stimulation, B2R-CFP separated from the lyn-rGFP, and moved into the endosomes where it colocalized with the mCherry-endofinFYVE (bottom panel). Only the receptor redistributed from one cellular compartment to another upon agonist, as both the plasma membrane and endosomal markers (i.e. lyn-rGFP and GFP-endofinFYVE, respectively) remained in their respective compartments, making this system suitable to dynamically track receptor trafficking using BRET.

Figure 2A:
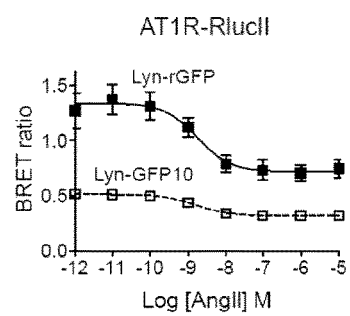
FIGS. 2A to 2F show the dose and time-dependent AT1R endocytosis measured by BRET.
Figure 2B:
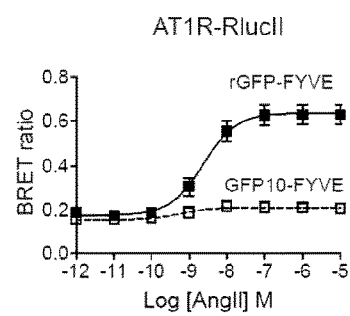
Figure 2C:
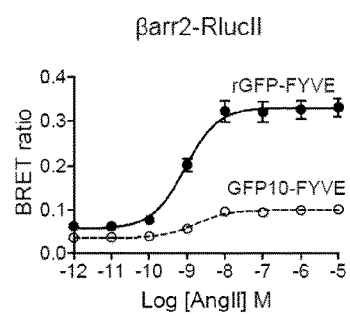
Figure 2D:
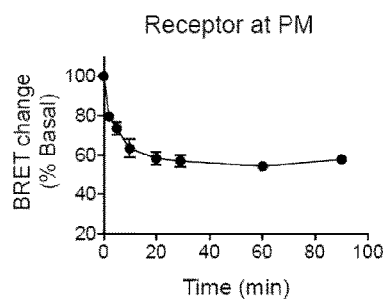
Figure 2E:
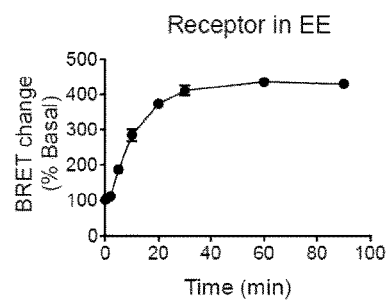
Figure 2F:
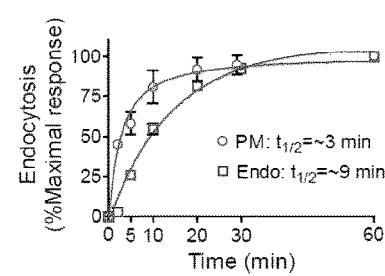

Example 3: Assessing AT1R Internalization and its Trafficking to Endosomes with β-Arrestin BRET experiments were performed to monitor receptor endocytosis. The RlucII was fused onto the C-terminal domain of the angiotensin type 1 receptor (AT1R-RlucII), another GPCR, which traffic with β-arrestin through the clathrin pathway and is targeted to endosomes (Hein, Meinel et al. 1997; Zhang, Barak et al. 1999; Anborgh, Seachrist et al. 2000; Oakley, Laporte et al. 2000; Gaborik, Szaszak et al. 2001). Using radio-ligand binding, it was first validated that the engineered AT1R-RlucII internalized to the same extent as the untagged receptor (FIG. 7A). Co-expression of AT1R-RlucII and lyn-rGFP did not prevent efficient agonist-mediated removal of receptors from the plasma membrane (FIG. 7A), which internalization increased furthermore by the expression of β-arrestin2 or was inhibited with the dominant negative Dynamin K44A (DynK44A; FIG. 7B). Consistent with their co-localization at the plasma membrane, expressing AT1R-RlucII and lyn-rGFP revealed a high BRET ratio at basal state (FIG. 2A). The signal rapidly decreased in a concentration-dependent manner following challenge of live cells with AngII and the removal of receptor from the plasma membrane. Expressing lyn-GFP10, on the other hand, generated both a lower basal and AngII-induced BRET ratio changes. Remarkably, expressing AT1R-RlucII with rGFP-endofinFYVE rather than GFP10-endofinFYVE resulted in a 7.7-fold increase in AngII-mediated BRET changes (ΔBRET) (FIG. 2B). Similarly, expressing AT1R with β-arrestin2-RlucII and rGFP-endofinFYVE instead of GFP10-endofinFYVE resulted in an increase of 4.5-fold in BRET (FIG. 2C). The temporal process of receptor endocytosis from the plasma membrane and its targeting to endosomes was next resolved using AT1R-RlucII with either the plasma membrane or endosome BRET acceptor sensors (e.g. lyn-rGFP and rGFP-endofinFYVE, respectively). AT1R disappearance from the plasma membrane was faster ($t_{1/2} \approx 3$ min) than its accumulation in endosomes ($t_{1/2} \approx 9$ min) (FIGS. 2D-F).

Figure 3A:
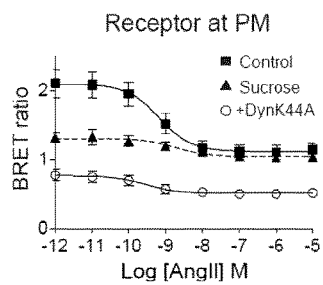
FIGS. 3A to 3F show the effect of blocking receptor endocytosis and overexpression of β-arrestin2 on AngII-induced BRET changes. HEK293SL cells were transfected with AT1R-RlucII/lyn-rGFP (FIG. 3A), AT1R-RlucII/rGFP-endofinFYVE (FIG. 3B), or AT1R/βarr2-RlucII/rGFP-endofinFYVE (FIG. 3C) along with either pcDNA or dynamin K44A. Cells were incubated in the absence (control, ■; DynK44A, O) or presence of 0.45 M sucrose (▲) for 20 min then stimulated with various concentrations of AngII for 40 min before BRET measurement. HEK293SL cells were transfected with AT1R-RlucII/lyn-rGFP (FIG. 3D) or AT1R-RlucII/rGFP-endofinFYVE (FIG. 3E) along with either pcDNA or β-arrestin2.
Figure 3B:
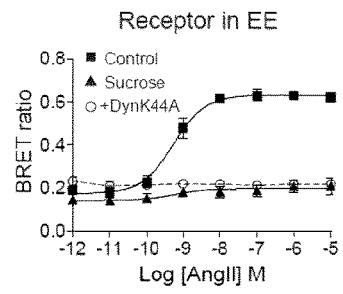
Figure 3C:
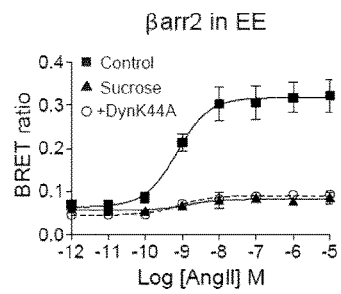
Figure 3D:
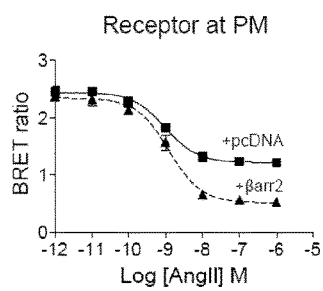
Figure 3E:
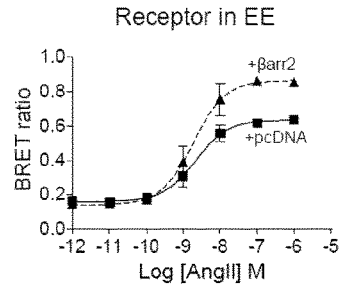
Figure 3F:
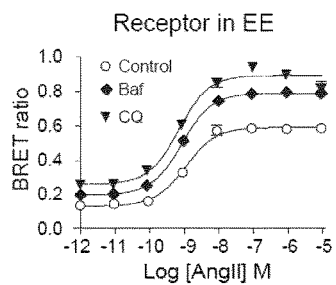

The extent to which AT1R internalization and its targeting to endosomes with β-arrestin could be regulated was next investigated. Dynamin K44A (DynK44A), a dominant negative of Dynamin, which is key for clathrin-coated pit invagination, and sucrose have both been used as endocytosis blockers (Zhang, Ferguson et al. 1996). AngII-mediated BRET responses at the plasma membrane and in the endosomes (AT1R-RlucII/lyn-rGFP and AT1R-RlucII/rGFP-endofinFYVE, respectively) were efficiently inhibited by the expression of DynK44A (FIGS. 3A and B). Consistent with the lack of accumulation of AT1R/β-arrestin complexes in endosomes in presence of DynK44A, very little AngII-mediated BRET ratio changes were observed between β-arrestin2-RlucII and rGFP-endofinFYVE (FIG. 3C). Similarly, sucrose efficiently blocked the AngII-induced BRET responses between AT1R-RlucII and lyn-rGFP at the plasma membrane and in the endosomes between AT1R-RlucII and either β-arrestin2-RlucII or rGFP-endofinFYVE (FIGS. 3A-C). Surprisingly, over-expression of DynK44A or sucrose treatment decreased the basal BRET ratio at the plasma membrane (with Lyn-rGFP) (FIG. 3A), but not in the endosome (with rGFP-endofinFYVE). β-arrestin expression facilitates AT1R endocytosis (Gaborik, Szaszak et al. 2001). The vesicle acidification inhibitors bafilomycin A (Baf) and Chloroquine (CQ), which prevent receptor degradation and AT1R recycling (Heinz et al, Mol Endocrinol. 1997 August; 11(9):1266-77), both increased the agonist-mediated accumulation of AT1R in endosomes (FIG. 3F). Consistent with its important role in agonist-mediated GPCRs endocytosis, over-expression of βarrestin2 enhanced AngII-mediated BRET by more than 50% for both receptor internalization (AT1R-RlucII and lyn-rGFP) and its targeting to endosomes (AT1R-RlucII and rGFP-endofinFYVE) (FIGS. 3D and E). The effects of DynK44A or β-arrestin2 on AngII-mediated AT1R endocytosis were also validated by ligand binding experiments, and found consistent with what observed in the BRET assay (FIG. 7B). Together, these results highlight the utility of the BRET-based assays to monitor, in a dose- and time-dependent fashion, AT1R endocytosis and its trafficking with β-arrestin into endosomes.

Figure 4A:
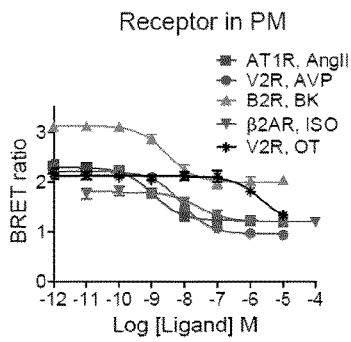
FIGS. 4A to 4E show dose-response curves obtained with the endocytosis BRET biosensors with various receptors.
Figure 4B:
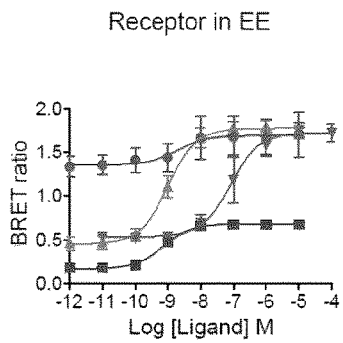
Figure 4C:
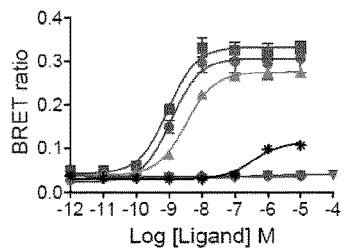
Figure 4D:
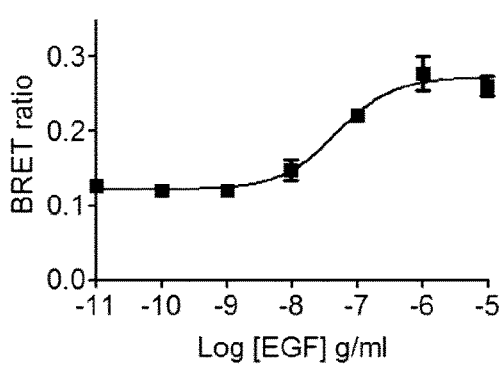
Figure 4E:
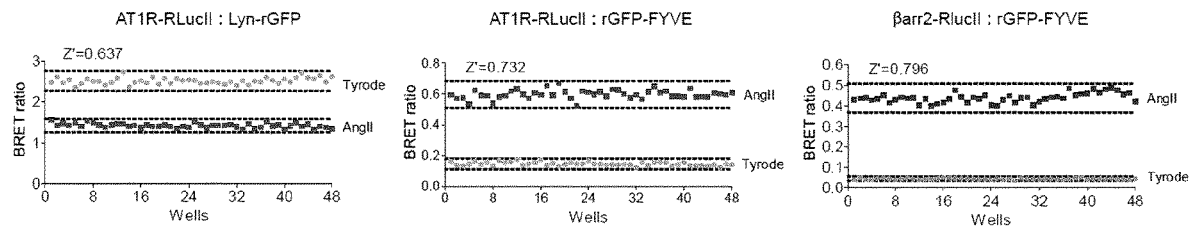

Example 4: Measurement of the Endocytosis and Trafficking of Various Receptors to Endosomes Different GPCRs were tagged with RlucII in order to examine their trafficking. When the vasopressin V2 receptor-RlucII (V2R-RlucII) was expressed with lyn-rGFP, AVP-dose dependently decreased the BRET ratio response. Similarly to AngII-stimulated AT1R, AVP promoted the internalization of V2R with an $EC_{50}$ in the nM range (1.1 nM and 7.8 nM, respectively) (FIG. 4A). On the other hand, oxytocin, which has low affinity for V2R (Barberis, Audigier et al. 1992), promoted the internalization of the receptor with lower potency (FIG. 4A, $EC_{50}$=2.2 µM). B2R-RlucII and β2-adrenergic receptor (β2AR)-RlucII also respectively showed dose-dependent decrease in the BRET ratio by their cognate ligands, bradykinin and isoproterenol. However, we observed differences in the basal BRET ratio between receptors. When receptor trafficking into the endosome was vetted, B2R-RlucII and β2AR-RlucII also showed different potencies in agonist-mediated increasing in BRET ratio (FIG. 4B). Notably, V2R-RlucII and rGFPendofinFYVE showed high basal BRET ratio (FIG. 4B), as compared to B2R and the other receptors, though we could still detect robust increased in the BRET ratio upon AVP stimulation. The higher basal signal was likely caused by high basal endosomal localization of V2R as suggested by microscopy (FIG. 8). Indeed, contrarily to B2R, colocalization of V2R with mCherry-endofinFYVE was more present in absence of agonist stimulus (FIGS. 1 and 8). Next, the agonist-mediated receptor/β-arrestin targeting to endosomes was examined using βarr2-RlucII and rGFPendofinFYVE with different GPCRs. AT1R, V2R and B2R promoted a 6-8-fold increase over basal in BRET ratios upon agonist stimulation (FIG. 4C), which is consistent with the trafficking of class B GPCR (Oakley, Laporte et al. 2000), which traffic to endosomes with β-arrestins. However, isoproterenol stimulation of β2AR failed to generate a BRET signal, consistent with the internalization of a Class A GPCR in endosomes without β-arrestins (Oakley, Laporte et al. 2000). Oxytocin showed very marginal trafficking of the V2R/β-arrestin complex to endosome, while for the PGF2α receptor (FP), which does not internalize (Goupil, Wisehart et al. 2012), no increase over basal in the BRET ratio was detected upon agonist stimulation (FIG. 4C). These results support the use of these plasma membrane and endosome BRET sensors for studying the ligand-mediated trafficking of different classes of GPCRs. FIG. 4D shows the plasma membrane and endosome BRET sensors may also be used to study the endocytosis and trafficking of other types of receptors (i.e., non-GPCRs), such as the epidermal growth factor receptor (EGFR), a receptor tyrosine kinase (RTK). FIG. 4E shows that the Z' factor of over 0.73 for the AT1R-RlucII/rGFP-endofinFYVE biosensors following AngII stimulation, which indicates a robust and HTS compliant assay for receptor internalization in endosomes.

Example 5: Studying Receptor Recycling Using BRET

Figure 5A:
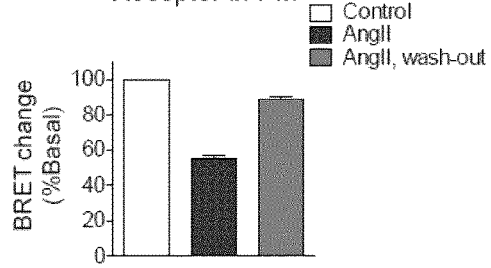
FIGS. 5A to 5C show the monitoring of receptor recycling after ligand removal by endocytosis BRET assays.
Figure 5B:
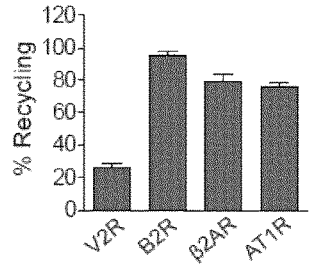
Figure 5C:
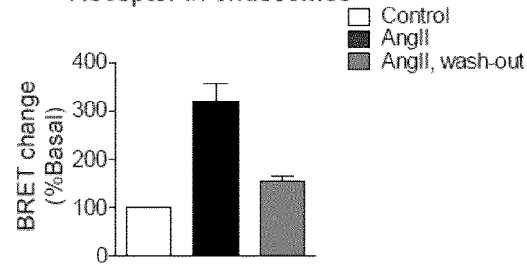

Following GPCR internalization, many receptors have been shown to recycle back to the plasma membrane or to traffic to other intracellular compartments (Tsao, Cao et al. 2001). The dynamics of receptor trafficking following agonist removal was assessed using the different rGFP/RlucII BRET sensor pairs. For receptor recycling at the plasma membrane, cells expressing AT1R-RlucII and lyn-rGFP that have been challenged with AngII for 30 min, were washed to remove the agonist, and left to recover for another 45 min, before BRET measurements. Results show that in cells pre-treated with AngII, BRET ratio decreased by around 50% compared to control, and the signal recovered to about ~90% of control after 45 min of agonist removal (i.e. ~80% of receptor recycling to the plasma membrane; FIG. 5A). The same paradigm was applied to the RlucII-tagged B2R, β2AR, and V2R. These findings revealed that more than 80% of the endocytosed B2R and β2AR recycled to the cell surface, while only about 30% of the endocytosed V2R recycled back to the plasma membrane (FIG. 5B). These results are in good agreement with previous studies (Innamorati, Sadeghi et al. 1998; Tsao and von Zastrow 2000; Zimmerman, Simaan et al. 2011). The disappearance of receptor for the early endosomes was next monitored using the AT1R-RlucII and rGFP-endofinFYVE. AngII treatment for 30 min increased the BRET ratio by 3-fold compared to unstimulated cells (control, FIG. 5C). 45 min after AngII removal, BRET ratio was 1.5-fold of basal, implying that 75% of AT1R disappeared from early endosomes, either by recycling back to the cell surface or other endocytotic sorting. These results provide evidence that the endocytosis BRET assays can be applied to monitor receptor recycling to the plasma membrane and the dynamics of endosomal sorting.

Figure 26A:
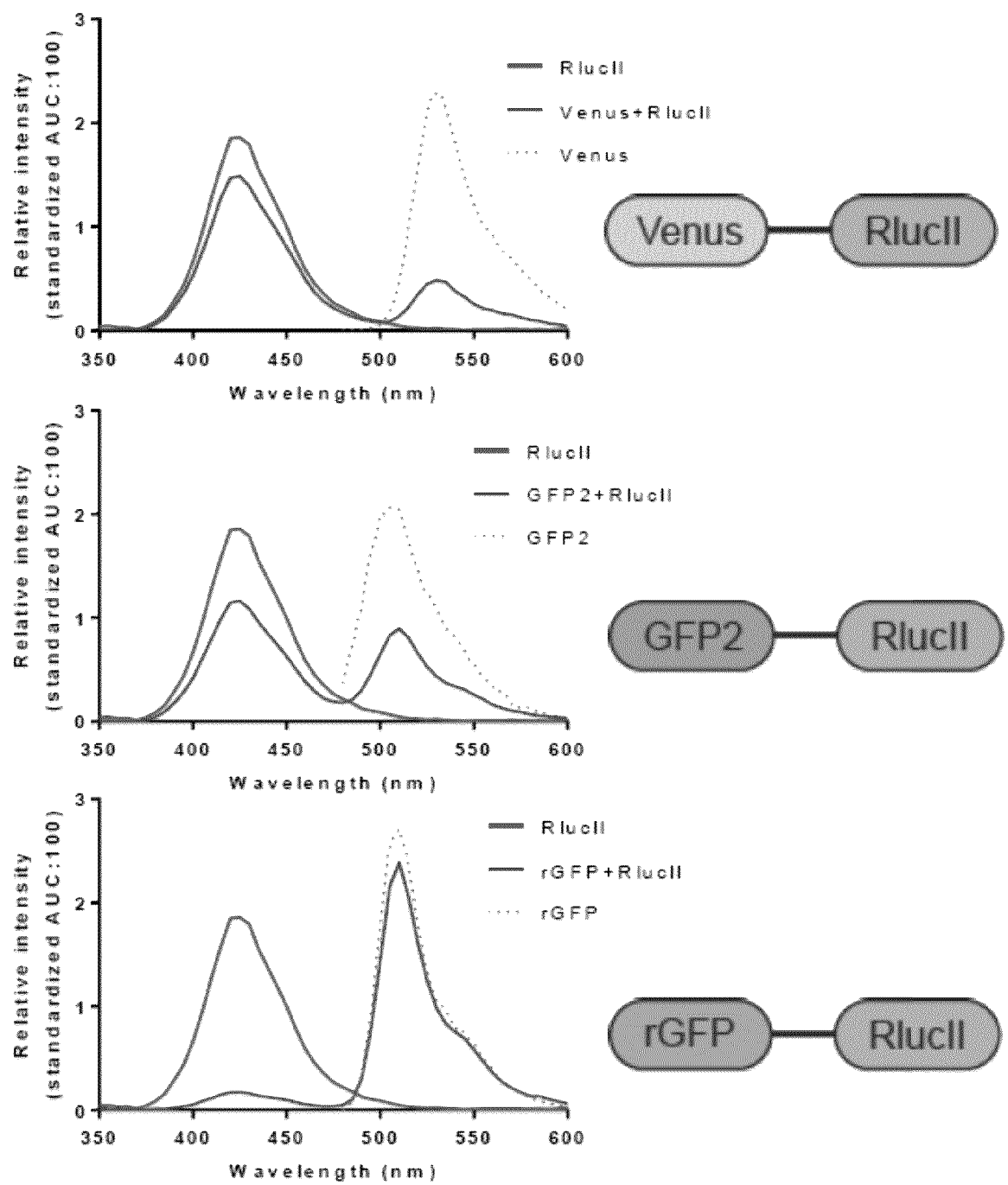
FIGS. 26A and 26B show the BRET transfer obtained between RlucII and different BRET acceptors for unimolecular fusion constructs. The BRET signal obtained using rGFP was more than 10-fold higher than that obtained with typical BRET1 (Venus) and BRET2 (GFP2) acceptors.
Figure 26B:
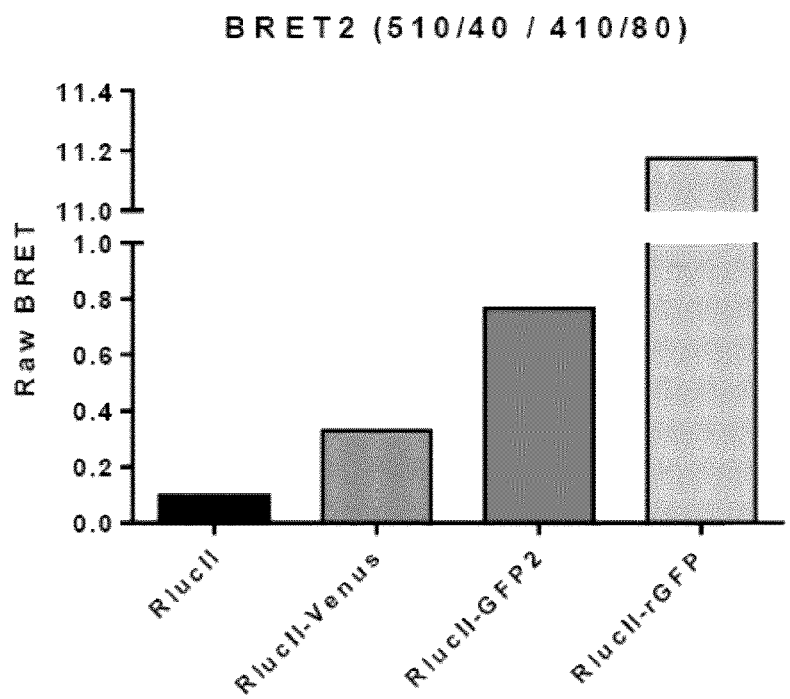
Figure 26C:
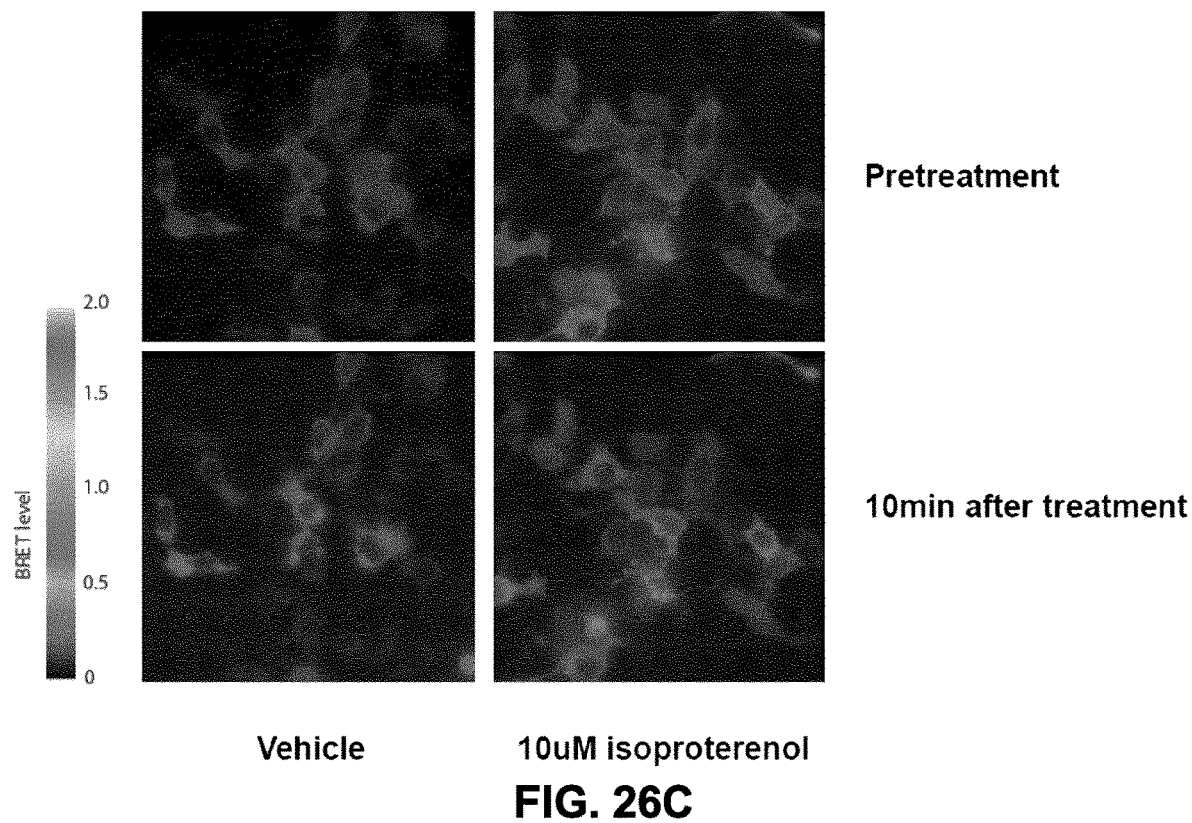
FIG. 26C shows that the rGFP-enhanced BRET signal can be used to monitor BRET in microscopy, even for a density-BRET based assay such as the recruitment of beta-arrestin to the plasma membrane. The assay used in this experiment is similar to that presented in FIG. 19C as measured using a plate reader. HEK293 cells were transiently transfected with constructs encoding the β2AR, the βarrestin2-RlucII and the plasma membrane marker: rGFP-CAAX(Kras). Isoproterenol stimulation induced the increase of BRET signal level only at the plasma membrane, indicating that an increase in BRET signal is a reflection of βarrestin recruitment to the plasma membrane.

FIGS. 26A to 26C show that the changes in BRET signal resulting from βarrestin translocation/recruitment to different compartments may be measured by BRET microscopy, and that the use of rGFP as the BRET acceptor results in a stronger BRET signal as compared to other BRET acceptors such as Venus and GFP2. BRET-based microscopy imaging opens up the possibility of image-based multiplexing for monitoring the translocation of an Rluc-tagged protein to distinct subcellular compartments in response to diverse stimuli.

Example 6: Differential Sorting of AT1R by Angiotensin Analogs

Figure 6A:
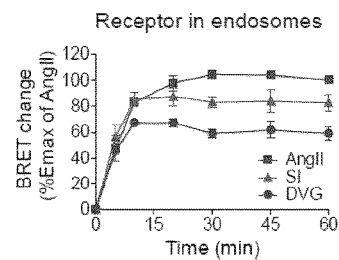
Figure 6B:
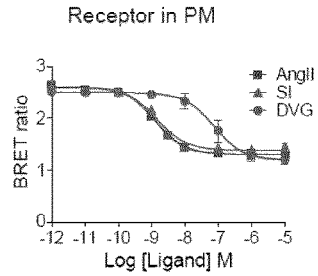
Figure 6C:
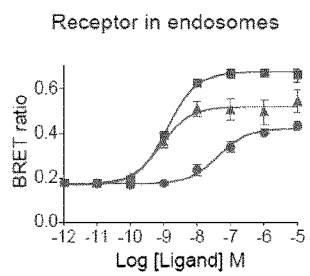

The ligand-mediated receptor endocytosis was next examined using different AT1R ligands: AngII, SI, and DVG, which were previously shown to have distinct biased signalling properties (Zimmerman, Beautrait et al. 2012). Their ability to temporally regulate the trafficking of AT1R-RlucII to endosomes was first evaluated using rGFP-endofinFYVE. Results revealed that the initial rates of AT1R trafficking to endosomes were similar upon ligand incubation (e.g. 0-5 min; FIG. 6A). However, DVG-bound AT1R reached maximal internalization at 10 min, while SI produced it maximal effect only after 20 min, and both ligands were respectively 40% and 20% less efficacious than AngII at promoting AT1R concentration in early endosomes. Taking the time of maximal internalization of 40 min as reference, the potency and efficacy of the different AngII ligands to promote AT1R internalization was compared. As shown in FIG. 6B, AngII, SI, and DVG decreased the BRET ratio between AT1R-RlucII and lyn-rGFP to the same extent at maximal concentrations of ligand. While AngII and SI had the same propensity to promote AT1R internalization (1.3 nM and 1.5 nM, respectively), DVG was less potent (75 nM). Both SI and DVG promoted less receptor accumulation in endosomes, as compared to AngII (FIG. 6C), although their relative order of potency remained the same as for promoting AT1R internalization. Interestingly, SI and DVG weakly promoted β-arrestin2 trafficking to endosomes with receptors as compared to AngII (FIG. 6D). Together, these finding provide evidence that the different AngII ligands cause distinct AT1R/β-arrestin2 complex sorting.

Figure 9A:
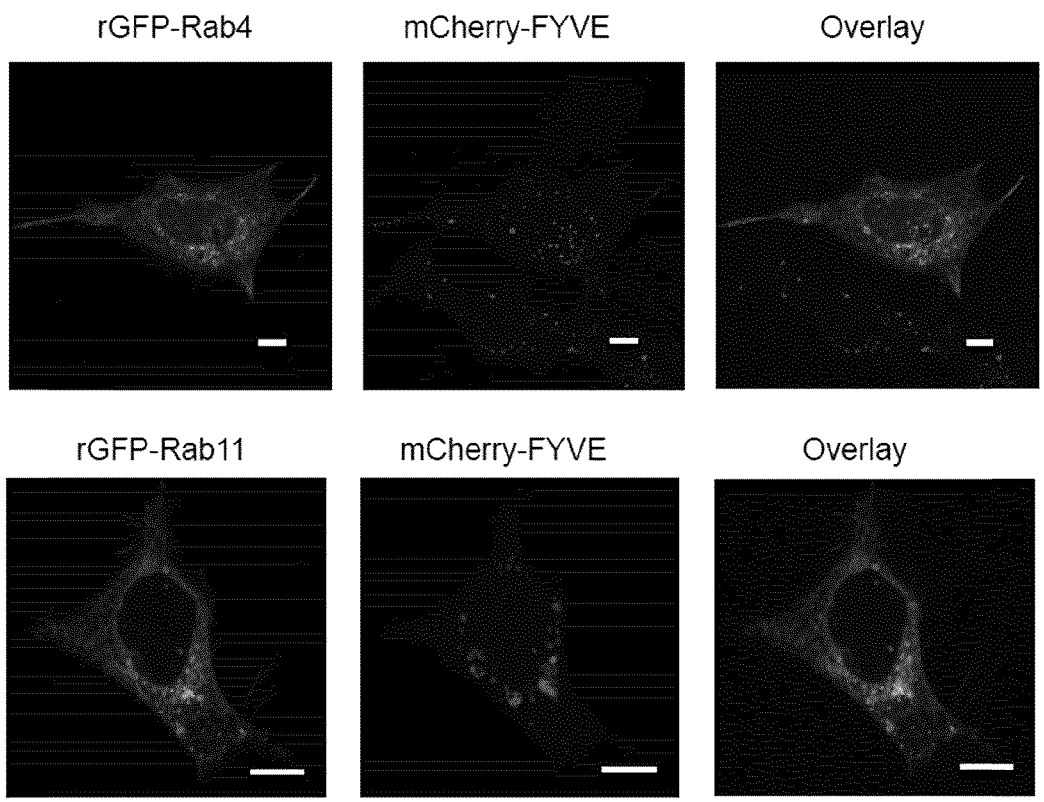
FIG. 9A shows the vesicular localization of rGFP-rab4 and rGFP-rab11 with mCherry-FYVE. HEK293SL cells were transfected either rGFP-rab4 (left) or rGFP-rab11 (right), then subjected to a confocal microscopy.

To test the potential differential intracellular trafficking of AT1R, other BRET-based sensors of endosomes were generated by tagging Rab proteins (Rabs) with rGFP. Rabs coordinate vesicle transport between a number of intracellular compartments and have been used to identify the pathways followed by GPCR trafficking (Seachrist and Ferguson 2003). Rab5 is found on both endocytosed and recycling vesicles of the short cycle, while rab4 is on recycling vesicles of short and long cycles, and rab11 on recycling vesicles of the long cycle and vesicles directed to lysosomes (Seachrist and Ferguson 2003). rGFP-tagged Rab4 (rGFP-rab4) and rab11 (rGFP-Rab11) were generated, since the rGFP-endofinFYVE labelled endosomes are mainly Rab5-positive. Both rGFP-rab4 and rGFP-rab11 showed good vesicular localizations when expressed in HEK293 cells (FIG. 9A). When AT1R-RlucII/rGFP-rab4 expressing cells were incubated with AngII, SI, or DVG, the BRET ratios were increased over time (FIG. 6E). Interestingly, SI and DVG stimulation generated a significantly higher BRET signal than AngII (5 and 10 min, FIG. 6E). At 10 min, the BRET ratio increased by SI and DVG were more than 2-fold of that of AngII. The signals plateaued after 10 min with SI and DVG, and at 30 min with AngII. Similarly to rGFP-rab4, rGFP-rab11 also revealed overall higher BRET signals with SI and DVG, than with AngII (FIG. 6F). Signals from AT1R-RlucII/rGFP-rab11 slowly increased over time as compared to rGFP-rab4, in good agreement with previous findings involving rab4 and rab11 in fast and slow recycling, respectively (Hunyady, Baukal et al. 2002; Li, Li et al. 2008). In both rGFP-rab4 and rGFP-rab11 BRET assays, SI and DVG showed no significant difference. These results provide evidence that SI and DVG drive AT1R into rab4- or rab11-positive vesicles and less into rab5-positive vesicles, relative to AngII.

Figure 9B:
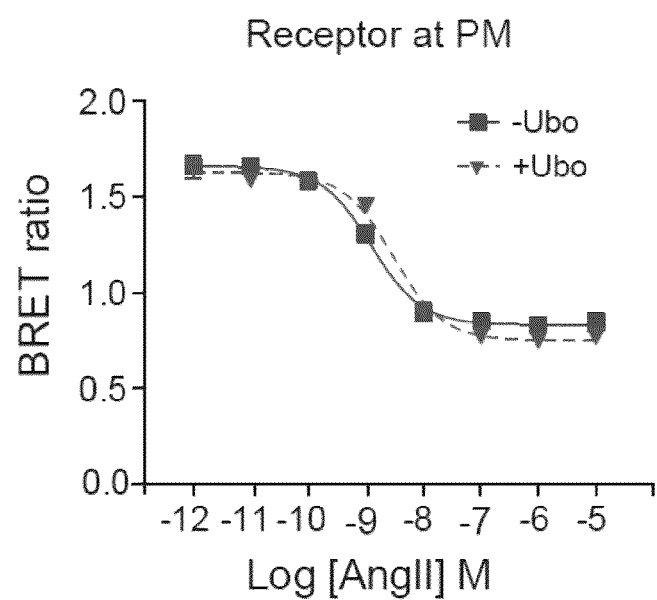
FIGS. 9B to 9D show the effect of Gαq inhibition on AngII-mediated AT1R internalization.
Figure 9C:
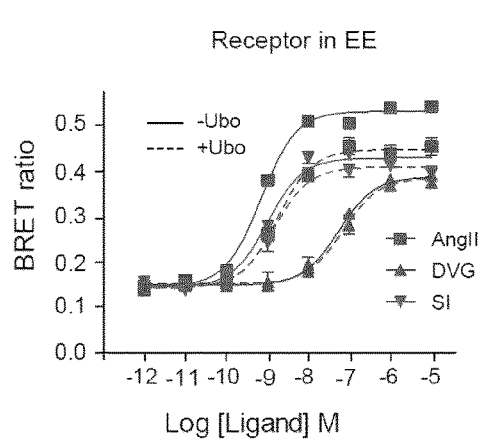
Figure 9D:
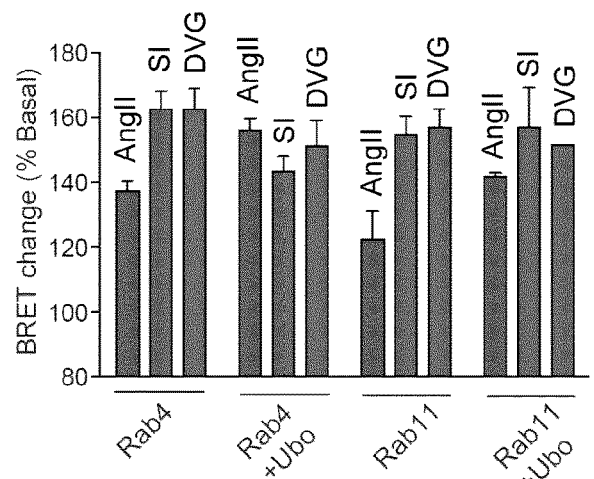

Recent evidence suggests that G proteins play some functions in membrane trafficking, but the role of Gαq in AT1R trafficking is ill studied. The BRET-based sensors was used to assess how inhibiting Gαq affected receptor internalization. Treating cells with Ubo-QIC, an inhibitor that locks specifically Gαq in its inactive state, did not prevent the AngII-dependent AT1R internalization as assessed by the PM EsBRET assay (FIG. 9B). Interestingly however, inhibiting Gαq reduced by more than 25% the targeting of AngII-bound AT1R to Rab5 containing endosomes (FIG. 9C). Consistent with the lack of DVG and SI in activating Gαq, Ubo-QIC had no effect on the ligand-mediated accumulation of receptors in these endosomes. Inhibiting Gαq, increased AngII-bound AT1R in Rab 4 and Rab11 vesicles, whereas it had little effects on the sorting of the receptor to endosomes promoted by either DVG or SI (FIG. 9D). These finding suggest that AT1R sorting can be biased by different ligands.

Figure 10A:
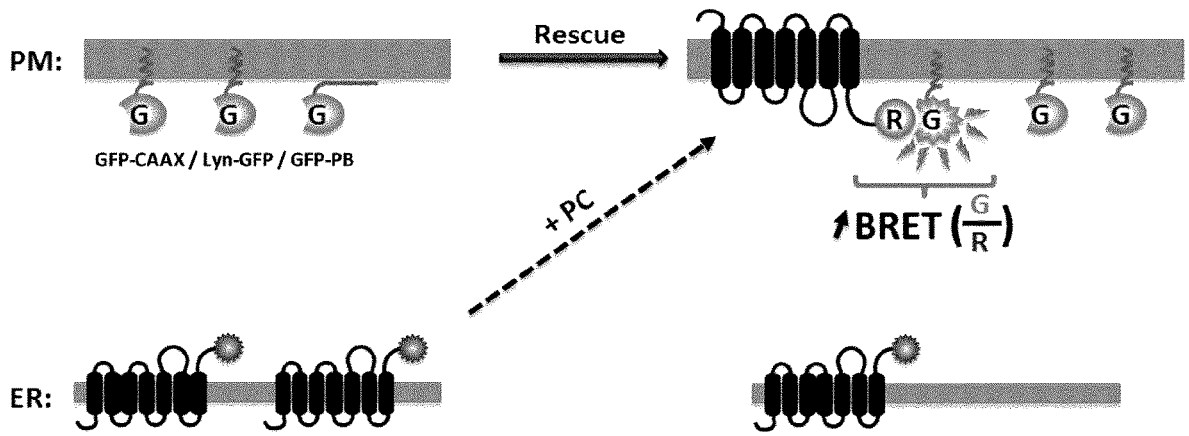
FIGS. 10A and 10B depict the principle of a BRET-based pharmacological chaperone (PC) assay and sequestration assay to assess functional rescue.
Figure 10B:
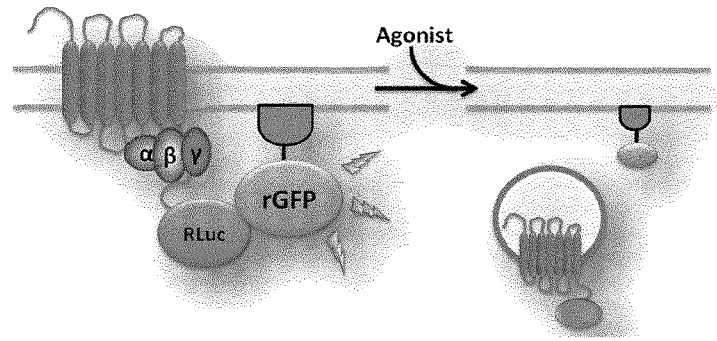

Example 7: BRET-Based Pharmacological Chaperone (PC) Assay and Sequestration Assay to Assess Functional Rescue In order to measure cell surface expression, an assay was developed based on plasma density of an RlucII-tagged protein (in FIG. 10A, a receptor) as detected in BRET between the RlucII-tagged protein and an energy acceptor (rGFP) located at the plasma-membrane by a subcellular localization tag. In FIG. 10A, examples of tags used for rGFP localization: the polybasic sequence and prenylation signal sequence from KRAS splice variant b (CAAX), the palmitoylation and myristoylation signal sequence from the Lyn kinase (Lyn) and plasma-membrane targeting polybasic sequence from the human GRK5 (PB). A schematic representation of an assay for evaluation of cell surface expression PC-rescue of otherwise ER-retained proteins tagged with RlucII is presented and described in FIG. 10A. A BRET-based assay to evaluate cell surface expression can also be used to evaluate agonist-induced sequestration of receptors as depicted and described in FIG. 10B. Most of GPCRs and other receptors internalize or are sequestered to sub-domains of the plasma-membrane upon agonist stimulation. A sequestration assay post PC-rescue of cell surface expression of receptors can be used to evaluate receptor activation, which reflects agonist binding and thus functionality. The different constructs used in this study are described in FIG. 11; FIG. 11A: description of MC4R-RlucII; FIG. 11B: description of V2R-RlucII, FIG. 11C: description of a voltage-gated Potassium channel (hERG) that was used as an example of a non-GPCR. Three different rGFP constructs with distinct plasma-membrane targeting sequences were tested as described in FIG. 11D. For most of the assays presented, the rGFP-CAAX and MC4R-RlucII constructs were used to illustrate the robustness of the assay, resistance to DMSO and functional rescue, as evaluated by using a MC4R agonist (α-MSH) to induce agonist-promoted sequestration.

Figure 12A:
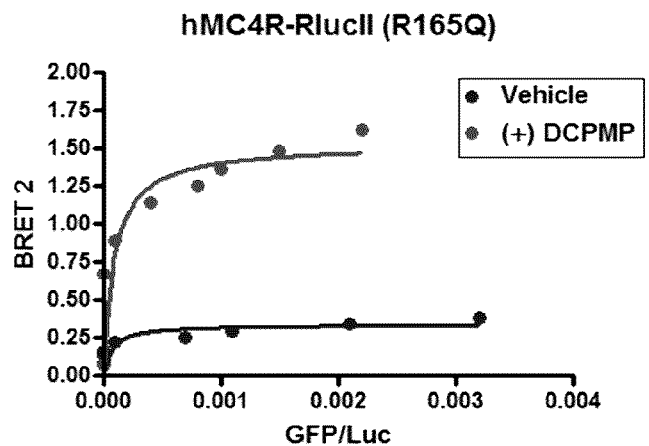
FIGS. 12A and B show the testing of different ratios (titration) of two forms of rGFP targeted to the plasma membrane. Titrations of BRET donor to acceptor and PC-rescue assay were performed on transfected cells (variable amount of rGFP construct+24 ng of receptor construct for 10 wells of a 96-well plate), following a 16 h treatment with either a chaperone: (DCPMP (N-((2R)-3(2,4-dichloroPhenyl)-1-(4-(2-((1-methoxypropan-2-ylamino)methyl)phenyl) piperazin-1-yl)-1-oxopropan-2-yl)propionamide), 10 μM) or vehicle (DMSO). HEK293 were transfected with hMC4R (R165Q)-RlucII construct and different quantities of rGFP-CAAX (FIG. 12A); and rGFP-PB construct (FIG. 12B). The BRET ratio is reported in function of GFP-construct expression (evaluated in fluorescence) over RlucII construct expression (evaluated in bioluminescence).
Figure 12B:
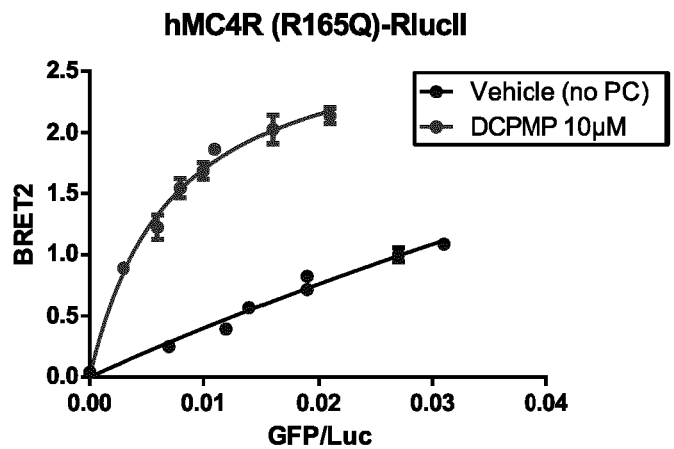

For optimization of the cell surface expression assay, two different plasma-membrane targeting sequences were tested for rGFP (constructs and tags described in FIG. 11D); the KRAS fragment-tag is targeted to the plasma-membrane by a combination of lipidation (rGFP-CAAX; prenylation) and a polybasic domain and the GRK5 fragment-tag is targeted to the plasma membrane by a polybasic domain (rGFP-PB), not requiring a lipidation of the rGFP fusion protein. In FIG. 12, titrations of the two rGFP constructs (FIG. 12A=rGFP-CAAX and FIG. 12B=rGFP-PB) were obtained from cells transiently expressing the mutant hMC4R (R165Q)-RlucII. As shown in FIG. 12A, a DCPMP-treatment leads to saturable BRET response for rGFP-CAAX, and this construct was selected for the subsequent experiments.

Figure 13A:
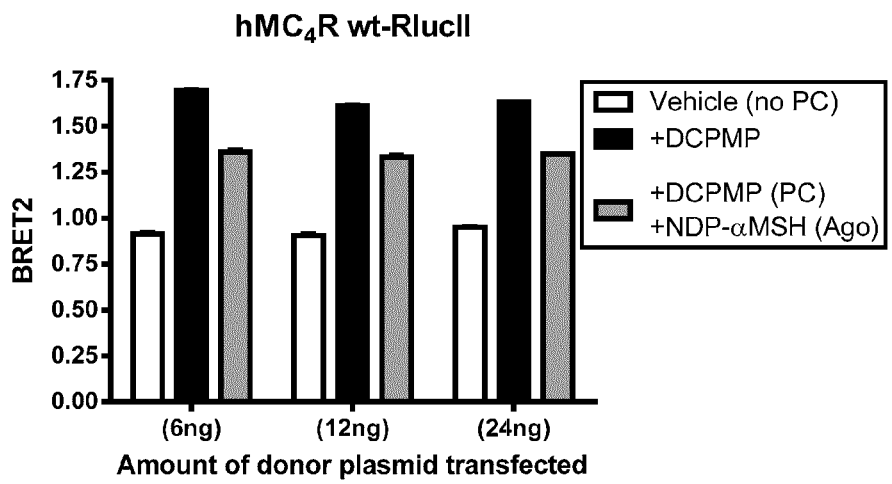
FIGS. 13A to C show the cell surface expression and functional PC-mediated rescue of wt and mutant MC4R at different ratios of receptor and rGFP-CAAX. HEK293 were co-transfected with an rGFP-CAAX construct (72 ng of plasmid for 10 wells of a 96-well plate) and 3 different quantities (as indicated on the graphs: 6, 12 and 24 ng for 10 wells) of hMC4R wt-RlucII (FIG. 13A); hMC4R (P299H)-RlucII (FIG. 13B); and hMC4R (R165Q)-RlucII (FIG. 13C). The PC-mediated rescue of cell surface expression and functionality (agonist-induced sequestration) was evaluated in BRET2, on transfected cells, following a 16 h-treatment with either a chaperone: (DCPMP, 10 µM; solid black and grey bars) or vehicle (DMSO; white bars). The grey bars represent data obtained from DCPMP-treated cells, exposed 1 h to an agonist (alpha-MSH) to induce receptor sequestration. As expected, DCPMP-treatment induces an increase in cell surface expression, as revealed by an increase in BRET signal, compared to non-treated cells (with bars). Agonist-treatment induces sequestration as revealed by a decrease in BRET signal (grey bars) as compared to cells treated with DCPMP but not exposed to an agonist (black bars). The wt (FIG. 13A) and R165Q mutant (FIG. 13C) receptors were sensitive to both DCPMP and α-MSH (10 µM, 1 h at 37C) while the P299H mutant MC4R was not PC-rescued (FIG. 13B). The optimal window for this assay is already obtained at 6 ng of donor and, increasing the quantity of transfected donor construct did not lead to a measurable rescue of hMC4R (P299H).
Figure 13B:
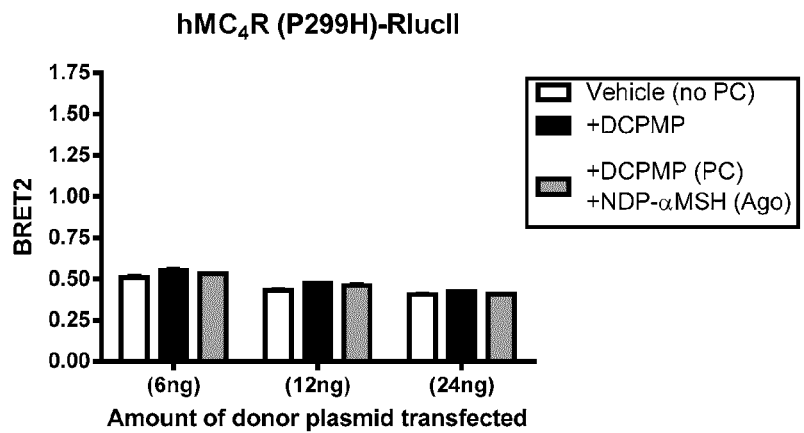
Figure 13C:
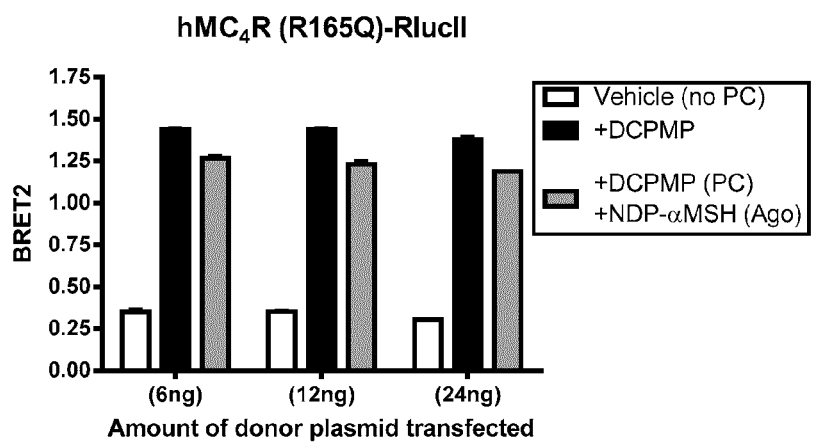
Figure 13D:
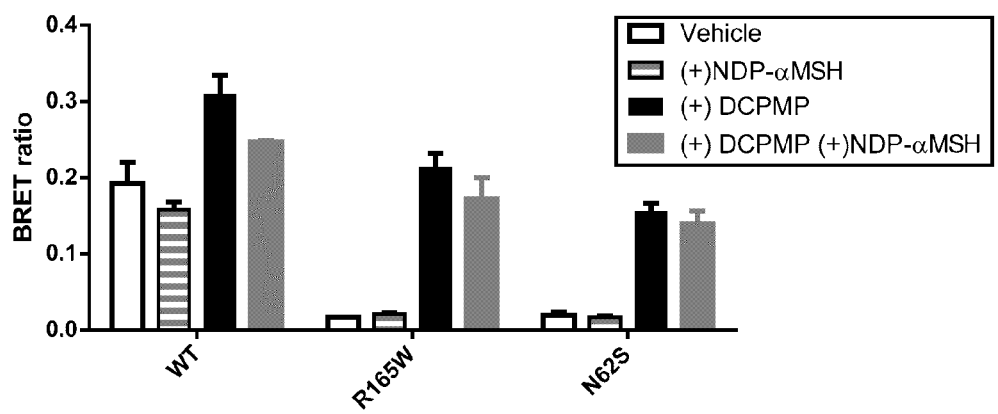
FIG. 13D shows polycistronic constructs encoding rGFP-CAAX(Kras) and either a WT or mutant hMC4R were transiently expressed in Hek293 cells. This figure shows that similar results for PC rescue of cell surface expression (white bars: DMSO vs. black bars: 10 µM DCPMP) and functionnal rescue can be obtained, as measured by agonist-induced sequestration (+alpha-MSH; grey bars), from polycistronic and non-polycistronic constructs (FIGS. 13A-C). Agonist-induced sequestration for cells not pretreated with a chaperonne is presented (hashed-bars).
Figure 13E:
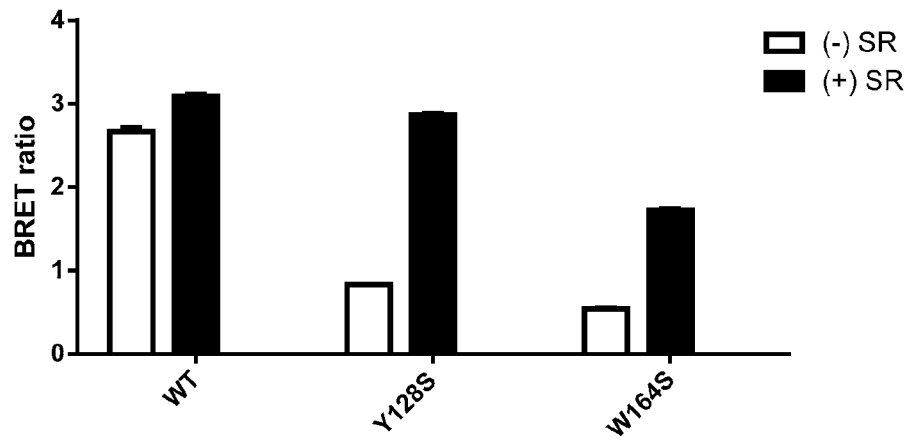
FIG. 13E shows the PC-mediated rescue of V2R mutants known to be intracellularly retained, as evidenced by the increase in BRET at the plasma membrane. The PC-mediated rescue of cell surface expression was evaluated in BRET1, on transfected cells, following a 16 h-treatment with either a chaperone: (SR121463, 10 µM; solid black bars) or vehicle (DMSO; white bars).

For optimization and validation of PC-mediated rescue of the cell surface expression and functionality of MC4R, cells transiently expressing rGFP-CAAX and 3 forms of the hMC4R, the wt receptor (hMC4R wt-RlucII), a PC rescuable mutant MC4R (hMC4R-R165Q-rlucII) and a mutant MC4R known as resistant to DCPMP-treatment (non PC-rescuable), were tested for cell surface expression following PC treatment and a 1 h-agonist treatment to induce agonist-mediated sequestration. Three different ratios receptor to rGFP-CAAX were tested. As shown, DCPMP-treatment led to an increase in BRET signal for the WT and R165Q MC4R but not for the P299H-mutant MC4R. Both wt and R165Q mutant MC4R expressed at the cell surface post-DCPMP treatment showed agonist-induced sequestration as described in FIGS. 13A to C. The condition equivalent to 24 ng of plasmid DNA per 10 wells of a 96-well plate was selected for the subsequent assays. FIG. 13D shows that the different components of the biosensors may be encoded and co-expressed from the same mRNA (polycistronic construct). Polycistronic constructs encoding rGFP-CAAX (Kras) and either a WT or mutant hMC4R was used to show the PC rescue of cell surface expression. Polycistronic constructs offer the advantage of a fixed ratio of donor to acceptor and the possibility of using only one construct for viral infection or for establishing stable cell lines. FIG. 13E shows the PC-mediated rescue of V2R mutants known to be intracellularly retained (Y128S and W164S) by the chaperone SR121463.

Figure 14A:
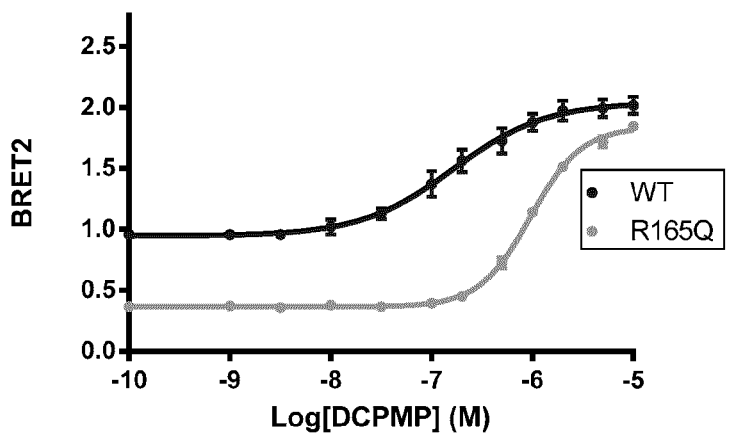
FIGS. 14A and 14B show dose-response curves for 2 PC-mediated functional rescue of WT and mutant (R165Q) MC4R cell surface expression. HEK293 were co-transfected with an rGFP-CAAX construct and, the hMC4R wt-RlucII or hMC4R (R165Q)-RlucII constructs (72 ng of rGFP construct+24 ng of receptor construct for 10 wells of a 96-well plate). Dose-responses of PC-mediated rescue of cell surface expression, following a 16 h-treatment with variable concentrations of DCPMP (FIG. 14A) and with Compound 1 (FIG. 14B), were evaluated in BRET2. Results obtained with hMC4R wt-RlucII (upper curves) or hMC4R (R165Q)-RlucII (lower curves) are reported in function of the chaperone concentration expressed in a logarithmic scale. EC50 and other curve parameters are indicated below each graph.
Figure 14B:
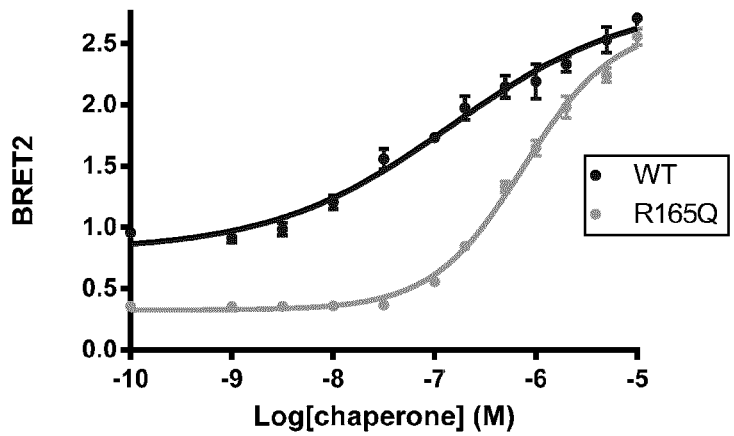

Example 8: BRET-Based Cell Surface Expression Assay Can Be Used for Pharmalogical Evaluation of Chaperone Potency and Efficacy In order to verify whether this assay could be used to characterize drugs with PC properties, dose-response curves were obtained with 2 different PC (DCPMP and Compound 1) treatment of cells coexpressing rGFP-CAAX and either the hMC4R wt-RlucII construct or the hMC4R (R165Q)-rlucII construct (FIG. 14). Characteristics of the dose-response curves were compatible with data obtained with a previously described FACS-based assay (P. René et al. *J Pharmacol Exp Ther.* 2010 December; 335(3):520-32), indicating that the BRET-based assay can be used to characterize ligands.

Figure 15A:
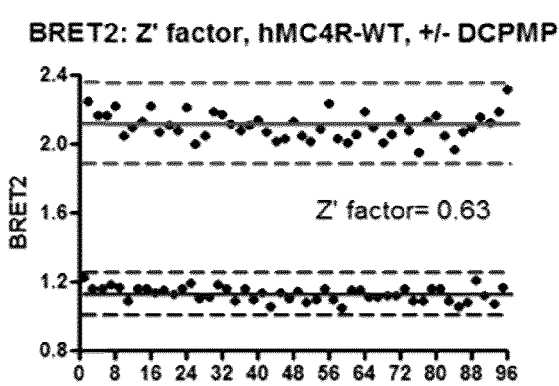
FIGS. 15A to 15D show the assessment of Z' factor as an indication of robustness of the assay. HEK293 were co-transfected with an rGFP-CAAX construct and, the hMC4R wt-RlucII (FIGS. 15A and 15B) or hMC4R (R165Q)-RlucII (FIGS. 15C and 15D) constructs (72 ng of rGFP construct+ 24 ng of receptor construct for 10 wells of a 96-well plate). Cell surface expression was evaluated in BRET2 in FIGS. 15A and 15C using coelenterazine 400a, and in BRET1 using coelenterazine H (FIGS. 15B and 15D) following a 16 h-treatment with 10 µM DCPMP (48 wells) vs. vehicle (DMSO) (48 wells). BRET values are expressed per well in the presented graphs and Z' factor evaluated over 0.63 with the hMC4R wt receptor and over 0.82 with the mutant R165Q mutant hMC4R, which indicates a robust assay with both receptors.
Figure 15B:
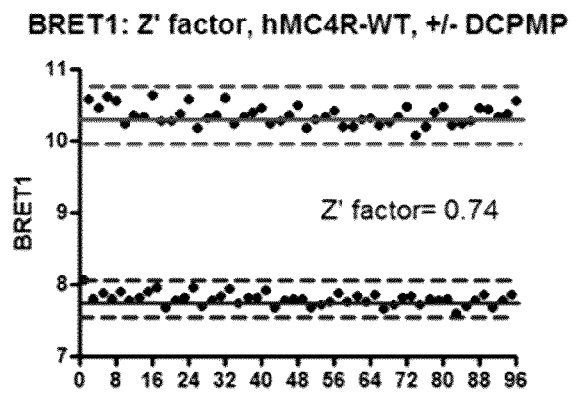
Figure 15C:
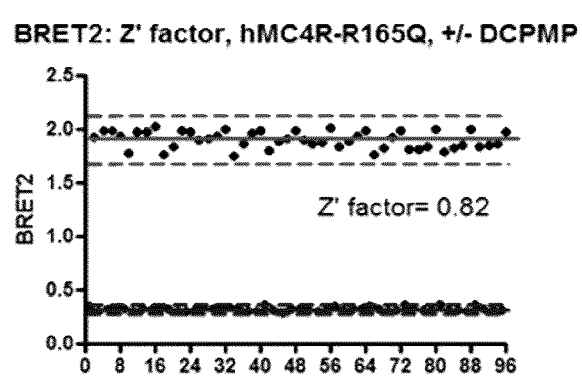
Figure 15D:
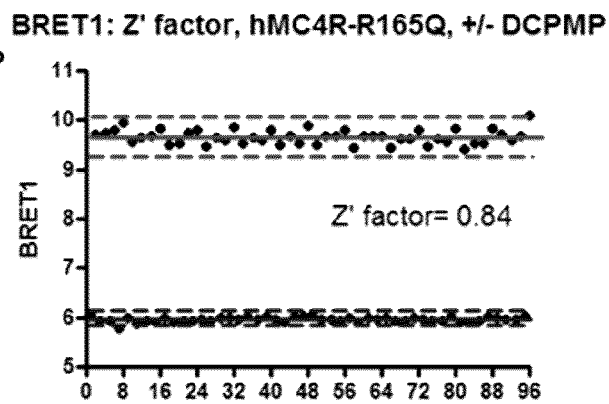
Figure 16A:
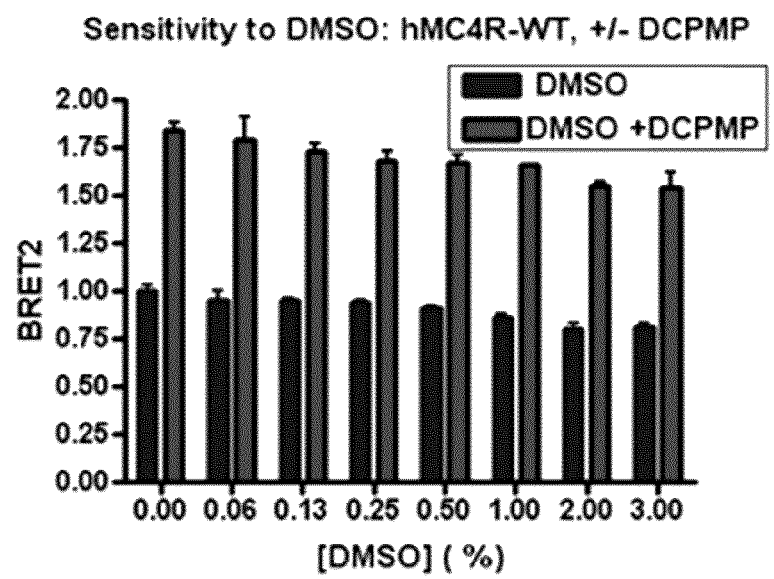
FIGS. 16A and 16B show the assessment of the impact of DMSO on the BRET-based cell surface expression assay. HEK293 were co-transfected with an rGFP-CAAX construct and, the hMC4R wt-RlucII (FIG. 16A) or hMC4R (R165Q)-RlucII (FIG. 16B) constructs (72 ng of rGFP construct+24 ng of receptor construct for 10 wells of a 96-well plate). Cell surface expression was evaluated in BRET2, following a 16 h-treatment with 10 µM DCPMP (right bars) or vehicle (DMSO, left bars) in presence of an increasing concentration of DMSO (up to 3%) during the PC-treatment, in order to evaluate whether the BRET-based assay for cell surface evaluation is sensitive to different levels of DMSO. As presented, the results obtained indicate that this assay is resistant to at least 3% DMSO, which is compatible with HTS applications and characterization of compounds.
Figure 16B:
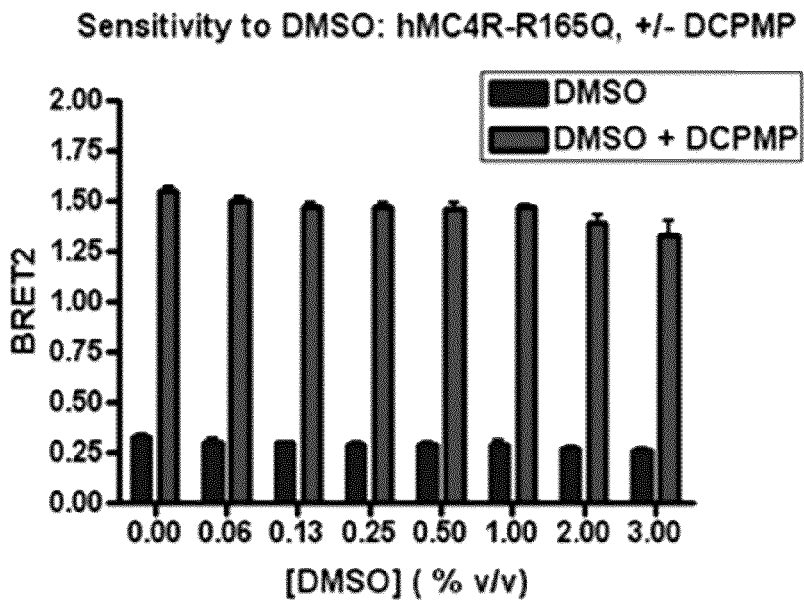
Figure 17A:
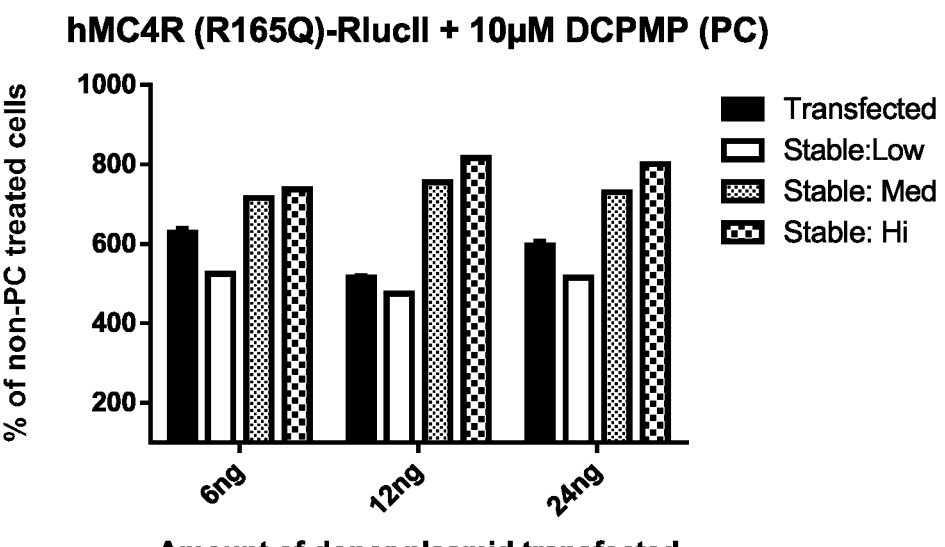
FIGS. 17A and 17B show PC-mediated rescue of MC4R and V2R expression in transfected and stable rGFP cell lines. HEK293 were co-transfected with an rGFP-CAAX construct (72 ng of plasmid for 10 wells of a 96-well plate) and 3 different quantities (as indicated on the graphs: 6, 12 and 24 ng for 10 wells) of hMC4R (R165Q)-RlucII (FIG. 17A) or in hV2R (Y128S)-RlucII (FIG. 17B). HEK293 cells selected for stably expressing different levels of rGFP-CAAX (low, medium (Med) & high (Hi)) were transfected with the same quantity of receptor constructs. The PC-mediated rescue of cell surface expression for MC4R was evaluated in BRET2, following a 16 h-treatment with 10 µM DCPMP, and for the V2R (Y128S)-RlucII expressing cells with the SR121463 chaperone (a known antagonist with inverse agonist and pharmalogical chaperone properties; Serradeil-Le Gal C., Cardiovasc Drug Rev. 2001, 19(3): 201-14) at 10 µM or vehicle (DMSO). The data is presented for the MC4R and V2R expressing cells as a % of BRET signal observed with cells treated with vehicle (DMSO). The presented data indicates that a better response can be obtained with stable cell lines expressing higher levels of rGFP-CAAX. The stable cell line expressing high levels of rGFP-CAAX (Stable:Hi) could be used to establish cell lines co-expressing a receptor-RlucII.
Figure 17B:
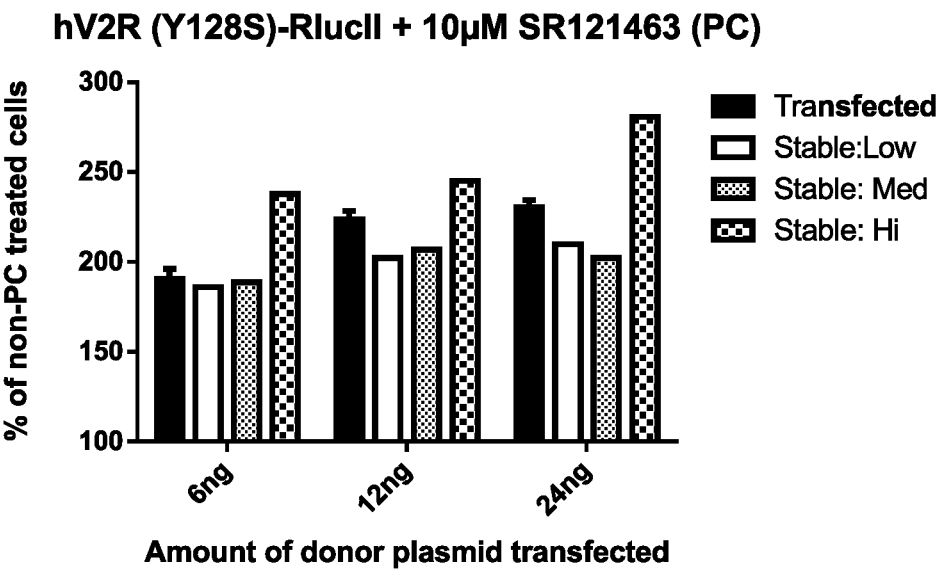

Z'-factors were determined for the PC-mediated rescue of MC4R cell surface expression, to evaluate the robustness of the developed BRET-based assay. Z' factors were obtained for both hMC4R wt-RlucII (FIGS. 15A and 15B) and hMC4R (R165Q)-RlucII (FIGS. 15C and 15D). Cell surface expression was evaluated in BRET2 in FIGS. 15A and 15C using coelenterazine 400a, and in BRET1 using coelenterazine H (FIGS. 15B and 15D) following a 16 h-treatment with 10 µM DCPMP vs. vehicle. Z' factor were evaluated to over 0.63 with the hMC4R wt receptor and over 0.82 with the mutant R165Q mutant hMC4R. The results show that the robustness of this assay is compatible with the requirements of screening applications, even with the WT MC4R.

Example 9: Evaluation of Resistance to DMSO

Libraries of ligands and compounds are often dissolved in DMSO. To evaluate whether the BRET-based assay for cell surface evaluation is sensitive to concentrations of DMSO usually reached with dose-response curves of ligands selected from library of compounds, hMC4R wt-RlucII and hMC4R (R165Q)-RlucII expressing cells were DCPMP-treated at 10 uM or with vehicle (DMSO) in well containing different concentrations of DMSO. As indicated in FIG. 16, this assay is resistant to at least 3% DMSO, which is compatible with high throughput screening (HTS) applications and characterization of compounds in dose-response curves.

Example 10: Generation of Stable Cell Lines

Cells stably expressing biosensors are usually preferred for screening purposes. PC-mediated rescue of MC4R and V2R expression was then evaluated in cells transiently expressing rGFP-CAAX and in stable rGFP-CAAX cell lines, in order to determine if the level of rGFP-CAAX reached in stable cell lines is compatible with a robust assay for screening applications. 3 different amounts (as indicated on the graphs: 6, 12 and 24 ng for 10 wells) of hMC4R (R165Q)-RlucII (FIG. 16A) or in hV2R (Y128S)-RlucII (FIG. 16B) were transfected in stable lines expressing different levels of rGFP-CAAX (low, med, high) or co-transfected in HEK293 cells along with the rGFP-CAAX construct in order to test different ratios of BRET donor to acceptor. The PC-mediated rescue of cell surface expression for MC4R was evaluated in BRET2, as indicated in FIG. 17. The data presented indicates that better responses can be obtained with stable cell lines expressing higher levels of rGFP. These stable cell lines could be used to establish cell lines expressing both receptor-RlucII and rGFP-CAAX, which would be useful for screening applications.

Figure 18A:
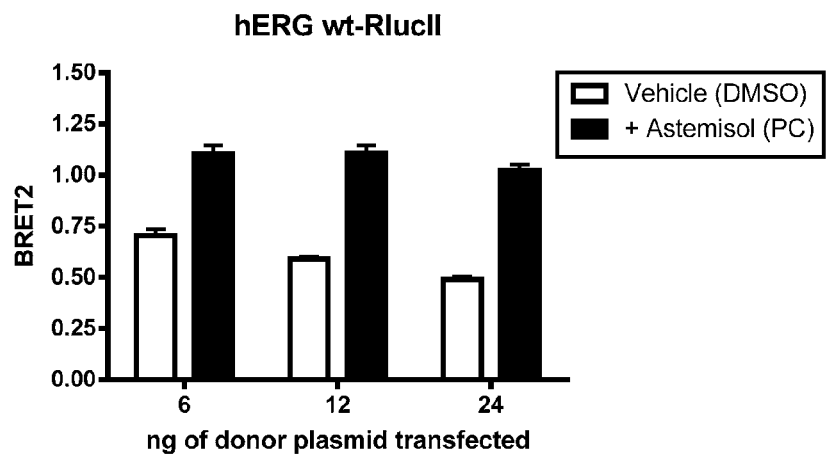
FIGS. 18A to 18E: PC-rescue assay for detecting ligands of hERG channel (a non-GPCR). Cell-surface expression and functionnal PC-mediated rescue of wt (FIG. 18A) and mutant (G601S.
Figure 18B:
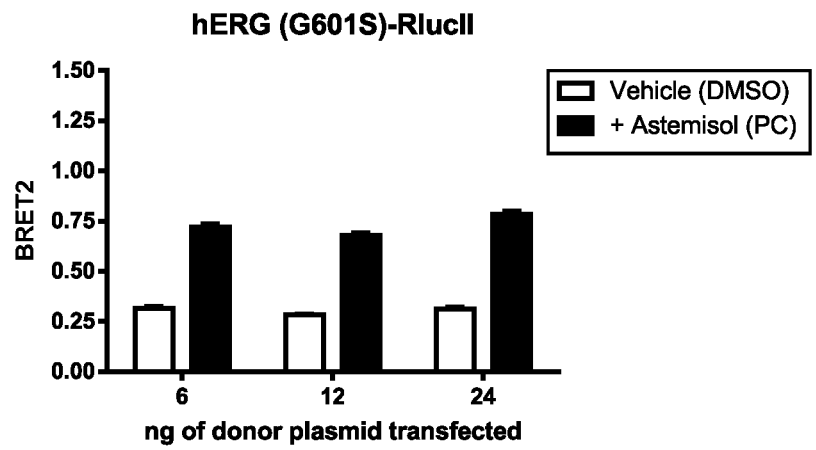
Figure 18C:
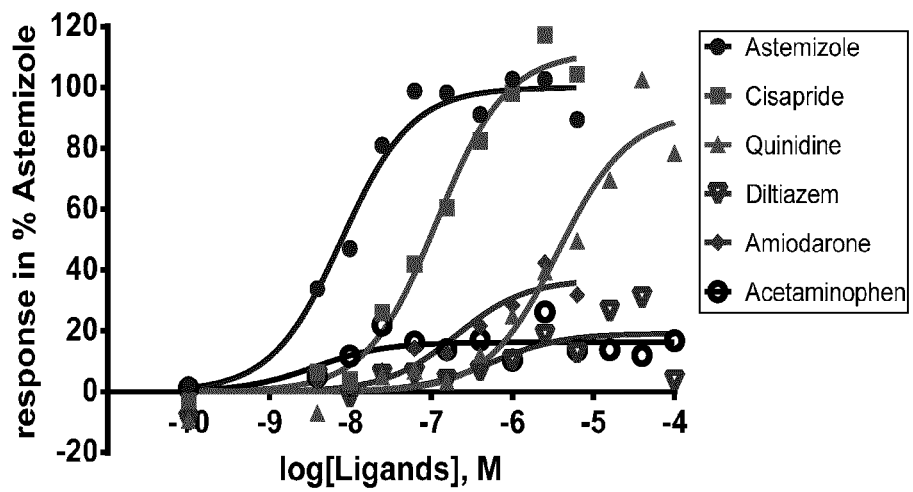
Figure 18D:
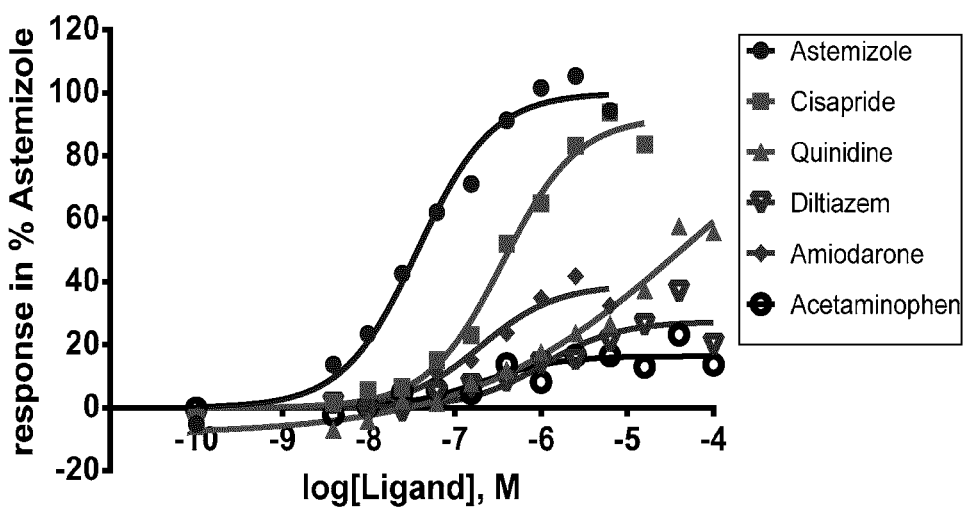
Figure 18E:
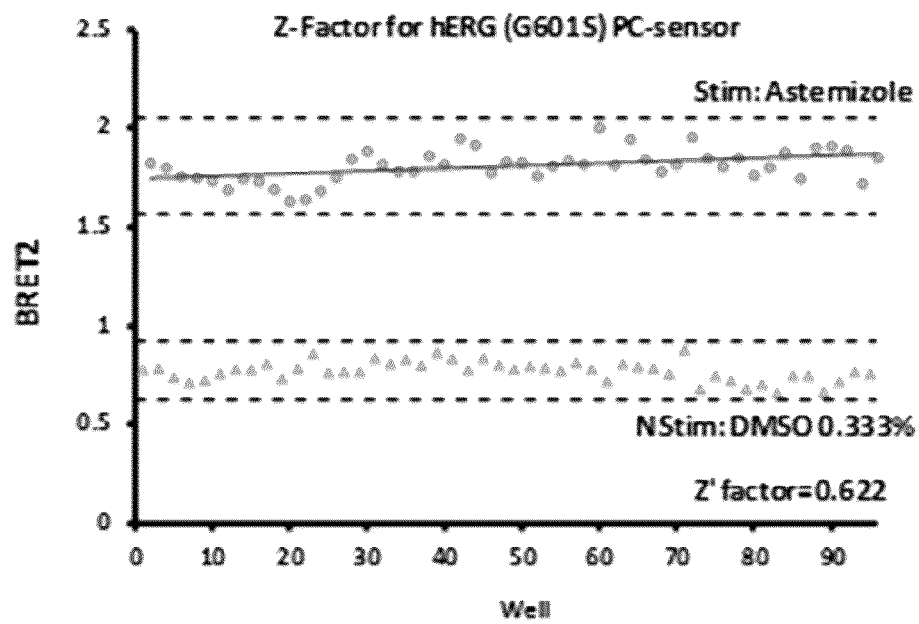

Example 11: Biosensors to Detect the PC-Mediated Cell Surface Rescue of an Ion Channel In order to verify whether a BRET-based PC-mediated cell surface expression assay could be used to identify and characterize drugs that would bind hERG, RlucII-tagged constructs were created using the WT sequence of hERG and a known intracellularly retained mutant (G601S) and tested for Astemizole-mediated rescue of cell surface expression (FIGS. 18A and B). Dose-response curves were obtained with the wt-hERG (FIG. 18C) and mutant (FIG. 18D) constructs, for drugs that are known to act as ligands and pharmalogical chaperones on hERG with different efficacy and potency. Characteristics of the dose-response curves were compatible with data obtained with an ELISA-based assay (HERG-Lite: Wible B A et al. *J Pharmacol Toxicol Methods.* 2005, 52(1):136-45). The Z' factor obtained using the hERG-(G601S) (FIG. 18E) indicates that this BRET-based assay is robust and could be used for high throughput application such as HTS to identify hERG chaperones capable of rescuing cell surface expression of different naturally occuring mutant hERG or to identify drugs that could have off-target effects mediated throug hERG binding.

Example 12: Biosensors to Monitor β-Arrestin Recruitment to GPCRs

Figure 19A:
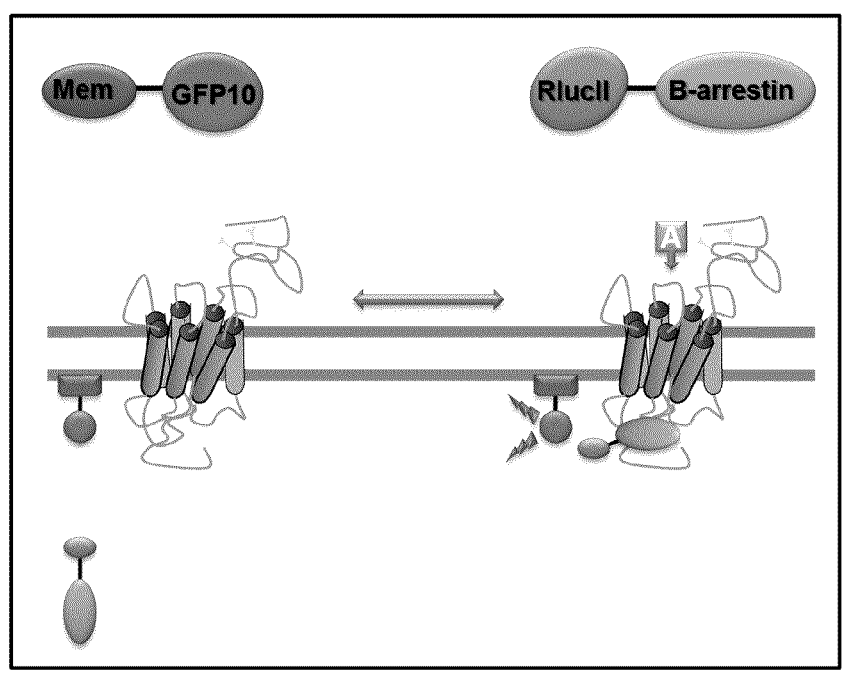
FIG. 19A shows the configuration of a biosensor for monitoring β-arrestin recruitment to a GPCR at the plasma membrane. A BRET acceptor (e.g., rGFP, GFP10) is tagged with a PM targeting moiety (thus tethering the BRET acceptor at the PM), and a β-arrestin is tagged with a BRET donor (e.g., RlucII). In the presence of a GPCR agonist (represented by A), β-arr is recruited to the GPCR, thus increasing the concentration of RlucII-β-arr at the plasma membrane, which in turn results in an increase in energy transfer (BRET) between RlucII and the PM-tagged GFP.

It was next tested whether it is possible to monitor β-arrestin (β-arr) recruitment to GPCRs (i.e. to the plasma membrane where GPCRs are localized) using a BRET biosensor that rely on changes in the concentration/density of the donor relative to the acceptor at the plasma membrane. As shown in FIG. 19A, a BRET acceptor (e.g., GFP) is tagged with a PM targeting moiety (thus tethering the BRET acceptor at the PM), and a β-arrestin is tagged with a BRET donor (e.g., RlucII). In the presence of a GPCR agonist, β-arr is recruited to the GPCR, thus increasing the concentration of RlucII-β-arr at the plasma membrane, which in turn results in an increase in energy transfer (BRET) between RlucII and the PM-tagged GFP.

Figure 19B:
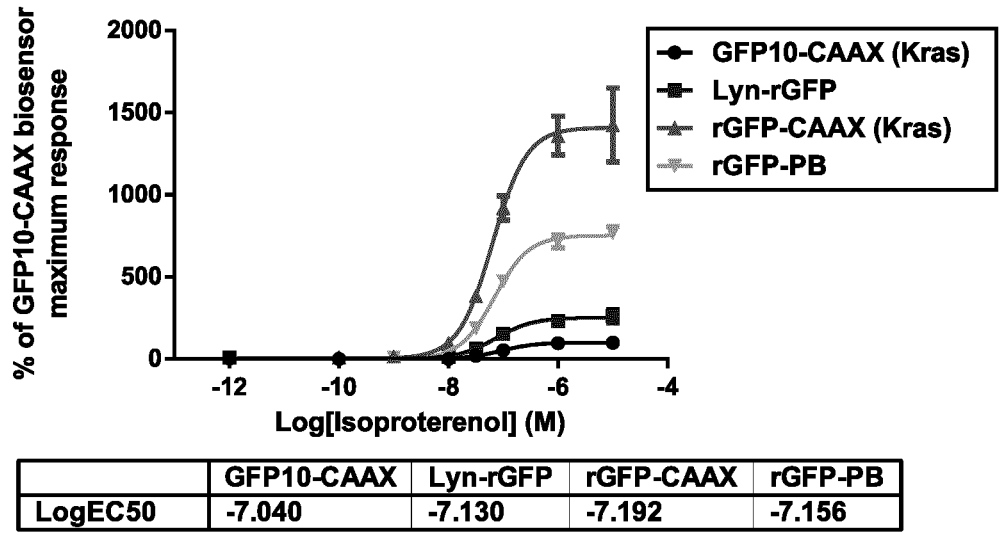
FIGS. 19B and 19C show the increase in the BRET ratio for the recruitment of β-arrestin$_1$ and β-arrestin$_2$, respectively, at the class A GPCR β2AR, for different PM-targeting moieties (Lyn, CAAX and PB-GRK5) and BRET acceptors (rGFP and GFP10), following stimulation with increasing doses of the agonist isoproterenol (iso). The β-arrestin-RlucII translocation sensor with rGFP-CAAX (squares) offers the best window with both receptors.
Figure 19C:
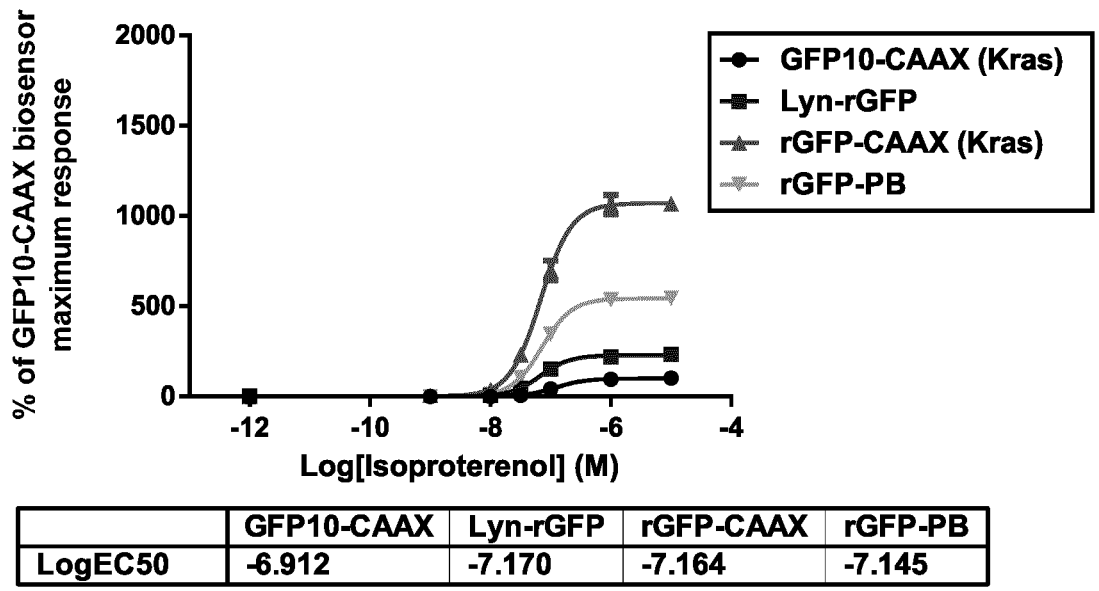
Figure 19D:
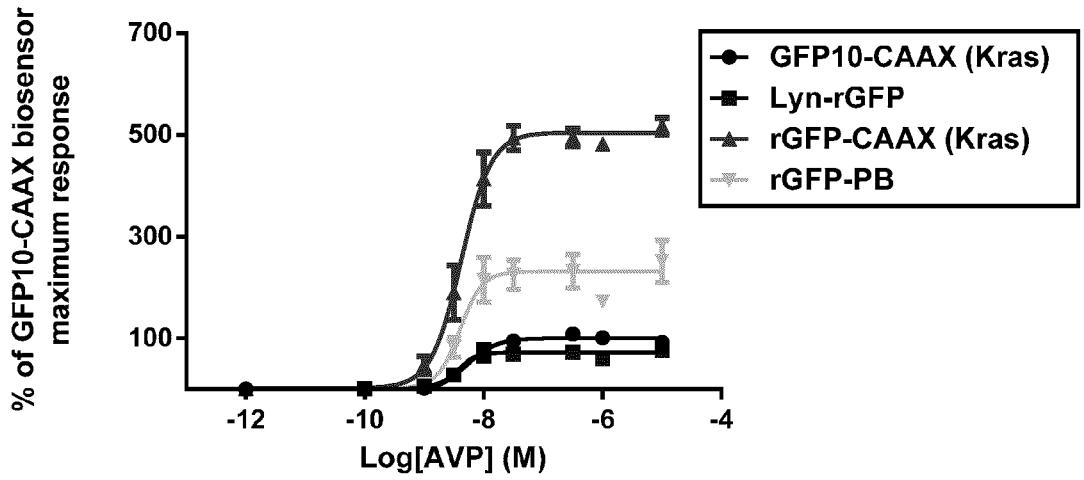
FIGS. 19D and 19E show the increase in the BRET ratio for the recruitment of β-arrestin$_1$ and β-arrestin$_2$, respectively, at the class B GPCR V$_2$R, for different PM-targeting moieties (Lyn, CAAX and PB-GRK5) and BRET acceptors (rGFP and GFP10), following stimulation with increasing doses of the agonist AVP.
Figure 19E:
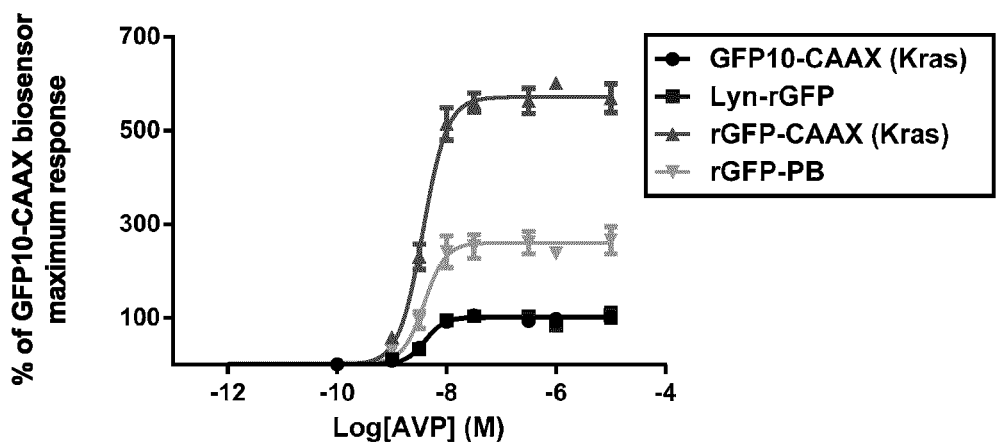

FIGS. 19B and 19C show the increase in the BRET ratio for β-arrestin$_2$ (FIGS. 19B and 19D) and β-arrestin$_2$ (FIGS. 19C and 19E) with two different GPCRs, a class A receptor that has lower affinity for β-arrestin: β$_2$AR (FIGS. 19B and 19C) and a class B receptor that has higher affinity for β-arrestin: V$_2$R (FIGS. 19D and 19E), following stimulation with increasing doses of isoproterenol (iso) and AVP, respectively. The results show that a suitable BRET signal is obtained using different PM targeting moieties (including a non-lipid based targetting moiety such as the polybasic domain of GRKS) and different BRET acceptors, and the best signal being obtained using the CAAX (Kras) PM targeting moiety and rGFP as the BRET acceptor (triangles).

Figure 19F:
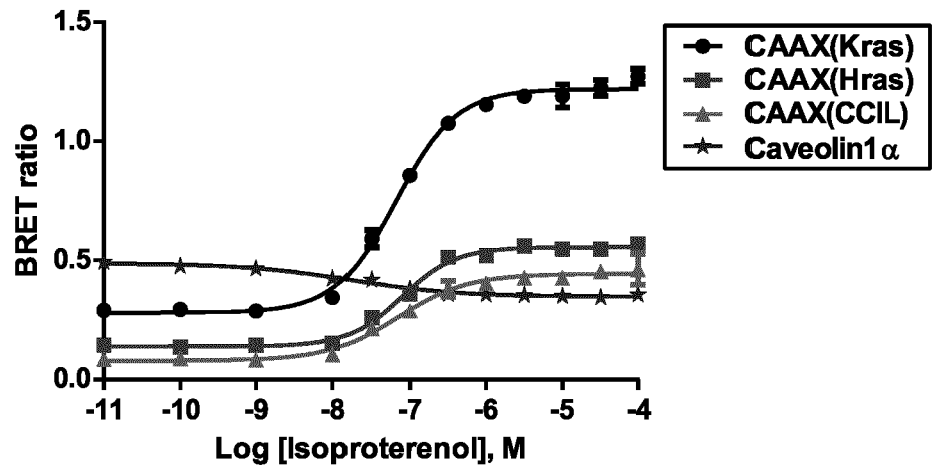
FIG. 19F shows the recruitment of β-arrestin$_2$ to β2AR following stimulation with increasing doses of the agonist isoproterenol (iso), as assessed using different PM-targeting moieties (CAAX from Kras, CAAX from Hras, the plasma-membrane targetting palmitoylation sequence from hRas and prenylation signal sequence from Ral1 (CCIL) and the marker of the caveolae structures Caveolin1α tagged with rGFP. The β-arrestin-RlucII translocation sensor with rGFP-CAAX (squares) show an increase of density at the plasma-membrane. In contrast to the response obtained with the rGFP-CAAX markers, a stimulation of β2AR lead to a decrease in density of β-arrestin$_2$ at the caveolae.
Figure 19G:
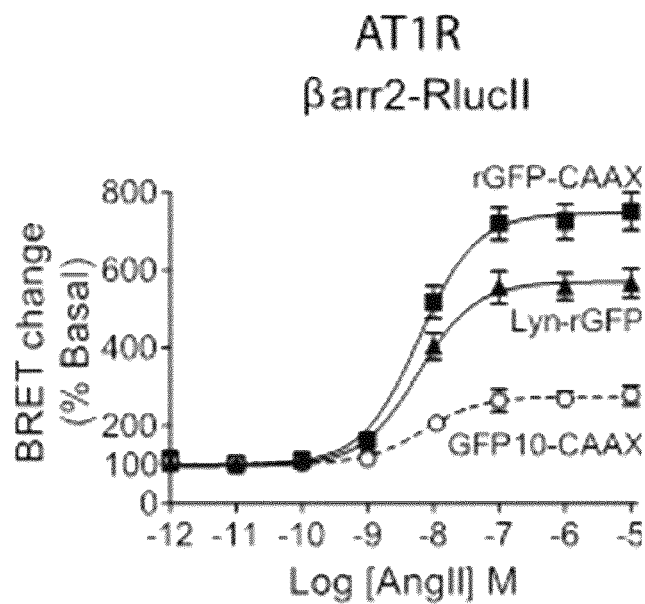
FIG. 19G shows dose-response curves for translocation of βarrestin2 at the plasma membrane after AT1R stimulation. HEK293SL cells were transfected with AT1R and βarr2-RlucII along with either Lyn-rGFP, or rGFP-CAAX or GFP10-CAAX. Cells were incubated with various concentrations of AngII for 6 min at room temperature before BRET measurements. Data are expressed as percent basal BRET. Data are the means±S.E. of 3 independent experiments.
Figure 19H:
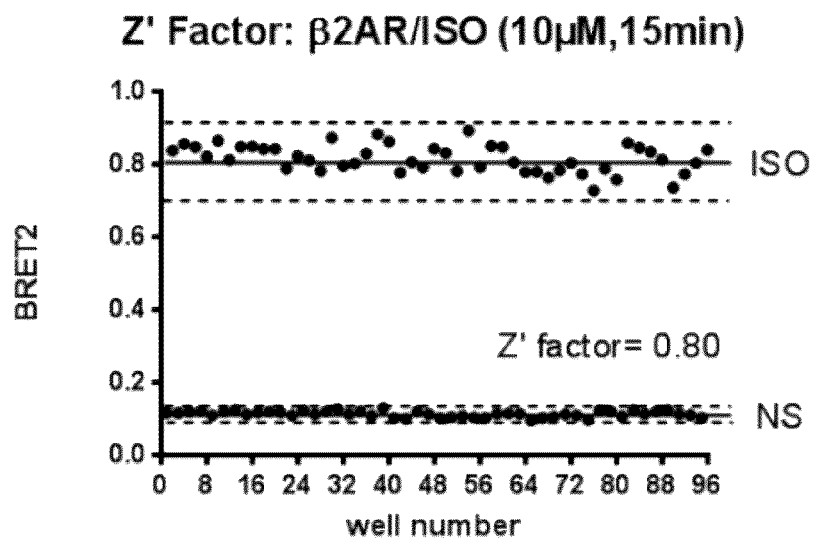
FIGS. 19H-19J show the Z' factors obtained for the βarrestin$_2$-RlucII/rGFP-CAAX biosensor and receptors of FIGS. 19C, 19E and 19G, respectively. This assay, to monitor receptor-mediated βarrestin recruitment, results in Z' factors of at least 0.74 (0.74, 0.80 and 0.838), which would be amenable to screening (including high-throughput screening) applications for both class A and B GPCRs.
Figure 19I:
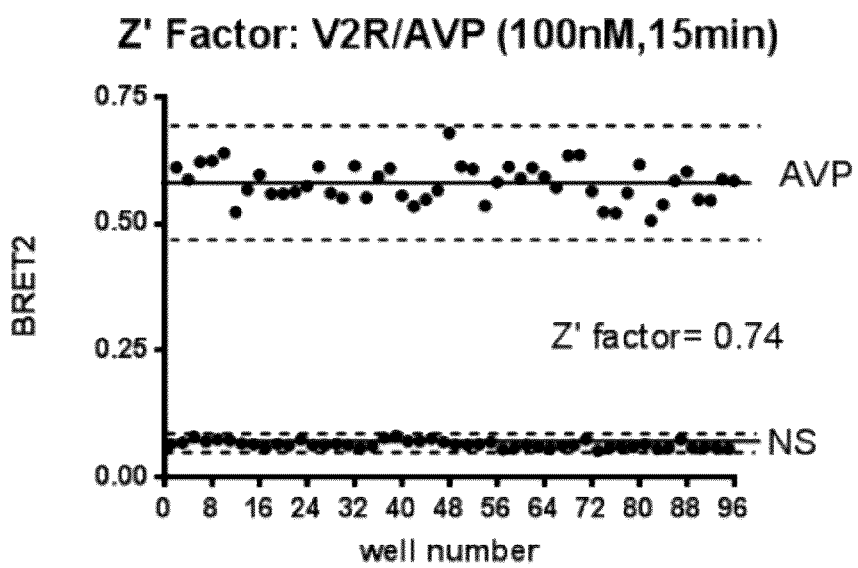
Figure 19J:
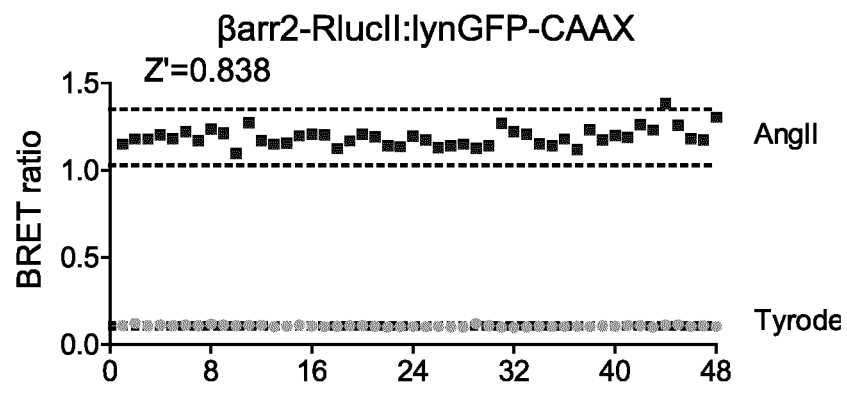
Figure 21C:
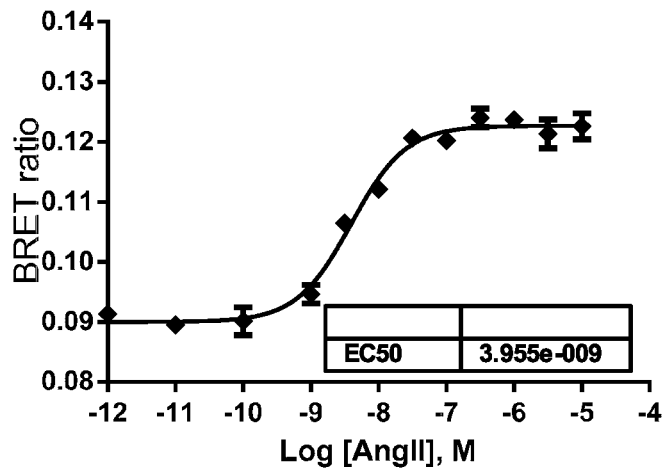
FIGS. 21C to 21E show dose-response curves for the recruitment of β-arrestin$_2$ at different GPCRs (AT1R, V2R and β2AR) using unimolecular biosensors.
Figure 21D:
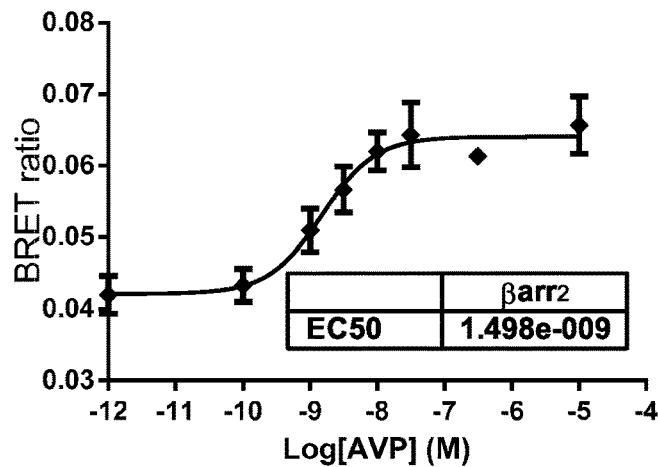
Figure 21E:
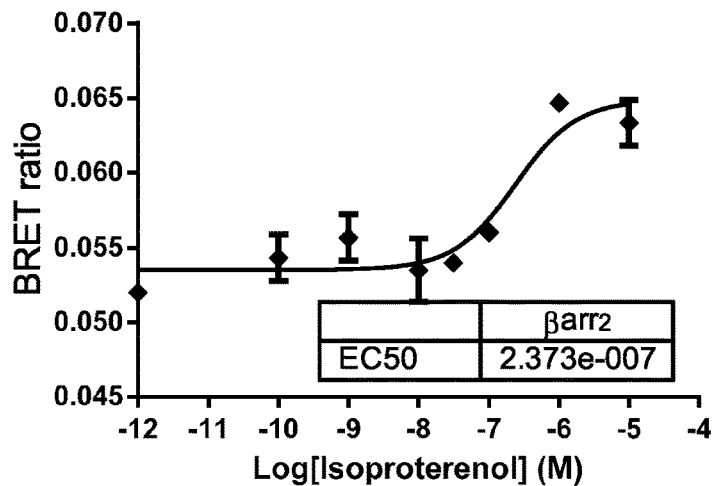

FIG. 19F shows that using βarr-RlucII with rGFP-CAAX, lyn or PB, all generated greater BRET responses than the traditional RlucII:GFP10 BRET pair such as with GFP10-CAAX. This assay to monitor beta-arrestin recruitment advantageously does not require modification of the receptor and also offers a robust assay (Z' factor of at least 0.74; FIGS. 19G and H) amenable to screening applications (including HTS) for both class A and B receptors. FIGS. 21A to 21E show the assessment of β-arrestin translocation using a unimolecular biosensor, which allows performing the experiments in membrane extracts, for example. A flexible polypeptide linker of 300 amino acids provided a better BRET signal relative to shorter polypeptide linkers (FIG. 21C).

Figure 20A:
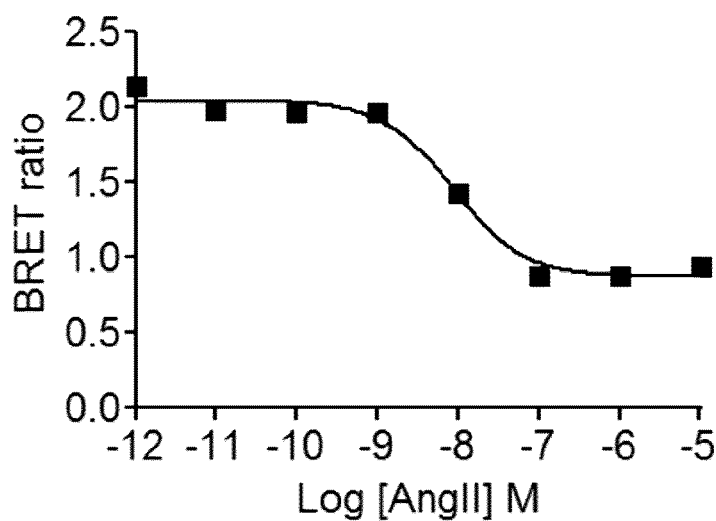
FIGS. 20A and 20B show the AngII-dose dependent decrease in plasma PIP2 amount as detected by BRET between RlucII-PH(PLCδ1) and rGFP-PH(PLCδ1) or Lyn-rGFP or rGFP-CAAX. HEK293SL cells were transfected with AT1R and HA-RlucII-PH(PLCδ1) along with either rGFP-PH(PLCδ1), Lyn-rGFP, or rGFP-CAAX. Cells were incubated with various concentrations of AngII for 1 min at RT then BRET was measured. Results are means±S.E. of triplicates in a single representative experiment.
Figure 20B:
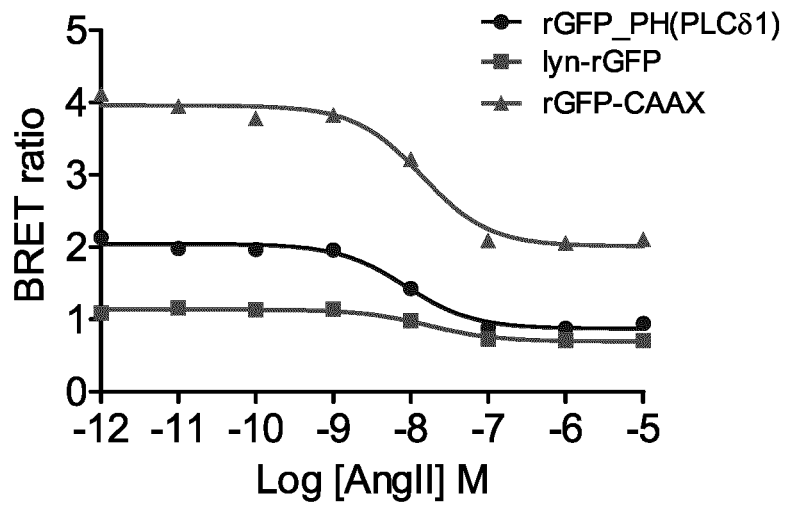

Example 13: Biosensors to Monitor PI(4,5)P$_2$ Amount at the Plasma Membrane The biosensor was applied to detect membrane PI(4,5)P$_2$ generation using PLCδ1-PH domain. In the basal state, PLCδ1-PH-RlucII and PLCδ1-PH-rGFP (or lyn-rGFP or rGFP-CAAX) are localized at the PM where PI(4,5)P$_2$ is located, so their local concentration/density is high enough to generate a detectable BRET signal. When the phospholipase C (PLC) was activated through activation of AT1R by its ligand AngII (thus inducing PI(4,5)P$_2$ hydrolysis), the PLCδ1-PH domain tagged with RlucII and rGFP diffused into the cytosol, thereby reducing the local concentration of rGFP and RlucII and consequently the BRET signal in a dose-dependent manner (FIGS. 20A and B).

Figure 22F:
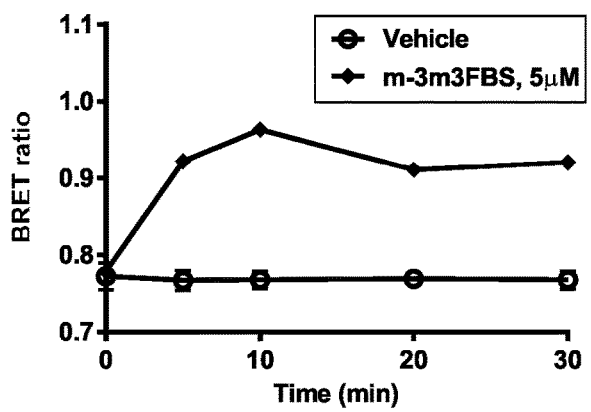
FIG. 22F shows that the BRET response measured with the unimolecular DAG sensor reflects PLC activation and the concomitant production of diacyl glycerol. HEK293 cells transiently expressing the unimolecular DAG sensor were exposed to 5 uM of m-3m3FBS, a direct activator of PLC (β2, β3, γ1, γ2, δ1 isoforms), for the indicated time. The PLC activation lead to an increase in BRET, reflecting a sustained increase of DAG level at the plasma membrane.
Figure 22G:
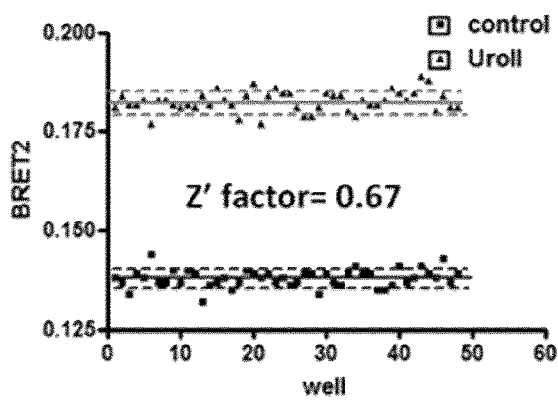
FIGS. 22G and 22H show the robustness of the DAG biosensor. A Z-factor was determined for the DAG biosensor using HEK293 transiently expressing the urotensin-II (FIG. 23G) or the prostaglandin F receptor (FIG. 23H) along with the DAG biosensor. The cells were exposed to 100 nM of agonist (Uroll in FIG. 23G or PGF2α in FIG. 23H) for x min prior to BRET measurements.
Figure 22H:
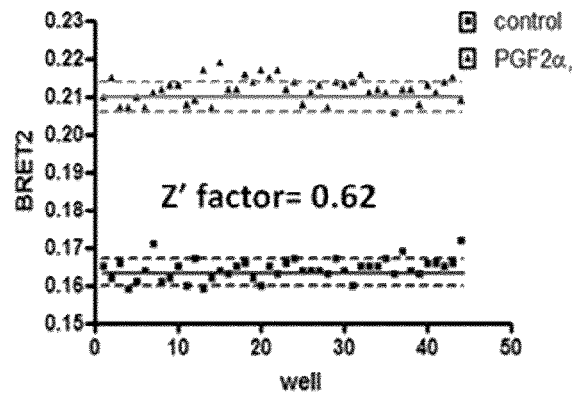

Example 14: Biosensors to Monitor Diacylglycerol (DAG) at the Plasma Membrane Upon activation of PLC, membrane PIP$_2$ is hydrolysed into IP$_3$ and DAG. Although inositol trisphosphate diffuses into the cytosol, DAG remains within the plasma membrane, due to its hydrophobic properties. FIGS. 22A and 23A show schematic representations of biosensors for measuring the translocation of the diacylglycerol-(DAG-) binding domain of PKCdelta (C1b) to the plasma membrane. The biosensors comprise a PM-targeting domain/moiety attached to a BRET acceptor (e.g., rGFP, GFP10) and a BRET donor (e.g., RlucII) linked to the DAG-binding domain of PKCδ, C1b. The DAG enrichment at the membrane following PIP$_2$ causes the C1b domain to bind to the membrane, bringing the BRET acceptor (e.g., rGFP) and BRET donor (e.g., RlucII) closer to each other, inducing a higher BRET signal. In the biosensor depicted in FIG. 22A, the BRET acceptor and BRET donor components are linked together (unimolecular biosensor), which allows performing the experiments in membrane extracts, for example, whereas these components are expressed separely in the biosensor depicted in FIG. 23A. The results depicted in FIGS. 22B to 22H and FIGS. 23B to 23E show that DAG accumulation at the plasma membrane may be monitored using both biosensors. FIG. 22F shows that direct activation of PLC using N-(3-Trifluoromethylphenyl)-2,4,6-trimethylbenzenesulfonamide (m-3M3FBS), which induces the hydrolysis of membrane PIP$_2$ into IP$_3$ and DAG (thus increasing the amount of DAG at the membrane), led to an increase of the BRET signal detected using the unimolecular biosensor.

Example 15: Biosensors to Monitor G Protein Subunit Sequestration

Figure 24C:
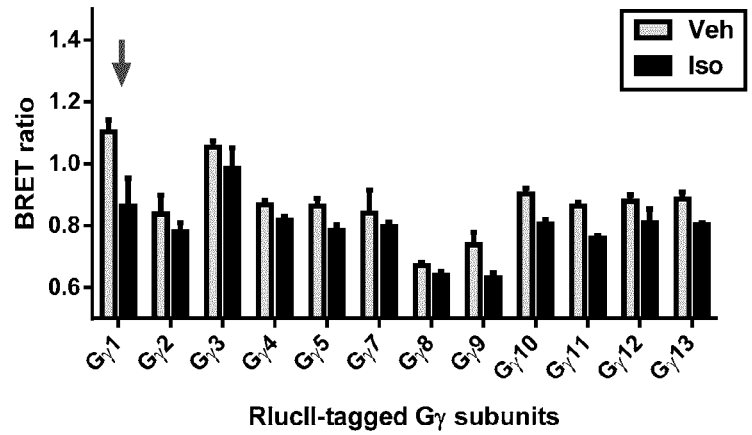
Figure 24D:
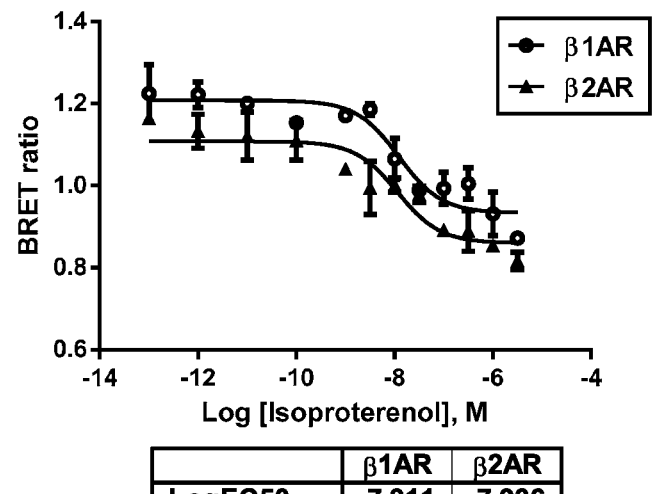
FIG. 24D shows a dose-response curve for the agonist-promoted RlucII-tagged Gγ1 sequestration from rGFP-CAAX (Kras) following β1AR (circles) and β2AR (tri-angles) stimulation with isoproterenol of HEK293 cells transiently transfected with constructs encoding a β-adren-ergic receptor, a WT Gβ1 subunit, an RlucII-tagged Gγ1 subunit and WT Gα15. The observed $EC_{50}$ are similar to the reported kd of isoproterenol for those receptors.
Figure 24E:
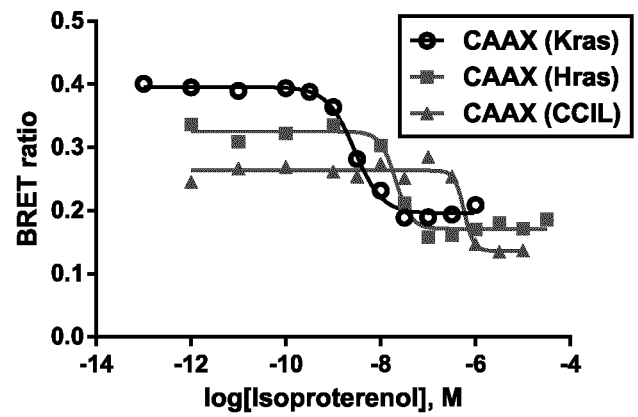
FIG. 24E shows dose-response curves for the agonist-promoted RlucII-tagged Gs sequestration from rGFP-CAAX Kras (circles), rGFP-CAAX Hras (squares) and rGFP-CAAX CCIL (triangles) following β1AR stimulation with isoproterenol. The potency observed with the 3 PM-markers is spanning from 4.4 nM (with rGFP-CAAX Kras) to 847 nM (with rGFP-CAAX CCIL), indicating that the pharmacology of different ligands could be distinct in domains monitored with specific markers.
Figure 24F:
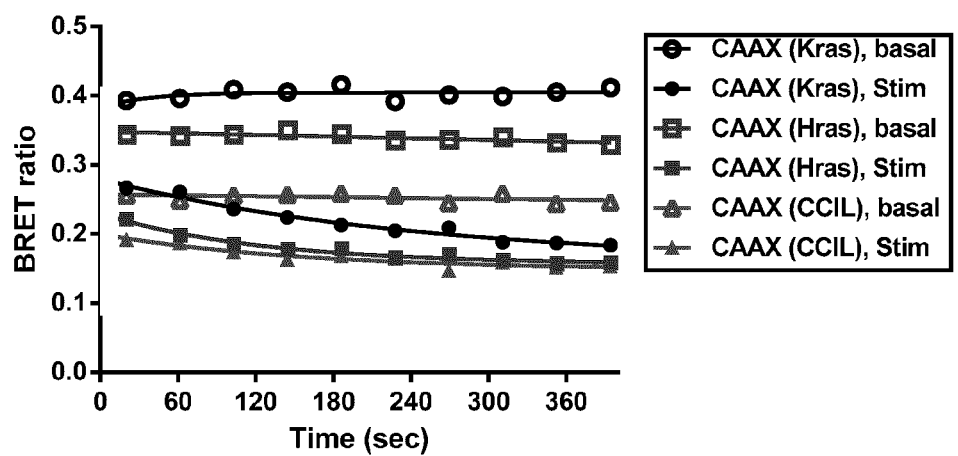
FIG. 24F shows the kinetics of agonist-promoted RlucII-tagged Gs sequestration from rGFP-CAAX Kras (circles), rGFP-CAAX Hras (squares) and rGFP-CAAX CCIL (tri-angles) following β1 AR stimulation with 1 μM isoprotere-nol for the indicated time. The maximal response is mostly reached within 5 min of stimulation as measured with the three PM-markers. The differences of $EC_{50}$ in FIG. 24E are thus not driven by differences in kinetics as the dose-response curves were establish at maximal response.
Figure 24G:
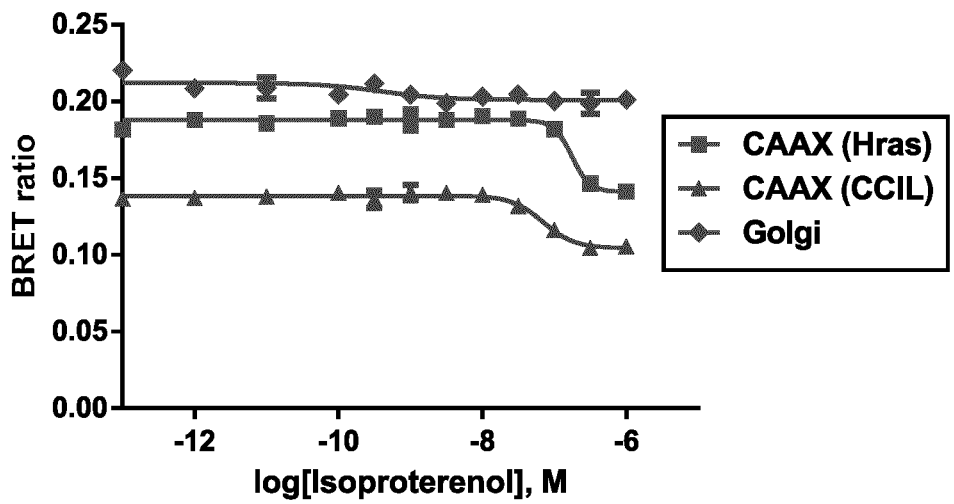
FIG. 24G shows dose-response curves for the agonist-promoted RlucII-tagged G12 sequestration from rGFP-CAAX CCIL (triangles), rGFP-CAAX Hras (squares) and Golgi-rGFP (Golgi targetting domain of eNOS1; diamonds) following β1AR stimulation with isoproterenol. The basal BRET indicates that G12 colocalized with the Golgi marker. However, most of the agonist-induced translocation of G12 is observed using the PM-markers and only minimally from Golgi. These results show that both Gs and G12 can be observed following the stimulation of a receptor.
Figure 24H:
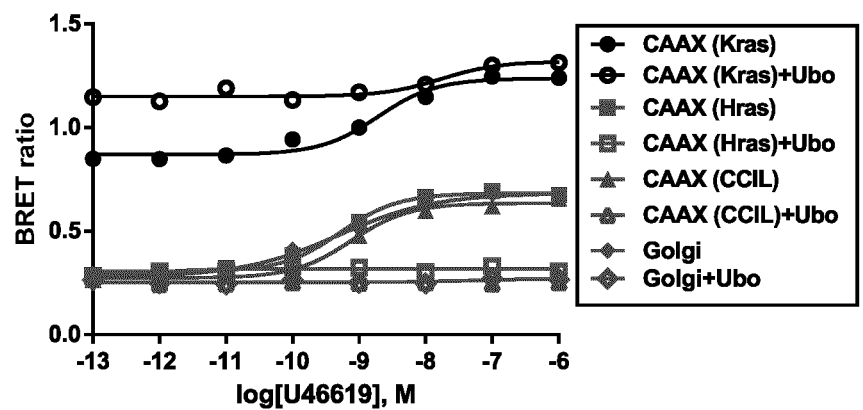
FIG. 24H shows dose-response curves for the agonist-promoted RlucII-tagged Gq translocation to rGFP-CAAX Kras (circles), rGFP-CAAX Hras (squares), rGFP-CAAX CCIL (triangles) and Golgi-rGFP (Golgi targetting domain of eNOS1; diamonds) following the thromboxane A2 recep-tor isoforme α (TpaR) stimulation with a prototypical ago-nist: U46619. The dose response curves were obtained from HEK293 cells transiently transfected with constructs encod-ing: TpaR, Gαq pos118RlucII (RlucII inserted after residue 118 of Gαq), WT Gγ5 and Gβ1, pretreated or not for 20 min with Ubo-Qic, a specific Gq inhibitor. The basal BRET indicates that Gq is mostly colocalized with rGFP-CAAX Kras (solid circles) and pretreatment with Ubo-Qic (open circles) further increase the density of Gq with this marker, blunting the window of response to U46619. The dose-response curves obtained with the other markers show an increase of density of Gq (an increase in BRET; solid squares, solid triangles and solid diamonds for rGFP-CAAX Hras, rGFP-CAAX CCIL and Golgi, respectively) only with cells not exposed to a Gq blocker. No response is observed with these markers with cells pretreated with the Gq inhibi-tor (open squares, open triangles and open diamonds for rGFP-CAAX Hras, rGFP-CAAX CCIL and Golgi, respec-tively). These results demonstrated that G protein translo-cation is linked, at least for Gq, to their activation and that it is possible to observe both sequestration or recruitment to subdomains, in response to an agonist stimulation.

In the absence of agonist, the G protein subunits are localized at the plasma membrane. Upon GPCR activation using an agonist (A), the G protein subunits are released from the plasma membrane. Using a PM-targeting domain/moiety attached to a BRET acceptor (e.g., rGFP, GFP10) and a BRET donor linked to a G protein subunit, it is possible to monitor GPCR activation by measuring the decrease in the BRET signal that results from the release of the G protein subunits from the PM (FIG. 24A). FIGS. 24B and 24C show the changes in BRET ratio following activation of β1AR and β2AR, respectively, with isoproterenol using different RlucII-tagged Gγ subunits, which provides evidence that Gγ1 and Gγ1 are mainly involved in signaling of β1AR, and Gγ1 is mainly involved in signaling of β2AR. FIGS. 24D to 24H show that the sequestration/translocation of different G protein subunits to different cellular compartments following agonist stimulation of GPCRs may be monitored using the biosensors.

Example 16: Biosensors to Monitor RhoA Activation

Figure 25A:
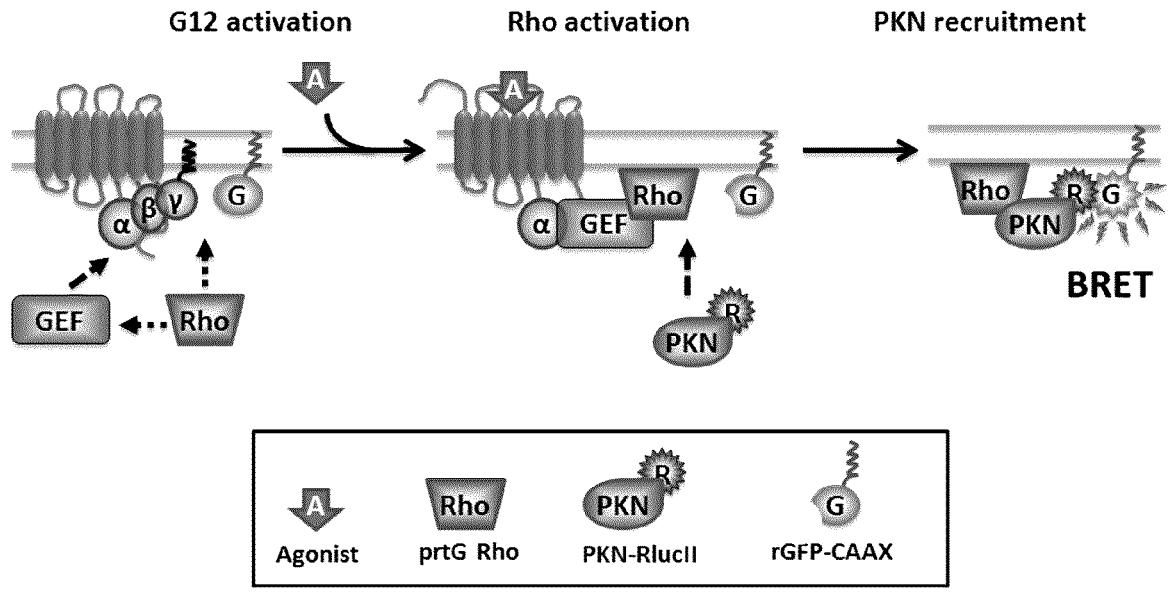
FIG. 25A shows a schematic representation of a biosensor for measuring Rho activation by the translocation of the Rho binding domain of Protein kinase N1 (PKN) to the plasma-membrane. The biosensor comprises a PM-targeting domain/moiety attached to a BRET acceptor (e.g., rGFP) and a BRET donor (e.g., RlucII) linked to the Rho binding domain of PKN. Upon G protein activation, a RhoGEF is recruited to an activated Gα subunit such as of the Gq and G12/13 family or to the Gβγ released from the activated Gα. This GEF activates a small G protein of the Rho family. Once activated, Rho recruits specific effectors with a domain that interact specifically with an activated Rho; PKN is one of those effectors. Based on this property, a sensor to monitor Rho activation was created by subcloning of PKN1 Rho-binding domain (CRIB) in an expression vector con-taining a BRET donor, RlucII, and by monitoring its trans-location to the plasma membrane where the activated Rho is located. The translocation is bringing the BRET acceptor (e.g., rGFP) and BRET donor (e.g., RlucII) closer to each other, inducing a higher BRET signal.
Figure 25B:
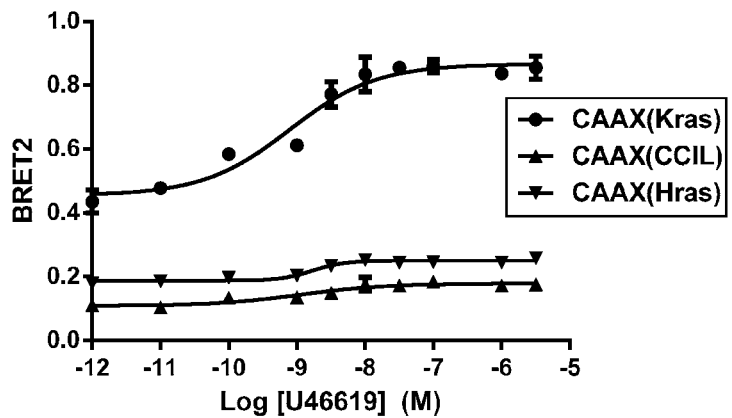
FIG. 25B shows dose-response curves for the agonist-promoted PKN-RlucII translocation to plasma membrane markers: rGFP-CAAX Kras (circles), rGFP-CAAX Hras (inverted triangles) and rGFP-CAAX (CCIL; triangles) following TpαR stimulation with an agonist (U46619). The dose response curves were obtained from HEK293 cells transiently transfected with constructs encoding: TPαR, PKN-RlucII, and a plasma membrane rGFP-marker. TPαR is a prototypical Gq/12/13-coupled receptor known to activate RhoA.
Figure 25C:
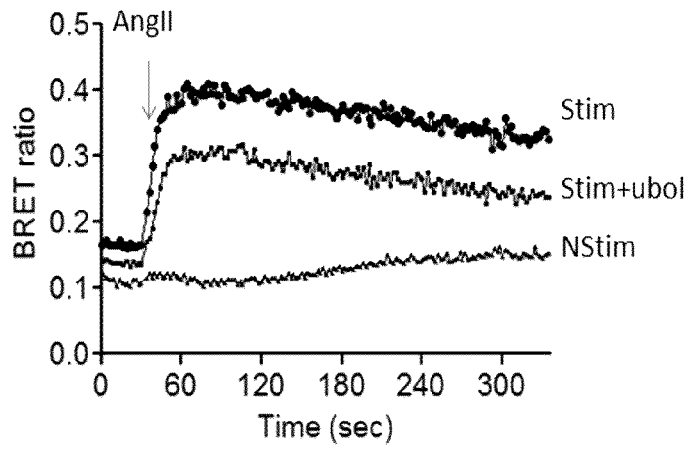
FIG. 25C shows kinetics of Rho sensor activation following AT1R exposure to angiotensin II. HEK293SL cells were transfected with constructs encoding AT1R along with PKN-crib-RlucII and rGFP-CAAX. Cells were first incubated in the absence or presence of 100 nM Ubo-Qic (a specific Gq inhibitor also known as FR900359) for 30 min before BRET measurements at every 2 sec. Tyrode (non-stimulated) or AngII (Stimulated; final concentration of 100 nM) were injected after 30 s. Data are the average of duplicate reading at different time points of a representative experiment.
Figure 25D:
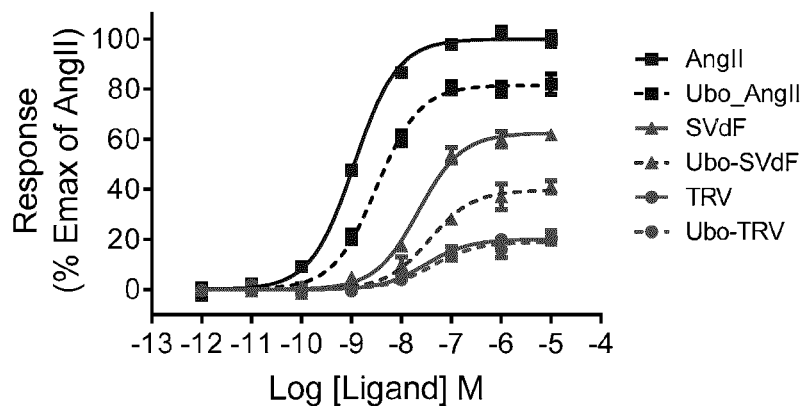
FIG. 25D to 25F shows the impact of Gq inhibition on Rho activation by different AngII ligands. HEK293SL cells were transfected with constructs encoding AT1R along with PKN-CRIB-RlucII and rGFP-CAAX. Cells were incubated in the absence (solid line) or presence (dotted line) of 100 nM Ubo-Qic (Gq inhibitor) for 30 min, then stimulated with various concentrations of AngII or analogs for 4 min before BRET measurements. Data were normalized to the Emax of AngII. Data represent as the means+/−S.E. from 3-4 independent experiments. Gq-activating ligands, such as AngII, hAngIII, SVdF, SBpa, hSarmesin, and SI showed a reduced efficacy and a rightward-shifted potency in the presence of ubo (FIGS. 25D and E). Blocking of Gq did not affect DVG, Saralasin, and TRV-mediated Rho activation since these ligands do not activate Gq. SII showed only changing $EC_{50}$ by ubo treatment, suggesting that SII weakly activates Gq/11.
Figure 25E:
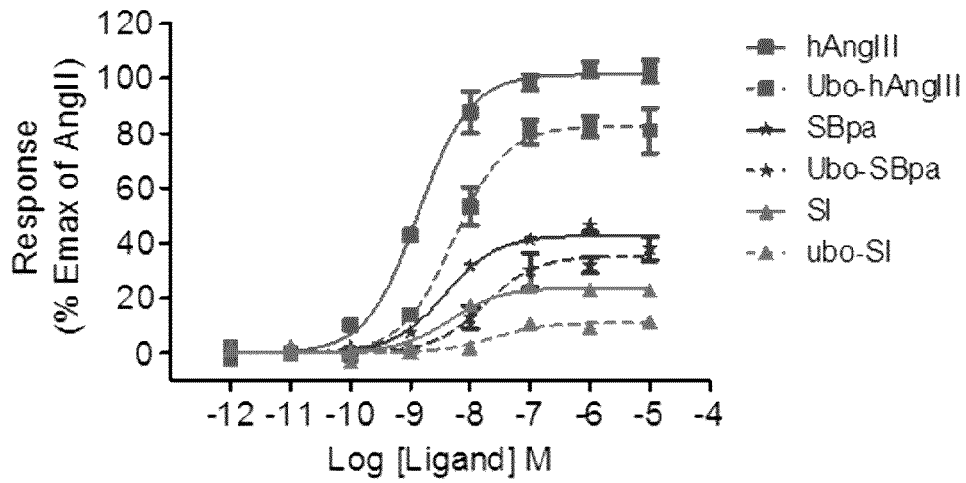
Figure 25F:
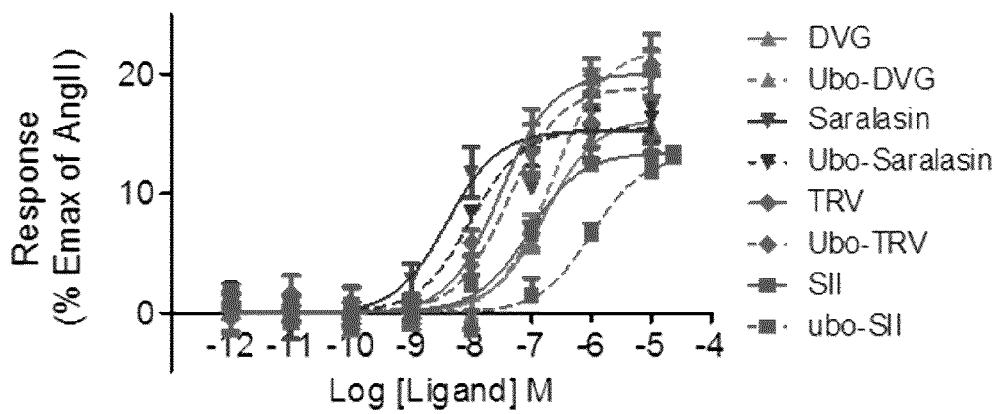
Figure 25G:
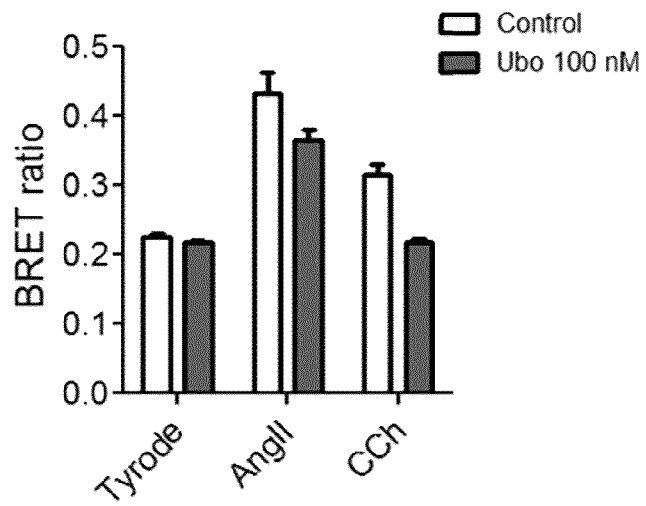
FIG. 25G shows the impact of Gq inhibition on Rho activation by AT1R and Acetylcholine receptors. HEK293SL Cells were transfected with constructs encoding AT1R along with PKN-CRIB-RlucII and rGFP-CAAX. Cells were incubated in the absence (control) or presence of 100 nM Ubo before being stimulated either with 100 nM AngII or 100 µM carbachol (CCh) for 70 s before BRET measurements. Results show that Ubo partially blocked AngII-mediated BRET increase and completely blocked CCh-mediated responses; suggesting that Gq plays a role in Rho activation by AngII and CCh. Data are mean+/−SD of triplicates from a representative experiment.
Figure 25H:
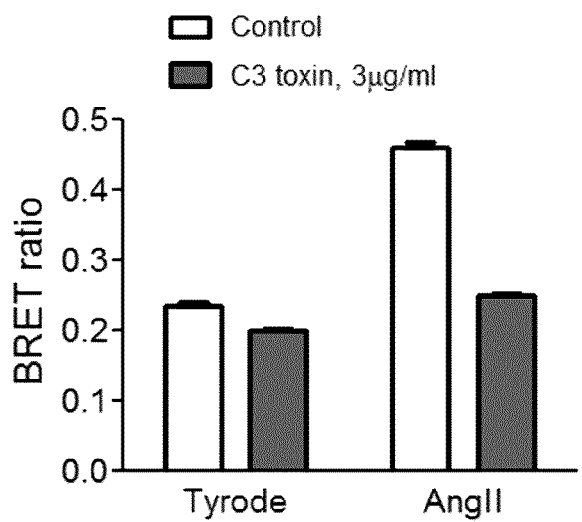
FIG. 25H shows the Effects on a Rho inhibitor of the Rho sensor activation. HEK293SL expressing AT1R, PKN-crib-RlucII and rGFP-CAAX, were incubated with 3 µg/ml of C3 toxin (Rho inhibitor, Cytoskeleton, Inc.) in Tyrode for ~4 hr at 37° C. then stimulated with 100 nM AngII for 70 s at RT. C3 toxin completely abolished agonist-mediated BRET increases, validating the sensor for monitoring Rho activity.
Figure 25I:
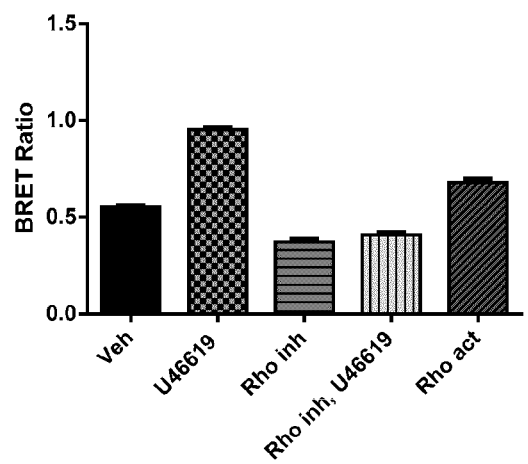
FIG. 25I shows that PKN translocation to the plasma membrane is dependent on Rho activation. HEK293 cells transiently expressing TPaR and the PKN sensor (PKN-RlucII+CAAX-rGFP), were pretreated or not, overnight, with of a Rho inhibitor (CT04; Cytoskeleton, Inc) and exposed to 100 nM of U46619 (TPαR agonist), 1 µg/ml of Rho activator II (CN03; Cytoskeleton, Inc) or vehicle. The Rho inhibitor abolished the TPαR-mediated response while the Rho activatitor is inducing a response, validating this sensor for monitoring Rho activity.

A biosensor of Rho activation was designed by monitoring the recruitment of PKN's CRIB domain, which binds the active form of Rho (Rho-GTP) that localizes at the plasma membrane, to the plasma membrane using BRET. The BRET pair is the RlucII-tagged CRIB domain of PKN as a BRET donor and the plasma membrane bound rGFP (rGFP-CAAX) as an acceptor (FIG. 25A). FIGS. 25B to 25G show that PKN CRIB domain is translocated to the plasma membrane upon agonist stimulation of GPCRs coupled to Gq/12/13, and that the translocation is decreased in the presence of specific Gq inhibitors. FIGS. 25H to 25J show the effect of Rho modulators on the BRET ratio measured using the Rho biosensor. The BRET ratio is increased in the presence of Rho activators, and decreased in the presence of Rho inhibitors, confirming the specificity of the assay.

Figure 27A:
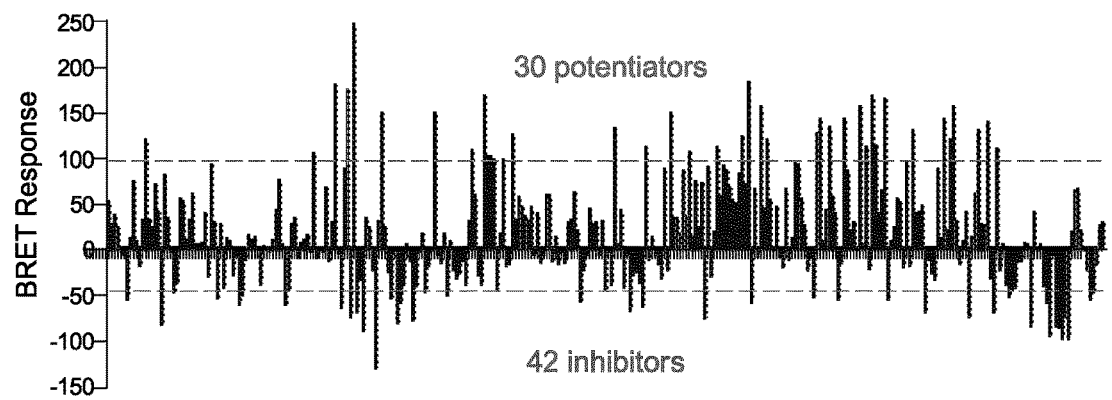
FIG. 27A shows the results of a screening of modulators of AT1R endocytosis. Following transient transfection of AT1R-RlucII and rGFP-FYVE, HEK293 cells were dispensed to 384-well white tissue culture treated plate (Greiner) and grown for an additional 24 h. Compounds are added using a 384 magnetic pintool (V&P scientific) at a final concentration of 15 µM or 5 µg/ml depending on the compound sub-library. For the agonist mode, compounds were incubated for 30 min at 37° C. GFP fluorescence was red using an Envision™ (Perkin-Elmer®) and coelenterazine 400a was added at a final concentration of 5 µM using a multidrop 384 (Thermo-Scientific®). Cells were incubated at room temperature before reading the BRET signal (RLuc at 480 nm and rGFP at 530 nm). For the antagonist mode, compounds were incubated for 30 min at 37° C. Angiotensin II was added at 10 nM ($EC_{80}$) and incubated for an additional 30 minutes at 37° C. The rest of the assay was performed as the agonist mode. Data were analysed using ActivityBase (IDBS) and reported as % agonist or % inhibition based on the angiotensin II activation. Shown are respectively 30 and 42 compounds that act as potentiators (increased the signal over 100%) and inhibitors (blocked more than 50% the signal) for AT1R targeting to endosomes.
Figure 27B:
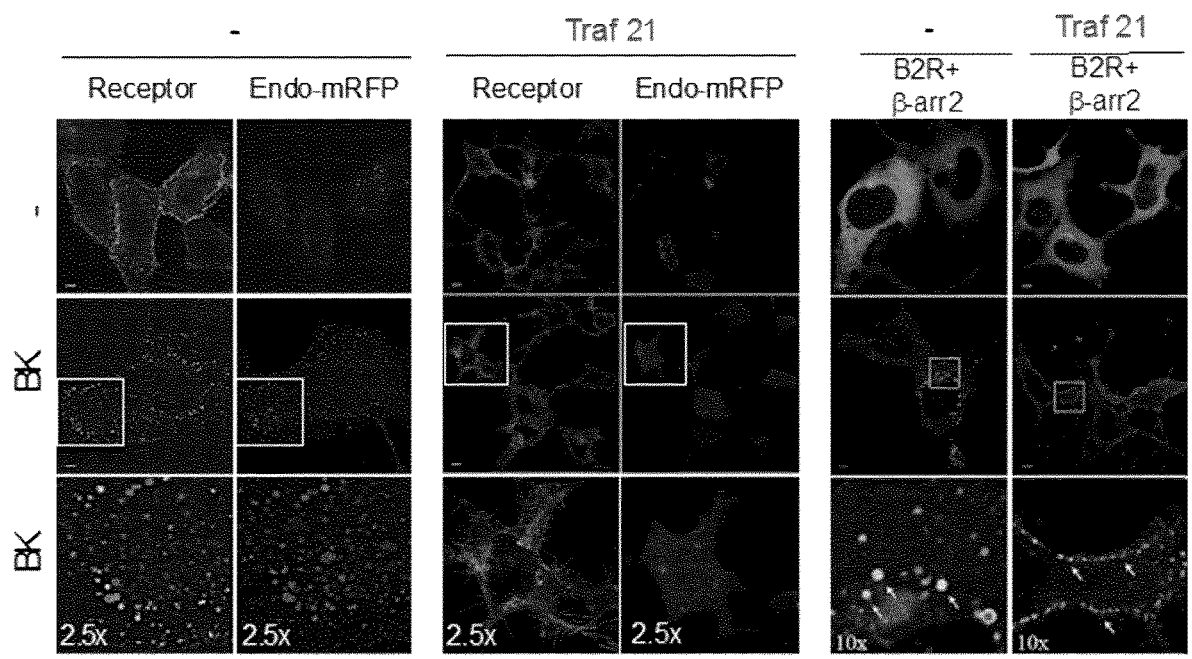
FIG. 27B shows the effects of compound #21 in the screening on B2R and βarrestin2 endocytosis to endosomes.
Figure 27C:
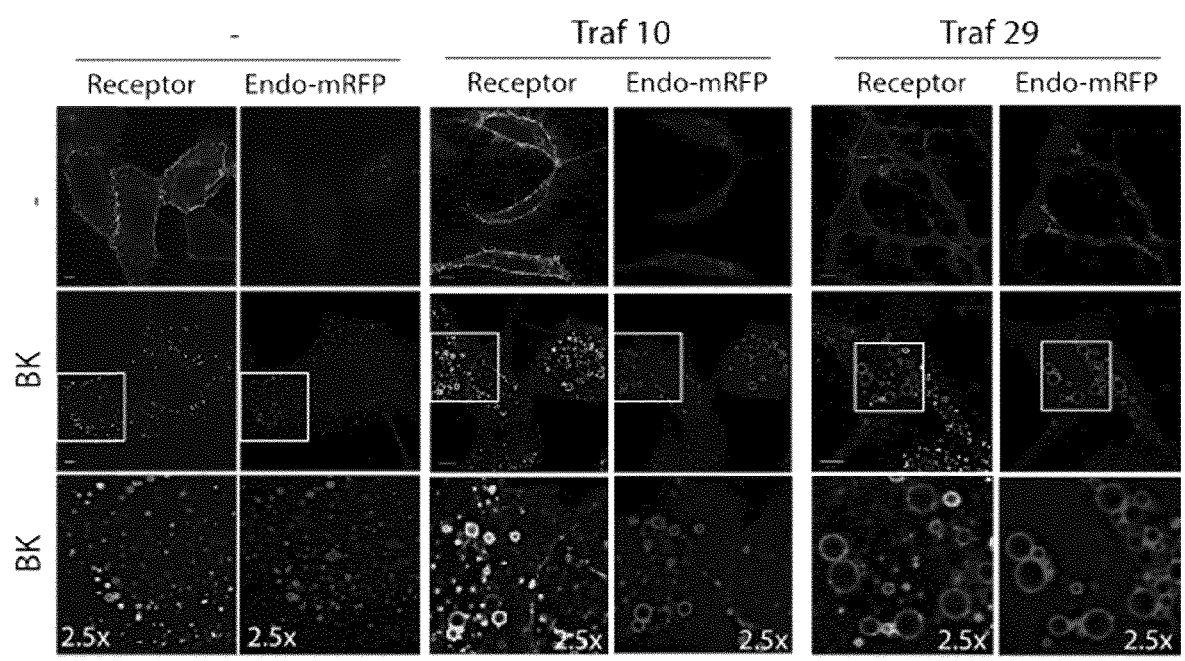
FIG. 27C shows the effects of compound #10 and #29 identified in the screening on B2R endocytosis to endosomes. One day before transfection, HEK293SL cells were seeded in 35 mm glass-bottom dishes at a density of 100,000 cells/dish. Cells were transfected with B2R-YFP+mCherry-FYVE (FIGS. 27B left and middle and 27C) or B2R+βarrestin2-YFP (FIG. 27C). Forty-eight hours post-transfection, cells were serum starved for 30 min and pretreated with either vehicle (FIGS. 27B left and 27C left), compound 21 (FIG. 27B middle and right), compound 10 (FIG. 27C middle), or compound 29 (FIG. 27C right) for 30 min at 37° C. Then cells were stimulated with or without (non treated) bradykinin (1 µM) for 15 min. Samples were analyzed on a Zeiss™ LSM-510 Meta laser scanning microscope using argon (514 nm) and HeNe I (543 nm) lasers, and images (2048×2048 pixels) were collected using a 63× oil immersion lens.

Example 17: Identification of Regulators of AT1R by High-Throughput Screening Using a Localization/Trafficking Biosensor Using the AT1R with βarr2-RlucII and rGFP-FYVE, 115,000 were screened to identify by a BRET assay compounds that either potentiated or inhibited AngII-mediated internalization of AT1R in endosomes. 30 potentiators and 42 inhibitors were identified (FIG. 27A). FIG. 27B shows that compound #21 (Traf 21) identified in the screen blocks the targeting of B2R-YFP or βarr2-YFP to endosomes, as compare to untreated, agonist-stimulated cells. FIG. 27C shows that compounds #10 (Traf 10) and #29 (Traf 29) identified in the screen which enhanced the targeting of B2R-YFP or βarr2-YFP to endosomes, as compare to untreated, agonist-stimulated cells. These results show that the biosensors described herein may be used to identify regulators (e.g., agonists, antagonists) of protein localization/trafficking by high-throughput screening.

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

REFERENCES

Claing, A., S. A. Laporte, et al. (2002). "Endocytosis of G protein-coupled receptors: roles of G protein-coupled receptor kinases and beta-arrestin proteins." Prog Neurobiol 66(2): 61-79.

Hanyaloglu, A. C. and M. von Zastrow (2008). "Regulation of GPCRs by endocytic membrane trafficking and its potential implications." Annu Rev Pharmacol Toxicol 48: 537-568.

Hunyady, L. and K. J. Catt (2006). "Pleiotropic AT1 receptor signaling pathways mediating physiological and pathogenic actions of angiotensin II." Mol Endocrinol 20(5): 953-970.

Molinari, P., I. Casella, et al. (2008). "Functional complementation of high-efficiency resonance energy transfer: a new tool for the study of protein binding interactions in living cells." Biochem J 409(1): 251-261.

Posner, B. I. and S. A. Laporte (2010). "Cellular signalling: Peptide hormones and growth factors." Prog Brain Res 181: 1-16.

Toth, D. J., J. T. Toth, et al. (2012). "Acute depletion of plasma membrane phosphatidylinositol 4,5-bisphosphate impairs specific steps in endocytosis of the G-protein-coupled receptor." J Cell Sci 125(Pt 9): 2185-2197.

Ward, W. W. and H. H. Seliger (1976). "Action spectrum and quantum yield for the photoinactivation of mnemiopsin, a bioluminescent photoprotein from the Ctenophore mnemiopsis SP." Photochem Photobiol 23(5): 351-363.

P. René et al. J Pharmacol Exp Ther. 2010 December; 335(3):520-32

Morello, J. P., et al., J Clin Invest, 2000. 105(7): p. 887-95

Wible B A et al. J Pharmacol Toxicol Methods. 2005, 52(1):136-45 Serradeil-Le Gal C. Cardiovasc Drug Rev. 2001, 19(3):201-14

Anborgh, P. H., J. L. Seachrist, et al. (2000). "Receptor/beta-arrestin complex formation and the differential trafficking and resensitization of beta2-adrenergic and angiotensin II type 1A receptors." Mol Endocrinol 14(12): 2040-2053.

Barberis, C., S. Audigier, et al. (1992). "Pharmacology of oxytocin and vasopressin receptors in the central and peripheral nervous system." Ann NY Acad Sci 652: 39-45.

Fessart, D., M. Simaan, et al. (2005). "c-Src regulates clathrin adapter protein 2 interaction with beta-arrestin and the angiotensin II type 1 receptor during clathrin-mediated internalization." Mol Endocrinol 19(2): 491-503.

Gaborik, Z., M. Szaszak, et al. (2001). "Beta-arrestin- and dynamin-dependent endocytosis of the AT1 angiotensin receptor." Mol Pharmacol 59(2): 239-247.

Goupil, E., V. Wisehart, et al. (2012). "Biasing the prostaglandin F2alpha receptor responses toward EGFR-dependent transactivation of MAPK." Mol Endocrinol 26(7): 1189-1202.

Hein, L., L. Meinel, et al. (1997). "Intracellular trafficking of angiotensin II and its AT1 and AT2 receptors: evidence for selective sorting of receptor and ligand." Mol Endocrinol 11(9): 1266-1277.

Hunyady, L., A. J. Baukal, et al. (2002). "Differential PI 3-kinase dependence of early and late phases of recycling of the internalized AT1 angiotensin receptor." J Cell Biol 157(7): 1211-1222.

Innamorati, G., H. M. Sadeghi, et al. (1998). "A serine cluster prevents recycling of the V2 vasopressin receptor." Proc Natl Acad Sci USA 95(5): 2222-2226.

Li, H., H. F. Li, et al. (2008). "Rab4 and Rab11 coordinately regulate the recycling of angiotensin II type I receptor as demonstrated by fluorescence resonance energy transfer microscopy." J Biomed Opt 13(3): 031206.

Oakley, R. H., S. A. Laporte, et al. (2000). "Differential affinities of visual arrestin, beta arrestin1, and beta arrestin2 for G protein-coupled receptors delineate two major classes of receptors." J Biol Chem 275(22): 17201-17210.

Quoyer, J., J. M. Janz, et al. (2013). "Pepducin targeting the C-X-C chemokine receptor type 4 acts as a biased agonist favoring activation of the inhibitory G protein." Proceedings of the National Academy of Sciences of the United States of America 110(52): E5088-5097.

Seachrist, J. L. and S. S. Ferguson (2003). "Regulation of G protein-coupled receptor endocytosis and trafficking by Rab GTPases." Life Sci 74(2-3): 225-235.

Tsao, P., T. Cao, et al. (2001). "Role of endocytosis in mediating downregulation of G-protein-coupled receptors." Trends Pharmacol Sci 22(2): 91-96.

Tsao, P. I. and M. von Zastrow (2000). "Type-specific sorting of G protein-coupled receptors after endocytosis." J Biol Chem 275(15): 11130-11140.

Zhang, J., L. S. Barak, et al. (1999). "Cellular trafficking of G protein-coupled receptor/beta-arrestin endocytic complexes." J Biol Chem 274(16): 10999-11006.

Zhang, J., S. S. Ferguson, et al. (1996). "Dynamin and beta-arrestin reveal distinct mechanisms for G protein-coupled receptor internalization." J Biol Chem 271(31): 18302-18305.

Zimmerman, B., A. Beautrait, et al. (2012). "Differential beta-arrestin-dependent conformational signaling and cellular responses revealed by angiotensin analogs." Sci Signal 5(221): ra33.

Zimmerman, B., M. Simaan, et al. (2011). "Role of ssarrestins in bradykinin B2 receptor-mediated signalling." Cell Signal 23(4): 648-659.

What is claimed is:

1. A biosensor for assessing the trafficking and/or localization of a protein of interest comprising;
   a first component comprising said protein of interest tagged with a *Renilla* green fluorescent protein (*Renilla* GFP) or a *Renilla* luciferase protein (*Renilla* Luc);
   a second component comprising a cellular compartment targeting moiety tagged with a *Renilla* GFP or a *Renilla* Luc, wherein said cellular compartment targeting moiety is:
   (i) a plasma membrane (PM) targeting moiety comprising the amino acid sequence MGCIKSKGKDS(SEQ ID NO:1), GKKKKKKSKTKCVIM (SEQ ID NO:7), CMSCKCVLS (SEQ ID NO:47), CMSCKCCIL (SEQ ID NO:43), or SPKKGLLQRLFKRQHQNNSKS (SEQ ID NO:8); or
   (ii) an endosomal targeting moiety comprising residues 739 to 806 of human endofin (SEQ ID NO:20);
   wherein if said protein of interest is tagged with said *Renilla* GFP, said cellular compartment targeting moiety is tagged with said *Renilla* Luc, and if said protein of interest is tagged with said *Renilla* Luc, said cellular compartment targeting moiety is tagged with said *Renilla* GFP.

2. The biosensor of claim 1, wherein said protein of interest is tagged with said *Renilla* Luc and said cellular compartment targeting moiety is tagged with said *Renilla* GFP.

3. The biosensor of claim 1, wherein said protein of interest is i) a signalling polypeptide or a fragment thereof, ii) a protein recruited to the plasma membrane upon stimulation of a receptor, or a fragment thereof, iii) a protein sequestered away from the plasma membrane upon stimulation of a receptor, or a fragment thereof, or iv) a cell surface receptor or a fragment thereof.

4. The biosensor of claim 3, wherein said cell surface receptor is a G protein-coupled receptor (GPCR) or a receptor tyrosine kinase (RTK).

5. The biosensor of claim 1, which comprises said PM targeting moiety.

6. The biosensor of claim 1, wherein said PM targeting moiety is fused to the C-terminal end of said *Renilla* Luc or said *Renilla* GFP.

7. The biosensor of claim 1, which comprises said endosomal targeting moiety.

8. The biosensor of claim 1, wherein said endosomal targeting moiety is fused to the C-terminal end of said *Renilla* Luc or said *Renilla* GFP; and/or said protein of interest is fused to the N-terminal end of said *Renilla* Luc or said *Renilla* GFP.

9. The biosensor of claim 1, wherein said first and second component are covalently linked through a flexible linker.

10. A method for determining whether an agent modulates the trafficking of a protein of interest in a cell, said method comprising:
    measuring the BRET signal in the biosensor of claim 1 in the presence and absence of said agent;
    wherein a difference in said BRET signal in the presence of said agent relative to the absence thereof is indicative that said agent modulates the trafficking of said protein of interest in said cell.

11. The biosensor of claim 1, wherein said *Renilla* Luc is *Renilla reniformis* luciferase II (RlucII) and/or said *Renilla* GFP is a *Renilla reniformis* GFP (rGFP).

12. The biosensor of claim 3, wherein said signalling protein or fragment thereof is a G protein effector or a fragment thereof, a β-arrestin polypeptide or a fragment thereof, a G protein subunit polypeptide or a fragment thereof, an adaptor protein or a fragment thereof, or a Rho-binding polypeptide or a fragment thereof.

13. The biosensor of claim 12, wherein said signalling protein or fragment thereof is an adaptor protein or a fragment thereof.

14. The biosensor of claim 13, wherein said adaptor protein or fragment thereof comprises at least one SH2 and/or SH3 domains.

15. The biosensor of claim 3, wherein said signalling protein or fragment thereof is a polypeptide that binds to a second messenger or to a second messenger precursor.

16. The biosensor of claim 15, wherein said second messenger precursor is phosphatidylinositol 4,5-bisphosphate ($PIP_2$).

17. The biosensor of claim 16, wherein said signalling protein or fragment thereof comprises a Pleckstrin homology (PH) domain.

18. The biosensor of claim 15, wherein said second messenger is diacylglycerol (DAG).

19. The biosensor of claim 18, wherein said signalling protein or fragment thereof comprises a phorbol esters/diacylglycerol binding domain.

20. The biosensor of claim 12, wherein the signalling protein or fragment thereof is a β-arrestin polypeptide or a fragment thereof fused to the N-terminal of said *Renilla* Luc, and the cellular compartment targeting moiety is a plasma membrane (PM) targeting moiety or an endosomal targeting moiety, fused to the C-terminal of said *Renilla* GFP.

21. The biosensor of claim 4, wherein the GPCR is fused to the N-terminal of said *Renilla* Luc, and the cellular compartment targeting moiety is fused to the C-terminal of said *Renilla* GFP.

22. The biosensor of claim 1, wherein said biosensor is comprised within a cell.

23. The biosensor of claim 1, wherein the protein of interest is a Grb2 polypeptide or a fragment thereof.

24. The biosensor of claim 23, wherein the Grb2 polypeptide comprises the amino acid sequence of SEQ ID NO: 24.

25. The biosensor of claim 16, wherein the signalling protein or fragment thereof comprising a PH domain is a phospholipase C delta 1 (PLCδ1) protein or a fragment thereof.

26. The biosensor of claim 25, wherein the PLCδ1 protein or fragment thereof comprises the amino acid sequence of SEQ ID NO: 25.

* * * * *

UNITED STATES PATENT AND TRADEMARK OFFICE
CERTIFICATE OF CORRECTION

PATENT NO. : 10,584,159 B2
APPLICATION NO. : 15/512267
DATED : March 10, 2020
INVENTOR(S) : Laporte et al.

Page 1 of 2

It is certified that error appears in the above-identified patent and that said Letters Patent is hereby corrected as shown below:

On the Title Page

Item (56) References Cited, OTHER PUBLICATIONS, Column 2, Violin et al. cite: Please correct "p-arrestin" to read -- β-arrestin --

In the Specification

Column 8, Line 27: Please correct "V2R-Rluc1II" to read -- V2R-RlucII --

Column 14, Line 20: Please insert a paragraph break between "AVP." and "FIGS. 21C"

Column 16, Line 22: Please correct "(TpaR)" to read -- (TpαR) --

Column 16, Line 25: Please correct "TpaR" to read -- TpαR --

Column 17, Line 56: Please correct "TpaR" to read -- TpαR --

Column 24, Line 5: Please correct "5130A" to read -- S130A --

Column 25, Line 47: Please correct "KISKEEKTPGCVK/KK<u>CIIM</u>;"
to read -- KISKEEKTPGCVKIKK<u>CIIM</u>; --

Column 26, Line 65: Please correct "(HSPAS)" to read -- (HSPA5) --

Column 37, Line 63: Please correct "Luc)," to read -- Luc, --

Column 38, Line 60: Please correct "NO:)" to read -- NO:45) --

Column 40, Line 8: Please correct "(0601S)" to read -- (G601S) --

Signed and Sealed this
Seventh Day of July, 2020

Andrei Iancu
*Director of the United States Patent and Trademark Office*

CERTIFICATE OF CORRECTION (continued)
U.S. Pat. No. 10,584,159 B2

Column 40, Line 26: Please correct "GRKS-plasma" to read -- GRK5-plasma --

Column 41, Line 12: Please correct "25,000" to read -- ~25,000 --

Column 41, Line 27: Please correct "3-4" to read -- 3~4 --

Column 65, Line 2: Please correct "BRET" to read -- ΔBRET --

Column 68, Line 15: Please correct "GRKS" to read -- GRK5 --

Column 70, Line 56: Please correct "β-arrestin$_2$" to read -- β-arrestin$_1$ --

Column 70, Line 65: Please correct "GRKS" to read -- GRK5 --

Column 72, Line 11: Please correct "Gγ1" to read -- Gγ11 --

SEQUENCE LISTING

```
<160> NUMBER OF SEQ ID NOS: 88

<210> SEQ ID NO 1
<211> LENGTH: 11
<212> TYPE: PRT
<213> ORGANISM: Homo sapiens

<400> SEQUENCE: 1

Met Gly Cys Ile Lys Ser Lys Gly Lys Asp Ser
1               5                   10

<210> SEQ ID NO 2
<211> LENGTH: 11
<212> TYPE: PRT
<213> ORGANISM: Artificial Sequence
<220> FEATURE:
```

```
<223> OTHER INFORMATION: synthetic linker

<400> SEQUENCE: 2

Val Gly Gly Gly Gly Ser Lys Leu Pro Ala Thr
1               5                   10

<210> SEQ ID NO 3
<211> LENGTH: 10
<212> TYPE: PRT
<213> ORGANISM: Artificial Sequence
<220> FEATURE:
<223> OTHER INFORMATION: synthetic linker

<400> SEQUENCE: 3

Gly Gly Ser Gly Leu Lys Leu Pro Ala Thr
1               5                   10

<210> SEQ ID NO 4
<211> LENGTH: 8
<212> TYPE: PRT
<213> ORGANISM: Artificial Sequence
<220> FEATURE:
<223> OTHER INFORMATION: synthetic linker

<400> SEQUENCE: 4

Asn Ala Ala Ile Arg Ser Gly Gly
1               5

<210> SEQ ID NO 5
<211> LENGTH: 8
<212> TYPE: PRT
<213> ORGANISM: Artificial Sequence
<220> FEATURE:
<223> OTHER INFORMATION: synthetic linker

<400> SEQUENCE: 5

Gly Gly Asn Ala Ala Ile Arg Ser
1               5

<210> SEQ ID NO 6
<211> LENGTH: 14
<212> TYPE: PRT
<213> ORGANISM: Artificial Sequence
<220> FEATURE:
<223> OTHER INFORMATION: synthetic linker

<400> SEQUENCE: 6

Gly Ser Ala Gly Thr Met Ala Ser Asn Asn Thr Ala Ser Gly
1               5                   10

<210> SEQ ID NO 7
<211> LENGTH: 15
<212> TYPE: PRT
<213> ORGANISM: Homo sapiens

<400> SEQUENCE: 7

Gly Lys Lys Lys Lys Lys Ser Lys Thr Lys Cys Val Ile Met
1               5                   10                  15

<210> SEQ ID NO 8
<211> LENGTH: 21
<212> TYPE: PRT
<213> ORGANISM: Homo sapiens

<400> SEQUENCE: 8

Ser Pro Lys Lys Gly Leu Leu Gln Arg Leu Phe Lys Arg Gln His Gln
```

Asn Asn Ser Lys Ser
              20

<210> SEQ ID NO 9
<211> LENGTH: 5
<212> TYPE: PRT
<213> ORGANISM: Artificial Sequence
<220> FEATURE:
<223> OTHER INFORMATION: synthetic linker

<400> SEQUENCE: 9

Gly Ser Ala Gly Thr
1               5

<210> SEQ ID NO 10
<211> LENGTH: 311
<212> TYPE: PRT
<213> ORGANISM: Renilla reniformis

<400> SEQUENCE: 10

Met Thr Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
                20                  25                  30

Phe Ile Asn Tyr Tyr Asp Ser Glu Lys His Ala Glu Asn Ala Val Ile
            35                  40                  45

Phe Leu His Gly Asn Ala Thr Ser Ser Tyr Leu Trp Arg His Val Val
        50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310

<210> SEQ ID NO 11
<211> LENGTH: 233
<212> TYPE: PRT
<213> ORGANISM: Renilla reniformis

<400> SEQUENCE: 11

Met Asp Leu Ala Lys Leu Gly Leu Lys Glu Val Met Pro Thr Lys Ile
1               5                   10                  15

Asn Leu Glu Gly Leu Val Gly Asp His Ala Phe Ser Met Glu Gly Val
            20                  25                  30

Gly Glu Gly Asn Ile Leu Glu Gly Thr Gln Glu Val Lys Ile Ser Val
        35                  40                  45

Thr Lys Gly Ala Pro Leu Pro Phe Ala Phe Asp Ile Val Ser Val Ala
    50                  55                  60

Phe Ser Tyr Gly Asn Arg Ala Tyr Thr Gly Tyr Pro Glu Glu Ile Ser
65                  70                  75                  80

Asp Tyr Phe Leu Gln Ser Phe Pro Glu Gly Phe Thr Tyr Glu Arg Asn
                85                  90                  95

Ile Arg Tyr Gln Asp Gly Gly Thr Ala Ile Val Lys Ser Asp Ile Ser
            100                 105                 110

Leu Glu Asp Gly Lys Phe Ile Val Asn Val Asp Phe Lys Ala Lys Asp
        115                 120                 125

Leu Arg Arg Met Gly Pro Val Met Gln Gln Asp Ile Val Gly Met Gln
    130                 135                 140

Pro Ser Tyr Glu Ser Met Tyr Thr Asn Val Thr Ser Val Ile Gly Glu
145                 150                 155                 160

Cys Ile Ile Ala Phe Lys Leu Gln Thr Gly Lys His Phe Thr Tyr His
                165                 170                 175

Met Arg Thr Val Tyr Lys Ser Lys Lys Pro Val Glu Thr Met Pro Leu
            180                 185                 190

Tyr His Phe Ile Gln His Arg Leu Val Lys Thr Asn Val Asp Thr Ala
        195                 200                 205

Ser Gly Tyr Val Val Gln His Glu Thr Ala Ile Ala Ala His Ser Thr
    210                 215                 220

Ile Lys Lys Ile Glu Gly Ser Leu Pro
225                 230

<210> SEQ ID NO 12
<211> LENGTH: 239
<212> TYPE: PRT
<213> ORGANISM: Aequorea victoria

<400> SEQUENCE: 12

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Pro His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Phe Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 13
<211> LENGTH: 332
<212> TYPE: PRT
<213> ORGANISM: Homo sapiens

<400> SEQUENCE: 13

Met Val Asn Ser Thr His Arg Gly Met His Thr Ser Leu His Leu Trp
1               5                   10                  15

Asn Arg Ser Ser Tyr Arg Leu His Ser Asn Ala Ser Glu Ser Leu Gly
            20                  25                  30

Lys Gly Tyr Ser Asp Gly Gly Cys Tyr Glu Gln Leu Phe Val Ser Pro
        35                  40                  45

Glu Val Phe Val Thr Leu Gly Val Ile Ser Leu Leu Glu Asn Ile Leu
    50                  55                  60

Val Ile Val Ala Ile Ala Lys Asn Lys Asn Leu His Ser Pro Met Tyr
65                  70                  75                  80

Phe Phe Ile Cys Ser Leu Ala Val Ala Asp Met Leu Val Ser Val Ser
                85                  90                  95

Asn Gly Ser Glu Thr Ile Val Ile Thr Leu Leu Asn Ser Thr Asp Thr
            100                 105                 110

Asp Ala Gln Ser Phe Thr Val Asn Ile Asp Asn Val Ile Asp Ser Val
        115                 120                 125

Ile Cys Ser Ser Leu Leu Ala Ser Ile Cys Ser Leu Leu Ser Ile Ala
130                 135                 140

Val Asp Arg Tyr Phe Thr Ile Phe Tyr Ala Leu Gln Tyr His Asn Ile
145                 150                 155                 160

Met Thr Val Lys Arg Val Gly Ile Ile Ile Ser Cys Ile Trp Ala Ala
                165                 170                 175

Cys Thr Val Ser Gly Ile Leu Phe Ile Ile Tyr Ser Asp Ser Ser Ala
            180                 185                 190

Val Ile Ile Cys Leu Ile Thr Met Phe Phe Thr Met Leu Ala Leu Met 195                 200                 205
Ala Ser Leu Tyr Val His Met Phe Leu Met Ala Arg Leu His Ile Lys
    210                 215                 220

Arg Ile Ala Val Leu Pro Gly Thr Gly Ala Ile Arg Gln Gly Ala Asn
225                 230                 235                 240

Met Lys Gly Ala Ile Thr Leu Thr Ile Leu Ile Gly Val Phe Val Val
                245                 250                 255

Cys Trp Ala Pro Phe Phe Leu His Leu Ile Phe Tyr Ile Ser Cys Pro
                260                 265                 270

Gln Asn Pro Tyr Cys Val Cys Phe Met Ser His Phe Asn Leu Tyr Leu
            275                 280                 285

Ile Leu Ile Met Cys Asn Ser Ile Ile Asp Pro Leu Ile Tyr Ala Leu
        290                 295                 300

Arg Ser Gln Glu Leu Arg Lys Thr Phe Lys Glu Ile Ile Cys Cys Tyr
305                 310                 315                 320

Pro Leu Gly Gly Leu Cys Asp Leu Ser Ser Arg Tyr
                325                 330

<210> SEQ ID NO 14
<211> LENGTH: 332
<212> TYPE: PRT
<213> ORGANISM: Homo sapiens

<400> SEQUENCE: 14

Met Val Asn Ser Thr His Arg Gly Met His Thr Ser Leu His Leu Trp
1               5                   10                  15

Asn Arg Ser Ser Tyr Arg Leu His Ser Asn Ala Ser Glu Ser Leu Gly
            20                  25                  30

Lys Gly Tyr Ser Asp Gly Gly Cys Tyr Glu Gln Leu Phe Val Ser Pro
        35                  40                  45

Glu Val Phe Val Thr Leu Gly Val Ile Ser Leu Leu Glu Asn Ile Leu
    50                  55                  60

Val Ile Val Ala Ile Ala Lys Asn Lys Asn Leu His Ser Pro Met Tyr
65                  70                  75                  80

Phe Phe Ile Cys Ser Leu Ala Val Ala Asp Met Leu Val Ser Val Ser
                85                  90                  95

Asn Gly Ser Glu Thr Ile Val Ile Thr Leu Leu Asn Ser Thr Asp Thr
            100                 105                 110

Asp Ala Gln Ser Phe Thr Val Asn Ile Asp Asn Val Ile Asp Ser Val
        115                 120                 125

Ile Cys Ser Ser Leu Leu Ala Ser Ile Cys Ser Leu Leu Ser Ile Ala
    130                 135                 140

Val Asp Arg Tyr Phe Thr Ile Phe Tyr Ala Leu Gln Tyr His Asn Ile
145                 150                 155                 160

Met Thr Val Lys Gln Val Gly Ile Ile Ile Ser Cys Ile Trp Ala Ala
                165                 170                 175

Cys Thr Val Ser Gly Ile Leu Phe Ile Ile Tyr Ser Asp Ser Ser Ala
            180                 185                 190

Val Ile Ile Cys Leu Ile Thr Met Phe Phe Thr Met Leu Ala Leu Met
        195                 200                 205

Ala Ser Leu Tyr Val His Met Phe Leu Met Ala Arg Leu His Ile Lys
    210                 215                 220

Arg Ile Ala Val Leu Pro Gly Thr Gly Ala Ile Arg Gln Gly Ala Asn
225                 230                 235                 240

Met Lys Gly Ala Ile Thr Leu Thr Ile Leu Ile Gly Val Phe Val Val
            245                 250                 255

Cys Trp Ala Pro Phe Phe Leu His Leu Ile Phe Tyr Ile Ser Cys Pro
        260                 265                 270

Gln Asn Pro Tyr Cys Val Cys Phe Met Ser His Phe Asn Leu Tyr Leu
        275                 280                 285

Ile Leu Ile Met Cys Asn Ser Ile Ile Asp Pro Leu Ile Tyr Ala Leu
        290                 295                 300

Arg Ser Gln Glu Leu Arg Lys Thr Phe Lys Glu Ile Ile Cys Cys Tyr
305                 310                 315                 320

Pro Leu Gly Gly Leu Cys Asp Leu Ser Ser Arg Tyr
                325                 330

<210> SEQ ID NO 15
<211> LENGTH: 332
<212> TYPE: PRT
<213> ORGANISM: Homo sapiens

<400> SEQUENCE: 15

Met Val Asn Ser Thr His Arg Gly Met His Thr Ser Leu His Leu Trp
1               5                   10                  15

Asn Arg Ser Ser Tyr Arg Leu His Ser Asn Ala Ser Glu Ser Leu Gly
            20                  25                  30

Lys Gly Tyr Ser Asp Gly Gly Cys Tyr Glu Gln Leu Phe Val Ser Pro
        35                  40                  45

Glu Val Phe Val Thr Leu Gly Val Ile Ser Leu Leu Glu Asn Ile Leu
    50                  55                  60

Val Ile Val Ala Ile Ala Lys Asn Lys Asn Leu His Ser Pro Met Tyr
65                  70                  75                  80

Phe Phe Ile Cys Ser Leu Ala Val Ala Asp Met Leu Val Ser Val Ser
                85                  90                  95

Asn Gly Ser Glu Thr Ile Val Ile Thr Leu Leu Asn Ser Thr Asp Thr
            100                 105                 110

Asp Ala Gln Ser Phe Thr Val Asn Ile Asp Asn Val Ile Asp Ser Val
        115                 120                 125

Ile Cys Ser Ser Leu Leu Ala Ser Ile Cys Ser Leu Leu Ser Ile Ala
    130                 135                 140

Val Asp Arg Tyr Phe Thr Ile Phe Tyr Ala Leu Gln Tyr His Asn Ile
145                 150                 155                 160

Met Thr Val Lys Arg Val Gly Ile Ile Ser Cys Ile Trp Ala Ala
                165                 170                 175

Cys Thr Val Ser Gly Ile Leu Phe Ile Ile Tyr Ser Asp Ser Ser Ala
            180                 185                 190

Val Ile Ile Cys Leu Ile Thr Met Phe Phe Thr Met Leu Ala Leu Met
        195                 200                 205

Ala Ser Leu Tyr Val His Met Phe Leu Met Ala Arg Leu His Ile Lys
    210                 215                 220

Arg Ile Ala Val Leu Pro Gly Thr Gly Ala Ile Arg Gln Gly Ala Asn
225                 230                 235                 240

Met Lys Gly Ala Ile Thr Leu Thr Ile Leu Ile Gly Val Phe Val Val
                245                 250                 255

Cys Trp Ala Pro Phe Phe Leu His Leu Ile Phe Tyr Ile Ser Cys Pro
            260                 265                 270

Gln Asn Pro Tyr Cys Val Cys Phe Met Ser His Phe Asn Leu Tyr Leu
        275                 280                 285

Ile Leu Ile Met Cys Asn Ser Ile Ile Asp His Leu Ile Tyr Ala Leu
    290                 295                 300

Arg Ser Gln Glu Leu Arg Lys Thr Phe Lys Glu Ile Ile Cys Cys Tyr
305                 310                 315                 320

Pro Leu Gly Gly Leu Cys Asp Leu Ser Ser Arg Tyr
                325                 330

<210> SEQ ID NO 16
<211> LENGTH: 371
<212> TYPE: PRT
<213> ORGANISM: Homo sapiens

<400> SEQUENCE: 16

Met Leu Met Ala Ser Thr Thr Ser Ala Val Pro Gly His Pro Ser Leu
1               5                   10                  15

Pro Ser Leu Pro Ser Asn Ser Ser Gln Glu Arg Pro Leu Asp Thr Arg
                20                  25                  30

Asp Pro Leu Leu Ala Arg Ala Glu Leu Ala Leu Leu Ser Ile Val Phe
            35                  40                  45

Val Ala Val Ala Leu Ser Asn Gly Leu Val Leu Ala Ala Leu Ala Arg
50                  55                  60

Arg Gly Arg Arg Gly His Trp Ala Pro Ile His Val Phe Ile Gly His
65                  70                  75                  80

Leu Cys Leu Ala Asp Leu Ala Val Ala Leu Phe Gln Val Leu Pro Gln
                85                  90                  95

Leu Ala Trp Lys Ala Thr Asp Arg Phe Arg Gly Pro Asp Ala Leu Cys
            100                 105                 110

Arg Ala Val Lys Tyr Leu Gln Met Val Gly Met Tyr Ala Ser Ser Tyr
            115                 120                 125

Met Ile Leu Ala Met Thr Leu Asp Arg His Arg Ala Ile Cys Arg Pro
130                 135                 140

Met Leu Ala Tyr Arg His Gly Ser Gly Ala His Trp Asn Arg Pro Val
145                 150                 155                 160

Leu Val Ala Trp Ala Phe Ser Leu Leu Leu Ser Leu Pro Gln Leu Phe
                165                 170                 175

Ile Phe Ala Gln Arg Asn Val Glu Gly Gly Ser Gly Val Thr Asp Cys
            180                 185                 190

Trp Ala Cys Phe Ala Glu Pro Trp Gly Arg Arg Thr Tyr Val Thr Trp
            195                 200                 205

Ile Ala Leu Met Val Phe Val Ala Pro Thr Leu Gly Ile Ala Ala Cys
210                 215                 220

Gln Val Leu Ile Phe Arg Glu Ile His Ala Ser Leu Val Pro Gly Pro
225                 230                 235                 240

Ser Glu Arg Pro Gly Gly Arg Arg Gly Arg Arg Thr Gly Ser Pro
                245                 250                 255

Gly Glu Gly Ala His Val Ser Ala Ala Val Ala Lys Thr Val Arg Met
            260                 265                 270

Thr Leu Val Ile Val Val Val Tyr Val Leu Cys Trp Ala Pro Phe Phe
            275                 280                 285

Leu Val Gln Leu Trp Ala Ala Trp Asp Pro Glu Ala Pro Leu Glu Gly
            290                 295                 300

Ala Pro Phe Val Leu Leu Met Leu Leu Ala Ser Leu Asn Ser Cys Thr
305                 310                 315                 320

Asn Pro Trp Ile Tyr Ala Ser Phe Ser Ser Ser Val Ser Ser Glu Leu 325                 330                 335
Arg Ser Leu Leu Cys Cys Ala Arg Gly Arg Thr Pro Pro Ser Leu Gly
                340                 345                 350

Pro Gln Asp Glu Ser Cys Thr Thr Ala Ser Ser Ser Leu Ala Lys Asp
            355                 360                 365

Thr Ser Ser
    370

<210> SEQ ID NO 17
<211> LENGTH: 371
<212> TYPE: PRT
<213> ORGANISM: Homo sapiens

<400> SEQUENCE: 17

Met Leu Met Ala Ser Thr Thr Ser Ala Val Pro Gly His Pro Ser Leu
1               5                   10                  15

Pro Ser Leu Pro Ser Asn Ser Ser Gln Glu Arg Pro Leu Asp Thr Arg
            20                  25                  30

Asp Pro Leu Leu Ala Arg Ala Glu Leu Ala Leu Leu Ser Ile Val Phe
        35                  40                  45

Val Ala Val Ala Leu Ser Asn Gly Leu Val Leu Ala Ala Leu Ala Arg
    50                  55                  60

Arg Gly Arg Arg Gly His Trp Ala Pro Ile His Val Phe Ile Gly His
65                  70                  75                  80

Leu Cys Leu Ala Asp Leu Ala Val Ala Leu Phe Gln Val Leu Pro Gln
                85                  90                  95

Leu Ala Trp Lys Ala Thr Asp Arg Phe Arg Gly Pro Asp Ala Leu Cys
            100                 105                 110

Arg Ala Val Lys Tyr Leu Gln Met Val Gly Met Tyr Ala Ser Ser Ser
        115                 120                 125

Met Ile Leu Ala Met Thr Leu Asp Arg His Arg Ala Ile Cys Arg Pro
    130                 135                 140

Met Leu Ala Tyr Arg His Gly Ser Gly Ala His Trp Asn Arg Pro Val
145                 150                 155                 160

Leu Val Ala Trp Ala Phe Ser Leu Leu Leu Ser Leu Pro Gln Leu Phe
                165                 170                 175

Ile Phe Ala Gln Arg Asn Val Glu Gly Gly Ser Gly Val Thr Asp Cys
            180                 185                 190

Trp Ala Cys Phe Ala Glu Pro Trp Gly Arg Arg Thr Tyr Val Thr Trp
        195                 200                 205

Ile Ala Leu Met Val Phe Val Ala Pro Thr Leu Gly Ile Ala Ala Cys
    210                 215                 220

Gln Val Leu Ile Phe Arg Glu Ile His Ala Ser Leu Val Pro Gly Pro
225                 230                 235                 240

Ser Glu Arg Pro Gly Gly Arg Arg Gly Arg Arg Thr Gly Ser Pro
                245                 250                 255

Gly Glu Gly Ala His Val Ser Ala Ala Val Ala Lys Thr Val Arg Met
            260                 265                 270

Thr Leu Val Ile Val Val Tyr Val Leu Cys Trp Ala Pro Phe Phe
        275                 280                 285

Leu Val Gln Leu Trp Ala Ala Trp Asp Pro Glu Ala Pro Leu Glu Gly
    290                 295                 300

Ala Pro Phe Val Leu Leu Met Leu Leu Ala Ser Leu Asn Ser Cys Thr
305                 310                 315                 320

```
Asn Pro Trp Ile Tyr Ala Ser Phe Ser Ser Ser Val Ser Ser Glu Leu
            325                 330                 335

Arg Ser Leu Leu Cys Cys Ala Arg Gly Arg Thr Pro Pro Ser Leu Gly
            340                 345                 350

Pro Gln Asp Glu Ser Cys Thr Thr Ala Ser Ser Leu Ala Lys Asp
            355                 360                 365

Thr Ser Ser
    370

<210> SEQ ID NO 18
<211> LENGTH: 1159
<212> TYPE: PRT
<213> ORGANISM: Homo sapiens

<400> SEQUENCE: 18

Met Pro Val Arg Arg Gly His Val Ala Pro Gln Asn Thr Phe Leu Asp
1               5                   10                  15

Thr Ile Ile Arg Lys Phe Glu Gly Gln Ser Arg Lys Phe Ile Ile Ala
            20                  25                  30

Asn Ala Arg Val Glu Asn Cys Ala Val Ile Tyr Cys Asn Asp Gly Phe
        35                  40                  45

Cys Glu Leu Cys Gly Tyr Ser Arg Ala Glu Val Met Gln Arg Pro Cys
    50                  55                  60

Thr Cys Asp Phe Leu His Gly Pro Arg Thr Gln Arg Arg Ala Ala Ala
65                  70                  75                  80

Gln Ile Ala Gln Ala Leu Leu Gly Ala Glu Arg Lys Val Glu Ile
                85                  90                  95

Ala Phe Tyr Arg Lys Asp Gly Ser Cys Phe Leu Cys Leu Val Asp Val
            100                 105                 110

Val Pro Val Lys Asn Glu Asp Gly Ala Val Ile Met Phe Ile Leu Asn
            115                 120                 125

Phe Glu Val Val Met Glu Lys Asp Met Val Gly Ser Pro Ala His Asp
    130                 135                 140

Thr Asn His Arg Gly Pro Pro Thr Ser Trp Leu Ala Pro Gly Arg Ala
145                 150                 155                 160

Lys Thr Phe Arg Leu Lys Leu Pro Ala Leu Leu Ala Leu Thr Ala Arg
                165                 170                 175

Glu Ser Ser Val Arg Ser Gly Gly Ala Gly Gly Ala Gly Ala Pro Gly
            180                 185                 190

Ala Val Val Val Asp Val Asp Leu Thr Pro Ala Ala Pro Ser Ser Glu
            195                 200                 205

Ser Leu Ala Leu Asp Glu Val Thr Ala Met Asp Asn His Val Ala Gly
        210                 215                 220

Leu Gly Pro Ala Glu Glu Arg Arg Ala Leu Val Gly Pro Gly Ser Pro
225                 230                 235                 240

Pro Arg Ser Ala Pro Gly Gln Leu Pro Ser Pro Arg Ala His Ser Leu
                245                 250                 255

Asn Pro Asp Ala Ser Gly Ser Ser Cys Ser Leu Ala Arg Thr Arg Ser
            260                 265                 270

Arg Glu Ser Cys Ala Ser Val Arg Arg Ala Ser Ser Ala Asp Asp Ile
        275                 280                 285

Glu Ala Met Arg Ala Gly Val Leu Pro Pro Pro Arg His Ala Ser
    290                 295                 300

Thr Gly Ala Met His Pro Leu Arg Ser Gly Leu Leu Asn Ser Thr Ser
305                 310                 315                 320
```

-continued

```
Asp Ser Asp Leu Val Arg Tyr Arg Thr Ile Ser Lys Ile Pro Gln Ile
            325                 330                 335

Thr Leu Asn Phe Val Asp Leu Lys Gly Asp Pro Phe Leu Ala Ser Pro
            340                 345                 350

Thr Ser Asp Arg Glu Ile Ile Ala Pro Lys Ile Lys Glu Arg Thr His
            355                 360                 365

Asn Val Thr Glu Lys Val Thr Gln Val Leu Ser Leu Gly Ala Asp Val
            370                 375                 380

Leu Pro Glu Tyr Lys Leu Gln Ala Pro Arg Ile His Arg Trp Thr Ile
385                 390                 395                 400

Leu His Tyr Ser Pro Phe Lys Ala Val Trp Asp Trp Leu Ile Leu Leu
                405                 410                 415

Leu Val Ile Tyr Thr Ala Val Phe Thr Pro Tyr Ser Ala Ala Phe Leu
                420                 425                 430

Leu Lys Glu Thr Glu Glu Gly Pro Pro Ala Thr Glu Cys Gly Tyr Ala
            435                 440                 445

Cys Gln Pro Leu Ala Val Val Asp Leu Ile Val Asp Ile Met Phe Ile
            450                 455                 460

Val Asp Ile Leu Ile Asn Phe Arg Thr Thr Tyr Val Asn Ala Asn Glu
465                 470                 475                 480

Glu Val Val Ser His Pro Gly Arg Ile Ala Val His Tyr Phe Lys Gly
                485                 490                 495

Trp Phe Leu Ile Asp Met Val Ala Ala Ile Pro Phe Asp Leu Leu Ile
                500                 505                 510

Phe Gly Ser Gly Ser Glu Glu Leu Ile Gly Leu Leu Lys Thr Ala Arg
            515                 520                 525

Leu Leu Arg Leu Val Arg Val Ala Arg Lys Leu Asp Arg Tyr Ser Glu
            530                 535                 540

Tyr Gly Ala Ala Val Leu Phe Leu Leu Met Cys Thr Phe Ala Leu Ile
545                 550                 555                 560

Ala His Trp Leu Ala Cys Ile Trp Tyr Ala Ile Gly Asn Met Glu Gln
                565                 570                 575

Pro His Met Asp Ser Arg Ile Gly Trp Leu His Asn Leu Gly Asp Gln
            580                 585                 590

Ile Gly Lys Pro Tyr Asn Ser Ser Gly Leu Gly Gly Pro Ser Ile Lys
            595                 600                 605

Asp Lys Tyr Val Thr Ala Leu Tyr Phe Thr Phe Ser Ser Leu Thr Ser
            610                 615                 620

Val Gly Phe Gly Asn Val Ser Pro Asn Thr Asn Ser Glu Lys Ile Phe
625                 630                 635                 640

Ser Ile Cys Val Met Leu Ile Gly Ser Leu Met Tyr Ala Ser Ile Phe
                645                 650                 655

Gly Asn Val Ser Ala Ile Ile Gln Arg Leu Tyr Ser Gly Thr Ala Arg
                660                 665                 670

Tyr His Thr Gln Met Leu Arg Val Arg Glu Phe Ile Arg Phe His Gln
            675                 680                 685

Ile Pro Asn Pro Leu Arg Gln Arg Leu Glu Glu Tyr Phe Gln His Ala
            690                 695                 700

Trp Ser Tyr Thr Asn Gly Ile Asp Met Asn Ala Val Leu Lys Gly Phe
705                 710                 715                 720

Pro Glu Cys Leu Gln Ala Asp Ile Cys Leu His Leu Asn Arg Ser Leu
                725                 730                 735
```

```
Leu Gln His Cys Lys Pro Phe Arg Gly Ala Thr Lys Gly Cys Leu Arg
            740                 745                 750

Ala Leu Ala Met Lys Phe Lys Thr Thr His Ala Pro Pro Gly Asp Thr
            755                 760                 765

Leu Val His Ala Gly Asp Leu Leu Thr Ala Leu Tyr Phe Ile Ser Arg
            770                 775                 780

Gly Ser Ile Glu Ile Leu Arg Gly Asp Val Val Ala Ile Leu Gly
785                 790                 795                 800

Lys Asn Asp Ile Phe Gly Glu Pro Leu Asn Leu Tyr Ala Arg Pro Gly
                805                 810                 815

Lys Ser Asn Gly Asp Val Arg Ala Leu Thr Tyr Cys Asp Leu His Lys
            820                 825                 830

Ile His Arg Asp Asp Leu Leu Glu Val Leu Asp Met Tyr Pro Glu Phe
            835                 840                 845

Ser Asp His Phe Trp Ser Ser Leu Glu Ile Thr Phe Asn Leu Arg Asp
            850                 855                 860

Thr Asn Met Ile Pro Gly Ser Pro Gly Ser Thr Glu Leu Glu Gly Gly
865                 870                 875                 880

Phe Ser Arg Gln Arg Lys Arg Lys Leu Ser Phe Arg Arg Thr Asp
                885                 890                 895

Lys Asp Thr Glu Gln Pro Gly Glu Val Ser Ala Leu Gly Pro Gly Arg
            900                 905                 910

Ala Gly Ala Gly Pro Ser Ser Arg Gly Arg Pro Gly Gly Pro Trp Gly
            915                 920                 925

Glu Ser Pro Ser Ser Gly Pro Ser Ser Pro Gly Ser Ser Glu Asp Glu
            930                 935                 940

Gly Pro Gly Arg Ser Ser Ser Pro Leu Arg Leu Val Pro Phe Ser Ser
945                 950                 955                 960

Pro Arg Pro Pro Gly Glu Pro Pro Gly Gly Glu Pro Leu Met Glu Asp
                965                 970                 975

Cys Glu Lys Ser Ser Asp Thr Cys Asn Pro Leu Ser Gly Ala Phe Ser
            980                 985                 990

Gly Val Ser Asn Ile Phe Ser Phe Trp Gly Asp Ser Arg Gly Arg Gln
            995                 1000                1005

Tyr Gln Glu Leu Pro Arg Cys Pro Ala Pro Thr Pro Ser Leu Leu
            1010                1015                1020

Asn Ile Pro Leu Ser Ser Pro Gly Arg Arg Pro Arg Gly Asp Val
            1025                1030                1035

Glu Ser Arg Leu Asp Ala Leu Gln Arg Gln Leu Asn Arg Leu Glu
            1040                1045                1050

Thr Arg Leu Ser Ala Asp Met Ala Thr Val Leu Gln Leu Leu Gln
            1055                1060                1065

Arg Gln Met Thr Leu Val Pro Pro Ala Tyr Ser Ala Val Thr Thr
            1070                1075                1080

Pro Gly Pro Gly Pro Thr Ser Thr Ser Pro Leu Leu Pro Val Ser
            1085                1090                1095

Pro Leu Pro Thr Leu Thr Leu Asp Ser Leu Ser Gln Val Ser Gln
            1100                1105                1110

Phe Met Ala Cys Glu Glu Leu Pro Pro Gly Ala Pro Glu Leu Pro
            1115                1120                1125

Gln Glu Gly Pro Thr Arg Arg Leu Ser Leu Pro Gly Gln Leu Gly
            1130                1135                1140

Ala Leu Thr Ser Gln Pro Leu His Arg His Gly Ser Asp Pro Gly
```

Ser

<210> SEQ ID NO 19
<211> LENGTH: 1159
<212> TYPE: PRT
<213> ORGANISM: Homo sapiens

<400> SEQUENCE: 19

```
Met Pro Val Arg Arg Gly His Val Ala Pro Gln Asn Thr Phe Leu Asp
1               5                   10                  15

Thr Ile Ile Arg Lys Phe Glu Gly Gln Ser Arg Lys Phe Ile Ile Ala
            20                  25                  30

Asn Ala Arg Val Glu Asn Cys Ala Val Ile Tyr Cys Asn Asp Gly Phe
        35                  40                  45

Cys Glu Leu Cys Gly Tyr Ser Arg Ala Glu Val Met Gln Arg Pro Cys
    50                  55                  60

Thr Cys Asp Phe Leu His Gly Pro Arg Thr Gln Arg Arg Ala Ala Ala
65                  70                  75                  80

Gln Ile Ala Gln Ala Leu Leu Gly Ala Glu Glu Arg Lys Val Glu Ile
                85                  90                  95

Ala Phe Tyr Arg Lys Asp Gly Ser Cys Phe Leu Cys Leu Val Asp Val
            100                 105                 110

Val Pro Val Lys Asn Glu Asp Gly Ala Val Ile Met Phe Ile Leu Asn
        115                 120                 125

Phe Glu Val Val Met Glu Lys Asp Met Val Gly Ser Pro Ala His Asp
130                 135                 140

Thr Asn His Arg Gly Pro Pro Thr Ser Trp Leu Ala Pro Gly Arg Ala
145                 150                 155                 160

Lys Thr Phe Arg Leu Lys Leu Pro Ala Leu Leu Ala Leu Thr Ala Arg
                165                 170                 175

Glu Ser Ser Val Arg Ser Gly Gly Ala Gly Ala Gly Ala Pro Gly
            180                 185                 190

Ala Val Val Val Asp Val Asp Leu Thr Pro Ala Ala Pro Ser Ser Glu
        195                 200                 205

Ser Leu Ala Leu Asp Glu Val Thr Ala Met Asp Asn His Val Ala Gly
    210                 215                 220

Leu Gly Pro Ala Glu Glu Arg Arg Ala Leu Val Gly Pro Gly Ser Pro
225                 230                 235                 240

Pro Arg Ser Ala Pro Gly Gln Leu Pro Ser Pro Arg Ala His Ser Leu
                245                 250                 255

Asn Pro Asp Ala Ser Gly Ser Ser Cys Ser Leu Ala Arg Thr Arg Ser
            260                 265                 270

Arg Glu Ser Cys Ala Ser Val Arg Arg Ala Ser Ser Ala Asp Asp Ile
        275                 280                 285

Glu Ala Met Arg Ala Gly Val Leu Pro Pro Pro Arg His Ala Ser
    290                 295                 300

Thr Gly Ala Met His Pro Leu Arg Ser Gly Leu Leu Asn Ser Thr Ser
305                 310                 315                 320

Asp Ser Asp Leu Val Arg Tyr Arg Thr Ile Ser Lys Ile Pro Gln Ile
                325                 330                 335

Thr Leu Asn Phe Val Asp Leu Lys Gly Asp Pro Phe Leu Ala Ser Pro
            340                 345                 350

Thr Ser Asp Arg Glu Ile Ile Ala Pro Lys Ile Lys Glu Arg Thr His
```

-continued

```
            355                 360                 365
Asn Val Thr Glu Lys Val Thr Gln Val Leu Ser Leu Gly Ala Asp Val
            370                 375                 380
Leu Pro Glu Tyr Lys Leu Gln Ala Pro Arg Ile His Arg Trp Thr Ile
385                 390                 395                 400
Leu His Tyr Ser Pro Phe Lys Ala Val Trp Asp Trp Leu Ile Leu Leu
                405                 410                 415
Leu Val Ile Tyr Thr Ala Val Phe Thr Pro Tyr Ser Ala Ala Phe Leu
            420                 425                 430
Leu Lys Glu Thr Glu Glu Gly Pro Pro Ala Thr Glu Cys Gly Tyr Ala
            435                 440                 445
Cys Gln Pro Leu Ala Val Val Asp Leu Ile Val Asp Ile Met Phe Ile
            450                 455                 460
Val Asp Ile Leu Ile Asn Phe Arg Thr Thr Tyr Val Asn Ala Asn Glu
465                 470                 475                 480
Glu Val Val Ser His Pro Gly Arg Ile Ala Val His Tyr Phe Lys Gly
                485                 490                 495
Trp Phe Leu Ile Asp Met Val Ala Ala Ile Pro Phe Asp Leu Leu Ile
                500                 505                 510
Phe Gly Ser Gly Ser Glu Glu Leu Ile Gly Leu Leu Lys Thr Ala Arg
            515                 520                 525
Leu Leu Arg Leu Val Arg Val Ala Arg Lys Leu Asp Arg Tyr Ser Glu
            530                 535                 540
Tyr Gly Ala Ala Val Leu Phe Leu Leu Met Cys Thr Phe Ala Leu Ile
545                 550                 555                 560
Ala His Trp Leu Ala Cys Ile Trp Tyr Ala Ile Gly Asn Met Glu Gln
                565                 570                 575
Pro His Met Asp Ser Arg Ile Gly Trp Leu His Asn Leu Gly Asp Gln
            580                 585                 590
Ile Gly Lys Pro Tyr Asn Ser Ser Leu Gly Gly Pro Ser Ile Lys
            595                 600                 605
Asp Lys Tyr Val Thr Ala Leu Tyr Phe Thr Phe Ser Ser Leu Thr Ser
            610                 615                 620
Val Gly Phe Gly Asn Val Ser Pro Asn Thr Asn Ser Glu Lys Ile Phe
625                 630                 635                 640
Ser Ile Cys Val Met Leu Ile Gly Ser Leu Met Tyr Ala Ser Ile Phe
                645                 650                 655
Gly Asn Val Ser Ala Ile Ile Gln Arg Leu Tyr Ser Gly Thr Ala Arg
                660                 665                 670
Tyr His Thr Gln Met Leu Arg Val Arg Glu Phe Ile Arg Phe His Gln
            675                 680                 685
Ile Pro Asn Pro Leu Arg Gln Arg Leu Glu Glu Tyr Phe Gln His Ala
            690                 695                 700
Trp Ser Tyr Thr Asn Gly Ile Asp Met Asn Ala Val Leu Lys Gly Phe
705                 710                 715                 720
Pro Glu Cys Leu Gln Ala Asp Ile Cys Leu His Leu Asn Arg Ser Leu
                725                 730                 735
Leu Gln His Cys Lys Pro Phe Arg Gly Ala Thr Lys Gly Cys Leu Arg
            740                 745                 750
Ala Leu Ala Met Lys Phe Lys Thr Thr His Ala Pro Pro Gly Asp Thr
            755                 760                 765
Leu Val His Ala Gly Asp Leu Leu Thr Ala Leu Tyr Phe Ile Ser Arg
            770                 775                 780
```

-continued

```
Gly Ser Ile Glu Ile Leu Arg Gly Asp Val Val Ala Ile Leu Gly
785                 790                 795                 800

Lys Asn Asp Ile Phe Gly Glu Pro Leu Asn Leu Tyr Ala Arg Pro Gly
            805                 810                 815

Lys Ser Asn Gly Asp Val Arg Ala Leu Thr Tyr Cys Asp Leu His Lys
        820                 825                 830

Ile His Arg Asp Asp Leu Leu Glu Val Leu Asp Met Tyr Pro Glu Phe
            835                 840                 845

Ser Asp His Phe Trp Ser Ser Leu Glu Ile Thr Phe Asn Leu Arg Asp
        850                 855                 860

Thr Asn Met Ile Pro Gly Ser Pro Gly Ser Thr Glu Leu Glu Gly Gly
865                 870                 875                 880

Phe Ser Arg Gln Arg Lys Arg Lys Leu Ser Phe Arg Arg Thr Asp
            885                 890                 895

Lys Asp Thr Glu Gln Pro Gly Glu Val Ser Ala Leu Gly Pro Gly Arg
            900                 905                 910

Ala Gly Ala Gly Pro Ser Ser Arg Gly Arg Pro Gly Gly Pro Trp Gly
            915                 920                 925

Glu Ser Pro Ser Ser Gly Pro Ser Ser Pro Glu Ser Ser Glu Asp Glu
930                 935                 940

Gly Pro Gly Arg Ser Ser Ser Pro Leu Arg Leu Val Pro Phe Ser Ser
945                 950                 955                 960

Pro Arg Pro Pro Gly Glu Pro Gly Gly Glu Pro Leu Met Glu Asp
            965                 970                 975

Cys Glu Lys Ser Ser Asp Thr Cys Asn Pro Leu Ser Gly Ala Phe Ser
            980                 985                 990

Gly Val Ser Asn Ile Phe Ser Phe Trp Gly Asp Ser Arg Gly Arg Gln
            995                 1000                1005

Tyr Gln Glu Leu Pro Arg Cys Pro Ala Pro Thr Pro Ser Leu Leu
        1010                1015                1020

Asn Ile Pro Leu Ser Ser Pro Gly Arg Arg Pro Arg Gly Asp Val
        1025                1030                1035

Glu Ser Arg Leu Asp Ala Leu Gln Arg Gln Leu Asn Arg Leu Glu
        1040                1045                1050

Thr Arg Leu Ser Ala Asp Met Ala Thr Val Leu Gln Leu Leu Gln
        1055                1060                1065

Arg Gln Met Thr Leu Val Pro Pro Ala Tyr Ser Ala Val Thr Thr
        1070                1075                1080

Pro Gly Pro Gly Pro Thr Ser Thr Ser Pro Leu Leu Pro Val Ser
        1085                1090                1095

Pro Leu Pro Thr Leu Thr Leu Asp Ser Leu Ser Gln Val Ser Gln
        1100                1105                1110

Phe Met Ala Cys Glu Glu Leu Pro Pro Gly Ala Pro Glu Leu Pro
        1115                1120                1125

Gln Glu Gly Pro Thr Arg Arg Leu Ser Leu Pro Gly Gln Leu Gly
        1130                1135                1140

Ala Leu Thr Ser Gln Pro Leu His Arg His Gly Ser Asp Pro Gly
        1145                1150                1155

Ser
```

<210> SEQ ID NO 20
<211> LENGTH: 68
<212> TYPE: PRT

<213> ORGANISM: Homo sapiens

<400> SEQUENCE: 20

Gln Lys Gln Pro Thr Trp Val Pro Asp Ser Glu Ala Pro Asn Cys Met
1               5                   10                  15

Asn Cys Gln Val Lys Phe Thr Phe Thr Lys Arg Arg His His Cys Arg
            20                  25                  30

Ala Cys Gly Lys Val Phe Cys Gly Val Cys Cys Asn Arg Lys Cys Lys
        35                  40                  45

Leu Gln Tyr Leu Glu Lys Glu Ala Arg Val Cys Val Val Cys Tyr Glu
    50                  55                  60

Thr Ile Ser Lys
65

<210> SEQ ID NO 21
<211> LENGTH: 213
<212> TYPE: PRT
<213> ORGANISM: Homo sapiens

<400> SEQUENCE: 21

Met Ser Glu Thr Tyr Asp Phe Leu Phe Lys Phe Leu Val Ile Gly Asn
1               5                   10                  15

Ala Gly Thr Gly Lys Ser Cys Leu Leu His Gln Phe Ile Glu Lys Lys
            20                  25                  30

Phe Lys Asp Asp Ser Asn His Thr Ile Gly Val Glu Phe Gly Ser Lys
        35                  40                  45

Ile Ile Asn Val Gly Gly Lys Tyr Val Lys Leu Gln Ile Trp Asp Thr
    50                  55                  60

Ala Gly Gln Glu Arg Phe Arg Ser Val Thr Arg Ser Tyr Tyr Arg Gly
65              70                  75                  80

Ala Ala Gly Ala Leu Leu Val Tyr Asp Ile Thr Ser Arg Glu Thr Tyr
            85                  90                  95

Asn Ala Leu Thr Asn Trp Leu Thr Asp Ala Arg Met Leu Ala Ser Gln
        100                 105                 110

Asn Ile Val Ile Ile Leu Cys Gly Asn Lys Lys Asp Leu Asp Ala Asp
    115                 120                 125

Arg Glu Val Thr Phe Leu Glu Ala Ser Arg Phe Ala Gln Glu Asn Glu
130                 135                 140

Leu Met Phe Leu Glu Thr Ser Ala Leu Thr Gly Glu Asn Val Glu Glu
145                 150                 155                 160

Ala Phe Val Gln Cys Ala Arg Lys Ile Leu Asn Lys Ile Glu Ser Gly
                165                 170                 175

Glu Leu Asp Pro Glu Arg Met Gly Ser Gly Ile Gln Tyr Gly Asp Ala
            180                 185                 190

Ala Leu Arg Gln Leu Arg Ser Pro Arg Arg Ala Gln Ala Pro Asn Ala
        195                 200                 205

Gln Glu Cys Gly Cys
    210

<210> SEQ ID NO 22
<211> LENGTH: 216
<212> TYPE: PRT
<213> ORGANISM: Homo sapiens

<400> SEQUENCE: 22

Met Gly Thr Arg Asp Asp Glu Tyr Asp Tyr Leu Phe Lys Val Val Leu
1               5                   10                  15

```
Ile Gly Asp Ser Gly Val Gly Lys Ser Asn Leu Leu Ser Arg Phe Thr
            20                  25                  30

Arg Asn Glu Phe Asn Leu Glu Ser Lys Ser Thr Ile Gly Val Glu Phe
        35                  40                  45

Ala Thr Arg Ser Ile Gln Val Asp Gly Lys Thr Ile Lys Ala Gln Ile
    50                  55                  60

Trp Asp Thr Ala Gly Gln Glu Arg Tyr Arg Ala Ile Thr Ser Ala Tyr
 65                  70                  75                  80

Tyr Arg Gly Ala Val Gly Ala Leu Leu Val Tyr Asp Ile Ala Lys His
                85                  90                  95

Leu Thr Tyr Glu Asn Val Glu Arg Trp Leu Lys Glu Leu Arg Asp His
            100                 105                 110

Ala Asp Ser Asn Ile Val Ile Met Leu Val Gly Asn Lys Ser Asp Leu
        115                 120                 125

Arg His Leu Arg Ala Val Pro Thr Asp Glu Ala Arg Ala Phe Ala Glu
    130                 135                 140

Lys Asn Gly Leu Ser Phe Ile Glu Thr Ser Ala Leu Asp Ser Thr Asn
145                 150                 155                 160

Val Glu Ala Ala Phe Gln Thr Ile Leu Thr Glu Ile Tyr Arg Ile Val
                165                 170                 175

Ser Gln Lys Gln Met Ser Asp Arg Arg Glu Asn Asp Met Ser Pro Ser
            180                 185                 190

Asn Asn Val Val Pro Ile His Val Pro Pro Thr Thr Glu Asn Lys Pro
        195                 200                 205

Lys Val Gln Cys Cys Gln Asn Ile
    210                 215

<210> SEQ ID NO 23
<211> LENGTH: 383
<212> TYPE: PRT
<213> ORGANISM: Homo sapiens

<400> SEQUENCE: 23

Met Lys Thr Ile Ile Ala Leu Ser Tyr Ile Phe Cys Leu Val Phe Ala
 1               5                  10                  15

Asp Tyr Lys Asp Asp Asp Ala Met Ile Leu Asn Ser Ser Thr Glu
            20                  25                  30

Asp Gly Ile Lys Arg Ile Gln Asp Asp Cys Pro Lys Ala Gly Arg His
        35                  40                  45

Asn Tyr Ile Phe Val Met Ile Pro Thr Leu Tyr Ser Ile Ile Phe Val
    50                  55                  60

Val Gly Ile Phe Gly Asn Ser Leu Val Val Ile Val Ile Tyr Phe Tyr
 65                  70                  75                  80

Met Lys Leu Lys Thr Val Ala Ser Val Phe Leu Leu Asn Leu Ala Leu
                85                  90                  95

Ala Asp Leu Cys Phe Leu Leu Thr Leu Pro Leu Trp Ala Val Tyr Thr
            100                 105                 110

Ala Met Glu Tyr Arg Trp Pro Phe Gly Asn Tyr Leu Cys Lys Ile Ala
        115                 120                 125

Ser Ala Ser Val Ser Phe Asn Leu Tyr Ala Ser Val Phe Leu Leu Thr
    130                 135                 140

Cys Leu Ser Ile Asp Arg Tyr Leu Ala Ile Val His Pro Met Lys Ser
145                 150                 155                 160

Arg Leu Arg Arg Thr Met Leu Val Ala Lys Val Thr Cys Ile Ile Ile
```

-continued

```
                165                 170                 175
Trp Leu Leu Ala Gly Leu Ala Ser Leu Pro Ala Ile Ile His Arg Asn
                180                 185                 190

Val Phe Phe Ile Glu Asn Thr Asn Ile Thr Val Cys Ala Phe His Tyr
                195                 200                 205

Glu Ser Gln Asn Ser Thr Leu Pro Ile Gly Leu Gly Leu Thr Lys Asn
                210                 215                 220

Ile Leu Gly Phe Leu Phe Pro Phe Leu Ile Ile Leu Thr Ser Tyr Thr
225                 230                 235                 240

Leu Ile Trp Lys Ala Leu Lys Lys Ala Tyr Glu Ile Gln Lys Asn Lys
                245                 250                 255

Pro Arg Asn Asp Asp Ile Phe Lys Ile Ile Met Ala Ile Val Leu Phe
                260                 265                 270

Phe Phe Phe Ser Trp Ile Pro His Gln Ile Phe Thr Phe Leu Asp Val
                275                 280                 285

Leu Ile Gln Leu Gly Ile Ile Arg Asp Cys Arg Ile Ala Asp Ile Val
                290                 295                 300

Asp Thr Ala Met Pro Ile Thr Ile Cys Ile Ala Tyr Phe Asn Asn Cys
305                 310                 315                 320

Leu Asn Pro Leu Phe Tyr Gly Phe Leu Gly Lys Lys Phe Lys Arg Tyr
                325                 330                 335

Phe Leu Gln Leu Leu Lys Tyr Ile Pro Pro Lys Ala Lys Ser His Ser
                340                 345                 350

Asn Leu Ser Thr Lys Met Ser Thr Leu Ser Tyr Arg Pro Ser Asp Asn
                355                 360                 365

Val Ser Ser Thr Lys Lys Pro Ala Pro Cys Phe Glu Val Glu
                370                 375                 380

<210> SEQ ID NO 24
<211> LENGTH: 176
<212> TYPE: PRT
<213> ORGANISM: Homo sapiens

<400> SEQUENCE: 24

Met Glu Ala Ile Ala Lys Tyr Asp Phe Lys Ala Thr Ala Asp Asp Glu
1               5                   10                  15

Leu Ser Phe Lys Arg Gly Asp Ile Leu Lys Val Leu Asn Glu Glu Cys
                20                  25                  30

Asp Gln Asn Trp Tyr Lys Ala Glu Leu Asn Gly Lys Asp Gly Phe Ile
                35                  40                  45

Pro Lys Asn Tyr Ile Glu Met Lys Pro His Pro Phe Gly Asn Asp Val
                50                  55                  60

Gln His Phe Lys Val Leu Arg Asp Gly Ala Gly Lys Tyr Phe Leu Trp
65                  70                  75                  80

Val Val Lys Phe Asn Ser Leu Asn Glu Leu Val Asp Tyr His Arg Ser
                85                  90                  95

Thr Ser Val Ser Arg Asn Gln Gln Ile Phe Leu Arg Asp Ile Glu Gln
                100                 105                 110

Val Pro Gln Gln Pro Thr Tyr Val Gln Ala Leu Phe Asp Phe Asp Pro
                115                 120                 125

Gln Glu Asp Gly Glu Leu Gly Phe Arg Arg Gly Asp Phe Ile His Val
                130                 135                 140

Met Asp Asn Ser Asp Pro Asn Trp Trp Lys Gly Ala Cys His Gly Gln
145                 150                 155                 160
```

```
Thr Gly Met Phe Pro Arg Asn Tyr Val Thr Pro Val Asn Arg Asn Val
                165                 170                 175

<210> SEQ ID NO 25
<211> LENGTH: 173
<212> TYPE: PRT
<213> ORGANISM: Homo sapiens

<400> SEQUENCE: 25

Asp Ser Gly Arg Asp Phe Leu Thr Leu His Gly Leu Gln Asp Glu
1               5                   10                  15

Asp Leu Gln Ala Leu Leu Lys Gly Ser Gln Leu Leu Lys Val Lys Ser
                20                  25                  30

Ser Ser Trp Arg Arg Glu Arg Phe Tyr Lys Leu Gln Glu Asp Cys Lys
            35                  40                  45

Thr Ile Trp Gln Glu Ser Arg Lys Val Met Arg Thr Pro Glu Ser Gln
    50                  55                  60

Leu Phe Ser Ile Glu Asp Ile Gln Glu Val Arg Met Gly His Arg Thr
65                  70                  75                  80

Glu Gly Leu Glu Lys Phe Ala Arg Asp Val Pro Glu Asp Arg Cys Phe
                85                  90                  95

Ser Ile Val Phe Lys Asp Gln Arg Asn Thr Leu Asp Leu Ile Ala Pro
                100                 105                 110

Ser Pro Ala Asp Ala Gln His Trp Val Leu Gly Leu His Lys Ile Ile
                115                 120                 125

His His Ser Gly Ser Met Asp Gln Arg Gln Lys Leu Gln His Trp Ile
            130                 135                 140

His Ser Cys Leu Arg Lys Ala Asp Lys Asn Lys Asp Asn Lys Met Ser
145                 150                 155                 160

Phe Lys Glu Leu Gln Asn Phe Leu Lys Glu Leu Asn Ile
                165                 170

<210> SEQ ID NO 26
<211> LENGTH: 10
<212> TYPE: PRT
<213> ORGANISM: Influenza A virus

<400> SEQUENCE: 26

Met Tyr Pro Tyr Asp Val Pro Asp Tyr Ala
1               5                   10

<210> SEQ ID NO 27
<211> LENGTH: 5
<212> TYPE: PRT
<213> ORGANISM: Artificial Sequence
<220> FEATURE:
<223> OTHER INFORMATION: synthetic linker

<400> SEQUENCE: 27

Leu Ser Asn Ala Thr
1               5

<210> SEQ ID NO 28
<211> LENGTH: 14
<212> TYPE: PRT
<213> ORGANISM: Artificial Sequence
<220> FEATURE:
<223> OTHER INFORMATION: synthetic linker

<400> SEQUENCE: 28

Gly Ser Ala Gly Thr Met Ala Ser Asn Asn Thr Ala Ser Gly
```

```
<210> SEQ ID NO 29
<211> LENGTH: 11
<212> TYPE: PRT
<213> ORGANISM: Artificial Sequence
<220> FEATURE:
<223> OTHER INFORMATION: synthetic linker

<400> SEQUENCE: 29

Gly Ser Gly Gly Ser Gly Ser Gly Gly Leu Glu
1               5                   10

<210> SEQ ID NO 30
<211> LENGTH: 10
<212> TYPE: PRT
<213> ORGANISM: Artificial Sequence
<220> FEATURE:
<223> OTHER INFORMATION: GGSGGKLPAT

<400> SEQUENCE: 30

Gly Gly Ser Gly Gly Lys Leu Pro Ala Thr
1               5                   10

<210> SEQ ID NO 31
<211> LENGTH: 18
<212> TYPE: PRT
<213> ORGANISM: Artificial Sequence
<220> FEATURE:
<223> OTHER INFORMATION: synthetic linker

<400> SEQUENCE: 31

Gly Asn Ala Ser Gly Thr Gly Ser Gly Gly Ser Gly Ser Gly Gly Leu
1               5                   10                  15

Glu Met

<210> SEQ ID NO 32
<211> LENGTH: 5
<212> TYPE: PRT
<213> ORGANISM: Artificial Sequence
<220> FEATURE:
<223> OTHER INFORMATION: synthetic linker

<400> SEQUENCE: 32

Ser Asn Ala Lys Leu
1               5

<210> SEQ ID NO 33
<211> LENGTH: 20
<212> TYPE: PRT
<213> ORGANISM: Homo sapiens

<400> SEQUENCE: 33

Lys Leu Asn Pro Pro Asp Glu Ser Gly Pro Gly Cys Met Ser Cys Lys
1               5                   10                  15

Cys Val Leu Ser
            20

<210> SEQ ID NO 34
<211> LENGTH: 20
<212> TYPE: PRT
<213> ORGANISM: Homo sapiens

<400> SEQUENCE: 34

Lys Leu Asn Ser Ser Asp Asp Gly Thr Gln Gly Cys Met Gly Leu Pro
```

```
                1               5                   10                  15

Cys Val Val Met
            20

<210> SEQ ID NO 35
<211> LENGTH: 20
<212> TYPE: PRT
<213> ORGANISM: Homo sapiens

<400> SEQUENCE: 35

Lys Ile Ser Lys Glu Glu Lys Thr Pro Gly Cys Val Lys Ile Lys Lys
1               5                   10                  15

Cys Ile Ile Met
            20

<210> SEQ ID NO 36
<211> LENGTH: 20
<212> TYPE: PRT
<213> ORGANISM: Homo sapiens

<400> SEQUENCE: 36

Lys Met Ser Lys Asp Gly Lys Lys Lys Lys Lys Ser Lys Thr Lys
1               5                   10                  15

Cys Val Ile Met
            20

<210> SEQ ID NO 37
<211> LENGTH: 21
<212> TYPE: PRT
<213> ORGANISM: Homo sapiens

<400> SEQUENCE: 37

Lys Asn Gly Lys Lys Lys Arg Lys Ser Leu Ala Lys Arg Ile Arg Glu
1               5                   10                  15

Arg Cys Cys Ile Leu
            20

<210> SEQ ID NO 38
<211> LENGTH: 7
<212> TYPE: PRT
<213> ORGANISM: Homo sapiens

<400> SEQUENCE: 38

Pro Lys Lys Lys Arg Arg Val
1               5

<210> SEQ ID NO 39
<211> LENGTH: 16
<212> TYPE: PRT
<213> ORGANISM: Homo sapiens

<400> SEQUENCE: 39

Lys Arg Pro Ala Ala Thr Lys Lys Ala Gly Gln Ala Lys Lys Lys Lys
1               5                   10                  15

<210> SEQ ID NO 40
<211> LENGTH: 15
<212> TYPE: PRT
<213> ORGANISM: Homo sapiens

<400> SEQUENCE: 40

Val Gln Ser Glu Pro Arg Ser Trp Ser Leu Leu Glu Gln Leu Gly
1               5                   10                  15
```

```
<210> SEQ ID NO 41
<211> LENGTH: 5
<212> TYPE: PRT
<213> ORGANISM: Artificial Sequence
<220> FEATURE:
<223> OTHER INFORMATION: Synthetic linker

<400> SEQUENCE: 41

Gly Ser Asn Ala Thr
1               5

<210> SEQ ID NO 42
<211> LENGTH: 73
<212> TYPE: PRT
<213> ORGANISM: Homo sapiens

<400> SEQUENCE: 42

Met Gly Asn Leu Lys Ser Val Ala Gln Glu Pro Gly Pro Pro Cys Gly
1               5                   10                  15

Leu Gly Leu Gly Leu Gly Leu Gly Leu Cys Gly Lys Gln Gly Pro Ala
                20                  25                  30

Thr Pro Ala Pro Glu Pro Ser Arg Ala Pro Ala Ser Leu Leu Pro Pro
            35                  40                  45

Ala Pro Glu His Ser Pro Pro Ser Ser Pro Leu Thr Gln Pro Pro Glu
        50                  55                  60

Gly Pro Lys Phe Pro Arg Val Lys Asn
65                  70

<210> SEQ ID NO 43
<211> LENGTH: 9
<212> TYPE: PRT
<213> ORGANISM: Homo sapiens

<400> SEQUENCE: 43

Cys Met Ser Cys Lys Cys Cys Ile Leu
1               5

<210> SEQ ID NO 44
<211> LENGTH: 178
<212> TYPE: PRT
<213> ORGANISM: Homo sapiens

<400> SEQUENCE: 44

Met Ser Gly Gly Lys Tyr Val Asp Ser Glu Gly His Leu Tyr Thr Val
1               5                   10                  15

Pro Ile Arg Glu Gln Gly Asn Ile Tyr Lys Pro Asn Asn Lys Ala Met
                20                  25                  30

Ala Asp Glu Leu Ser Glu Lys Gln Val Tyr Asp Ala His Thr Lys Glu
            35                  40                  45

Ile Asp Leu Val Asn Arg Asp Pro Lys His Leu Asn Asp Asp Val Val
        50                  55                  60

Lys Ile Asp Phe Glu Asp Val Ile Ala Glu Pro Gly Thr His Ser
65                  70                  75                  80

Phe Asp Gly Ile Trp Lys Ala Ser Phe Thr Thr Phe Thr Val Thr Lys
                85                  90                  95

Tyr Trp Phe Tyr Arg Leu Leu Ser Ala Leu Phe Gly Ile Pro Met Ala
                100                 105                 110

Leu Ile Trp Gly Ile Tyr Phe Ala Ile Leu Ser Phe Leu His Ile Trp
                115                 120                 125
```

```
Ala Val Val Pro Cys Ile Lys Ser Phe Leu Ile Glu Ile Gln Cys Ile
            130                 135                 140

Ser Arg Val Tyr Ser Ile Tyr Val His Thr Val Cys Asp Pro Leu Phe
145                 150                 155                 160

Glu Ala Val Gly Lys Ile Phe Ser Asn Val Arg Ile Asn Leu Gln Lys
                165                 170                 175

Glu Ile

<210> SEQ ID NO 45
<211> LENGTH: 8
<212> TYPE: PRT
<213> ORGANISM: Homo sapiens

<400> SEQUENCE: 45

Asp Arg Val Tyr Ile His Pro Phe
1               5

<210> SEQ ID NO 46
<211> LENGTH: 371
<212> TYPE: PRT
<213> ORGANISM: Homo sapiens

<400> SEQUENCE: 46

Met Leu Met Ala Ser Thr Thr Ser Ala Val Pro Gly His Pro Ser Leu
1               5                   10                  15

Pro Ser Leu Pro Ser Asn Ser Ser Gln Glu Arg Pro Leu Asp Thr Arg
                20                  25                  30

Asp Pro Leu Leu Ala Arg Ala Glu Leu Ala Leu Leu Ser Ile Val Phe
            35                  40                  45

Val Ala Val Ala Leu Ser Asn Gly Leu Val Leu Ala Ala Leu Ala Arg
50                  55                  60

Arg Gly Arg Arg Gly His Trp Ala Pro Ile His Val Phe Ile Gly His
65                  70                  75                  80

Leu Cys Leu Ala Asp Leu Ala Val Ala Leu Phe Gln Val Leu Pro Gln
                85                  90                  95

Leu Ala Trp Lys Ala Thr Asp Arg Phe Arg Gly Pro Asp Ala Leu Cys
            100                 105                 110

Arg Ala Val Lys Tyr Leu Gln Met Val Gly Met Tyr Ala Ser Ser Tyr
            115                 120                 125

Met Ile Leu Ala Met Thr Leu Asp Arg His Arg Ala Ile Cys Arg Pro
130                 135                 140

Met Leu Ala Tyr Arg His Gly Ser Gly Ala His Trp Asn Arg Pro Val
145                 150                 155                 160

Leu Val Ala Ser Ala Phe Ser Leu Leu Leu Ser Leu Pro Gln Leu Phe
                165                 170                 175

Ile Phe Ala Gln Arg Asn Val Glu Gly Gly Ser Gly Val Thr Asp Cys
            180                 185                 190

Trp Ala Cys Phe Ala Glu Pro Trp Gly Arg Arg Thr Tyr Val Thr Trp
            195                 200                 205

Ile Ala Leu Met Val Phe Val Ala Pro Thr Leu Gly Ile Ala Ala Cys
            210                 215                 220

Gln Val Leu Ile Phe Arg Glu Ile His Ala Ser Leu Val Pro Gly Pro
225                 230                 235                 240

Ser Glu Arg Pro Gly Gly Arg Arg Gly Arg Arg Thr Gly Ser Pro
                245                 250                 255
```

```
Gly Glu Gly Ala His Val Ser Ala Ala Val Ala Lys Thr Val Arg Met
            260                 265                 270

Thr Leu Val Ile Val Val Tyr Val Leu Cys Trp Ala Pro Phe Phe
        275                 280                 285

Leu Val Gln Leu Trp Ala Ala Trp Asp Pro Glu Ala Pro Leu Glu Gly
            290                 295                 300

Ala Pro Phe Val Leu Leu Met Leu Leu Ala Ser Leu Asn Ser Cys Thr
305                 310                 315                 320

Asn Pro Trp Ile Tyr Ala Ser Phe Ser Ser Val Ser Ser Glu Leu
            325                 330                 335

Arg Ser Leu Leu Cys Cys Ala Arg Gly Arg Thr Pro Pro Ser Leu Gly
            340                 345                 350

Pro Gln Asp Glu Ser Cys Thr Thr Ala Ser Ser Ser Leu Ala Lys Asp
            355                 360                 365

Thr Ser Ser
    370

<210> SEQ ID NO 47
<211> LENGTH: 9
<212> TYPE: PRT
<213> ORGANISM: Homo sapiens

<400> SEQUENCE: 47

Cys Met Ser Cys Lys Cys Val Leu Ser
1               5

<210> SEQ ID NO 48
<211> LENGTH: 332
<212> TYPE: PRT
<213> ORGANISM: Homo sapiens

<400> SEQUENCE: 48

Met Val Asn Ser Thr His Arg Gly Met His Thr Ser Leu His Leu Trp
1               5                   10                  15

Asn Arg Ser Ser Tyr Arg Leu His Ser Asn Ala Ser Glu Ser Leu Gly
            20                  25                  30

Lys Gly Tyr Ser Asp Gly Gly Cys Tyr Glu Gln Leu Phe Val Ser Pro
        35                  40                  45

Glu Val Phe Val Thr Leu Gly Val Ile Ser Leu Leu Glu Ser Ile Leu
    50                  55                  60

Val Ile Val Ala Ile Ala Lys Asn Lys Asn Leu His Ser Pro Met Tyr
65              70                  75                  80

Phe Phe Ile Cys Ser Leu Ala Val Ala Asp Met Leu Val Ser Val Ser
                85                  90                  95

Asn Gly Ser Glu Thr Ile Val Ile Thr Leu Leu Asn Ser Thr Asp Thr
            100                 105                 110

Asp Ala Gln Ser Phe Thr Val Asn Ile Asp Asn Val Ile Asp Ser Val
        115                 120                 125

Ile Cys Ser Ser Leu Leu Ala Ser Ile Cys Ser Leu Leu Ser Ile Ala
    130                 135                 140

Val Asp Arg Tyr Phe Thr Ile Phe Tyr Ala Leu Gln Tyr His Asn Ile
145                 150                 155                 160

Met Thr Val Lys Arg Val Gly Ile Ile Ile Ser Cys Ile Trp Ala Ala
                165                 170                 175

Cys Thr Val Ser Gly Ile Leu Phe Ile Ile Tyr Ser Asp Ser Ser Ala
            180                 185                 190
```

```
Val Ile Ile Cys Leu Ile Thr Met Phe Phe Thr Met Leu Ala Leu Met
        195                 200                 205

Ala Ser Leu Tyr Val His Met Phe Leu Met Ala Arg Leu His Ile Lys
210                 215                 220

Arg Ile Ala Val Leu Pro Gly Thr Gly Ala Ile Arg Gln Gly Ala Asn
225                 230                 235                 240

Met Lys Gly Ala Ile Thr Leu Thr Ile Leu Ile Gly Val Phe Val Val
                245                 250                 255

Cys Trp Ala Pro Phe Phe Leu His Leu Ile Phe Tyr Ile Ser Cys Pro
                260                 265                 270

Gln Asn Pro Tyr Cys Val Cys Phe Met Ser His Phe Asn Leu Tyr Leu
                275                 280                 285

Ile Leu Ile Met Cys Asn Ser Ile Ile Asp Pro Leu Ile Tyr Ala Leu
                290                 295                 300

Arg Ser Gln Glu Leu Arg Lys Thr Phe Lys Glu Ile Ile Cys Cys Tyr
305                 310                 315                 320

Pro Leu Gly Gly Leu Cys Asp Leu Ser Ser Arg Tyr
                325                 330

<210> SEQ ID NO 49
<211> LENGTH: 332
<212> TYPE: PRT
<213> ORGANISM: Homo sapiens

<400> SEQUENCE: 49

Met Val Asn Ser Thr His Arg Gly Met His Thr Ser Leu His Leu Trp
1               5                   10                  15

Asn Arg Ser Ser Tyr Arg Leu His Ser Asn Ala Ser Glu Ser Leu Gly
                20                  25                  30

Lys Gly Tyr Ser Asp Gly Gly Cys Tyr Glu Gln Leu Phe Val Ser Pro
            35                  40                  45

Glu Val Phe Val Thr Leu Gly Val Ile Ser Leu Leu Glu Asn Ile Leu
        50                  55                  60

Val Ile Val Ala Ile Ala Lys Asn Lys Asn Leu His Ser Pro Met Tyr
65                  70                  75                  80

Phe Phe Ile Cys Ser Leu Ala Val Ala Asp Met Leu Val Ser Val Ser
                85                  90                  95

Asn Gly Ser Glu Thr Ile Val Ile Thr Leu Leu Asn Ser Thr Asp Thr
            100                 105                 110

Asp Ala Gln Ser Phe Thr Val Asn Ile Asp Asn Val Ile Asp Ser Val
        115                 120                 125

Ile Cys Ser Ser Leu Leu Ala Ser Ile Cys Ser Leu Leu Ser Ile Ala
130                 135                 140

Val Asp Arg Tyr Phe Thr Ile Phe Tyr Ala Leu Gln Tyr His Asn Ile
145                 150                 155                 160

Met Thr Val Lys Trp Val Gly Ile Ile Ser Cys Ile Trp Ala Ala
                165                 170                 175

Cys Thr Val Ser Gly Ile Leu Phe Ile Ile Tyr Ser Asp Ser Ser Ala
                180                 185                 190

Val Ile Ile Cys Leu Ile Thr Met Phe Phe Thr Met Leu Ala Leu Met
        195                 200                 205

Ala Ser Leu Tyr Val His Met Phe Leu Met Ala Arg Leu His Ile Lys
210                 215                 220

Arg Ile Ala Val Leu Pro Gly Thr Gly Ala Ile Arg Gln Gly Ala Asn
225                 230                 235                 240
```

```
Met Lys Gly Ala Ile Thr Leu Thr Ile Leu Ile Gly Val Phe Val Val
                245                 250                 255

Cys Trp Ala Pro Phe Phe Leu His Leu Ile Phe Tyr Ile Ser Cys Pro
            260                 265                 270

Gln Asn Pro Tyr Cys Val Cys Phe Met Ser His Phe Asn Leu Tyr Leu
        275                 280                 285

Ile Leu Ile Met Cys Asn Ser Ile Ile Asp Pro Leu Ile Tyr Ala Leu
    290                 295                 300

Arg Ser Gln Glu Leu Arg Lys Thr Phe Lys Glu Ile Ile Cys Cys Tyr
305                 310                 315                 320

Pro Leu Gly Gly Leu Cys Asp Leu Ser Ser Arg Tyr
                325                 330

<210> SEQ ID NO 50
<211> LENGTH: 941
<212> TYPE: PRT
<213> ORGANISM: Homo sapiens

<400> SEQUENCE: 50

Met Gly Cys Ile Lys Ser Lys Gly Lys Asp Ser Leu Ser Asn Ala Met
1               5                   10                  15

Val Ser Lys Gly Glu Glu Leu Phe Thr Gly Val Val Pro Ile Leu Val
            20                  25                  30

Glu Leu Asp Gly Asp Val Asn Gly His Lys Phe Ser Val Ser Gly Glu
        35                  40                  45

Gly Glu Gly Asp Ala Thr Tyr Gly Lys Leu Thr Leu Lys Phe Ile Cys
    50                  55                  60

Thr Thr Gly Lys Leu Pro Val Pro Trp Pro Thr Leu Val Thr Thr Leu
65                  70                  75                  80

Ser Tyr Gly Val Gln Cys Phe Ser Arg Tyr Pro Asp His Met Lys Gln
                85                  90                  95

His Asp Phe Phe Lys Ser Ala Met Pro Glu Gly Tyr Val Gln Glu Arg
            100                 105                 110

Thr Ile Phe Phe Lys Asp Asp Gly Asn Tyr Lys Thr Arg Ala Glu Val
        115                 120                 125

Lys Phe Glu Gly Asp Thr Leu Val Asn Arg Ile Glu Leu Lys Gly Ile
    130                 135                 140

Asp Phe Lys Glu Asp Gly Asn Ile Leu Gly His Lys Leu Glu Tyr Asn
145                 150                 155                 160

Tyr Asn Pro His Asn Val Tyr Ile Met Ala Asp Lys Gln Lys Asn Gly
                165                 170                 175

Ile Lys Val Asn Phe Lys Ile Arg His Asn Ile Glu Asp Gly Ser Val
            180                 185                 190

Gln Leu Ala Asp His Tyr Gln Gln Asn Thr Pro Ile Gly Asp Gly Pro
        195                 200                 205

Val Leu Leu Pro Asp Asn His Tyr Leu Phe Thr Gln Ser Ala Leu Ser
    210                 215                 220

Lys Asp Pro Asn Glu Lys Arg Asp His Met Val Leu Leu Glu Phe Val
225                 230                 235                 240

Thr Ala Ala Gly Ile Thr Leu Gly Met Asp Glu Leu Tyr Lys Gly Thr
                245                 250                 255

Gly Thr Ala Ala Lys Glu Gly Glu Lys Gln Lys Gly Ala Met Gln Pro
            260                 265                 270

Ser Glu Gln Gln Arg Gly Lys Glu Ala Gln Lys Glu Lys Asn Gly Lys
```

```
            275                 280                 285
Glu Pro Asn Pro Arg Pro Glu Gln Pro Lys Pro Ala Lys Val Glu Gln
290                 295                 300

Gln Glu Asp Glu Pro Glu Arg Pro Lys Arg Glu Pro Met Gln Leu
305                 310                 315                 320

Glu Pro Ala Glu Ser Ala Lys Gln Gly Arg Asn Leu Pro Gln Lys Val
                325                 330                 335

Glu Gln Gly Glu Glu Arg Pro Gln Glu Ala Asp Met Pro Gly Gln Ala
                340                 345                 350

Gln Ser Ala Met Arg Pro Gln Leu Ser Asn Ser Glu Glu Gly Pro Ala
                355                 360                 365

Arg Gly Lys Pro Ala Pro Glu Glu Pro Asp Glu Gln Leu Gly Glu Pro
370                 375                 380

Glu Glu Ala Gln Gly Glu His Ala Asp Glu Pro Ala Pro Ser Lys Pro
385                 390                 395                 400

Ser Glu Lys His Met Val Pro Gln Met Ala Glu Pro Lys Gly Glu
                405                 410                 415

Glu Ala Arg Glu Pro Gln Gly Ala Glu Asp Lys Pro Ala Pro Val His
                420                 425                 430

Lys Pro Lys Lys Glu Pro Gln Arg Pro Asn Glu Lys Ala Pro
                435                 440                 445

Lys Pro Lys Gly Arg His Val Gly Arg Gln Glu Asn Asp Asp Ser Ala
450                 455                 460

Gly Lys Pro Glu Pro Gly Arg Pro Asp Arg Lys Gly Lys Glu Lys Glu
465                 470                 475                 480

Pro Glu Glu Glu Pro Ala Gln Gly His Ser Leu Pro Gln Glu Pro Glu
                485                 490                 495

Pro Met Pro Arg Pro Lys Pro Glu Val Arg Lys Pro His Pro Gly
                500                 505                 510

Ala Ser Pro His Gln Val Ser Asp Val Glu Asp Ala Lys Gly Pro Glu
                515                 520                 525

Arg Lys Val Asn Pro Met Glu Gly Glu Glu Ser Ala Lys Gln Ala Gln
530                 535                 540

Gln Glu Gly Pro Ala Glu Asn Asp Glu Ala Glu Arg Pro Glu Arg Pro
545                 550                 555                 560

Ala Ser Gly Gly Ala Arg Glu Ala Met Thr Ser Lys Val Tyr Asp Pro
                565                 570                 575

Glu Gln Arg Lys Arg Met Ile Thr Gly Pro Gln Trp Trp Ala Arg Cys
                580                 585                 590

Lys Gln Met Asn Val Leu Asp Ser Phe Ile Asn Tyr Tyr Asp Ser Glu
                595                 600                 605

Lys His Ala Glu Asn Ala Val Ile Phe Leu His Gly Asn Ala Thr Ser
                610                 615                 620

Ser Tyr Leu Trp Arg His Val Pro His Ile Glu Pro Val Ala Arg
625                 630                 635                 640

Cys Ile Ile Pro Asp Leu Ile Gly Met Gly Lys Ser Gly Lys Ser Gly
                645                 650                 655

Asn Gly Ser Tyr Arg Leu Leu Asp His Tyr Lys Tyr Leu Thr Ala Trp
                660                 665                 670

Phe Glu Leu Leu Asn Leu Pro Lys Lys Ile Ile Phe Val Gly His Asp
                675                 680                 685

Trp Gly Ala Ala Leu Ala Phe His Tyr Ser Tyr Glu His Gln Asp Lys
690                 695                 700
```

-continued

```
Ile Lys Ala Ile Val His Ala Glu Ser Val Val Asp Val Ile Glu Ser
705                 710                 715                 720

Trp Asp Glu Trp Pro Asp Ile Glu Asp Ile Ala Leu Ile Lys Ser
            725                 730                 735

Glu Glu Gly Glu Lys Met Val Leu Glu Asn Asn Phe Val Glu Thr
            740                 745                 750

Val Leu Pro Ser Lys Ile Met Arg Lys Leu Glu Pro Glu Phe Ala
            755                 760                 765

Ala Tyr Leu Glu Pro Phe Lys Glu Lys Gly Glu Val Arg Arg Pro Thr
                770                 775                 780

Leu Ser Trp Pro Arg Glu Ile Pro Leu Val Lys Gly Gly Lys Pro Asp
785                 790                 795                 800

Val Val Gln Ile Val Arg Asn Tyr Asn Ala Tyr Leu Arg Ala Ser Asp
            805                 810                 815

Asp Leu Pro Lys Met Phe Ile Glu Ser Asp Pro Gly Phe Phe Ser Asn
            820                 825                 830

Ala Ile Val Glu Gly Ala Lys Lys Phe Pro Asn Thr Glu Phe Val Lys
            835                 840                 845

Val Lys Gly Leu His Phe Ser Gln Glu Asp Ala Pro Asp Glu Met Gly
            850                 855                 860

Lys Tyr Ile Lys Ser Phe Val Glu Arg Val Leu Lys Asn Glu Gln Gly
865                 870                 875                 880

Ser Gly Ser Gly Phe Asn Ile Asp Met Pro His Arg Phe Lys Val His
                885                 890                 895

Asn Tyr Met Ser Pro Thr Phe Cys Asp His Cys Gly Ser Leu Leu Trp
            900                 905                 910

Gly Leu Val Lys Gln Gly Leu Lys Cys Glu Asp Cys Gly Met Asn Val
            915                 920                 925

His His Lys Cys Arg Glu Lys Val Ala Asn Leu Cys Gly
    930                 935                 940
```

<210> SEQ ID NO 51
<211> LENGTH: 1304
<212> TYPE: PRT
<213> ORGANISM: Homo sapiens

<400> SEQUENCE: 51

```
Met Gly Cys Ile Lys Ser Lys Gly Lys Asp Ser Leu Ser Asn Ala Met
1               5                   10                  15

Val Ser Lys Gly Glu Glu Leu Phe Thr Gly Val Val Pro Ile Leu Val
            20                  25                  30

Glu Leu Asp Gly Asp Val Asn Gly His Lys Phe Ser Val Ser Gly Glu
        35                  40                  45

Gly Glu Gly Asp Ala Thr Tyr Gly Lys Leu Thr Leu Lys Phe Ile Cys
    50                  55                  60

Thr Thr Gly Lys Leu Pro Val Pro Trp Pro Thr Leu Val Thr Thr Leu
65                  70                  75                  80

Ser Tyr Gly Val Gln Cys Phe Ser Arg Tyr Pro Asp His Met Lys Gln
                85                  90                  95

His Asp Phe Phe Lys Ser Ala Met Pro Glu Gly Tyr Val Gln Glu Arg
            100                 105                 110

Thr Ile Phe Phe Lys Asp Asp Gly Asn Tyr Lys Thr Arg Ala Glu Val
            115                 120                 125

Lys Phe Glu Gly Asp Thr Leu Val Asn Arg Ile Glu Leu Lys Gly Ile
```

```
            130                 135                 140
Asp Phe Lys Glu Asp Gly Asn Ile Leu Gly His Lys Leu Glu Tyr Asn
145                 150                 155                 160

Tyr Asn Pro His Asn Val Tyr Ile Met Ala Asp Lys Gln Lys Asn Gly
                165                 170                 175

Ile Lys Val Asn Phe Lys Ile Arg His Asn Ile Glu Asp Gly Ser Val
            180                 185                 190

Gln Leu Ala Asp His Tyr Gln Gln Asn Thr Pro Ile Gly Asp Gly Pro
        195                 200                 205

Val Leu Leu Pro Asp Asn His Tyr Leu Phe Thr Gln Ser Ala Leu Ser
    210                 215                 220

Lys Asp Pro Asn Glu Lys Arg Asp His Met Val Leu Leu Glu Phe Val
225                 230                 235                 240

Thr Ala Ala Gly Ile Thr Leu Gly Met Asp Glu Leu Tyr Lys Gly Thr
                245                 250                 255

Gly Thr Ala Ala Lys Glu Gly Glu Lys Gln Lys Gly Ala Met Gln Pro
            260                 265                 270

Ser Glu Gln Gln Arg Gly Lys Glu Ala Gln Lys Glu Lys Asn Gly Lys
        275                 280                 285

Glu Pro Asn Pro Arg Pro Glu Gln Pro Lys Pro Ala Lys Val Glu Gln
    290                 295                 300

Gln Glu Asp Glu Pro Glu Arg Pro Lys Arg Glu Pro Met Gln Leu
305                 310                 315                 320

Glu Pro Ala Glu Ser Ala Lys Gln Gly Arg Asn Leu Pro Gln Lys Val
                325                 330                 335

Glu Gln Gly Glu Glu Arg Pro Gln Glu Ala Asp Met Pro Gly Gln Ala
            340                 345                 350

Gln Ser Ala Met Arg Pro Gln Leu Ser Asn Ser Glu Glu Gly Pro Ala
        355                 360                 365

Arg Gly Lys Pro Ala Pro Glu Glu Pro Asp Glu Gln Leu Gly Glu Pro
    370                 375                 380

Glu Glu Ala Gln Gly Glu His Ala Asp Glu Pro Ala Pro Ser Lys Pro
385                 390                 395                 400

Ser Glu Lys His Met Val Pro Gln Met Ala Glu Pro Glu Lys Gly Glu
                405                 410                 415

Glu Ala Arg Glu Pro Gln Gly Ala Glu Asp Lys Pro Ala Pro Val His
            420                 425                 430

Lys Pro Lys Lys Glu Glu Pro Gln Arg Pro Asn Glu Glu Lys Ala Pro
        435                 440                 445

Lys Pro Lys Gly Arg His Val Gly Arg Gln Glu Asn Asp Asp Ser Ala
    450                 455                 460

Gly Lys Pro Glu Pro Gly Arg Pro Asp Arg Lys Gly Lys Glu Lys Glu
465                 470                 475                 480

Pro Glu Glu Pro Ala Gln Gly His Ser Leu Pro Gln Glu Pro Glu
                485                 490                 495

Pro Met Pro Arg Pro Lys Pro Glu Val Arg Lys Lys Pro His Pro Gly
            500                 505                 510

Ala Ser Pro His Gln Val Ser Asp Val Glu Asp Ala Lys Gly Pro Glu
        515                 520                 525

Arg Lys Val Asn Pro Met Glu Gly Glu Glu Ser Ala Lys Gln Ala Gln
    530                 535                 540

Gln Glu Gly Pro Ala Glu Asn Asp Glu Ala Glu Arg Pro Glu Arg Pro
545                 550                 555                 560
```

-continued

```
Ala Ser Gly Gly Ala Arg Glu Ala Met Thr Ser Lys Val Tyr Asp Pro
                565                 570                 575

Glu Gln Arg Lys Arg Met Ile Thr Gly Pro Gln Trp Trp Ala Arg Cys
            580                 585                 590

Lys Gln Met Asn Val Leu Asp Ser Phe Ile Asn Tyr Tyr Asp Ser Glu
        595                 600                 605

Lys His Ala Glu Asn Ala Val Ile Phe Leu His Gly Asn Ala Thr Ser
    610                 615                 620

Ser Tyr Leu Trp Arg His Val Pro His Ile Glu Pro Val Ala Arg
625                 630                 635                 640

Cys Ile Ile Pro Asp Leu Ile Gly Met Gly Lys Ser Gly Lys Ser Gly
                645                 650                 655

Asn Gly Ser Tyr Arg Leu Leu Asp His Tyr Lys Tyr Leu Thr Ala Trp
            660                 665                 670

Phe Glu Leu Leu Asn Leu Pro Lys Lys Ile Ile Phe Val Gly His Asp
        675                 680                 685

Trp Gly Ala Ala Leu Ala Phe His Tyr Ser Tyr Glu His Gln Asp Lys
    690                 695                 700

Ile Lys Ala Ile Val His Ala Glu Ser Val Val Asp Val Ile Glu Ser
705                 710                 715                 720

Trp Asp Glu Trp Pro Asp Ile Glu Glu Asp Ile Ala Leu Ile Lys Ser
                725                 730                 735

Glu Glu Gly Glu Lys Met Val Leu Glu Asn Asn Phe Val Glu Thr
            740                 745                 750

Val Leu Pro Ser Lys Ile Met Arg Lys Leu Glu Pro Glu Glu Phe Ala
        755                 760                 765

Ala Tyr Leu Glu Pro Phe Lys Glu Lys Gly Val Arg Arg Pro Thr
    770                 775                 780

Leu Ser Trp Pro Arg Glu Ile Pro Leu Val Lys Gly Gly Lys Pro Asp
785                 790                 795                 800

Val Val Gln Ile Val Arg Asn Tyr Asn Ala Tyr Leu Arg Ala Ser Asp
                805                 810                 815

Asp Leu Pro Lys Met Phe Ile Glu Ser Asp Pro Gly Phe Phe Ser Asn
            820                 825                 830

Ala Ile Val Glu Gly Ala Lys Lys Phe Pro Asn Thr Glu Phe Val Lys
        835                 840                 845

Val Lys Gly Leu His Phe Ser Gln Glu Asp Ala Pro Asp Glu Met Gly
    850                 855                 860

Lys Tyr Ile Lys Ser Phe Val Glu Arg Val Leu Lys Asn Glu Gln Gly
865                 870                 875                 880

Ser Gly Ser Ala Gly Thr Ala Gly Asp Lys Gly Thr Arg Val Phe Lys
                885                 890                 895

Lys Ala Ser Pro Asn Gly Lys Leu Thr Val Tyr Leu Gly Lys Arg Asp
            900                 905                 910

Phe Val Asp His Ile Asp Leu Val Asp Pro Val Asp Gly Val Val Leu
        915                 920                 925

Val Asp Pro Glu Tyr Leu Lys Glu Arg Arg Val Tyr Val Thr Leu Thr
    930                 935                 940

Cys Ala Phe Arg Tyr Gly Arg Glu Asp Leu Asp Val Leu Gly Leu Thr
945                 950                 955                 960

Phe Arg Lys Asp Leu Phe Val Ala Asn Val Gln Ser Phe Pro Pro Ala
                965                 970                 975
```

Pro Glu Asp Lys Lys Pro Leu Thr Arg Leu Gln Glu Arg Leu Ile Lys
                980                 985                 990

Lys Leu Gly Glu His Ala Tyr Pro Phe Thr Phe Glu Ile Pro Pro Asn
            995                 1000                1005

Leu Pro Cys Ser Val Thr Leu Gln Pro Gly Pro Glu Asp Thr Gly
        1010                1015                1020

Lys Ala Cys Gly Val Asp Tyr Glu Val Lys Ala Phe Cys Ala Glu
        1025                1030                1035

Asn Leu Glu Glu Lys Ile His Lys Arg Asn Ser Val Arg Leu Val
        1040                1045                1050

Ile Arg Lys Val Gln Tyr Ala Pro Glu Arg Pro Gly Pro Gln Pro
        1055                1060                1065

Thr Ala Glu Thr Thr Arg Gln Phe Leu Met Ser Asp Lys Pro Leu
        1070                1075                1080

His Leu Glu Ala Ser Leu Asp Lys Glu Ile Tyr Tyr His Gly Glu
        1085                1090                1095

Pro Ile Ser Val Asn Val His Val Thr Asn Asn Thr Asn Lys Thr
        1100                1105                1110

Val Lys Lys Ile Lys Ile Ser Val Arg Gln Tyr Ala Asp Ile Cys
        1115                1120                1125

Leu Phe Asn Thr Ala Gln Tyr Lys Cys Pro Val Ala Met Glu Glu
        1130                1135                1140

Ala Asp Asp Thr Val Ala Pro Ser Ser Thr Phe Cys Lys Val Tyr
        1145                1150                1155

Thr Leu Thr Pro Phe Leu Ala Asn Asn Arg Glu Lys Arg Gly Leu
        1160                1165                1170

Ala Leu Asp Gly Lys Leu Lys His Glu Asp Thr Asn Leu Ala Ser
        1175                1180                1185

Ser Thr Leu Leu Arg Glu Gly Ala Asn Arg Glu Ile Leu Gly Ile
        1190                1195                1200

Ile Val Ser Tyr Lys Val Lys Val Lys Leu Val Val Ser Arg Gly
        1205                1210                1215

Gly Leu Leu Gly Asp Leu Ala Ser Ser Asp Val Ala Val Glu Leu
        1220                1225                1230

Pro Phe Thr Leu Met His Pro Lys Pro Lys Glu Glu Pro Pro His
        1235                1240                1245

Arg Glu Val Pro Glu Asn Glu Thr Pro Val Asp Thr Asn Leu Ile
        1250                1255                1260

Glu Leu Asp Thr Asn Asp Asp Asp Ile Val Phe Glu Asp Phe Ala
        1265                1270                1275

Arg Gln Arg Leu Lys Gly Met Lys Asp Asp Lys Glu Glu Glu Glu
        1280                1285                1290

Asp Gly Thr Gly Ser Pro Gln Leu Asn Asn Arg
        1295                1300

<210> SEQ ID NO 52
<211> LENGTH: 1295
<212> TYPE: PRT
<213> ORGANISM: Homo sapiens

<400> SEQUENCE: 52

Met Gly Cys Ile Lys Ser Lys Gly Lys Asp Ser Leu Ser Asn Ala Met
1               5                   10                  15

Val Ser Lys Gly Glu Glu Leu Phe Thr Gly Val Val Pro Ile Leu Val
            20                  25                  30

```
Glu Leu Asp Gly Asp Val Asn Gly His Lys Phe Ser Val Ser Gly Glu
         35                  40                  45

Gly Glu Gly Asp Ala Thr Tyr Gly Lys Leu Thr Leu Lys Phe Ile Cys
 50                  55                  60

Thr Thr Gly Lys Leu Pro Val Pro Trp Pro Thr Leu Val Thr Thr Leu
 65                  70                  75                  80

Ser Tyr Gly Val Gln Cys Phe Ser Arg Tyr Pro Asp His Met Lys Gln
                 85                  90                  95

His Asp Phe Phe Lys Ser Ala Met Pro Glu Gly Tyr Val Gln Glu Arg
             100                 105                 110

Thr Ile Phe Phe Lys Asp Asp Gly Asn Tyr Lys Thr Arg Ala Glu Val
         115                 120                 125

Lys Phe Glu Gly Asp Thr Leu Val Asn Arg Ile Glu Leu Lys Gly Ile
 130                 135                 140

Asp Phe Lys Glu Asp Gly Asn Ile Leu Gly His Lys Leu Glu Tyr Asn
145                 150                 155                 160

Tyr Asn Pro His Asn Val Tyr Ile Met Ala Asp Lys Gln Lys Asn Gly
                 165                 170                 175

Ile Lys Val Asn Phe Lys Ile Arg His Asn Ile Glu Asp Gly Ser Val
             180                 185                 190

Gln Leu Ala Asp His Tyr Gln Gln Asn Thr Pro Ile Gly Asp Gly Pro
         195                 200                 205

Val Leu Leu Pro Asp Asn His Tyr Leu Phe Thr Gln Ser Ala Leu Ser
 210                 215                 220

Lys Asp Pro Asn Glu Lys Arg Asp His Met Val Leu Leu Glu Phe Val
225                 230                 235                 240

Thr Ala Ala Gly Ile Thr Leu Gly Met Asp Glu Leu Tyr Lys Gly Thr
                 245                 250                 255

Gly Thr Ala Ala Lys Glu Gly Glu Lys Gln Lys Gly Ala Met Gln Pro
             260                 265                 270

Ser Glu Gln Gln Arg Gly Lys Glu Ala Gln Lys Glu Lys Asn Gly Lys
         275                 280                 285

Glu Pro Asn Pro Arg Pro Glu Gln Pro Lys Pro Ala Lys Val Glu Gln
 290                 295                 300

Gln Glu Asp Glu Pro Glu Arg Pro Lys Arg Glu Pro Met Gln Leu
305                 310                 315                 320

Glu Pro Ala Glu Ser Ala Lys Gln Gly Arg Asn Leu Pro Gln Lys Val
                 325                 330                 335

Glu Gln Gly Glu Glu Arg Pro Gln Glu Ala Asp Met Pro Gly Gln Ala
             340                 345                 350

Gln Ser Ala Met Arg Pro Gln Leu Ser Asn Ser Glu Glu Gly Pro Ala
         355                 360                 365

Arg Gly Lys Pro Ala Pro Glu Glu Pro Asp Glu Gln Leu Gly Glu Pro
 370                 375                 380

Glu Glu Ala Gln Gly Glu His Ala Asp Glu Pro Ala Pro Ser Lys Pro
385                 390                 395                 400

Ser Glu Lys His Met Val Pro Gln Met Ala Glu Pro Glu Lys Gly Glu
                 405                 410                 415

Glu Ala Arg Glu Pro Gln Gly Ala Glu Asp Lys Pro Ala Pro Val His
             420                 425                 430

Lys Pro Lys Lys Glu Gly Pro Gln Arg Pro Asn Glu Glu Lys Ala Pro
         435                 440                 445
```

Lys Pro Lys Gly Arg His Val Gly Arg Gln Glu Asn Asp Asp Ser Ala
450                 455                 460

Gly Lys Pro Glu Pro Gly Arg Pro Asp Arg Lys Gly Lys Glu Lys Glu
465                 470                 475                 480

Pro Glu Glu Pro Ala Gln Gly His Ser Leu Pro Gln Glu Pro Glu
            485                 490                 495

Pro Met Pro Arg Pro Lys Pro Glu Val Arg Lys Lys Pro His Pro Gly
            500                 505                 510

Ala Ser Pro His Gln Val Ser Asp Val Glu Asp Ala Lys Gly Pro Glu
            515                 520                 525

Arg Lys Val Asn Pro Met Glu Gly Glu Glu Ser Ala Lys Gln Ala Gln
530                 535                 540

Gln Glu Gly Pro Ala Glu Asn Asp Glu Ala Glu Arg Pro Glu Arg Pro
545                 550                 555                 560

Ala Ser Gly Gly Ala Arg Glu Ala Met Thr Ser Lys Val Tyr Asp Pro
            565                 570                 575

Glu Gln Arg Lys Arg Met Ile Thr Gly Pro Gln Trp Trp Ala Arg Cys
            580                 585                 590

Lys Gln Met Asn Val Leu Asp Ser Phe Ile Asn Tyr Tyr Asp Ser Glu
            595                 600                 605

Lys His Ala Glu Asn Ala Val Ile Phe Leu His Gly Asn Ala Thr Ser
610                 615                 620

Ser Tyr Leu Trp Arg His Val Val Pro His Ile Glu Pro Val Ala Arg
625                 630                 635                 640

Cys Ile Ile Pro Asp Leu Ile Gly Met Gly Lys Ser Gly Lys Ser Gly
            645                 650                 655

Asn Gly Ser Tyr Arg Leu Leu Asp His Tyr Lys Tyr Leu Thr Ala Trp
            660                 665                 670

Phe Glu Leu Leu Asn Leu Pro Lys Lys Ile Ile Phe Val Gly His Asp
            675                 680                 685

Trp Gly Ala Ala Leu Ala Phe His Tyr Ser Tyr Glu His Gln Asp Lys
690                 695                 700

Ile Lys Ala Ile Val His Ala Glu Ser Val Val Asp Val Ile Glu Ser
705                 710                 715                 720

Trp Asp Glu Trp Pro Asp Ile Glu Glu Asp Ile Ala Leu Ile Lys Ser
            725                 730                 735

Glu Glu Gly Glu Lys Met Val Leu Glu Asn Asn Phe Phe Val Glu Thr
            740                 745                 750

Val Leu Pro Ser Lys Ile Met Arg Lys Leu Glu Pro Glu Glu Phe Ala
755                 760                 765

Ala Tyr Leu Glu Pro Phe Lys Glu Lys Gly Glu Val Arg Arg Pro Thr
770                 775                 780

Leu Ser Trp Pro Arg Glu Ile Pro Leu Val Lys Gly Gly Lys Pro Asp
785                 790                 795                 800

Val Val Gln Ile Val Arg Asn Tyr Asn Ala Tyr Leu Arg Ala Ser Asp
            805                 810                 815

Asp Leu Pro Lys Met Phe Ile Glu Ser Asp Pro Gly Phe Phe Ser Asn
            820                 825                 830

Ala Ile Val Glu Gly Ala Lys Lys Phe Pro Asn Thr Glu Phe Val Lys
            835                 840                 845

Val Lys Gly Leu His Phe Ser Gln Glu Asp Ala Pro Asp Glu Met Gly
850                 855                 860

Lys Tyr Ile Lys Ser Phe Val Glu Arg Val Leu Lys Asn Glu Gln Gly

```
                    865                 870                 875                 880
            Ser Gly Ser Ala Gly Thr Ala Gly Glu Lys Pro Gly Thr Arg Val Phe
                            885                 890                 895
            Lys Lys Ser Ser Pro Asn Cys Lys Leu Thr Val Tyr Leu Gly Lys Arg
                        900                 905                 910
            Asp Phe Val Asp His Leu Asp Lys Val Asp Pro Val Asp Gly Val Val
                        915                 920                 925
            Leu Val Asp Pro Asp Tyr Leu Lys Asp Arg Lys Val Phe Val Thr Leu
                    930                 935                 940
            Thr Cys Ala Phe Arg Tyr Gly Arg Glu Asp Leu Asp Val Leu Gly Leu
            945                 950                 955                 960
            Ser Phe Arg Lys Asp Leu Phe Ile Ala Thr Tyr Gln Ala Phe Pro Pro
                                965                 970                 975
            Val Pro Asn Pro Pro Arg Pro Thr Arg Leu Gln Asp Arg Leu Leu
                            980                 985                 990
            Arg Lys Leu Gly Gln His Ala His Pro Phe Phe Phe Thr Ile Pro Gln
                                995                 1000                1005
            Asn Leu Pro Cys Ser Val Thr Leu Gln Pro Gly Pro Glu Asp Thr
                    1010                1015                1020
            Gly Lys Ala Cys Gly Val Asp Phe Glu Ile Arg Ala Phe Cys Ala
                    1025                1030                1035
            Lys Ser Leu Glu Glu Lys Ser His Lys Arg Asn Ser Val Arg Leu
                    1040                1045                1050
            Val Ile Arg Lys Val Gln Phe Ala Pro Glu Lys Pro Gly Pro Gln
                    1055                1060                1065
            Pro Ser Ala Glu Thr Thr Arg His Phe Leu Met Ser Asp Arg Ser
                    1070                1075                1080
            Leu His Leu Glu Ala Ser Leu Asp Lys Glu Leu Tyr Tyr His Gly
                    1085                1090                1095
            Glu Pro Leu Asn Val Asn Val His Val Thr Asn Asn Ser Thr Lys
                    1100                1105                1110
            Thr Val Lys Lys Ile Lys Val Ser Val Arg Gln Tyr Ala Asp Ile
                    1115                1120                1125
            Cys Leu Phe Ser Thr Ala Gln Tyr Lys Cys Pro Val Ala Gln Leu
                    1130                1135                1140
            Glu Gln Asp Asp Gln Val Ser Pro Ser Ser Thr Phe Cys Lys Val
                    1145                1150                1155
            Tyr Thr Ile Thr Pro Leu Leu Ser Asp Asn Arg Glu Lys Arg Gly
                    1160                1165                1170
            Leu Ala Leu Asp Gly Lys Leu Lys His Glu Asp Thr Asn Leu Ala
                    1175                1180                1185
            Ser Ser Thr Ile Val Lys Glu Gly Ala Asn Lys Glu Val Leu Gly
                    1190                1195                1200
            Ile Leu Val Ser Tyr Arg Val Lys Val Lys Leu Val Val Ser Arg
                    1205                1210                1215
            Gly Gly Asp Val Ser Val Glu Leu Pro Phe Val Leu Met His Pro
                    1220                1225                1230
            Lys Pro His Asp His Ile Pro Leu Pro Arg Pro Gln Ser Ala Ala
                    1235                1240                1245
            Pro Glu Thr Asp Val Pro Val Asp Thr Asn Leu Ile Glu Phe Asp
                    1250                1255                1260
            Thr Asn Tyr Ala Thr Asp Asp Asp Ile Val Phe Glu Asp Phe Ala
                    1265                1270                1275
```

-continued

```
Arg Leu Arg Leu Lys Gly Met Lys Asp Asp Asp Tyr Asp Asp Gln
    1280                1285                1290

Leu Cys
    1295

<210> SEQ ID NO 53
<211> LENGTH: 707
<212> TYPE: PRT
<213> ORGANISM: Homo sapiens

<400> SEQUENCE: 53

Met Ser Gly Val Val Arg Thr Leu Ser Arg Cys Leu Leu Pro Ala Glu
1               5                   10                  15

Ala Gly Gly Ala Arg Glu Arg Arg Ala Gly Ser Gly Ala Arg Asp Ala
            20                  25                  30

Glu Arg Glu Ala Arg Arg Ser Arg Asp Ile Asp Ala Leu Leu Ala
        35                  40                  45

Arg Glu Arg Arg Ala Val Arg Leu Val Lys Ile Leu Leu Leu Gly
    50                  55                  60

Ala Gly Glu Ser Gly Lys Ser Thr Phe Leu Lys Gln Met Arg Ile Ile
65                  70                  75                  80

His Gly Arg Glu Gly Ser Gly Gly Gly Ser Met Thr Ser Lys Val
                85                  90                  95

Tyr Asp Pro Glu Gln Arg Lys Arg Met Ile Thr Gly Pro Gln Trp Trp
                100                 105                 110

Ala Arg Cys Lys Gln Met Asn Val Leu Asp Ser Phe Ile Asn Tyr Tyr
            115                 120                 125

Asp Ser Glu Lys His Ala Glu Asn Ala Val Ile Phe Leu His Gly Asn
        130                 135                 140

Ala Ala Ser Ser Tyr Leu Trp Arg His Val Val Pro His Ile Glu Pro
145                 150                 155                 160

Val Ala Arg Cys Ile Ile Pro Asp Leu Ile Gly Met Gly Lys Ser Gly
                165                 170                 175

Lys Ser Gly Asn Gly Ser Tyr Arg Leu Leu Asp His Tyr Lys Tyr Leu
            180                 185                 190

Thr Ala Trp Phe Glu Leu Leu Asn Leu Pro Lys Lys Ile Ile Phe Val
        195                 200                 205

Gly His Asp Trp Gly Ala Ala Leu Ala Phe His Tyr Ser Tyr Glu His
    210                 215                 220

Gln Asp Lys Ile Lys Ala Ile Val His Ala Glu Ser Val Val Asp Val
225                 230                 235                 240

Ile Glu Ser Trp Asp Glu Trp Pro Asp Ile Glu Glu Asp Ile Ala Leu
                245                 250                 255

Ile Lys Ser Glu Glu Gly Glu Lys Met Val Leu Glu Asn Asn Phe Phe
            260                 265                 270

Val Glu Thr Val Leu Pro Ser Lys Ile Met Arg Lys Leu Glu Pro Glu
        275                 280                 285

Glu Phe Ala Ala Tyr Leu Glu Pro Phe Lys Glu Lys Gly Glu Val Arg
    290                 295                 300

Arg Pro Thr Leu Ser Trp Pro Arg Glu Ile Pro Leu Val Lys Gly Gly
305                 310                 315                 320

Lys Pro Asp Val Val Gln Ile Val Arg Asn Tyr Asn Ala Tyr Leu Arg
                325                 330                 335

Ala Ser Asp Asp Leu Pro Lys Met Phe Ile Glu Ser Asp Pro Gly Phe
```

```
                340                 345                 350
Phe Ser Asn Ala Ile Val Glu Gly Ala Lys Lys Phe Pro Asn Thr Glu
        355                 360                 365
Phe Val Lys Val Lys Gly Leu His Phe Ser Gln Glu Asp Ala Pro Asp
370                 375                 380
Glu Met Gly Lys Tyr Ile Lys Ser Phe Val Glu Arg Val Leu Lys Asn
385                 390                 395                 400
Glu Gln Ser Gly Gly Gly Ser Gly Thr Phe Asp Gln Lys Ala Leu
                405                 410                 415
Leu Glu Phe Arg Asp Thr Ile Phe Asp Asn Ile Leu Lys Gly Ser Arg
                420                 425                 430
Val Leu Val Asp Ala Arg Asp Lys Leu Gly Ile Pro Trp Gln Tyr Ser
            435                 440                 445
Glu Asn Glu Glu His Gly Met Phe Leu Met Ala Phe Glu Asn Lys Ala
        450                 455                 460
Gly Leu Pro Val Glu Pro Ala Thr Phe Gln Leu Tyr Val Pro Ala Leu
465                 470                 475                 480
Ser Ala Leu Trp Arg Asp Ser Gly Ile Arg Glu Ala Phe Ser Arg Arg
                485                 490                 495
Ser Glu Phe Gln Leu Gly Glu Ser Val Lys Tyr Phe Leu Asp Asn Leu
                500                 505                 510
Asp Arg Ile Gly Gln Leu Glu Tyr Met Pro Thr Glu Gln Asp Ile Leu
                515                 520                 525
Leu Ala Arg Lys Ala Thr Lys Gly Ile Val Glu His Asp Phe Val Ile
            530                 535                 540
Lys Lys Ile Pro Phe Lys Met Val Asp Val Gly Gly Gln Arg Ser Gln
545                 550                 555                 560
Arg Gln Lys Trp Phe Gln Cys Phe Asp Gly Ile Thr Ser Ile Leu Phe
                565                 570                 575
Met Val Ser Ser Ser Glu Tyr Asp Gln Val Leu Met Glu Asp Arg Arg
                580                 585                 590
Thr Asn Arg Leu Val Glu Ser Met Asn Ile Phe Glu Thr Ile Val Asn
                595                 600                 605
Asn Lys Leu Phe Phe Asn Val Ser Ile Ile Leu Phe Leu Asn Lys Met
        610                 615                 620
Asp Leu Leu Val Glu Lys Val Lys Thr Val Ser Ile Lys Lys His Phe
625                 630                 635                 640
Pro Asp Phe Arg Gly Asp Pro His Arg Leu Glu Asp Val Gln Arg Tyr
                645                 650                 655
Leu Val Gln Cys Phe Asp Arg Lys Arg Arg Asn Arg Ser Lys Pro Leu
                660                 665                 670
Phe His His Phe Thr Thr Ala Ile Asp Thr Glu Asn Val Arg Phe Val
            675                 680                 685
Phe His Ala Val Lys Asp Thr Ile Leu Gln Glu Asn Leu Lys Asp Ile
        690                 695                 700
Met Leu Gln
705

<210> SEQ ID NO 54
<211> LENGTH: 686
<212> TYPE: PRT
<213> ORGANISM: Homo sapiens

<400> SEQUENCE: 54
```

```
Met Thr Leu Glu Ser Ile Met Ala Cys Cys Leu Ser Glu Glu Ala Lys
1               5                   10                  15

Glu Ala Arg Arg Ile Asn Asp Glu Ile Glu Arg Gln Leu Arg Arg Asp
            20                  25                  30

Lys Arg Asp Ala Arg Arg Glu Leu Lys Leu Leu Leu Leu Gly Thr Gly
            35                  40                  45

Glu Ser Gly Lys Ser Thr Phe Ile Lys Gln Met Arg Ile Ile His Gly
50                  55                  60

Ser Gly Tyr Ser Asp Glu Asp Lys Arg Gly Phe Thr Lys Leu Val Tyr
65                  70                  75                  80

Gln Asn Ile Phe Thr Ala Met Gln Ala Met Ile Arg Ala Met Asp Thr
                85                  90                  95

Leu Lys Ile Pro Tyr Lys Tyr Glu His Asn Lys Ala His Ala Gln Leu
                100                 105                 110

Val Arg Glu Val Asp Val Asn Ala Ala Ile Arg Ser Thr Arg Met Thr
            115                 120                 125

Ser Lys Val Tyr Asp Pro Glu Gln Arg Lys Arg Met Ile Thr Gly Pro
130                 135                 140

Gln Trp Trp Ala Arg Cys Lys Gln Met Asn Val Leu Asp Ser Phe Ile
145                 150                 155                 160

Asn Tyr Tyr Asp Ser Glu Lys His Ala Glu Asn Ala Val Ile Phe Leu
                165                 170                 175

His Gly Asn Ala Ala Ser Ser Tyr Leu Trp Arg His Val Val Pro His
                180                 185                 190

Ile Glu Pro Val Ala Arg Cys Ile Ile Pro Asp Leu Ile Gly Met Gly
            195                 200                 205

Lys Ser Gly Lys Ser Gly Asn Gly Ser Tyr Arg Leu Leu Asp His Tyr
210                 215                 220

Lys Tyr Leu Thr Ala Trp Phe Glu Leu Leu Asn Leu Pro Lys Lys Ile
225                 230                 235                 240

Ile Phe Val Gly His Asp Trp Gly Ala Ala Leu Ala Phe His Tyr Ser
                245                 250                 255

Tyr Glu His Gln Asp Lys Ile Lys Ala Ile Val His Ala Glu Ser Val
                260                 265                 270

Val Asp Val Ile Glu Ser Trp Asp Glu Trp Pro Asp Ile Glu Glu Asp
            275                 280                 285

Ile Ala Leu Ile Lys Ser Glu Gly Glu Lys Met Val Leu Glu Asn
290                 295                 300

Asn Phe Phe Val Glu Thr Val Leu Pro Ser Lys Ile Met Arg Lys Leu
305                 310                 315                 320

Glu Pro Glu Glu Phe Ala Ala Tyr Leu Glu Pro Phe Lys Glu Lys Gly
                325                 330                 335

Glu Val Arg Arg Pro Thr Leu Ser Trp Pro Arg Glu Ile Pro Leu Val
            340                 345                 350

Lys Gly Gly Lys Pro Asp Val Val Gln Ile Val Arg Asn Tyr Asn Ala
            355                 360                 365

Tyr Leu Arg Ala Ser Asp Asp Leu Pro Lys Met Phe Ile Glu Ser Asp
370                 375                 380

Pro Gly Phe Phe Ser Asn Ala Ile Val Glu Gly Ala Lys Lys Phe Pro
385                 390                 395                 400

Asn Thr Glu Phe Val Lys Val Lys Gly Leu His Phe Ser Gln Glu Asp
                405                 410                 415

Ala Pro Asp Glu Met Gly Lys Tyr Ile Lys Ser Phe Val Glu Arg Val
```

```
            420                 425                 430
Leu Lys Asn Glu Gln Cys Thr Asn Ala Ala Ile Arg Ser Glu Lys Val
        435                 440                 445

Ser Ala Phe Glu Asn Pro Tyr Val Asp Ala Ile Lys Ser Leu Trp Asn
    450                 455                 460

Asp Pro Gly Ile Gln Glu Cys Tyr Asp Arg Arg Glu Tyr Gln Leu
465                 470                 475                 480

Ser Asp Ser Thr Lys Tyr Tyr Leu Asn Asp Leu Asp Arg Val Ala Asp
                485                 490                 495

Pro Ala Tyr Leu Pro Thr Gln Gln Asp Val Leu Arg Val Arg Val Pro
            500                 505                 510

Thr Thr Gly Ile Ile Glu Tyr Pro Phe Asp Leu Gln Ser Val Ile Phe
        515                 520                 525

Arg Met Val Asp Val Gly Gly Gln Arg Ser Glu Arg Arg Lys Trp Ile
    530                 535                 540

His Cys Phe Glu Asn Val Thr Ser Ile Met Phe Leu Val Ala Leu Ser
545                 550                 555                 560

Glu Tyr Asp Gln Val Leu Val Glu Ser Asp Asn Glu Asn Arg Met Glu
                565                 570                 575

Glu Ser Lys Ala Leu Phe Arg Thr Ile Ile Thr Tyr Pro Trp Phe Gln
            580                 585                 590

Asn Ser Ser Val Ile Leu Phe Leu Asn Lys Lys Asp Leu Leu Glu Glu
        595                 600                 605

Lys Ile Met Tyr Ser His Leu Val Asp Tyr Phe Pro Glu Tyr Asp Gly
    610                 615                 620

Pro Gln Arg Asp Ala Gln Ala Ala Arg Glu Phe Ile Leu Lys Met Phe
625                 630                 635                 640

Val Asp Leu Asn Pro Asp Ser Asp Lys Ile Ile Tyr Ser His Phe Thr
                645                 650                 655

Cys Ala Thr Asp Thr Glu Asn Ile Arg Phe Val Phe Ala Ala Val Lys
            660                 665                 670

Asp Thr Ile Leu Gln Leu Asn Leu Lys Glu Tyr Asn Leu Val
        675                 680                 685

<210> SEQ ID NO 55
<211> LENGTH: 717
<212> TYPE: PRT
<213> ORGANISM: Homo sapiens

<400> SEQUENCE: 55

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
            20                  25                  30

Asp Lys Gln Val Tyr Arg Ala Thr His Arg Leu Leu Leu Leu Gly Ala
        35                  40                  45

Gly Glu Ser Gly Lys Ser Thr Ile Val Lys Gln Met Arg Ile Leu His
    50                  55                  60

Val Asn Gly Ser Gly Gly Gly Ser Met Thr Ser Lys Val Tyr Asp
65                  70                  75                  80

Pro Glu Gln Arg Lys Arg Met Ile Thr Gly Pro Gln Trp Trp Ala Arg
                85                  90                  95

Cys Lys Gln Met Asn Val Leu Asp Ser Phe Ile Asn Tyr Tyr Asp Ser
            100                 105                 110
```

```
Glu Lys His Ala Glu Asn Ala Val Ile Phe Leu His Gly Asn Ala Thr
        115                 120                 125
Ser Ser Tyr Leu Trp Arg His Val Val Pro His Ile Glu Pro Val Ala
130                 135                 140
Arg Cys Ile Ile Pro Asp Leu Ile Gly Met Gly Lys Ser Gly Lys Ser
145                 150                 155                 160
Gly Asn Gly Ser Tyr Arg Leu Leu Asp His Tyr Lys Tyr Leu Thr Ala
                165                 170                 175
Trp Phe Glu Leu Leu Asn Leu Pro Lys Lys Ile Ile Phe Val Gly His
                180                 185                 190
Asp Trp Gly Ala Ala Leu Ala Phe His Tyr Ser Tyr Glu His Gln Asp
            195                 200                 205
Lys Ile Lys Ala Ile Val His Ala Glu Ser Val Val Asp Val Ile Glu
        210                 215                 220
Ser Trp Asp Glu Trp Pro Asp Ile Glu Glu Asp Ile Ala Leu Ile Lys
225                 230                 235                 240
Ser Glu Glu Gly Glu Lys Met Val Leu Glu Asn Asn Phe Phe Val Glu
                245                 250                 255
Thr Val Leu Pro Ser Lys Ile Met Arg Lys Leu Glu Pro Glu Glu Phe
                260                 265                 270
Ala Ala Tyr Leu Glu Pro Phe Lys Glu Lys Gly Glu Val Arg Arg Pro
            275                 280                 285
Thr Leu Ser Trp Pro Arg Glu Ile Pro Leu Val Lys Gly Gly Lys Pro
        290                 295                 300
Asp Val Val Gln Ile Val Arg Asn Tyr Asn Ala Tyr Leu Arg Ala Ser
305                 310                 315                 320
Asp Asp Leu Pro Lys Met Phe Ile Glu Ser Asp Pro Gly Phe Phe Ser
                325                 330                 335
Asn Ala Ile Val Glu Gly Ala Lys Lys Phe Pro Asn Thr Glu Phe Val
            340                 345                 350
Lys Val Lys Gly Leu His Phe Ser Gln Glu Asp Ala Pro Asp Glu Met
        355                 360                 365
Gly Lys Tyr Ile Lys Ser Phe Val Glu Arg Val Leu Lys Asn Glu Gln
    370                 375                 380
Ser Gly Gly Gly Gly Ser Phe Asn Gly Glu Gly Gly Glu Glu Asp Pro
385                 390                 395                 400
Gln Ala Ala Arg Ser Asn Ser Asp Gly Glu Lys Ala Thr Lys Val Gln
                405                 410                 415
Asp Ile Lys Asn Asn Leu Lys Glu Ala Ile Glu Thr Ile Val Ala Ala
            420                 425                 430
Met Ser Asn Leu Val Pro Pro Val Glu Leu Ala Asn Pro Glu Asn Gln
        435                 440                 445
Phe Arg Val Asp Tyr Ile Leu Ser Val Met Asn Val Pro Asp Phe Asp
    450                 455                 460
Phe Pro Pro Glu Phe Tyr Glu His Ala Lys Ala Leu Trp Glu Asp Glu
465                 470                 475                 480
Gly Val Arg Ala Cys Tyr Glu Arg Ser Asn Glu Tyr Gln Leu Ile Asp
                485                 490                 495
Cys Ala Gln Tyr Phe Leu Asp Lys Ile Asp Val Ile Lys Gln Ala Asp
            500                 505                 510
Tyr Val Pro Ser Asp Gln Asp Leu Leu Arg Cys Arg Val Leu Thr Ser
        515                 520                 525
Gly Ile Phe Glu Thr Lys Phe Gln Val Asp Lys Val Asn Phe His Met
```

```
                530             535             540
Phe Asp Val Gly Gly Gln Arg Asp Glu Arg Arg Lys Trp Ile Gln Cys
545                 550                 555                 560

Phe Asn Asp Val Thr Ala Ile Ile Phe Val Val Ala Ser Ser Ser Tyr
                565                 570                 575

Asn Met Val Ile Arg Glu Asp Asn Gln Thr Asn Arg Leu Gln Glu Ala
                580                 585                 590

Leu Asn Leu Phe Lys Ser Ile Trp Asn Asn Arg Trp Leu Arg Thr Ile
                595                 600                 605

Ser Val Ile Leu Phe Leu Asn Lys Gln Asp Leu Leu Ala Glu Lys Val
                610                 615                 620

Leu Ala Gly Lys Ser Lys Ile Glu Asp Tyr Phe Pro Glu Phe Ala Arg
625                 630                 635                 640

Tyr Thr Thr Pro Glu Asp Ala Thr Pro Glu Pro Gly Glu Asp Pro Arg
                645                 650                 655

Val Thr Arg Ala Lys Tyr Phe Ile Arg Asp Glu Phe Leu Arg Ile Ser
                660                 665                 670

Thr Ala Ser Gly Asp Gly Arg His Tyr Cys Tyr Pro His Phe Thr Cys
                675                 680                 685

Ala Val Asp Thr Glu Asn Ile Arg Arg Val Phe Asn Asp Cys Arg Asp
                690                 695                 700

Ile Ile Gln Arg Met His Leu Arg Gln Tyr Glu Leu Leu
705                 710                 715

<210> SEQ ID NO 56
<211> LENGTH: 340
<212> TYPE: PRT
<213> ORGANISM: Homo sapiens

<400> SEQUENCE: 56

Met Ser Glu Leu Asp Gln Leu Arg Gln Glu Ala Glu Gln Leu Lys Asn
1               5                   10                  15

Gln Ile Arg Asp Ala Arg Lys Ala Cys Ala Asp Ala Thr Leu Ser Gln
                20                  25                  30

Ile Thr Asn Asn Ile Asp Pro Val Gly Arg Ile Gln Met Arg Thr Arg
                35                  40                  45

Arg Thr Leu Arg Gly His Leu Ala Lys Ile Tyr Ala Met His Trp Gly
            50                  55                  60

Thr Asp Ser Arg Leu Leu Val Ser Ala Ser Gln Asp Gly Lys Leu Ile
65              70                  75                  80

Ile Trp Asp Ser Tyr Thr Thr Asn Lys Val His Ala Ile Pro Leu Arg
                85                  90                  95

Ser Ser Trp Val Met Thr Cys Ala Tyr Ala Pro Ser Gly Asn Tyr Val
                100                 105                 110

Ala Cys Gly Gly Leu Asp Asn Ile Cys Ser Ile Tyr Asn Leu Lys Thr
            115                 120                 125

Arg Glu Gly Asn Val Arg Val Ser Arg Glu Leu Ala Gly His Thr Gly
        130                 135                 140

Tyr Leu Ser Cys Cys Arg Phe Leu Asp Asp Asn Gln Ile Val Thr Ser
145                 150                 155                 160

Ser Gly Asp Thr Thr Cys Ala Leu Trp Asp Ile Glu Thr Gly Gln Gln
                165                 170                 175

Thr Thr Thr Phe Thr Gly His Thr Gly Asp Val Met Ser Leu Ser Leu
                180                 185                 190
```

```
Ala Pro Asp Thr Arg Leu Phe Val Ser Gly Ala Cys Asp Ala Ser Ala
        195                 200                 205
Lys Leu Trp Asp Val Arg Glu Gly Met Cys Arg Gln Thr Phe Thr Gly
210                 215                 220
His Glu Ser Asp Ile Asn Ala Ile Cys Phe Phe Pro Asn Gly Asn Ala
225                 230                 235                 240
Phe Ala Thr Gly Ser Asp Ala Thr Cys Arg Leu Phe Asp Leu Arg
        245                 250                 255
Ala Asp Gln Glu Leu Met Thr Tyr Ser His Asp Asn Ile Ile Cys Gly
        260                 265                 270
Ile Thr Ser Val Ser Phe Ser Lys Ser Gly Arg Leu Leu Leu Ala Gly
        275                 280                 285
Tyr Asp Asp Phe Asn Cys Asn Val Trp Asp Ala Leu Lys Ala Asp Arg
290                 295                 300
Ala Gly Val Leu Ala Gly His Asp Asn Arg Val Ser Cys Leu Gly Val
305                 310                 315                 320
Thr Asp Asp Gly Met Ala Val Ala Thr Gly Ser Trp Asp Ser Phe Leu
                325                 330                 335
Lys Ile Trp Asn
            340

<210> SEQ ID NO 57
<211> LENGTH: 74
<212> TYPE: PRT
<213> ORGANISM: Homo sapiens

<400> SEQUENCE: 57

Met Pro Val Ile Asn Ile Glu Asp Leu Thr Glu Lys Asp Lys Leu Lys
1               5                   10                  15
Met Glu Val Asp Gln Leu Lys Lys Glu Val Thr Leu Glu Arg Met Leu
            20                  25                  30
Val Ser Lys Cys Cys Glu Glu Val Arg Asp Tyr Val Glu Glu Arg Ser
        35                  40                  45
Gly Glu Asp Pro Leu Val Lys Gly Ile Pro Glu Asp Lys Asn Pro Phe
    50                  55                  60
Lys Glu Leu Lys Gly Gly Cys Val Ile Ser
65                  70

<210> SEQ ID NO 58
<211> LENGTH: 71
<212> TYPE: PRT
<213> ORGANISM: Homo sapiens

<400> SEQUENCE: 58

Met Ala Ser Asn Asn Thr Ala Ser Ile Ala Gln Ala Arg Lys Leu Val
1               5                   10                  15
Glu Gln Leu Lys Met Glu Ala Asn Ile Asp Arg Ile Lys Val Ser Lys
            20                  25                  30
Ala Ala Ala Asp Leu Met Ala Tyr Cys Glu Ala His Ala Lys Glu Asp
        35                  40                  45
Pro Leu Leu Thr Pro Val Pro Ala Ser Glu Asn Pro Phe Arg Glu Lys
    50                  55                  60
Lys Phe Phe Cys Ala Ile Leu
65                  70

<210> SEQ ID NO 59
<211> LENGTH: 75
```

```
<212> TYPE: PRT
<213> ORGANISM: Homo sapiens

<400> SEQUENCE: 59

Met Lys Gly Glu Thr Pro Val Asn Ser Thr Met Ser Ile Gly Gln Ala
1               5                   10                  15

Arg Lys Met Val Glu Gln Leu Lys Ile Glu Ala Ser Leu Cys Arg Ile
            20                  25                  30

Lys Val Ser Lys Ala Ala Ala Asp Leu Met Thr Tyr Cys Asp Ala His
        35                  40                  45

Ala Cys Glu Asp Pro Leu Ile Thr Pro Val Pro Thr Ser Glu Asn Pro
    50                  55                  60

Phe Arg Glu Lys Lys Phe Phe Cys Ala Leu Leu
65                  70                  75

<210> SEQ ID NO 60
<211> LENGTH: 75
<212> TYPE: PRT
<213> ORGANISM: Homo sapiens

<400> SEQUENCE: 60

Met Lys Glu Gly Met Ser Asn Asn Ser Thr Thr Ser Ile Ser Gln Ala
1               5                   10                  15

Arg Lys Ala Val Glu Gln Leu Lys Met Glu Ala Cys Met Asp Arg Val
            20                  25                  30

Lys Val Ser Gln Ala Ala Ala Asp Leu Leu Ala Tyr Cys Glu Ala His
        35                  40                  45

Val Arg Glu Asp Pro Leu Ile Ile Pro Val Pro Ala Ser Glu Asn Pro
    50                  55                  60

Phe Arg Glu Lys Lys Phe Phe Cys Thr Ile Leu
65                  70                  75

<210> SEQ ID NO 61
<211> LENGTH: 68
<212> TYPE: PRT
<213> ORGANISM: Homo sapiens

<400> SEQUENCE: 61

Met Ser Gly Ser Ser Val Ala Ala Met Lys Lys Val Val Gln Gln Leu
1               5                   10                  15

Leu Arg Leu Glu Ala Gly Leu Asn Arg Val Lys Val Ser Gln Ala Ala
            20                  25                  30

Ala Asp Leu Lys Gln Phe Cys Leu Gln Asn Ala Gln His Asp Pro Leu
        35                  40                  45

Leu Thr Gly Val Ser Ser Ser Thr Asn Pro Phe Arg Pro Gln Lys Val
    50                  55                  60

Cys Ser Phe Leu
65

<210> SEQ ID NO 62
<211> LENGTH: 68
<212> TYPE: PRT
<213> ORGANISM: Homo sapiens

<400> SEQUENCE: 62

Met Ser Ala Thr Asn Asn Ile Ala Gln Ala Arg Lys Leu Val Glu Gln
1               5                   10                  15

Leu Arg Ile Glu Ala Gly Ile Glu Arg Ile Lys Val Ser Lys Ala Ala
            20                  25                  30
```

```
Ser Asp Leu Met Ser Tyr Cys Glu Gln His Ala Arg Asn Asp Pro Leu
        35                  40                  45

Leu Val Gly Val Pro Ala Ser Glu Asn Pro Phe Lys Asp Lys Lys Pro
 50                  55                  60

Cys Ile Ile Leu
 65

<210> SEQ ID NO 63
<211> LENGTH: 70
<212> TYPE: PRT
<213> ORGANISM: Homo sapiens

<400> SEQUENCE: 63

Met Ser Asn Asn Met Ala Lys Ile Ala Glu Ala Arg Lys Thr Val Glu
 1               5                  10                  15

Gln Leu Lys Leu Glu Val Asn Ile Asp Arg Met Lys Val Ser Gln Ala
             20                  25                  30

Ala Ala Glu Leu Leu Ala Phe Cys Glu Thr His Ala Lys Asp Asp Pro
         35                  40                  45

Leu Val Thr Pro Val Pro Ala Ala Glu Asn Pro Phe Arg Asp Lys Arg
 50                  55                  60

Leu Phe Cys Val Leu Leu
 65                  70

<210> SEQ ID NO 64
<211> LENGTH: 69
<212> TYPE: PRT
<213> ORGANISM: Homo sapiens

<400> SEQUENCE: 64

Met Ala Gln Asp Leu Ser Glu Lys Asp Leu Leu Lys Met Glu Val Glu
 1               5                  10                  15

Gln Leu Lys Lys Glu Val Lys Asn Thr Arg Ile Pro Ile Ser Lys Ala
             20                  25                  30

Gly Lys Glu Ile Lys Glu Tyr Val Glu Ala Gln Ala Gly Asn Asp Pro
         35                  40                  45

Phe Leu Lys Gly Ile Pro Glu Asp Lys Asn Pro Phe Lys Glu Lys Gly
 50                  55                  60

Gly Cys Leu Ile Ser
 65

<210> SEQ ID NO 65
<211> LENGTH: 68
<212> TYPE: PRT
<213> ORGANISM: Homo sapiens

<400> SEQUENCE: 65

Met Ser Ser Gly Ala Ser Ala Ser Ala Leu Gln Arg Leu Val Glu Gln
 1               5                  10                  15

Leu Lys Leu Glu Ala Gly Val Glu Arg Ile Lys Val Ser Gln Ala Ala
             20                  25                  30

Ala Glu Leu Gln Gln Tyr Cys Met Gln Asn Ala Cys Lys Asp Ala Leu
         35                  40                  45

Leu Val Gly Val Pro Ala Gly Ser Asn Pro Phe Arg Glu Pro Arg Ser
 50                  55                  60

Cys Ala Leu Leu
 65
```

<210> SEQ ID NO 66
<211> LENGTH: 73
<212> TYPE: PRT
<213> ORGANISM: Homo sapiens

<400> SEQUENCE: 66

Met Pro Ala Leu His Ile Glu Asp Leu Pro Glu Lys Glu Lys Leu Lys
1               5                   10                  15

Met Glu Val Glu Gln Leu Arg Lys Glu Val Lys Leu Gln Arg Gln Gln
                20                  25                  30

Val Ser Lys Cys Ser Glu Glu Ile Lys Asn Tyr Ile Glu Glu Arg Ser
            35                  40                  45

Gly Glu Asp Pro Leu Val Lys Gly Ile Pro Glu Asp Lys Asn Pro Phe
        50                  55                  60

Lys Glu Lys Gly Ser Cys Val Ile Ser
65                  70

<210> SEQ ID NO 67
<211> LENGTH: 72
<212> TYPE: PRT
<213> ORGANISM: Homo sapiens

<400> SEQUENCE: 67

Met Ser Ser Lys Thr Ala Ser Thr Asn Asn Ile Ala Gln Ala Arg Arg
1               5                   10                  15

Thr Val Gln Gln Leu Arg Leu Glu Ala Ser Ile Glu Arg Ile Lys Val
                20                  25                  30

Ser Lys Ala Ser Ala Asp Leu Met Ser Tyr Cys Glu His Ala Arg
            35                  40                  45

Ser Asp Pro Leu Leu Ile Gly Ile Pro Thr Ser Glu Asn Pro Phe Lys
        50                  55                  60

Asp Lys Lys Thr Cys Ile Ile Leu
65                  70

<210> SEQ ID NO 68
<211> LENGTH: 67
<212> TYPE: PRT
<213> ORGANISM: Homo sapiens

<400> SEQUENCE: 68

Met Glu Glu Trp Asp Val Pro Gln Met Lys Lys Glu Val Glu Ser Leu
1               5                   10                  15

Lys Tyr Gln Leu Ala Phe Gln Arg Glu Met Ala Ser Lys Thr Ile Pro
                20                  25                  30

Glu Leu Leu Lys Trp Ile Glu Asp Gly Ile Pro Lys Asp Pro Phe Leu
            35                  40                  45

Asn Pro Asp Leu Met Lys Asn Asn Pro Trp Val Glu Lys Gly Lys Cys
        50                  55                  60

Thr Ile Leu
65

<210> SEQ ID NO 69
<211> LENGTH: 374
<212> TYPE: PRT
<213> ORGANISM: Homo sapiens

<400> SEQUENCE: 69

Met Ala Arg Ser Leu Thr Trp Arg Cys Cys Pro Trp Cys Leu Thr Glu
1               5                   10                  15

Asp Glu Lys Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu
        35                  40                  45

Gly Pro Gly Glu Ser Gly Lys Ser Thr Phe Ile Lys Gln Met Arg Ile
50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
        100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
        180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
        260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Gln Asn Ile
        340                 345                 350

Arg Lys Val Phe Lys Asp Val Arg Asp Ser Val Leu Ala Arg Tyr Leu
        355                 360                 365

Asp Glu Ile Asn Leu Leu
        370

<210> SEQ ID NO 70
<211> LENGTH: 88
<212> TYPE: PRT
<213> ORGANISM: Homo sapiens

<400> SEQUENCE: 70

Val Gln Ser Glu Pro Arg Ser Trp Ser Leu Leu Glu Gln Leu Gly Leu

-continued

```
                1               5                  10                  15
Ala Gly Ala Asp Leu Ala Ala Pro Gly Val Gln Gln Gln Leu Glu Leu
                20                  25                  30

Glu Arg Glu Arg Leu Arg Arg Glu Ile Arg Lys Glu Leu Lys Leu Lys
            35                  40                  45

Glu Gly Ala Glu Asn Leu Arg Arg Ala Thr Thr Asp Leu Gly Arg Ser
        50                  55                  60

Leu Gly Pro Val Glu Leu Leu Arg Gly Ser Ser Arg Arg Leu Asp
65                  70                  75                  80

Leu Leu His Gln Gln Leu Gln Glu
                85
```

<210> SEQ ID NO 71
<211> LENGTH: 14
<212> TYPE: PRT
<213> ORGANISM: Homo sapiens

<400> SEQUENCE: 71

```
Gly Ser Ala Ser Ala Gly Thr Ala Thr Met Ala Ser Asp Ala
1               5                  10
```

<210> SEQ ID NO 72
<211> LENGTH: 57
<212> TYPE: PRT
<213> ORGANISM: Homo sapiens

<400> SEQUENCE: 72

```
Phe Asn Ile Asp Met Pro His Arg Phe Lys Val His Asn Tyr Met Ser
1               5                  10                  15

Pro Thr Phe Cys Asp His Cys Gly Ser Leu Leu Trp Gly Leu Val Lys
                20                  25                  30

Gln Gly Leu Lys Cys Glu Asp Cys Gly Met Asn Val His His Lys Cys
            35                  40                  45

Arg Glu Lys Val Ala Asn Leu Cys Gly
        50                  55
```

<210> SEQ ID NO 73
<211> LENGTH: 477
<212> TYPE: PRT
<213> ORGANISM: Homo sapiens

<400> SEQUENCE: 73

```
Met Gly Ala Gly Val Leu Val Leu Gly Ala Ser Glu Pro Gly Asn Leu
1               5                  10                  15

Ser Ser Ala Ala Pro Leu Pro Asp Gly Ala Ala Thr Ala Ala Arg Leu
                20                  25                  30

Leu Val Pro Ala Ser Pro Pro Ala Ser Leu Leu Pro Pro Ala Ser Glu
            35                  40                  45

Ser Pro Glu Pro Leu Ser Gln Gln Trp Thr Ala Gly Met Gly Leu Leu
        50                  55                  60

Met Ala Leu Ile Val Leu Leu Ile Val Ala Gly Asn Val Leu Val Ile
65                  70                  75                  80

Val Ala Ile Ala Lys Thr Pro Arg Leu Gln Thr Leu Thr Asn Leu Phe
                85                  90                  95

Ile Met Ser Leu Ala Ser Ala Asp Leu Val Met Gly Leu Leu Val Val
                100                 105                 110

Pro Phe Gly Ala Thr Ile Val Val Trp Gly Arg Trp Glu Tyr Gly Ser
            115                 120                 125
```

Phe Phe Cys Glu Leu Trp Thr Ser Val Asp Val Leu Cys Val Thr Ala
    130                 135                 140

Ser Ile Glu Thr Leu Cys Val Ile Ala Leu Asp Arg Tyr Leu Ala Ile
145                 150                 155                 160

Thr Ser Pro Phe Arg Tyr Gln Ser Leu Leu Thr Arg Ala Arg Ala Arg
                165                 170                 175

Gly Leu Val Cys Thr Val Trp Ala Ile Ser Ala Leu Val Ser Phe Leu
            180                 185                 190

Pro Ile Leu Met His Trp Trp Arg Ala Glu Ser Asp Glu Ala Arg Arg
        195                 200                 205

Cys Tyr Asn Asp Pro Lys Cys Cys Asp Phe Val Thr Asn Arg Ala Tyr
    210                 215                 220

Ala Ile Ala Ser Ser Val Val Ser Phe Tyr Val Pro Leu Cys Ile Met
225                 230                 235                 240

Ala Phe Val Tyr Leu Arg Val Phe Arg Glu Ala Gln Lys Gln Val Lys
                245                 250                 255

Lys Ile Asp Ser Cys Glu Arg Arg Phe Leu Gly Gly Pro Ala Arg Pro
            260                 265                 270

Pro Ser Pro Ser Pro Ser Pro Val Pro Ala Pro Ala Pro Pro Pro Gly
        275                 280                 285

Pro Pro Arg Pro Ala Ala Ala Ala Thr Ala Pro Leu Ala Asn Gly
    290                 295                 300

Arg Ala Gly Lys Arg Arg Pro Ser Arg Leu Val Ala Leu Arg Glu Gln
305                 310                 315                 320

Lys Ala Leu Lys Thr Leu Gly Ile Ile Met Gly Val Phe Thr Leu Cys
                325                 330                 335

Trp Leu Pro Phe Phe Leu Ala Asn Val Val Lys Ala Phe His Arg Glu
            340                 345                 350

Leu Val Pro Asp Arg Leu Phe Val Phe Phe Asn Trp Leu Gly Tyr Ala
        355                 360                 365

Asn Ser Ala Phe Asn Pro Ile Ile Tyr Cys Arg Ser Pro Asp Phe Arg
    370                 375                 380

Lys Ala Phe Gln Gly Leu Leu Cys Cys Ala Arg Arg Ala Ala Arg Arg
385                 390                 395                 400

Arg His Ala Thr His Gly Asp Arg Pro Arg Ala Ser Gly Cys Leu Ala
                405                 410                 415

Arg Pro Gly Pro Pro Pro Ser Pro Gly Ala Ala Ser Asp Asp Asp Asp
            420                 425                 430

Asp Asp Val Val Gly Ala Thr Pro Pro Ala Arg Leu Leu Glu Pro Trp
        435                 440                 445

Ala Gly Cys Asn Gly Gly Ala Ala Ala Asp Ser Asp Ser Ser Leu Asp
    450                 455                 460

Glu Pro Cys Arg Pro Gly Phe Ala Ser Glu Ser Lys Val
465                 470                 475

<210> SEQ ID NO 74
<211> LENGTH: 413
<212> TYPE: PRT
<213> ORGANISM: Homo sapiens

<400> SEQUENCE: 74

Met Gly Gln Pro Gly Asn Gly Ser Ala Phe Leu Leu Ala Pro Asn Arg
1               5                   10                  15

Ser His Ala Pro Asp His Asp Val Thr Gln Gln Arg Asp Glu Val Trp

Val Val Gly Met Gly Ile Val Met Ser Leu Ile Val Leu Ala Ile Val
           20                  25                  30
Phe Gly Asn Val Leu Val Ile Thr Ala Ile Ala Lys Phe Glu Arg Leu
 35                  40                  45
Gln Thr Val Thr Asn Tyr Phe Ile Thr Ser Leu Ala Cys Ala Asp Leu
 50                  55                  60
Val Met Gly Leu Ala Val Val Pro Phe Gly Ala His Ile Leu Met
 65                  70                  75                  80
Lys Met Trp Thr Phe Gly Asn Phe Trp Cys Glu Phe Trp Thr Ser Ile
 85                  90                  95
Asp Val Leu Cys Val Thr Ala Ser Ile Glu Thr Leu Cys Val Ile Ala
     100                 105                 110
Val Asp Arg Tyr Phe Ala Ile Thr Ser Pro Phe Lys Tyr Gln Ser Leu
     115                 120                 125
Leu Thr Lys Asn Lys Ala Arg Val Ile Ile Leu Met Val Trp Ile Val
     130                 135                 140
Ser Gly Leu Thr Ser Phe Leu Pro Ile Gln Met His Trp Tyr Arg Ala
145                 150                 155                 160
Thr His Gln Glu Ala Ile Asn Cys Tyr Ala Asn Glu Thr Cys Cys Asp
         165                 170                 175
Phe Phe Thr Asn Gln Ala Tyr Ala Ile Ala Ser Ser Ile Val Ser Phe
         180                 185                 190
Tyr Val Pro Leu Val Ile Met Val Phe Val Tyr Ser Arg Val Phe Gln
         195                 200                 205
Glu Ala Lys Arg Gln Leu Gln Lys Ile Asp Lys Ser Glu Gly Arg Phe
         210                 215                 220
His Val Gln Asn Leu Ser Gln Val Glu Gln Asp Gly Arg Thr Gly His
225                 230                 235                 240
Gly Leu Arg Arg Ser Ser Lys Phe Cys Leu Lys Glu His Lys Ala Leu
         245                 250                 255
Lys Thr Leu Gly Ile Ile Met Gly Thr Phe Thr Leu Cys Trp Leu Pro
         260                 265                 270
Phe Phe Ile Val Asn Ile Val His Val Ile Gln Asp Asn Leu Ile Arg
         275                 280                 285
Lys Glu Val Tyr Ile Leu Leu Asn Trp Ile Gly Tyr Val Asn Ser Gly
305                 290                 295                 300
Phe Asn Pro Leu Ile Tyr Cys Arg Ser Pro Asp Phe Arg Ile Ala Phe
         310                 315                 320
Gln Glu Leu Leu Cys Leu Arg Arg Ser Ser Leu Lys Ala Tyr Gly Asn
         325                 330                 335
Gly Tyr Ser Ser Asn Gly Asn Thr Gly Glu Gln Ser Gly Tyr His Val
         340                 345                 350
Glu Gln Glu Lys Glu Asn Lys Leu Leu Cys Glu Asp Leu Pro Gly Thr
         355                 360                 365
Glu Asp Phe Val Gly His Gln Gly Thr Val Pro Ser Asp Asn Ile Asp
370                 375                 380
Ser Gln Gly Arg Asn Cys Ser Thr Asn Asp Ser Leu Leu
385                 390                 395                 400
         405                 410

<210> SEQ ID NO 75
<211> LENGTH: 359
<212> TYPE: PRT
<213> ORGANISM: Homo sapiens

<400> SEQUENCE: 75

```
Met Ser Met Asn Asn Ser Lys Gln Leu Val Ser Pro Ala Ala Ala Leu
1               5                   10                  15

Leu Ser Asn Thr Thr Cys Gln Thr Glu Asn Arg Leu Ser Val Phe Phe
            20                  25                  30

Ser Val Ile Phe Met Thr Val Gly Ile Leu Ser Asn Ser Leu Ala Ile
        35                  40                  45

Ala Ile Leu Met Lys Ala Tyr Gln Arg Phe Arg Gln Lys Ser Lys Ala
    50                  55                  60

Ser Phe Leu Leu Leu Ala Ser Gly Leu Val Ile Thr Asp Phe Phe Gly
65                  70                  75                  80

His Leu Ile Asn Gly Ala Ile Ala Val Phe Val Tyr Ala Ser Asp Lys
                85                  90                  95

Glu Trp Ile Arg Phe Asp Gln Ser Asn Val Leu Cys Ser Ile Phe Gly
            100                 105                 110

Ile Cys Met Val Phe Ser Gly Leu Cys Pro Leu Leu Leu Gly Ser Val
        115                 120                 125

Met Ala Ile Glu Arg Cys Ile Gly Val Thr Lys Pro Ile Phe His Ser
    130                 135                 140

Thr Lys Ile Thr Ser Lys His Val Lys Met Met Leu Ser Gly Val Cys
145                 150                 155                 160

Leu Phe Ala Val Phe Ile Ala Leu Leu Pro Ile Leu Gly His Arg Asp
                165                 170                 175

Tyr Lys Ile Gln Ala Ser Arg Thr Trp Cys Phe Tyr Asn Thr Glu Asp
            180                 185                 190

Ile Lys Asp Trp Glu Asp Arg Phe Tyr Leu Leu Leu Phe Ser Phe Leu
        195                 200                 205

Gly Leu Leu Ala Leu Gly Val Ser Leu Leu Cys Asn Ala Ile Thr Gly
    210                 215                 220

Ile Thr Leu Leu Arg Val Lys Phe Lys Ser Gln Gln His Arg Gln Gly
225                 230                 235                 240

Arg Ser His His Leu Glu Met Val Ile Gln Leu Leu Ala Ile Met Cys
                245                 250                 255

Val Ser Cys Ile Cys Trp Ser Pro Phe Leu Val Thr Met Ala Asn Ile
            260                 265                 270

Gly Ile Asn Gly Asn His Ser Leu Glu Thr Cys Glu Thr Thr Leu Phe
        275                 280                 285

Ala Leu Arg Met Ala Thr Trp Asn Gln Ile Leu Asp Pro Trp Val Tyr
    290                 295                 300

Ile Leu Leu Arg Lys Ala Val Leu Lys Asn Leu Tyr Lys Leu Ala Ser
305                 310                 315                 320

Gln Cys Cys Gly Val His Val Ile Ser Leu His Ile Trp Glu Leu Ser
                325                 330                 335

Ser Ile Lys Asn Ser Leu Lys Val Ala Ala Ile Ser Glu Ser Pro Val
            340                 345                 350

Ala Glu Lys Ser Ala Ser Thr
        355
```

<210> SEQ ID NO 76
<211> LENGTH: 343
<212> TYPE: PRT
<213> ORGANISM: Homo sapiens

<400> SEQUENCE: 76

Met Trp Pro Asn Gly Ser Ser Leu Gly Pro Cys Phe Arg Pro Thr Asn
1               5                   10                  15

Ile Thr Leu Glu Glu Arg Arg Leu Ile Ala Ser Pro Trp Phe Ala Ala
                20                  25                  30

Ser Phe Cys Val Val Gly Leu Ala Ser Asn Leu Leu Ala Leu Ser Val
            35                  40                  45

Leu Ala Gly Ala Arg Gln Gly Gly Ser His Thr Arg Ser Ser Phe Leu
        50                  55                  60

Thr Phe Leu Cys Gly Leu Val Leu Thr Asp Phe Leu Gly Leu Leu Val
65                  70                  75                  80

Thr Gly Thr Ile Val Val Ser Gln His Ala Ala Leu Phe Glu Trp His
                85                  90                  95

Ala Val Asp Pro Gly Cys Arg Leu Cys Arg Phe Met Gly Val Val Met
            100                 105                 110

Ile Phe Phe Gly Leu Ser Pro Leu Leu Leu Gly Ala Ala Met Ala Ser
            115                 120                 125

Glu Arg Tyr Leu Gly Ile Thr Arg Pro Phe Ser Arg Pro Ala Val Ala
        130                 135                 140

Ser Gln Arg Arg Ala Trp Ala Thr Val Gly Leu Val Trp Ala Ala Ala
145                 150                 155                 160

Leu Ala Leu Gly Leu Leu Pro Leu Leu Gly Val Gly Arg Tyr Thr Val
                165                 170                 175

Gln Tyr Pro Gly Ser Trp Cys Phe Leu Thr Leu Gly Ala Glu Ser Gly
            180                 185                 190

Asp Val Ala Phe Gly Leu Leu Phe Ser Met Leu Gly Gly Leu Ser Val
            195                 200                 205

Gly Leu Ser Phe Leu Leu Asn Thr Val Ser Val Ala Thr Leu Cys His
        210                 215                 220

Val Tyr His Gly Gln Glu Ala Ala Gln Gln Arg Pro Arg Asp Ser Glu
225                 230                 235                 240

Val Glu Met Met Ala Gln Leu Leu Gly Ile Met Val Val Ala Ser Val
                245                 250                 255

Cys Trp Leu Pro Leu Leu Val Phe Ile Ala Gln Thr Val Leu Arg Asn
            260                 265                 270

Pro Pro Ala Met Ser Pro Ala Gly Gln Leu Ser Arg Thr Thr Glu Lys
        275                 280                 285

Glu Leu Leu Ile Tyr Leu Arg Val Ala Thr Trp Asn Gln Ile Leu Asp
        290                 295                 300

Pro Trp Val Tyr Ile Leu Phe Arg Arg Ala Val Leu Arg Arg Leu Gln
305                 310                 315                 320

Pro Arg Leu Ser Thr Arg Pro Arg Ser Leu Ser Leu Gln Pro Gln Leu
                325                 330                 335

Thr Gln Arg Ser Gly Leu Gln
            340

<210> SEQ ID NO 77
<211> LENGTH: 389
<212> TYPE: PRT
<213> ORGANISM: Homo sapiens

<400> SEQUENCE: 77

Met Ala Leu Thr Pro Glu Ser Pro Ser Ser Phe Pro Gly Leu Ala Ala
1               5                   10                  15

Thr Gly Ser Ser Val Pro Glu Pro Pro Gly Gly Pro Asn Ala Thr Leu

```
                20                  25                  30
Asn Ser Ser Trp Ala Ser Pro Thr Glu Pro Ser Ser Leu Glu Asp Leu
        35                  40                  45
Val Ala Thr Gly Thr Ile Gly Thr Leu Leu Ser Ala Met Gly Val Val
 50                  55                  60
Gly Val Val Gly Asn Ala Tyr Thr Leu Val Val Thr Cys Arg Ser Leu
 65                  70                  75                  80
Arg Ala Val Ala Ser Met Tyr Val Tyr Val Val Asn Leu Ala Leu Ala
                85                  90                  95
Asp Leu Leu Tyr Leu Leu Ser Ile Pro Phe Ile Val Ala Thr Tyr Val
                100                 105                 110
Thr Lys Glu Trp His Phe Gly Asp Val Gly Cys Arg Val Leu Phe Gly
                115                 120                 125
Leu Asp Phe Leu Thr Met His Ala Ser Ile Phe Thr Leu Thr Val Met
                130                 135                 140
Ser Ser Glu Arg Tyr Ala Ala Val Leu Arg Pro Leu Asp Thr Val Gln
145                 150                 155                 160
Arg Pro Lys Gly Tyr Arg Lys Leu Leu Ala Leu Gly Thr Trp Leu Leu
                165                 170                 175
Ala Leu Leu Leu Thr Leu Pro Val Met Leu Ala Met Arg Leu Val Arg
                180                 185                 190
Arg Gly Pro Lys Ser Leu Cys Leu Pro Ala Trp Gly Pro Arg Ala His
                195                 200                 205
Arg Ala Tyr Leu Thr Leu Leu Phe Ala Thr Ser Ile Ala Gly Pro Gly
                210                 215                 220
Leu Leu Ile Gly Leu Leu Tyr Ala Arg Leu Ala Arg Ala Tyr Arg Arg
225                 230                 235                 240
Ser Gln Arg Ala Ser Phe Lys Arg Ala Arg Pro Gly Ala Arg Ala
                245                 250                 255
Leu Arg Leu Val Leu Gly Ile Val Leu Leu Phe Trp Ala Cys Phe Leu
                260                 265                 270
Pro Phe Trp Leu Trp Gln Leu Leu Ala Gln Tyr His Gln Ala Pro Leu
                275                 280                 285
Ala Pro Arg Thr Ala Arg Ile Val Asn Tyr Leu Thr Thr Cys Leu Thr
                290                 295                 300
Tyr Gly Asn Ser Cys Ala Asn Pro Phe Leu Tyr Thr Leu Leu Thr Arg
305                 310                 315                 320
Asn Tyr Arg Asp His Leu Arg Gly Arg Val Arg Gly Pro Gly Ser Gly
                325                 330                 335
Gly Gly Arg Gly Pro Val Pro Ser Leu Gln Pro Arg Ala Arg Phe Gln
                340                 345                 350
Arg Cys Ser Gly Arg Ser Leu Ser Ser Cys Ser Pro Gln Pro Thr Asp
                355                 360                 365
Ser Leu Val Leu Ala Pro Ala Ala Pro Ala Arg Pro Ala Pro Glu Gly
                370                 375                 380
Pro Arg Ala Pro Ala
385

<210> SEQ ID NO 78
<211> LENGTH: 487
<212> TYPE: PRT
<213> ORGANISM: Homo sapiens

<400> SEQUENCE: 78
```

-continued

```
Met Ser Leu Pro Asn Ser Ser Cys Leu Leu Glu Asp Lys Met Cys Glu
1               5                   10                  15

Gly Asn Lys Thr Thr Met Ala Ser Pro Gln Leu Met Pro Leu Val Val
            20                  25                  30

Val Leu Ser Thr Ile Cys Leu Val Thr Val Gly Leu Asn Leu Leu Val
            35                  40                  45

Leu Tyr Ala Val Arg Ser Glu Arg Lys Leu His Thr Val Gly Asn Leu
    50                  55                  60

Tyr Ile Val Ser Leu Ser Val Ala Asp Leu Ile Val Gly Ala Val Val
65                  70                  75                  80

Met Pro Met Asn Ile Leu Tyr Leu Leu Met Ser Lys Trp Ser Leu Gly
                85                  90                  95

Arg Pro Leu Cys Leu Phe Trp Leu Ser Met Asp Tyr Val Ala Ser Thr
                100                 105                 110

Ala Ser Ile Phe Ser Val Phe Ile Leu Cys Ile Asp Arg Tyr Arg Ser
                115                 120                 125

Val Gln Gln Pro Leu Arg Tyr Leu Lys Tyr Arg Thr Lys Thr Arg Ala
    130                 135                 140

Ser Ala Thr Ile Leu Gly Ala Trp Phe Leu Ser Phe Leu Trp Val Ile
145                 150                 155                 160

Pro Ile Leu Gly Trp Asn His Phe Met Gln Gln Thr Ser Val Arg Arg
                165                 170                 175

Glu Asp Lys Cys Glu Thr Asp Phe Tyr Asp Val Thr Trp Phe Lys Val
                180                 185                 190

Met Thr Ala Ile Ile Asn Phe Tyr Leu Pro Thr Leu Leu Met Leu Trp
    195                 200                 205

Phe Tyr Ala Lys Ile Tyr Lys Ala Val Arg Gln His Cys Gln His Arg
    210                 215                 220

Glu Leu Ile Asn Arg Ser Leu Pro Ser Phe Ser Glu Ile Lys Leu Arg
225                 230                 235                 240

Pro Glu Asn Pro Lys Gly Asp Ala Lys Lys Pro Gly Lys Glu Ser Pro
                245                 250                 255

Trp Glu Val Leu Lys Arg Lys Pro Lys Asp Ala Gly Gly Gly Ser Val
                260                 265                 270

Leu Lys Ser Pro Ser Gln Thr Pro Lys Glu Met Lys Ser Pro Val Val
            275                 280                 285

Phe Ser Gln Glu Asp Asp Arg Glu Val Asp Lys Leu Tyr Cys Phe Pro
    290                 295                 300

Leu Asp Ile Val His Met Gln Ala Ala Ala Glu Gly Ser Ser Arg Asp
305                 310                 315                 320

Tyr Val Ala Val Asn Arg Ser His Gly Gln Leu Lys Thr Asp Glu Gln
                325                 330                 335

Gly Leu Asn Thr His Gly Ala Ser Glu Ile Ser Glu Asp Gln Met Leu
            340                 345                 350

Gly Asp Ser Gln Ser Phe Ser Arg Thr Asp Ser Asp Thr Thr Thr Glu
    355                 360                 365

Thr Ala Pro Gly Lys Gly Lys Leu Arg Ser Gly Ser Asn Thr Gly Leu
    370                 375                 380

Asp Tyr Ile Lys Phe Thr Trp Lys Arg Leu Arg Ser His Ser Arg Gln
385                 390                 395                 400

Tyr Val Ser Gly Leu His Met Asn Arg Glu Arg Lys Ala Ala Lys Gln
                405                 410                 415

Leu Gly Phe Ile Met Ala Ala Phe Ile Leu Cys Trp Ile Pro Tyr Phe
```

-continued

```
                420             425             430
Ile Phe Phe Met Val Ile Ala Phe Cys Lys Asn Cys Cys Asn Glu His
            435                 440                 445

Leu His Met Phe Thr Ile Trp Leu Gly Tyr Ile Asn Ser Thr Leu Asn
    450                 455                 460

Pro Leu Ile Tyr Pro Leu Cys Asn Glu Asn Phe Lys Lys Thr Phe Lys
465                 470                 475                 480

Arg Ile Leu His Ile Arg Ser
                485

<210> SEQ ID NO 79
<211> LENGTH: 391
<212> TYPE: PRT
<213> ORGANISM: Homo sapiens

<400> SEQUENCE: 79

Met Phe Ser Pro Trp Lys Ile Ser Met Phe Leu Ser Val Arg Glu Asp
1               5                   10                  15

Ser Val Pro Thr Thr Ala Ser Phe Ser Ala Asp Met Leu Asn Val Thr
            20                  25                  30

Leu Gln Gly Pro Thr Leu Asn Gly Thr Phe Ala Gln Ser Lys Cys Pro
        35                  40                  45

Gln Val Glu Trp Leu Gly Trp Leu Asn Thr Ile Gln Pro Pro Phe Leu
    50                  55                  60

Trp Val Leu Phe Val Leu Ala Thr Leu Glu Asn Ile Phe Val Leu Ser
65                  70                  75                  80

Val Phe Cys Leu His Lys Ser Ser Cys Thr Val Ala Glu Ile Tyr Leu
                85                  90                  95

Gly Asn Leu Ala Ala Ala Asp Leu Ile Leu Ala Cys Gly Leu Pro Phe
            100                 105                 110

Trp Ala Ile Thr Ile Ser Asn Asn Phe Asp Trp Leu Phe Gly Glu Thr
        115                 120                 125

Leu Cys Arg Val Val Asn Ala Ile Ile Ser Met Asn Leu Tyr Ser Ser
    130                 135                 140

Ile Cys Phe Leu Met Leu Val Ser Ile Asp Arg Tyr Leu Ala Leu Val
145                 150                 155                 160

Lys Thr Met Ser Met Gly Arg Met Arg Gly Val Arg Trp Ala Lys Leu
                165                 170                 175

Tyr Ser Leu Val Ile Trp Gly Cys Thr Leu Leu Leu Ser Ser Pro Met
            180                 185                 190

Leu Val Phe Arg Thr Met Lys Glu Tyr Ser Asp Glu Gly His Asn Val
        195                 200                 205

Thr Ala Cys Val Ile Ser Tyr Pro Ser Leu Ile Trp Glu Val Phe Thr
    210                 215                 220

Asn Met Leu Leu Asn Val Val Gly Phe Leu Leu Pro Leu Ser Val Ile
225                 230                 235                 240

Thr Phe Cys Thr Met Gln Ile Met Gln Val Leu Arg Asn Asn Glu Met
                245                 250                 255

Gln Lys Phe Lys Glu Ile Gln Thr Glu Arg Arg Ala Thr Val Leu Val
            260                 265                 270

Leu Val Val Leu Leu Leu Phe Ile Ile Cys Trp Leu Pro Phe Gln Ile
        275                 280                 285

Ser Thr Phe Leu Asp Thr Leu His Arg Leu Gly Ile Leu Ser Ser Cys
    290                 295                 300
```

```
Gln Asp Glu Arg Ile Ile Asp Val Ile Thr Gln Ile Ala Ser Phe Met
305                 310                 315                 320

Ala Tyr Ser Asn Ser Cys Leu Asn Pro Leu Val Tyr Ile Val Gly
            325                 330                 335

Lys Arg Phe Arg Lys Lys Ser Trp Glu Val Tyr Gln Gly Val Cys Gln
            340                 345                 350

Lys Gly Gly Cys Arg Ser Glu Pro Ile Gln Met Glu Asn Ser Met Gly
            355                 360                 365

Thr Leu Arg Thr Ser Ile Ser Val Glu Arg Gln Ile His Lys Leu Gln
            370                 375                 380

Asp Trp Ala Gly Ser Arg Gln
385                 390

<210> SEQ ID NO 80
<211> LENGTH: 443
<212> TYPE: PRT
<213> ORGANISM: Homo sapiens

<400> SEQUENCE: 80

Met Asp Pro Leu Asn Leu Ser Trp Tyr Asp Asp Leu Glu Arg Gln
1               5                   10                  15

Asn Trp Ser Arg Pro Phe Asn Gly Ser Asp Gly Lys Ala Asp Arg Pro
            20                  25                  30

His Tyr Asn Tyr Tyr Ala Thr Leu Leu Thr Leu Leu Ile Ala Val Ile
            35                  40                  45

Val Phe Gly Asn Val Leu Val Cys Met Ala Val Ser Arg Glu Lys Ala
    50                  55                  60

Leu Gln Thr Thr Thr Asn Tyr Leu Ile Val Ser Leu Ala Val Ala Asp
65                  70                  75                  80

Leu Leu Val Ala Thr Leu Val Met Pro Trp Val Val Tyr Leu Glu Val
                85                  90                  95

Val Gly Glu Trp Lys Phe Ser Arg Ile His Cys Asp Ile Phe Val Thr
            100                 105                 110

Leu Asp Val Met Met Cys Thr Ala Ser Ile Leu Asn Leu Cys Ala Ile
            115                 120                 125

Ser Ile Asp Arg Tyr Thr Ala Val Ala Met Pro Met Leu Tyr Asn Thr
130                 135                 140

Arg Tyr Ser Ser Lys Arg Arg Val Thr Val Met Ile Ser Ile Val Trp
145                 150                 155                 160

Val Leu Ser Phe Thr Ile Ser Cys Pro Leu Leu Phe Gly Leu Asn Asn
                165                 170                 175

Ala Asp Gln Asn Glu Cys Ile Ile Ala Asn Pro Ala Phe Val Val Tyr
            180                 185                 190

Ser Ser Ile Val Ser Phe Tyr Val Pro Phe Ile Val Thr Leu Leu Val
            195                 200                 205

Tyr Ile Lys Ile Tyr Ile Val Leu Arg Arg Arg Lys Arg Val Asn
210                 215                 220

Thr Lys Arg Ser Ser Arg Ala Phe Arg Ala His Leu Arg Ala Pro Leu
225                 230                 235                 240

Lys Gly Asn Cys Thr His Pro Glu Asp Met Lys Leu Cys Thr Val Ile
            245                 250                 255

Met Lys Ser Asn Gly Ser Phe Pro Val Asn Arg Arg Val Glu Ala
            260                 265                 270

Ala Arg Arg Ala Gln Glu Leu Glu Met Glu Met Leu Ser Ser Thr Ser
275                 280                 285
```

```
Pro Pro Glu Arg Thr Arg Tyr Ser Pro Ile Pro Pro Ser His His Gln
    290                 295                 300

Leu Thr Leu Pro Asp Pro Ser His His Gly Leu His Ser Thr Pro Asp
305                 310                 315                 320

Ser Pro Ala Lys Pro Glu Lys Asn Gly His Ala Lys Asp His Pro Lys
                325                 330                 335

Ile Ala Lys Ile Phe Glu Ile Gln Thr Met Pro Asn Gly Lys Thr Arg
                340                 345                 350

Thr Ser Leu Lys Thr Met Ser Arg Arg Lys Leu Ser Gln Gln Lys Glu
                355                 360                 365

Lys Lys Ala Thr Gln Met Leu Ala Ile Val Leu Gly Val Phe Ile Ile
        370                 375                 380

Cys Trp Leu Pro Phe Phe Ile Thr His Ile Leu Asn Ile His Cys Asp
385                 390                 395                 400

Cys Asn Ile Pro Pro Val Leu Tyr Ser Ala Phe Thr Trp Leu Gly Tyr
                405                 410                 415

Val Asn Ser Ala Val Asn Pro Ile Ile Tyr Thr Thr Phe Asn Ile Glu
                420                 425                 430

Phe Arg Lys Ala Phe Leu Lys Ile Leu His Cys
                435                 440

<210> SEQ ID NO 81
<211> LENGTH: 569
<212> TYPE: PRT
<213> ORGANISM: Homo sapiens

<400> SEQUENCE: 81

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
```

```
                    210                 215                 220
Val Thr Ala Ala Gly Ile Thr Leu Gly Met Asp Glu Leu Tyr Lys Gly
225                 230                 235                 240

Gly Gly Gly Gly Asp Ile Glu Phe Leu Gln Pro Gly Gly Ser Gly Gly
                245                 250                 255

Gly Gly Met Thr Ser Lys Val Tyr Asp Pro Glu Gln Arg Lys Arg Met
            260                 265                 270

Ile Thr Gly Pro Gln Trp Trp Ala Arg Cys Lys Gln Met Asn Val Leu
        275                 280                 285

Asp Ser Phe Ile Asn Tyr Tyr Asp Ser Glu Lys His Ala Glu Asn Ala
    290                 295                 300

Val Ile Phe Leu His Gly Asn Ala Ala Ser Ser Tyr Leu Trp Arg His
305                 310                 315                 320

Val Val Pro His Ile Glu Pro Val Ala Arg Cys Ile Ile Pro Asp Leu
                325                 330                 335

Ile Gly Met Gly Lys Ser Gly Lys Ser Gly Asn Gly Ser Tyr Arg Leu
            340                 345                 350

Leu Asp His Tyr Lys Tyr Leu Thr Ala Trp Phe Glu Leu Leu Asn Leu
        355                 360                 365

Pro Lys Lys Ile Ile Phe Val Gly His Asp Trp Gly Ala Ala Leu Ala
    370                 375                 380

Phe His Tyr Ser Tyr Glu His Gln Asp Lys Ile Lys Ala Ile Val His
385                 390                 395                 400

Ala Glu Ser Val Val Asp Val Ile Glu Ser Trp Asp Glu Trp Pro Asp
                405                 410                 415

Ile Glu Glu Asp Ile Ala Leu Ile Lys Ser Glu Glu Gly Glu Lys Met
            420                 425                 430

Val Leu Glu Asn Asn Phe Phe Val Glu Thr Val Leu Pro Ser Lys Ile
        435                 440                 445

Met Arg Lys Leu Glu Pro Glu Glu Phe Ala Ala Tyr Leu Glu Pro Phe
    450                 455                 460

Lys Glu Lys Gly Glu Val Arg Arg Pro Thr Leu Ser Trp Pro Arg Glu
465                 470                 475                 480

Ile Pro Leu Val Lys Gly Gly Lys Pro Asp Val Val Gln Ile Val Arg
                485                 490                 495

Asn Tyr Asn Ala Tyr Leu Arg Ala Ser Asp Asp Leu Pro Lys Met Phe
            500                 505                 510

Ile Glu Ser Asp Pro Gly Phe Phe Ser Asn Ala Ile Val Glu Gly Ala
        515                 520                 525

Lys Lys Phe Pro Asn Thr Glu Phe Val Lys Val Lys Gly Leu His Phe
    530                 535                 540

Ser Gln Glu Asp Ala Pro Asp Glu Met Gly Lys Tyr Ile Lys Ser Phe
545                 550                 555                 560

Val Glu Arg Val Leu Lys Asn Glu Gln
                565

<210> SEQ ID NO 82
<211> LENGTH: 563
<212> TYPE: PRT
<213> ORGANISM: Homo sapiens

<400> SEQUENCE: 82

Met Asp Leu Ala Lys Leu Gly Leu Lys Glu Val Met Pro Thr Lys Ile
1               5                   10                  15
```

```
Asn Leu Glu Gly Leu Val Gly Asp His Ala Phe Ser Met Glu Gly Val
                 20                  25                  30

Gly Glu Gly Asn Ile Leu Glu Gly Thr Gln Glu Val Lys Ile Ser Val
             35                  40                  45

Thr Lys Gly Ala Pro Leu Pro Phe Ala Phe Asp Ile Val Ser Val Ala
 50                  55                  60

Phe Ser Tyr Gly Asn Arg Ala Tyr Thr Gly Tyr Pro Glu Glu Ile Ser
 65                  70                  75                  80

Asp Tyr Phe Leu Gln Ser Phe Pro Glu Gly Phe Thr Tyr Glu Arg Asn
                 85                  90                  95

Ile Arg Tyr Gln Asp Gly Gly Thr Ala Ile Val Lys Ser Asp Ile Ser
             100                 105                 110

Leu Glu Asp Gly Lys Phe Ile Val Asn Val Asp Phe Lys Ala Lys Asp
             115                 120                 125

Leu Arg Arg Met Gly Pro Val Met Gln Gln Asp Ile Val Gly Met Gln
130                 135                 140

Pro Ser Tyr Glu Ser Met Tyr Thr Asn Val Thr Ser Val Ile Gly Glu
145                 150                 155                 160

Cys Ile Ile Ala Phe Lys Leu Gln Thr Gly Lys His Phe Thr Tyr His
                 165                 170                 175

Met Arg Thr Val Tyr Lys Ser Lys Pro Val Glu Thr Met Pro Leu
             180                 185                 190

Tyr His Phe Ile Gln His Arg Leu Val Lys Thr Asn Val Asp Thr Ala
             195                 200                 205

Ser Gly Tyr Val Val Gln His Glu Thr Ala Ile Ala Ala His Ser Thr
210                 215                 220

Ile Lys Lys Ile Glu Gly Ser Leu Pro Gly Gly Gly Gly Asp Ile
225                 230                 235                 240

Glu Phe Leu Gln Pro Gly Gly Ser Gly Gly Gly Met Thr Ser Lys
                 245                 250                 255

Val Tyr Asp Pro Glu Gln Arg Lys Arg Met Ile Thr Gly Pro Gln Trp
             260                 265                 270

Trp Ala Arg Cys Lys Gln Met Asn Val Leu Asp Ser Phe Ile Asn Tyr
             275                 280                 285

Tyr Asp Ser Glu Lys His Ala Glu Asn Ala Val Ile Phe Leu His Gly
290                 295                 300

Asn Ala Ala Ser Ser Tyr Leu Trp Arg His Val Val Pro His Ile Glu
305                 310                 315                 320

Pro Val Ala Arg Cys Ile Ile Pro Asp Leu Ile Gly Met Gly Lys Ser
                 325                 330                 335

Gly Lys Ser Gly Asn Gly Ser Tyr Arg Leu Leu Asp His Tyr Lys Tyr
             340                 345                 350

Leu Thr Ala Trp Phe Glu Leu Leu Asn Leu Pro Lys Lys Ile Ile Phe
             355                 360                 365

Val Gly His Asp Trp Gly Ala Ala Leu Ala Phe His Tyr Ser Tyr Glu
370                 375                 380

His Gln Asp Lys Ile Lys Ala Ile Val His Ala Glu Ser Val Val Asp
385                 390                 395                 400

Val Ile Glu Ser Trp Asp Glu Trp Pro Asp Ile Glu Glu Asp Ile Ala
                 405                 410                 415

Leu Ile Lys Ser Glu Glu Gly Glu Lys Met Val Leu Glu Asn Asn Phe
             420                 425                 430

Phe Val Glu Thr Val Leu Pro Ser Lys Ile Met Arg Lys Leu Glu Pro
```

435                 440                 445
Glu Glu Phe Ala Ala Tyr Leu Glu Pro Phe Lys Glu Lys Gly Glu Val
        450                 455                 460

Arg Arg Pro Thr Leu Ser Trp Pro Arg Glu Ile Pro Leu Val Lys Gly
465                 470                 475                 480

Gly Lys Pro Asp Val Val Gln Ile Val Arg Asn Tyr Asn Ala Tyr Leu
                485                 490                 495

Arg Ala Ser Asp Asp Leu Pro Lys Met Phe Ile Glu Ser Asp Pro Gly
        500                 505                 510

Phe Phe Ser Asn Ala Ile Val Glu Gly Ala Lys Lys Phe Pro Asn Thr
            515                 520                 525

Glu Phe Val Lys Val Lys Gly Leu His Phe Ser Gln Glu Asp Ala Pro
        530                 535                 540

Asp Glu Met Gly Lys Tyr Ile Lys Ser Phe Val Glu Arg Val Leu Lys
545                 550                 555                 560

Asn Glu Gln

<210> SEQ ID NO 83
<211> LENGTH: 569
<212> TYPE: PRT
<213> ORGANISM: Homo sapiens

<400> SEQUENCE: 83

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Gly Gly Gly Gly Asp Ile Glu Phe Leu Gln Pro Gly Gly Ser Gly Gly

```
                    245                 250                 255
        Gly Gly Met Thr Ser Lys Val Tyr Asp Pro Glu Gln Arg Lys Arg Met
                    260                 265                 270

Ile Thr Gly Pro Gln Trp Trp Ala Arg Cys Lys Gln Met Asn Val Leu
                    275                 280                 285

Asp Ser Phe Ile Asn Tyr Tyr Asp Ser Glu Lys His Ala Glu Asn Ala
                    290                 295                 300

Val Ile Phe Leu His Gly Asn Ala Ala Ser Ser Tyr Leu Trp Arg His
        305                 310                 315                 320

Val Val Pro His Ile Glu Pro Val Ala Arg Cys Ile Ile Pro Asp Leu
                            325                 330                 335

Ile Gly Met Gly Lys Ser Gly Lys Ser Gly Asn Gly Ser Tyr Arg Leu
                            340                 345                 350

Leu Asp His Tyr Lys Tyr Leu Thr Ala Trp Phe Glu Leu Leu Asn Leu
                            355                 360                 365

Pro Lys Lys Ile Ile Phe Val Gly His Asp Trp Gly Ala Ala Leu Ala
        370                 375                 380

Phe His Tyr Ser Tyr Glu His Gln Asp Lys Ile Lys Ala Ile Val His
        385                 390                 395                 400

Ala Glu Ser Val Val Asp Val Ile Glu Ser Trp Asp Glu Trp Pro Asp
                            405                 410                 415

Ile Glu Glu Asp Ile Ala Leu Ile Lys Ser Glu Glu Gly Glu Lys Met
                            420                 425                 430

Val Leu Glu Asn Asn Phe Phe Val Gly Thr Val Leu Pro Ser Lys Ile
                            435                 440                 445

Met Arg Lys Leu Glu Pro Glu Glu Phe Ala Ala Tyr Leu Glu Pro Phe
                    450                 455                 460

Lys Glu Lys Gly Glu Val Arg Arg Pro Thr Leu Ser Trp Pro Arg Glu
        465                 470                 475                 480

Ile Pro Leu Val Lys Gly Gly Lys Pro Asp Val Val Gln Ile Val Arg
                            485                 490                 495

Asn Tyr Asn Ala Tyr Leu Arg Ala Ser Asp Asp Leu Pro Lys Met Phe
                            500                 505                 510

Ile Glu Ser Asp Pro Gly Phe Phe Ser Asn Ala Ile Val Glu Gly Ala
                            515                 520                 525

Lys Lys Phe Pro Asn Thr Glu Phe Val Lys Val Lys Gly Leu His Phe
                    530                 535                 540

Ser Gln Glu Asp Ala Pro Asp Glu Met Gly Lys Tyr Ile Lys Ser Phe
        545                 550                 555                 560

Val Glu Arg Val Leu Lys Asn Glu Gln
                            565

<210> SEQ ID NO 84
<211> LENGTH: 5
<212> TYPE: PRT
<213> ORGANISM: Homo sapiens

<400> SEQUENCE: 84

Lys Leu Pro Ala Thr
1               5

<210> SEQ ID NO 85
<211> LENGTH: 418
<212> TYPE: PRT
<213> ORGANISM: Homo sapiens
```

```
<400> SEQUENCE: 85

Met Gly Asp Lys Gly Thr Arg Val Phe Lys Lys Ala Ser Pro Asn Gly
1               5                   10                  15

Lys Leu Thr Val Tyr Leu Gly Lys Arg Asp Phe Val Asp His Ile Asp
                20                  25                  30

Leu Val Asp Pro Val Asp Gly Val Val Leu Val Asp Pro Glu Tyr Leu
            35                  40                  45

Lys Glu Arg Arg Val Tyr Val Thr Leu Thr Cys Ala Phe Arg Tyr Gly
        50                  55                  60

Arg Glu Asp Leu Asp Val Leu Gly Leu Thr Phe Arg Lys Asp Leu Phe
65                  70                  75                  80

Val Ala Asn Val Gln Ser Phe Pro Pro Ala Pro Glu Asp Lys Lys Pro
                85                  90                  95

Leu Thr Arg Leu Gln Glu Arg Leu Ile Lys Lys Leu Gly Glu His Ala
            100                 105                 110

Tyr Pro Phe Thr Phe Glu Ile Pro Pro Asn Leu Pro Cys Ser Val Thr
        115                 120                 125

Leu Gln Pro Gly Pro Glu Asp Thr Gly Lys Ala Cys Gly Val Asp Tyr
    130                 135                 140

Glu Val Lys Ala Phe Cys Ala Glu Asn Leu Glu Glu Lys Ile His Lys
145                 150                 155                 160

Arg Asn Ser Val Arg Leu Val Ile Arg Lys Val Gln Tyr Ala Pro Glu
                165                 170                 175

Arg Pro Gly Pro Gln Pro Thr Ala Glu Thr Thr Arg Gln Phe Leu Met
            180                 185                 190

Ser Asp Lys Pro Leu His Leu Glu Ala Ser Leu Asp Lys Glu Ile Tyr
        195                 200                 205

Tyr His Gly Glu Pro Ile Ser Val Asn Val His Val Thr Asn Asn Thr
    210                 215                 220

Asn Lys Thr Val Lys Lys Ile Lys Ile Ser Val Arg Gln Tyr Ala Asp
225                 230                 235                 240

Ile Cys Leu Phe Asn Thr Ala Gln Tyr Lys Cys Pro Val Ala Met Glu
                245                 250                 255

Glu Ala Asp Asp Thr Val Ala Pro Ser Ser Thr Phe Cys Lys Val Tyr
            260                 265                 270

Thr Leu Thr Pro Phe Leu Ala Asn Asn Arg Glu Lys Arg Gly Leu Ala
        275                 280                 285

Leu Asp Gly Lys Leu Lys His Glu Asp Thr Asn Leu Ala Ser Ser Thr
    290                 295                 300

Leu Leu Arg Glu Gly Ala Asn Arg Glu Ile Leu Gly Ile Ile Val Ser
305                 310                 315                 320

Tyr Lys Val Lys Val Lys Leu Val Val Ser Arg Gly Gly Leu Leu Gly
                325                 330                 335

Asp Leu Ala Ser Ser Asp Val Ala Val Glu Leu Pro Phe Thr Leu Met
            340                 345                 350

His Pro Lys Pro Lys Glu Glu Pro Pro His Arg Glu Val Pro Glu Asn
        355                 360                 365

Glu Thr Pro Val Asp Thr Asn Leu Ile Glu Leu Asp Thr Asn Asp Asp
    370                 375                 380

Asp Ile Val Phe Glu Asp Phe Ala Arg Gln Arg Leu Lys Gly Met Lys
385                 390                 395                 400

Asp Asp Lys Glu Glu Glu Glu Asp Gly Thr Gly Ser Pro Gln Leu Asn
                405                 410                 415
```

Asn Arg

<210> SEQ ID NO 86
<211> LENGTH: 409
<212> TYPE: PRT
<213> ORGANISM: Homo sapiens

<400> SEQUENCE: 86

```
Met Gly Glu Lys Pro Gly Thr Arg Val Phe Lys Ser Ser Pro Asn
1               5                   10                  15

Cys Lys Leu Thr Val Tyr Leu Gly Lys Arg Asp Phe Val Asp His Leu
                20                  25                  30

Asp Lys Val Asp Pro Val Asp Gly Val Val Leu Val Asp Pro Asp Tyr
                35                  40                  45

Leu Lys Asp Arg Lys Val Phe Val Thr Leu Thr Cys Ala Phe Arg Tyr
50                  55                  60

Gly Arg Glu Asp Leu Asp Val Leu Gly Leu Ser Phe Arg Lys Asp Leu
65                  70                  75                  80

Phe Ile Ala Thr Tyr Gln Ala Phe Pro Pro Val Pro Asn Pro Pro Arg
                85                  90                  95

Pro Pro Thr Arg Leu Gln Asp Arg Leu Leu Arg Lys Leu Gly Gln His
                100                 105                 110

Ala His Pro Phe Phe Phe Thr Ile Pro Gln Asn Leu Pro Cys Ser Val
                115                 120                 125

Thr Leu Gln Pro Gly Pro Glu Asp Thr Gly Lys Ala Cys Gly Val Asp
                130                 135                 140

Phe Glu Ile Arg Ala Phe Cys Ala Lys Ser Leu Glu Glu Lys Ser His
145                 150                 155                 160

Lys Arg Asn Ser Val Arg Leu Val Ile Arg Lys Val Gln Phe Ala Pro
                165                 170                 175

Glu Lys Pro Gly Pro Gln Pro Ser Ala Glu Thr Thr Arg His Phe Leu
                180                 185                 190

Met Ser Asp Arg Ser Leu His Leu Glu Ala Ser Leu Asp Lys Glu Leu
                195                 200                 205

Tyr Tyr His Gly Glu Pro Leu Asn Val Asn Val His Val Thr Asn Asn
                210                 215                 220

Ser Thr Lys Thr Val Lys Lys Ile Lys Val Ser Val Arg Gln Tyr Ala
225                 230                 235                 240

Asp Ile Cys Leu Phe Ser Thr Ala Gln Tyr Lys Cys Pro Val Ala Gln
                245                 250                 255

Leu Glu Gln Asp Asp Gln Val Ser Pro Ser Ser Thr Phe Cys Lys Val
                260                 265                 270

Tyr Thr Ile Thr Pro Leu Leu Ser Asp Asn Arg Glu Lys Arg Gly Leu
                275                 280                 285

Ala Leu Asp Gly Lys Leu Lys His Glu Asp Thr Asn Leu Ala Ser Ser
                290                 295                 300

Thr Ile Val Lys Glu Gly Ala Asn Lys Glu Val Leu Gly Ile Leu Val
305                 310                 315                 320

Ser Tyr Arg Val Lys Val Lys Leu Val Val Ser Arg Gly Gly Asp Val
                325                 330                 335

Ser Val Glu Leu Pro Phe Val Leu Met His Pro Lys Pro His Asp His
                340                 345                 350

Ile Pro Leu Pro Arg Pro Gln Ser Ala Ala Pro Glu Thr Asp Val Pro
                355                 360                 365
```

```
Val Asp Thr Asn Leu Ile Glu Phe Asp Thr Asn Tyr Ala Thr Asp Asp
        370                 375                 380

Asp Ile Val Phe Glu Asp Phe Ala Arg Leu Arg Leu Lys Gly Met Lys
385                 390                 395                 400

Asp Asp Asp Tyr Asp Asp Gln Leu Cys
                405

<210> SEQ ID NO 87
<211> LENGTH: 30
<212> TYPE: PRT
<213> ORGANISM: Homo sapiens

<400> SEQUENCE: 87

Arg Lys Gly Gln Glu Arg Phe Asn Arg Trp Phe Leu Thr Gly Met Thr
1               5                   10                  15

Val Ala Gly Val Val Leu Leu Gly Ser Leu Phe Ser Arg Lys
                20                  25                  30

<210> SEQ ID NO 88
<211> LENGTH: 17
<212> TYPE: PRT
<213> ORGANISM: Homo sapiens

<400> SEQUENCE: 88

Met Gly Val Ala Asp Leu Ile Lys Lys Phe Glu Ser Ile Ser Lys Glu
1               5                   10                  15

Glu
```